US007462707B1

(12) United States Patent
Witcombe et al.

(10) Patent No.: US 7,462,707 B1
(45) Date of Patent: Dec. 9, 2008

(54) NUCLEIC ACIDS ENCODING A RECOMBINANT 250 KDA ANTIGEN FROM SPOROZOITES/MEROZOITES OF *EIMERIA MAXIMA* AND THEIR USES

(75) Inventors: David Witcombe, Eastwood (AU); Nicholas C. Smith, Rosevill (AU); Michael Wallach, St. Ives (AU)

(73) Assignees: University of Technology, Sydney, Broadway, N.S.W. (AU); Abic Biological Laboratories Teva, Ltd., Beit Shemesh (IL)

( * ) Notice: Subject to any disclaimer, the term of this patent is extended or adjusted under 35 U.S.C. 154(b) by 357 days.

(21) Appl. No.: 10/483,165

(22) PCT Filed: Jul. 3, 2002

(86) PCT No.: PCT/US02/21237

§ 371 (c)(1),
(2), (4) Date: Sep. 17, 2004

(87) PCT Pub. No.: WO03/004684

PCT Pub. Date: Jan. 16, 2003

Related U.S. Application Data

(60) Provisional application No. 60/303,670, filed on Jul. 6, 2001.

(51) Int. Cl.
*C07H 21/04* (2006.01)
*C07K 14/00* (2006.01)
*C12P 21/04* (2006.01)
*C12N 1/10* (2006.01)
*A61K 39/012* (2006.01)
*A61K 39/00* (2006.01)

(52) U.S. Cl. .................... 536/23.7; 435/69.3; 435/69.7; 435/258.4; 435/320.1; 530/300; 530/350; 424/265.1; 424/271.1

(58) Field of Classification Search ................ 536/23.7; 435/69.3, 69.7, 258.4, 320.1; 530/300, 350; 424/265.1, 271.1
See application file for complete search history.

(56) References Cited

U.S. PATENT DOCUMENTS

| | | | |
|---|---|---|---|
| 5,496,550 | A | 3/1996 | Wallach et al. |
| 5,932,225 | A | 8/1999 | Wallach et al. |

FOREIGN PATENT DOCUMENTS

| | | |
|---|---|---|
| EP | 0135712 | 3/1985 |
| EP | 0164176 | 11/1985 |
| EP | 0167443 | 1/1986 |
| EP | 0256536 | 1/1996 |
| WO | WO9000403 | 1/1990 |
| WO | WO 03004683 | 1/2003 |

OTHER PUBLICATIONS

Bumstead et al Clinical and Diagnostic Laboratory Immunology, Sep. 1995, p. 524-530.*

Rudinger et al, in "Peptide and Hormones", edited by Parsons, J.A., University Park Press, Jun. 1976.*

Danforth, H.D., et al., A Review of Progress in Coccidial Vaccine Development, *In Vith Intnl.Coccidiosis Conf.*, Guelph, Ontario, Canada, Barta, J.R. and Fernando, M.A.,(ed.), pp. 49-60 (1993).

Eschenbacher, K. H., et al., Characterization of a 14kDa oocytst wall protein of *Eimeria tenella* and *E. Acervulina, Parasitol.*, vol. 112:169-176 (1995) (Abstract).

Fried, M., et al., Developmental gene expression of a 230-kilodalton macrogamete-specific protein of the avian coccidial parasite, *Eimeria maxima, Mol. & Biochem. Parasitol.*, vol. 51:251-262 (1992).

Gilbert, et al., An Enzyme-Linked Immunosorbent Assay for Coccidiosis in chickens: Correlation of Antibody Levels with Prior Exposure to Coccidia in the Laboratory and in the Field, *Avian Disease*, vol. 32:688-694 (1988).

(Continued)

*Primary Examiner*—Shanon A. Foley
*Assistant Examiner*—Padma Baskar
(74) *Attorney, Agent, or Firm*—John P. White; Cooper & Dunham LLP

(57) ABSTRACT

The present invention provides an isolated nucleic acid comprising a nucleotide sequence encoding a 250 kDa polypeptide from Sporozoites/Merozoites of *Eimeria maxima*, or encoding a homolog of the polypeptide, or a complement of the nucleic acid and a method of producing a recombinant 250 kDa polypeptide of the same. The present invention also provides an isolated nucleic acid comprising a nucleotide sequence encoding an immunodominant portion of a 250 kDa polypeptide from Sporozoites/Merozoites of *Eimeria maxima* having the amino acid sequence described herein, or encoding a homolog of the polypeptide, or a complement of the nucleic acid. The subject invention also provides a vaccine against *Eimeria tenella, Eimeria maxima, Eimeria acervulina, Eimeria necatrix, Eimeriapraecax, Eimeria mitis* or *Eimeria brunetti*, or a microorganism expressing an immunologically cross-reactive antigen, comprising the isolated nucleic acid comprising a nucleotide sequence encoding a 250 kDa polypeptide from Sporozoites/Merozoites of *Eimeria maxima* or the immunodominant portion of a 250 kDa polypeptide from Sporozoites/Merozoites of *Eimeria maxima*, or encoding a homolog of the polypeptide, or a complement of the nucleic acid which may also contain a 56 kDa, 82 kDa or 230 kDa protein isolated from the gametocytes of *Eimeria maxima* and a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject any of the aforementioned vaccines.

26 Claims, 75 Drawing Sheets

OTHER PUBLICATIONS

Hein, H., Eimeria Brunette: Cross Infections in Chickens Immunized to *E. maxima, Experimental Parasitology*, vol. 29:367-374 (1971).

Karkhanis, Y.D., et al., Purification and characterization of a protective antigen for *Eimeria tenella, Infect. & Immun.*, vol. 59:983-989 (1991).

Kowlaczyk et al., Quantitation of Maternal-Fetal Egg Transport in the Chicken, *Immunology*, vol. 54:755-762 (1985).

Larsen, N.C., et al., Production and Partial Characterization of Monoclonal Antibodies Specific for the Gamonts of *Eimeria tenella, The J. Parasitology*, vol. 77(6):1012-1015 (1991).

Laxer, M.A., et al., Production of Monoclonal Antibodies Specific For *Eimeria tenella* Microgametocytes, *The J. Parasitology*, vol. 73(3):611-616 (1987).

Long, P.L., et al., Effects of Fowl Sera on Some Stages in the Life Cycle of *Eimeria tenella, Experimental Parasitology*, vol. 14:210-217 (1963).

Long, P.L., et al., Immunity to coccidiosis: effect of serum antibodies on cell invasion by sporozoites of *Eimeria* in vitro, *Parasitology*, vol. 65:437-445 (1972).

Losch et al., The Chicken Egg, an Antibody Source, *J. Vet Med B.* vol. 33:609-619 (1986).

Mencher, D. et al., Antigenic proteins of *Eimeria maxima* gametocytes: cell-free translation and detection with recovered chicken serum, *Exp. Parasitol.*, vol. 68:40-48 (1989) (Abstract).

Pugatsch, T., et al., *Eimeria maxima*: Isolation of Gametocyctes and Their Immunogenicity in Mice, Rabbits, and Chickens, *Experimental Parasitology*, vol. 68:127-134 (1989).

Rose, M.E., Immunity to *Eimeria brunetti* and *Eimeria maxima* infections in the fowl, *Parasitology*, vol. 57:363-370 (1967).

Rose et al., Immunity to coccidiosis: protective effects of transferred serum and cells investigated in chick embyros infected with *Eimeria tenella, Parasitology*, vol. 63:299-313, (1971).

Rose, M.E., Immunity to Coccidiosis: maternal transfer in *Eimeria maxima* Infections, *Parasitology*, vol. 65:273-282 (1972).

Rose, M.E., Protective antibodies in infections with *Eimeria maxima*: the reduction of pathogenic effects in vivo and a comparison between oral and subcutaneous administration of antiserum, *Parasitology*, vol. 68:285-292 (1974).

Rose, M.E., Immunity to *Eimeria maxima*: Reactions of Antisera in vitro and Protection in vivo, *The Journal of Parasitology*, vol. 60(3):528-530 (1974).

Rose, M.E., Immunity to coccidiosis: stages of the life- cycle of *Eimeria maxima* which induce, and are affected by, the response of the host, *Parasitology*, vol. 73:25-37 (1976).

Rose, M.E., *Eimeria, Current Topics in Microbiology and Immunology*, (A. Clarke, et al. eds.), vol. 120:7-17 (1985).

Shirley, M.W., et al., *Eimeria* spp. from the Chicken: from Merozoites to Oocysts in Embryonated Eggs, *Parasitology*, vol. 83:259-267 (1981).

Smith, N.C., et al., Maternal transmission of immunity to *Eimeria maxima*: western blot analysis of protective antibodies induced by infection, *Infection & Immunity*, 62(11): 4811-4817 (1994).

Song et al., Antibodies to the α-Subunit of Insulin Receptor from Eggs of Immunized Hens, *The Journal of Immunology*, vol. 135:3354-3359 (1986).

Stotish, R.L., et al., Preparation and Purification of Merozoites of *Eimeria tenella, The Journal of Parasitology*, vol. 61(4):700-703 (1975).

Wallach, M., et al., *Eimeria maxima*: Identification of Gametocyte Protein Antigens, *Experimental Parasitology*, vol. 68(1):49-56 (1989).

Wallach, M., et al., Passive Immunization of chickens against *Eimeria maxima* Infection with a Monoclonal Antibody Developed against a Gametocyte Antigen, *Infection and Immunity*, vol. 58:557-562 (1990).

Wallach, M., et al., *Eimeria maxima* gametocyte antigens: potential use in a subunit maternal vaccine against coccidiosis in chickens, *Vaccine*, vol. 13:347-354 (1995).

Wallach, M., et al., Progress Towards a Subunit Vaccine Against Coccidiosis, *Misset's World Poultry, Supplement Coccidiosis*, No. 2:22-24 (1996).

Belli, S.I. et al. (2002) Functional Genomics of *gam*56: Characterisation of the role of 56 Kilodalton Sexual Stage Antigen in Oocyst Wall Formation in *Eimeria maxima, Int. J. of Parasitology* 32:1727-1737.

Tomley, F.M. et al. (2001) EtMIC4: a Microneme Protein from *Eimeria tenella* that Contains Tandem Arrays of Epidermal Growth Factor-like Repeats and Thrombospondin Type-I Repeats, *Int. J. of Parasitology* 31:1303-1310.

Witcombe, D.M. et al. (2003) Molecular Characterization of EmTFP250: A Novel Member of the TRAP Protein Family in *Eimeria maxima, Int. J. of Parasitology* 33:691-702.

Wallach, M. et al. (1992) Maternal Immunization with Gametocyte Antigens as a Means of Providing Protective Immunity Against *Eimeria maxima* in Chickens, *Infection and Immunity* 60(5):2036-2039.

Database EMBL mic4 Gene, (2001) XP002313642, Abstract.

Belli, S.I., et al., Cloning And Characterization Of The 82 kDa Tyrosine-Rich Sexual Stage Glycoprotein, GAM82, and Its Role In Oocyst Wall Formation In The Apicomplexan Parasite, *Eimeria maxima*, Gene, vol. 307:201-212, (2003).

Belli, S.I., et al., Roles Of Tyrosine-Rich Precursor Gycoproteins And Dityrosine- and 3,4-Dihydroxyphenylalanine-Mediated Protein Cross-Linking In Development Of The Oocyst Wall In The Coccidian Parasite *Eimeria maxima, Eukaryotic Cell*, vol. 2:456-464 (2003).

* cited by examiner

230kDa 1 2 3 4

*FIGURE 6*

```
    CAACATTTCTTCTTCCTTTTTCTTCTTCGAGCTTCTTTAGCTCGATTTTCTGGCCCTTGC
  1 ---------+---------+---------+---------+---------+---------+ 60
    GTTGTAAAGAAGAAGGAAAAAGAAGAAGCTCGAAGAAATCGAGCTAAAAGACCGGGAACG

c    T  F  L  L  P  F  S  S  S  S  F  F  S  S  I  F  W  P  L  Q -

    AGCTCTCCGCGGGTGCAGGGCGCAGCCAGCTCACTACTGCCTTTCACAGCGTCGTTCCCC
 61 ---------+---------+---------+---------+---------+---------+ 120
    TCGAGAGGCGCCCACGTCCCGCGTCGGTCGAGTGATGACGGAAAGTGTCGCAGCAAGGGG

c    L  S  A  G  A  G  R  S  Q  L  T  T  A  F  H  S  V  V  P  H -

    ACCTTGGCCCATGTGCCACATGGTCATTTTTCTTCAGTTTGTTCATGAGAAGAGCTGCTA
121 ---------+---------+---------+---------+---------+---------+ 180
    TGGAACCGGGTACACGGTGTACCAGTAAAAAGAAGTCAAACAAGTACTCTTCTCGACGAT

c    L  G  P  C  A  T  W  S  F  F  F  S  L  F  M  R  R  A  A  T -

    CAGTGTAGCTCGAACTCAACTTTAAACGCAGCCGTTTCAGCGGCGACAATATGCTGCATC
181 ---------+---------+---------+---------+---------+---------+ 240
    GTCACATCGAGCTTGAGTTGAAATTTGCGTCGGCAAAGTCGCCGCTGTTATACGACGTAG

c    V  *  L  E  L  N  F  K  R  S  R  F  S  G  D  N  M  L  H  R -

    GCAACCCGCGGTGGGCGCTTTGTGCAGCCCTCGCTGCACTCTATGGCGGAACAGGAATCG
241 ---------+---------+---------+---------+---------+---------+ 300
    CGTTGGGCGCCACCCGCGAAACACGTCGGGAGCGACGTGAGATACCGCCTTGTCCTTAGC

c    N  P  R  W  A  L  C  A  A  L  A  A  L  Y  G  G  T  G  I  A -

    CCAGCGCCGAAGTTAACAATGAATTGAGCAAGTGCGAATCTGGGTGGACACCCTGGACTA
301 ---------+---------+---------+---------+---------+---------+ 360
    GGTCGCGGCTTCAATTGTTACTTAACTCGTTCACGCTTAGACCCACCTGTGGGACCTGAT

c    S  A  E  V  N  N  E  L  S  K  C  E  S  G  W  T  P  W  T  T -

    CCTGCAACCCGCAAACTGGTCTGCGGGAGAGGCACAATGCACAGTGCGAGACATGGGTGG
361 ---------+---------+---------+---------+---------+---------+ 420
    GGACGTTGGGCGTTTGACCAGACGCCCTCTCCGTGTTACGTGTCACGCTCTGTACCCACC

c    C  N  P  Q  T  G  L  R  E  R  H  N  A  Q  C  E  T  W  V  E -

    AGGTTGAGGAATGCCAGAAGCTGACAGGATGTGGCAACTGGACTCCTTGGTCTCCCGGCG
421 ---------+---------+---------+---------+---------+---------+ 480
    TCCAACTCCTTACGGTCTTCGACTGTCCTACACCGTTGACCTGAGGAACCAGAGGGCCGC

c    V  E  E  C  Q  K  L  T  G  C  G  N  W  T  P  W  S  P  G  D -
```

*FIGURE 6 (cont.)*

```
     ATATGTCGTGTGTGGTGGGACAGTTTCAAACCCGCAACAGGGAGGGCTGCCCAGAGGTGC
 481 ---------+---------+---------+---------+---------+---------+ 540
     TATACAGCACACACCACCCTGTCAAAGTTTGGGCGTTGTCCCTCCCGACGGGTCTCCACG

c     M  S  C  V  V  G  Q  F  Q  T  R  N  R  E  G  C  P  E  V  Q -

     AGGAAGTGAGGGCATGCAGGCCTGTACTTCTAGAATGCAACGATCAATGGACCCCCTGGA
 541 ---------+---------+---------+---------+---------+---------+ 600
     TCCTTCACTCCCGTACGTCCGGACATGAAGATCTTACGTTGCTAGTTACCTGGGGGACCT

c     E  V  R  A  C  R  P  V  L  L  E  C  N  D  Q  W  T  P  W  T -

     CAATGTGCGACACCAACCGCGTCCAGGAAAGATACAACTCAAAGTGCGGACCCGTCGAAG
 601 ---------+---------+---------+---------+---------+---------+ 660
     GTTACACGCTGTGGTTGGCGCAGGTCCTTTCTATGTTGAGTTTCACGCCTGGGCAGCTTC

c     N  C  D  T  N  R  V  Q  E  R  Y  N  S  K  C  G  P  V  E  V -

     TCCGCGAGTGCAACATGGACGACGCAGAGATCGAGAAATGCGGCGAGTTCGTGGAATGGG
 661 ---------+---------+---------+---------+---------+---------+ 720
     AGGCGCTCACGTTGTACCTGCTGCGTCTCTAGCTCTTTACGCCGCTCAAGCACCTTACCC

c     R  E  C  N  M  D  D  A  E  I  E  K  C  G  E  F  V  E  W  D -

     ATCCCCCTATGAATGGAGACTGCGTACGCGGGGGTACCCACACGCGTTACCGTCAAAACT
 721 ---------+---------+---------+---------+---------+---------+ 780
     TAGGGGGATACTTACCTCTGACGCATGCGCCCCCATGGGTGTGCGCAATGGCAGTTTTGA

c     P  P  M  N  G  D  C  V  R  G  G  T  H  T  R  Y  R  Q  N  C -

     GCCCAGACCGCAAAGAGGTGCGGGTGTGCGGAGCCTTTGATTGCAGTAGCTGCTCTGTAA
 781 ---------+---------+---------+---------+---------+---------+ 840
     CGGGTCTGGCGTTTCTCCACGCCCACACGCCTCGGAAACTAACGTCATCGACGAGACATT

c     P  D  R  K  E  V  R  V  C  G  A  F  D  C  S  S  C  S  V  N -

     ACGCCACTTGCGATCCCATTGGTGCATCCTGCGAATGCAAGCCTGGTTTCCGCGGCAATG
 841 ---------+---------+---------+---------+---------+---------+ 900
     TGCGGTGAACGCTAGGGTAACCACGTAGGACGCTTACGTTCGGACCAAAGGCGCCGTTAC

c     A  T  C  D  P  I  G  A  S  C  E  C  K  P  G  F  R  G  N  G -

     GGAAGACCTGCGAGGCCTTCAACCCCTGCGAAGATACCCCTGCACCTTGCGACAGCAACG
 901 ---------+---------+---------+---------+---------+---------+ 960
     CCTTCTGGACGCTCCGGAAGTTGGGGACGCTTCTATGGGGACGTGGAACGCTGTCGTTGC

c     K  T  C  E  A  F  N  P  C  E  D  T  P  A  P  C  D  S  N  A -

     CCATCTGCACCCCAGACGCAATGACGCCAAATGCCAGTGCAAGGCAGGCTGGGACGCAGA
 961 ---------+---------+---------+---------+---------+---------+ 1020
     GGTAGACGTGGGGTCTGCGTTACTGCGGTTTACGGTCACGTTCCGTCCGACCCTGCGTCT

c     I  C  T  P  D  A  M  T  P  N  A  S  A  R  Q  A  G  T  Q  I -

     TTCCGGAGCAGGCAGCAGCAAGAAGCCTTGCGTTGAGGTCGACGAGTGCGCATCCAACAC
1021 ---------+---------+---------+---------+---------+---------+ 1080
     AAGGCCTCGTCCGTCGTCGTTCTTCGGAACGCAACTCCAGCTGCTCACGCGTAGGTTGTG

c     P  E  Q  A  A  A  R  S  L  A  L  R  S  T  S  A  H  P  T  P -
```

*FIGURE 6 (cont.)*

```
      CCACCAGTGCCCGGCACACTCCACATGCATCAACACCAAGGGCTCTTATAAGTGCGACTG
1081  ---------+---------+---------+---------+---------+---------+ 1140
      GGTGGTCACGGGCCGTGTGAGGTGTACGTAGTTGTGGTTCCCGAGAATATTCACGCTGAC

c      T  S  A  R  H  T  P  H  A  S  T  P  R  A  L  I  S  A  T  A -

      CAACCAGGGATACCGTCAAGGGAGAGGACGGACAGTGTCATGACGTCGATGAATGCACCA
1141  ---------+---------+---------+---------+---------+---------+ 1200
      GTTGGTCCCTATGGCAGTTCCCTCTCCTGCCTGTCACAGTACTGCAGCTACTTACGTGGT

c      T  R  D  T  V  K  G  E  D  G  Q  C  H  D  V  D  E  C  T  N -

      ACGGAGAGCACACCTGCCCCGCTCACTCCACTTGTTTGAATACAGCTGGCAGCTACGAGT
1201  ---------+---------+---------+---------+---------+---------+ 1260
      TGCCTCTCGTGTGGACGGGGCGAGTGAGGTGAACAAACTTATGTCGACCGTCGATGCTCA

c      G  E  H  T  C  P  A  H  S  T  C  L  N  T  A  G  S  Y  E  C -

      GCCGCTGCGACACTGGGTACAGCGGAAATGCAACTGCAGACAGCCCTTGCAAGAACATTG
1261  ---------+---------+---------+---------+---------+---------+ 1320
      CGGCGACGCTGTGACCCATGTCGCCTTTACGTTGACGTCTGTCGGGAACGTTCTTGTAAC

c      R  C  D  T  G  Y  S  G  N  A  T  A  D  S  P  C  K  N  I  D -

      ACGAATGCGCCAACCCCAACGCCTGCTCGGCCAACGCTATCTGCACAGACACCGACGGCT
1321  ---------+---------+---------+---------+---------+---------+ 1380
      TGCTTACGCGGTTGGGGTTGCGGACGAGCCGGTTGCGATAGACGTGTCTGTGGCTGCCGA

c      E  C  A  N  P  N  A  C  S  A  N  A  I  C  T  D  T  D  G  S -

      CCTTCACCTGCAGCTGCCCCGAAGGGTACAGCGGCCAGGGAACCCATGACTCTCCCTGCT
1381  ---------+---------+---------+---------+---------+---------+ 1440
      GGAAGTGGACGTCGACGGGGCTTCCCATGTCGCCGGTCCCTTGGGTACTGAGAGGGACGA

c      F  T  C  S  C  P  E  G  Y  S  G  Q  G  T  H  D  S  P  C  S -

      CCAAGATCGACTTCTGCGCATACCCCTCACTCAATACATGCGGAGCCCACTCCACTTGCA
1441  ---------+---------+---------+---------+---------+---------+ 1500
      GGTTCTAGCTGAAGACGCGTATGGGGAGTGAGTTATGTACGCCTCGGGTGAGGTGAACGT

c      K  I  D  F  C  A  Y  P  S  L  N  T  C  G  A  H  S  T  C  N -

      ACACCCTCACATCTTTCAAGTGCATCTGCGATGCGGGATATGAAGGCGCCGGCACTCGCG
1501  ---------+---------+---------+---------+---------+---------+ 1560
      TGTGGGAGTGTAGAAAGTTCACGTAGACGCTACGCCCTATACTTCCGCGGCCGTGAGCGC

c      T  L  T  S  F  K  C  I  C  D  A  G  Y  E  G  A  G  T  R  E -

      AGAGCCCGTGCGTGGACGTGAACGAGTGCTCGAACGAGAAGCCCACAAACAACTGCAACA
1561  ---------+---------+---------+---------+---------+---------+ 1620
      TCTCGGGCACGCACCTGCACTTGCTCACGAGCTTGCTCTTCGGGTGTTTGTTGACGTTGT

c      S  P  C  V  D  V  N  E  C  S  N  E  K  P  T  N  N  C  N  R -
```

*FIGURE 6 (cont.)*

```
     GAAACGCAAAACTGCACCAACACCGAGGGATCCTACACTTGCGAATGCAAGCCCGGTTTCT
1621 ---------+---------+---------+---------+---------+---------+ 1680
     CTTTGCGTTTGACGTGGTTGTGGCTCCCTAGGATGTGAACGCTTACGTTCGGGCCAAAGA

c     N  A  N  C  T  N  T  E  G  S  Y  T  C  E  C  K  P  G  F  S -

     CTGGCGACGGCATGGGTCCCAACGGGTGTACCGACATCGACGAGTGCGCGGCGGAGCAGT
1681 ---------+---------+---------+---------+---------+---------+ 1740
     GACCGCTGCCGTACCCAGGGTTGCCCACATGGCTGTAGCTGCTCACGCGCCGCCTCGTCA

c     G  D  G  M  G  P  N  G  C  T  D  I  D  E  C  A  A  E  Q  S -

     CCCCCTGCGACCCTCACGCCTCCTGCAGCAACACTGAGGGCTCGTATGTATGCACCTGCA
1741 ---------+---------+---------+---------+---------+---------+ 1800
     GGGGGACGCTGGGAGTGCGGAGGACGTCGTTGTGACTCCCGAGCATACATACGTGGACGT

c     P  C  D  P  H  A  S  C  S  N  T  E  G  S  Y  V  C  T  C  N -

     ACACCGGCTACGAGCCAGCTTCAACCGACGGCCATGCATGCAAAGATATCGACGAGTGCG
1801 ---------+---------+---------+---------+---------+---------+ 1860
     TGTGGCCGATGCTCGGTCGAAGTTGGCTGCCGGTACGTACGTTTCTATAGCTGCTCACGC

c     T  G  Y  E  P  A  S  T  D  G  H  A  C  K  D  I  D  E  C  A -

     CCACCGGTGCAGCTGGGTGCCACGTGTCAGCACAGTGTCTGAACACGGACGGCAGCTACG
1861 ---------+---------+---------+---------+---------+---------+ 1920
     GGTGGCCACGTCGACCCACGGTGCACAGTCGTGTCACAGACTTGTGCCTGCCGTCGATGC

c     T  G  A  A  G  C  H  V  S  A  Q  C  L  N  T  D  G  S  Y  E -

     AGTGCAAGTGTCTTGAGGGCTTCGTCGGCGACGGAAAGACCTGCAACGACGTCGATGAGT
1921 ---------+---------+---------+---------+---------+---------+ 1980
     TCACGTTCACAGAACTCCCGAAGCAGCCGCTGCCTTTCTGGACGTTGCTGCAGCTACTCA

c     C  K  C  L  E  G  F  V  G  D  G  K  T  C  N  D  V  D  E  C -

     GCGCTGCGGCGACATCTCCTTGCGGTGACAACACTCACTGCCAGAACACAATTGGCAGCT
1981 ---------+---------+---------+---------+---------+---------+ 2040
     CGCGACGCCGCTGTAGAGGAACGCCACTGTTGTGAGTGACGGTCTTGTGTTAACCGTCGA

c     A  A  A  T  S  P  C  G  D  N  T  H  C  Q  N  T  I  G  S  Y -

     ACGAGTGCGAGTGCAAGGCTGGCTATGGCAACATGCAAGACAACGCATGCAGCGACATTG
2041 ---------+---------+---------+---------+---------+---------+ 2100
     TGCTCACGCTCACGTTCCGACCGATACCGTTGTACGTTCTGTTGCGTACGTCGCTGTAAC

c     E  C  E  C  K  A  G  Y  G  N  M  Q  D  N  A  C  S  D  I  D -

     ACGAGTGCAAGGATGCGAACACCAAGATCCCTGACAACTGTCTTTGCGTGAACAATGATG
2101 ---------+---------+---------+---------+---------+---------+ 2160
     TGCTCACGTTCCTACGCTTGTGGTTCTAGGGACTGTTGACAGAAACGCACTTGTTACTAC

c     E  C  K  D  A  N  T  K  I  P  D  N  C  L  C  V  N  N  D  G -

     GCAGCTACTCCCTTGAGGCGAAGGCTGGATACGAATTGGTGAACGGCGAGTGCATCAAGA
2161 ---------+---------+---------+---------+---------+---------+ 2220
     CGTCGATGAGGGAACTCCGCTTCCGACCTATGCTTAACCACTTGCCGCTCACGTAGTTCT
c     S  Y  S  L  E  A  K  A  G  Y  E  L  V  N  G  E  C  I  K  I -
```

*FIGURE 6 (cont.)*

```
     TCGACTTCTGCGCCCGCGGCGCATGCAACTCGCTGGCCTCCTGCAAGGAGAATGAAGAAG
2221 ---------+---------+---------+---------+---------+---------+ 2280
     AGCTGAAGACGCGGGCGCCGCGTACGTTGAGCGACCGGAGGACGTTCCTCTTACTTCTTC

c     D  F  C  A  R  G  A  C  N  S  L  A  S  C  K  E  N  E  E  G -

     GCACAGCGGCGATCTGCACCTGCCTGCCAGGCTACAGCGGCGACGGCACTGCTGAAGGCC
2281 ---------+---------+---------+---------+---------+---------+ 2340
     CGTGTCGCCGCTAGACGTGGACGGACGGTCCGATGTCGCCGCTGCCGTGACGACTTCCGG

c     T  A  A  I  C  T  C  L  P  G  Y  S  G  D  G  T  A  E  G  H -

     ACTGCAACGACATTGACGAGTGTGCAGGTCAGAATGACTGTGCTCCTGCCGAGCAGGGAG
2341 ---------+---------+---------+---------+---------+---------+ 2400
     TGACGTTGCTGTAACTGCTCACACGTCCAGTCTTACTGACACGAGGACGGCTCGTCCCTC

c     C  N  D  I  D  E  C  A  G  Q  N  D  C  A  P  A  E  Q  G  G -

     GCATCTGCGAGAACACTGTCGGCTCGTACACCTGCAAGTGCAAAGAGGGGTACAGGCAAG
2401 ---------+---------+---------+---------+---------+---------+ 2460
     CGTAGACGCTCTTGTGACAGCCGAGCATGTGGACGTTCACGTTTCTCCCCATGTCCGTTC

c     I  C  E  N  T  V  G  S  Y  T  C  K  C  K  E  G  Y  R  Q  D -

     ATGGAAACTCATGCACTGAGATCGACGAGTGCGCTGAGGGAACCCACAACTGCCACCCTT
2461 ---------+---------+---------+---------+---------+---------+ 2520
     TACCTTTGAGTACGTGACTCTAGCTGCTCACGCGACTCCCTTGGGTGTTGACGGTGGGAA

c     G  N  S  C  T  E  I  D  E  C  A  E  G  T  H  N  C  H  P  S -

     CCGCCACCTGCAGCAACACCCCCGGAAGCTTCACCTGCCAATGCAACAGTGGATTCACTG
2521 ---------+---------+---------+---------+---------+---------+ 2580
     GGCGGTGGACGTCGTTGTGGGGGCCTTCGAAGTGGACGGTTACGTTGTCACCTAAGTGAC

c     A  T  C  S  N  T  P  G  S  F  T  C  Q  C  N  S  G  F  T  G -

     GCAGCGGTGTGGAGTGCGAAGACATTGACGAGTGCTCAACTGAGGCAGATGATTGTGGTG
2581 ---------+---------+---------+---------+---------+---------+ 2640
     CGTCGCCACACCTCACGCTTCTGTAACTGCTCACGAGTTGACTCCGTCTACTAACACCAC

c     S  G  V  E  C  E  D  I  D  E  C  S  T  E  A  D  D  C  G  A -

     CAAACACCATCTGCAGCAACACCATTGGTGCTTTCGAGTGCAACTGCCGTGAAGGCTATG
2641 ---------+---------+---------+---------+---------+---------+ 2700
     GTTTGTGGTAGACGTCGTTGTGGTAACCACGAAAGCTCACGTTGACGGCACTTCCGATAC

c     N  T  I  C  S  N  T  I  G  A  F  E  C  N  C  R  E  G  Y  E -

     AACGCGCAGACGCAAAGACGTGCGTCGACATCGACGAATGCGCGACAGGCACACACACTT
2701 ---------+---------+---------+---------+---------+---------+ 2760
     TTGCGCGTCTGCGTTTCTGCACGCAGCTGTAGCTGCTTACGCGCTGTCCGTGTGTGTGAA

c     R  A  D  A  K  T  C  V  D  I  D  E  C  A  T  G  T  H  T  C -
```

*FIGURE 6 (cont.)*

```
      GCTCGAACCACGCCACCTGCACCAATACCGATGGGTCATTCACATGCCAGTGCAACCCCG
2761 ---------+---------+---------+---------+---------+---------+ 2820
      CGAGCTTGGTGCGGTGGACGTGGTTATGGCTACCCAGTAAGTGTACGGTCACGTTGGGGC

c     S  N  H  A  T  C  T  N  T  D  G  S  F  T  C  Q  C  N  P  G -

      GCTTCGAAGGTGACGGCCACAAGTGCGAGGACATCGACTTCTGCGGTGCTGGACAGCACG
2821 ---------+---------+---------+---------+---------+---------+ 2880
      CGAAGCTTCCACTGCCGGTGTTCACGCTCCTGTAGCTGAAGACGCCACGACCTGTCGTGC

c     F  E  G  D  G  H  K  C  E  D  I  D  F  C  G  A  G  Q  H  D -

      ACTGCAATGTGCATGCCGAGTGCTCTGAGAGCGAGGACAACACCACTTTCAAGTGCACCT
2881 ---------+---------+---------+---------+---------+---------+ 2940
      TGACGTTACACGTACGGCTCACGAGACTCTCGCTCCTGTTGTGGTGAAAGTTCACGTGGA

c     C  N  V  H  A  E  C  S  E  S  E  D  N  T  T  F  K  C  T  C -

      GTATAACAGGGTACGCTGGAGACGGCCATGGCGAGGCAGGCTGCCAAGACATTGATGAGT
2941 ---------+---------+---------+---------+---------+---------+ 3000
      CATATTGTCCCATGCGACCTCTGCCGGTACCGCTCCGTCCGACGGTTCTGTAACTACTCA

c     I  T  G  Y  A  G  D  G  H  G  E  A  G  C  Q  D  I  D  E  C -

      GCGCAGAAGAAAACATCTGCGGAAGCAACGCTGTCTGCACAAACACCGCAGGAAGCTACC
3001 ---------+---------+---------+---------+---------+---------+ 3060
      CGCGTCTTCTTTTGTAGACGCCTTCGTTGCGACAGACGTGTTTGTGGCGTCCTTCGATGG

c     A  E  E  N  I  C  G  S  N  A  V  C  T  N  T  A  G  S  Y  Q -

      AATGCGCATGCCGTGAGGGCTTCGTTGCATCAGCTGAACAGCAGCAGCAGGGAACCCCAG
3061 ---------+---------+---------+---------+---------+---------+ 3120
      TTACGCGTACGGCACTCCCGAAGCAACGTAGTCGACTTGTCGTCGTCGTCCCTTGGGGTC

c     C  A  C  R  E  G  F  V  A  S  A  E  Q  Q  Q  Q  G  T  P  A -

      CACTGGTTTGCGTGGACGTCGACGAGTGCAGCGACGCTTCGAAGAACACATGTGCCAAGC
3121 ---------+---------+---------+---------+---------+---------+ 3180
      GTGACCAAACGCACCTGCAGCTGCTCACGTCGCTGCGAAGCTTCTTGTGTACACGGTTCG

c     L  V  C  V  D  V  D  E  C  S  D  A  S  K  N  T  C  A  K  P -

      CAGCCGACGGAGGCATTTGCACAAACACTGAAGGCAGCTACGAATGCGCTTGCAAGCCAG
3181 ---------+---------+---------+---------+---------+---------+ 3240
      GTCGGCTGCCTCCGTAAACGTGTTTGTGACTTCCGTCGATGCTTACGCGAACGTTCGGTC

c     A  D  G  G  I  C  T  N  T  E  G  S  Y  E  C  A  C  K  P  G -

      GCTACCAAGGTGACGGCCACAGCTGCGCAGACATCAACGAATGCACTGCACAGGGCACCT
3241 ---------+---------+---------+---------+---------+---------+ 3300
      CGATGGTTCCACTGCCGGTGTCGACGCGTCTGTAGTTGCTTACGTGACGTGTCCCGTGGA

c     Y  Q  G  D  G  H  S  C  A  D  I  N  E  C  T  A  Q  G  T  C -

      GCGGCGAACACACAACTTGCAAGAACACACCCGGATCCTTCCAGTGCGACTGCGTTGAGG
3301 ---------+---------+---------+---------+---------+---------+ 3360
      CGCCGCTTGTGTGTTGAACGTTCTTGTGTGGGCCTAGGAAGGTCACGCTGACGCAACTCC

c     G  E  H  T  T  C  K  N  T  P  G  S  F  Q  C  D  C  V  E  G -
```

FIGURE 6 (cont.)

```
       GATTCGAGCGCGCTGATGAACGCACCTGCCGTGACATCAACGAGTGCGAGACAGGAGCAG
  3361 ------------+---------+---------+---------+---------+---------+ 3420
       CTAAGCTCGCGCGACTACTTGCGTGGACGGCACTGTAGTTGCTCACGCTCTGTCCTCGTC

c         F  E  R  A  D  E  R  T  C  R  D  I  N  E  C  E  T  G  A  V  -

       TCGTGCTGCCACCGAACTCCACCTGCGTCAACACTGAAGGCAGCTACGACTTCGACTGCG
  3421 ------------+---------+---------+---------+---------+---------+ 3480
       AGCACGACGGTGGCTTGAGGTGGACGCAGTTGTGACTTCCGTCGATGCTGAAGCTGACGC

c         V  L  P  P  N  S  T  C  V  N  T  E  G  S  Y  D  F  D  C  V  -

       TTGCTGGGTACCGCCGCACTGATGGAGCTTGTGTGAAGATCGACTTCTGCAAGGAGAAGG
  3481 ------------+---------+---------+---------+---------+---------+ 3540
       AACGACCCATGGCGGCGTGACTACCTCGAACACACTTCTAGCTGAAGACGTTCCTCTTCC

c         A  G  Y  R  R  T  D  G  A  C  V  K  I  D  F  C  K  E  K  G  -

       GATGCAACGCAAACGCCACATGCCGCGAAAACGATGCCGGCACCGAGGCCATCTGCACTT
  3541 ------------+---------+---------+---------+---------+---------+ 3600
       CTACGTTGCGTTTGCGGTGTACGGCGCTTTTGCTACGGCCGTGGCTCCGGTAGACGTGAA

c         C  N  A  N  A  T  C  R  E  N  D  A  G  T  E  A  I  C  T  C  -

       GCAAGGAAGGCTATGAAGGCAGCGGAGAAGGCGAAGATGGTTGCCAGAACATCAATGAGT
  3601 ------------+---------+---------+---------+---------+---------+ 3660
       CGTTCCTTCCGATACTTCCGTCGCCTCTTCCGCTTCTACCAACGGTCTTGTAGTTACTCA

c         K  E  G  Y  E  G  S  G  E  G  E  D  G  C  Q  N  I  N  E  C  -

       GCGAGAGAGGCGAACCCTGCAAGGACTTCGGCGAAGGCGGTGTTTGCGTCGACACACCAG
  3661 ------------+---------+---------+---------+---------+---------+ 3720
       CGCTCTCTCCGCTTGGGACGTTCCTGAAGCCGCTTCCGCCACAAACGCAGCTGTGTGGTC

c         E  R  G  E  P  C  K  D  F  G  E  G  G  V  C  V  D  T  P  G  -

       GATCATTCACTTGCGAGTGCGCTGCTGGATTCATTCAACGCCGCTCCGTTTGCCAAGATG
  3721 ------------+---------+---------+---------+---------+---------+ 3780
       CTAGTAAGTGAACGCTCACGCGACGACCTAAGTAAGTTGCGGCGAGGCAAACGGTTCTAC

c         S  F  T  C  E  C  A  A  G  F  I  Q  R  R  S  V  C  Q  D  V  -

       TTGACGAATGTCTCGACGGAAAGCTGAACACCTGCGCTGCCACCGGAGGCGTCTGCTCCA
  3781 ------------+---------+---------+---------+---------+---------+ 3840
       AACTGCTTACAGAGCTGCCTTTCGACTTGTGGACGCGACGGTGGCCTCCGCAGACGAGGT

c         D  E  C  L  D  G  K  L  N  T  C  A  A  T  G  G  V  C  S  N  -

       ACACCGTCGGTTCCTTCACCTGCTCGTGCGCCAGCGGCTTCGAAGGCGATGGCCACACCT
  3841 ------------+---------+---------+---------+---------+---------+ 3900
       TGTGGCAGCCAAGGAAGTGGACGAGCACGCGGTCGCCGAAGCTTCCGCTACCGGTGTGGA

c         T  V  G  S  F  T  C  S  C  A  S  G  F  E  G  D  G  H  T  C  -
```

*FIGURE 6 (cont.)*

```
      GCAATGATGTCGACGAATGCGCAACAGCACAGCACACCTGTGACCCGAATGCCACTTGCG
3901 ---------+---------+---------+---------+---------+---------+ 3960
      CGTTACTACAGCTGCTTACGCGTTGTCGTGTCGTGTGGACACTGGGCTTACGGTGAACGC

c      N  D  V  D  E  C  A  T  A  Q  H  T  C  D  P  N  A  T  C  V -

      TCAACACCGAAGGCAGCTTCGAGTGCCGCTGCAATGCCGGATTCGAGGGCGACGGACACA
3961 ---------+---------+---------+---------+---------+---------+ 4020
      AGTTGTGGCTTCCGTCGAAGCTCACGGCGACGTTACGGCCTAAGCTCCCGCTGCCTGTGT

c      N  T  E  G  S  F  E  C  R  C  N  A  G  F  E  G  D  G  H  T -

      CCTGCGCAGACATCGACGAATGCGCAGACCCAGCCAAAAACACATGCGATACACACAAGG
4021 ---------+---------+---------+---------+---------+---------+ 4080
      GGACGCGTCTGTAGCTGCTTACGCGTCTGGGTCGGTTTTTGTGTACGCTATGTGTGTTCC

c      C  A  D  I  D  E  C  A  D  P  A  K  N  T  C  D  T  H  K  G -

      GTGTATGCCAAAACACCACAGGGTCCTACACCTGCGGCTGCAAGACCGGATTCAGTCTTG
4081 ---------+---------+---------+---------+---------+---------+ 4140
      CACATACGGTTTTGTGGTGTCCCAGGATGTGGACGCCGACGTTCTGGCCTAAGTCAGAAC

c      V  C  Q  N  T  T  G  S  Y  T  C  G  C  K  T  G  F  S  L  A -

      CAGCTGACGGAAGCACATGCGAAAACGTCGACGAGTGCGCGGCGGGAACTGCAAACTGCA
4141 ---------+---------+---------+---------+---------+---------+ 4200
      GTCGACTGCCTTCGTGTACGCTTTTGCAGCTGCTCACGCGCCGCCCTTGACGTTTGACGT

c      A  D  G  S  T  C  E  N  V  D  E  C  A  A  G  T  A  N  C  N -

      ACGAGCGAAGCTTCTGTAAGGACACAGAGGGTTCCTACCAATGCGAGTGCAAGAACGGCT
4201 ---------+---------+---------+---------+---------+---------+ 4260
      TGCTCGCTTCGAAGACATTCCTGTGTCTCCCAAGGATGGTTACGCTCACGTTCTTGCCGA

c      E  R  S  F  C  K  D  T  E  G  S  Y  Q  C  E  C  K  N  G  Y -

      ACAAGGCTGCAGGAGAGGACTGTGTGGACGTTGACGAGTGCGAGGCTGGCGTGCATGGAT
4261 ---------+---------+---------+---------+---------+---------+ 4320
      TGTTCCGACGTCCTCTCCTGACACACCTGCAACTGCTCACGCTCCGACCGCACGTACCTA

c      K  A  A  G  E  D  C  V  D  V  D  E  C  E  A  G  V  H  G  C -

      GCAGCGAGCACGCAATCTGCACAAATACAGACGGCAGCTACTCCTGCGAATGCATGGAGG
4321 ---------+---------+---------+---------+---------+---------+ 4380
      CGTCGCTCGTGCGTTAGACGTGTTTATGTCTGCCGTCGATGAGGACGCTTACGTACCTCC

c      S  E  H  A  I  C  T  N  T  D  G  S  Y  S  C  E  C  M  E  G -

      GATACCAGGGAGACGGCAAGGCTTGCGAGAAGACAGTCGGCGTCTGCGACTCCGCTCCCT
4381 ---------+---------+---------+---------+---------+---------+ 4440
      CTATGGTCCCTCTGCCGTTCCGAACGCTCTTCTGTCAGCCGCAGACGCTGAGGCGAGGGA

c      Y  Q  G  D  G  K  A  C  E  K  T  V  G  V  C  D  S  A  P  C -

      GCGGTGCCCACGCCACCTGCGAGCCTGCAGGGGACAACTACACTTGCACATGCCACCCAG
4441 ---------+---------+---------+---------+---------+---------+ 4500
      CGCCACGGGTGCGGTGGACGCTCGGACGTCCCCTGTTGATGTGAACGTGTACGGTGGGTC
```

*FIGURE 6 (cont)*

```
c        G  A  H  A  T  C  E  P  A  G  D  N  Y  T  C  T  C  H  P  G -
         GCTACGAGATGCGCGAAGGAGCCTGCGTTGACATCGATGAGTGCACAGCAGGCAGCCTCA
4501     ---------+---------+---------+---------+---------+---------+ 4560
         CGATGCTCTACGCGCTTCCTCGGACGCAACTGTAGCTACTCACGTGTCGTCCGTCGGAGT

c        Y  E  M  R  E  G  A  C  V  D  I  D  E  C  T  A  G  S  L  N -
         ACTGCGACCCTCATGCCATTTGCACAAACACCGACGGCTCCTTCACTTGCGTCTGTGGCA
4561     ---------+---------+---------+---------+---------+---------+ 4620
         TGACGCTGGGAGTACGGTAAACGTGTTTGTGGCTGCCGAGGAAGTGAACGCAGACACCGT

c        C  D  P  H  A  I  C  T  N  T  D  G  S  F  T  C  V  C  G  S -
         GCGGCTATACCGGCCTTGGCACATCCTGCGAAGACATCGACGAGTGCGCGGGTAACGCAG
4621     ---------+---------+---------+---------+---------+---------+ 4680
         CGCCGATATGGCCGGAACCGTGTAGGACGCTTCTGTAGCTGCTCACGCGCCCATTGCGTC

c        G  Y  T  G  L  G  T  S  C  E  D  I  D  E  C  A  G  N  A  A -
         CAGGCTGCGACATCCACGCCGTCTGCACGAACACTCCCGGATCGTTCAAGTGCGAGTGCA
4681     ---------+---------+---------+---------+---------+---------+ 4740
         GTCCGACGCTGTAGGTGCGGCAGACGTGCTTGTGAGGGCCTAGCAAGTTCACGCTCACGT

c        G  C  D  I  H  A  V  C  T  N  T  P  G  S  F  K  C  E  C  K -
         AGAGCGGCTTCGAAGGCGATGGCACGCAATGCACGGAGAAGGTGTTGCTCCCCGGACAGA
4741     ---------+---------+---------+---------+---------+---------+ 4800
         TCTCGCCGAAGCTTCCGCTACCGTGCGTTACGTGCCTCTTCCACAACGAGGGGCCTGTCT

c        S  G  F  E  G  D  G  T  Q  C  T  E  K  V  L  L  P  G  Q  I -
         TTCACTGCGAAGCCTGGACTGCATGGACAGAGTGTACCGACGGCGCCAAAACCAGCACAC
4801     ---------+---------+---------+---------+---------+---------+ 4860
         AAGTGACGCTTCGGACCTGACGTACCTGTCTCACATGGCTGCCGCGGTTTTGGTCGTGTG

c        H  C  E  A  W  T  A  W  T  E  C  T  D  G  A  K  T  S  T  R -
         GCAGCTGCCTTGCACTGCCGCTTAAGAAGGAGATGCGCGCCTGCCCTGCAGCTGACTTCT
4861     ---------+---------+---------+---------+---------+---------+ 4920
         CGTCGACGGAACGTGACGGCGAATTCTTCCTCTACGCGCGGACGGGACGTCGACTGAAGA

c        S  C  L  A  L  P  L  K  K  E  M  R  A  C  P  A  A  D  F  S -
         CCCAGTGCGGAGAGTTCACTGAATGGACTGCCTGCCCTGGAACCAACAATAACCTGTCTC
4921     ---------+---------+---------+---------+---------+---------+ 4980
         GGGTCACGCCTCTCAAGTGACTTACCTGACGGACGGGACCTTGGTTGTTATTGGACAGAG

c        Q  C  G  E  F  T  E  W  T  A  C  P  G  T  N  N  N  L  S  R -
         ATAGGCGCACTGAAAGATTCGGAGAACCCGGATGCGAAGATGCAGAGGAAGTCCGCGAAT
4981     ---------+---------+---------+---------+---------+---------+ 5040
         TATCCGCGTGACTTTCTAAGCCTCTTGGGCCTACGCTTCTACGTCTCCTTCAGGCGCTTA

c        R  R  T  E  R  F  G  E  P  G  C  E  D  A  E  E  V  R  E  C -
         GCCCAGATGAAGAGACCGAGCAGAAATGCGGCGCCTGGGGTGAGTGGACCGCCTGCGGCG
```

*FIGURE 6 (cont.)*

```
5041 ---------+---------+---------+---------+---------+---------+ 5100
     CGGGTCTACTTCTCTGGCTCGTCTTTACGCCGCGGACCCCACTCACCTGGCGGACGCCGC

c     P  D  E  E  T  E  Q  K  C  G  A  W  G  E  W  T  A  C  G  D -

     ACCCATCCCCTGGCCTGAGAACTCGCGCACGCGAGAACTGCCCCGATGTGGTAGAGTTCG
5101 ---------+---------+---------+---------+---------+---------+ 5160
     TGGGTAGGGGACCGGACTCTTGAGCGCGTGCGCTCTTGACGGGGCTACACCATCTCAAGC

c     P  S  P  G  L  R  T  R  A  R  E  N  C  P  D  V  V  E  F  E -

     AGCGTTGCACTATGCCCAGTGAGCCTGAGGCTGGCGAAGTGACTGAGCCTCACACAGAAG
5161 ---------+---------+---------+---------+---------+---------+ 5220
     TCGCAACGTGATACGGGTCACTCGGACTCCGACCGCTTCACTGACTCGGAGTGTGTCTTC

c     R  C  T  M  P  S  E  P  E  A  G  E  V  T  E  P  H  T  E  G -

     GAGGAGCCGGAGTTGGTGGCGAAGTGACTGAGCCTGACACGGAAGAAGGAGCCGGAGTTG
5221 ---------+---------+---------+---------+---------+---------+ 5280
     CTCCTCGGCCTCAACCACCGCTTCACTGACTCGGACTGTGCCTTCTTCCTCGGCCTCAAC

c     G  A  G  V  G  G  E  V  T  E  P  D  T  E  E  G  A  G  V  G -

     GTGGTGAAGTGCAGCCCGGTACAGAAGAAGGAGCAGGAGTTGGTGGTGAAGTGCAGCCCG
5281 ---------+---------+---------+---------+---------+---------+ 5340
     CACCACTTCACGTCGGGCCATGTCTTCTTCCTCGTCCTCAACCACCACTTCACGTCGGGC

c     G  E  V  Q  P  G  T  E  E  G  A  G  V  G  G  E  V  Q  P  G -

     GTACAGAAGAAGGAGCCGGAGTTGGTGGTGAAGTGCAGCCCGGTACAGAAGAAGGAGCCG
5341 ---------+---------+---------+---------+---------+---------+ 5400
     CATGTCTTCTTCCTCGGCCTCAACCACCACTTCACGTCGGGCCATGTCTTCTTCCTCGGC

c     T  E  E  G  A  G  V  G  G  E  V  Q  P  G  T  E  E  G  A  G -

     GAGTTGGTGGTGAAGTGCAGCCCGGTACGGAAGAAGGAGCCGGCATTGGTGGCGAAGTGA
5401 ---------+---------+---------+---------+---------+---------+ 5460
     CTCAACCACCACTTCACGTCGGGCCATGCCTTCTTCCTCGGCCGTAACCACCGCTTCACT

c     V  G  G  E  V  Q  P  G  T  E  E  G  A  G  I  G  G  E  V  T -

     CTGAGCCTGACACCGAAGGAGGAGCCGGAGTTAGTGGCGAACCGACCGAAGAAGAGGGCA
5461 ---------+---------+---------+---------+---------+---------+ 5520
     GACTCGGACTGTGGCTTCGTCCTCGGCCTCAATCACCGCTTGGCTGGCTTCTTCTCCCGT

c     E  P  D  T  E  G  G  A  G  V  S  G  E  P  T  E  E  E  G  T -

     CCGAAAGCACCGGTCCATGCAAAGAGTTCGGACCCTGGACGGCCTGCAAGGAGGACGAGA
5521 ---------+---------+---------+---------+---------+---------+ 5580
     GGCTTTCGTGGCCAGGTACGTTTCTCAAGCCTGGGACCTGCCGGACGTTCCTCCTGCTCT

c     E  S  T  G  P  C  K  E  F  G  P  W  T  A  C  K  E  D  E  N -

     ACGGAGTCGGCATCCAACGCCGTATGTGCGCCGGCAGAGAAGACATCATCGAATCCAGAA
5581 ---------+---------+---------+---------+---------+---------+ 5640
     TGCCTCAGCCGTAGGTTGCGGCATACACGCGGCCGTCTCTTCTGTAGTAGCTTAGGTCTT
```

*FIGURE 6 (cont.)*

```
c          G  V  G  I  Q  R  R  M  C  A  G  R  E  D  I  I  E  S  R  I -
           TTTGCACTGTCACGGATCACTGCGGAGAATGGACCCCCTGGTCAACTTGCACTAACGGCA
      5641 ---------+---------+---------+---------+---------+---------+ 5700
           AAACGTGACAGTGCCTACTGACGCCTCTTACCTGGGGGACCAGTTGAACGTGATTGCCGT
c          C  T  V  T  D  D  C  G  E  W  T  P  W  S  T  C  T  N  G  S -
           GCCAGGCCAGAAACAAACGCTTCTGCACCAACGTTAGGGAAGTCCGTCTCTGCGGAGCTG
      5701 ---------+---------+---------+---------+---------+---------+ 5760
           CGGTCCGGTCTTTGTTTGCGAAGACGTGGTTGCAATCCCTTCAGGCAGAGACGCCTCGAC
c          Q  A  R  N  K  R  F  C  T  N  V  R  E  V  R  L  C  G  A  D -
           ACATTCCAGTTACAGACGGATGCACGTGGAGCGAGTGGACTTCTTGCAGTCTAGTCAATG
      5761 ---------+---------+---------+---------+---------+---------+ 5820
           TGTAAGGTCAATGTCTGCCTACGTGCACCTCGCTCACCTGAAGAACGTCAGATCAGTTAC
c          I  P  V  T  D  G  C  T  W  S  E  W  T  S  C  S  L  V  N  E -
           AGGAGGGCGGCTACTTCCGCACGCGCACATCCTCTGACTGCAACATGAATGAAGTGCAGG
      5821 ---------+---------+---------+---------+---------+---------+ 5880
           TCCTCCCGCCGATGAAGGCGTGCGCGTGTAGGAGACTGACGTTGTACTTACTTCACGTCC
c          E  G  G  Y  F  R  T  R  T  S  S  D  C  N  M  N  E  V  Q  A -
           CCTGCTCTCCCAGCAGCAGCACAACCGCAGACAGCGAAACAGAAGGCACCTGCTCTGCAT
      5881 ---------+---------+---------+---------+---------+---------+ 5940
           GGACGAGAGGGTCGTCGTCGTGTTGGCGTCTGTCGCTTTGTCTTCCGTGGACGAGACGTA
c          C  S  P  S  S  S  T  T  A  D  S  E  T  E  G  T  C  S  A  W -
           GGAACCCCTGGACGGAGTGCTCGAACGGCCACCAGACACGCAAGTGTGCCACAATGGAAG
      5941 ---------+---------+---------+---------+---------+---------+ 6000
           CCTTGGGGACCTGCCTCACGAGCTTGCCGGTGGTCTGTGCGTTCACACGGTGTTACCTTC
c          N  P  W  T  E  C  S  N  G  H  Q  T  R  K  C  A  T  M  E  A -
           CAGAAGAATCGCGCACTTGCGGAGAGACTCCAGAGAACTGCGGAGAATTCGGCCCCTTCG
      6001 ---------+---------+---------+---------+---------+---------+ 6060
           GTCTTCTTAGCGCGTGAACGCCTCTCTGAGGTCTCTTGACGCCTCTTAAGCCGGGGAAGC
c          E  E  S  R  T  C  G  E  T  P  E  N  C  G  E  F  G  P  F  E -
           AACCCGCAAACTGCACGGCCGGCCAAATGGTCACCAGGACGCGCACCTGCGGAGAGAAACCG
      6061 ---------+---------+---------+---------+---------+---------+ 6120
           TTGGGCGTTTGACGTGCCGGCCGGTTTACCAGTGGTCCTGCGCGTGGACGCCTCTTTGGC
c          P  A  N  C  T  A  G  Q  M  V  T  R  T  R  T  C  G  E  T  E -
           AGCAGAAGGAAACCAAACTGTGCGACGTCAGCTCCACCGAAGAAGGAAAACAATGCGGTC
      6121 ---------+---------+---------+---------+---------+---------+ 6180
           TCGTCTTCCTTTGGTTTGACACGCTGCAGTCGAGGTGGCTTCTTCCTTTTGTTACGCCAG
c          Q  K  E  T  K  L  C  D  V  S  S  T  E  E  G  K  Q  C  G  Q -
           AGTGGGGCCCATGGAGCGAATGCAACATCCACCTGGGCTCAGAGGACAATGTGCGTGTTC
```

*FIGURE 6 (cont.)*

```
6181 ---------+---------+---------+---------+---------+---------+ 6240
     TCACCCCGGGTACCTCGCTTACGTTGTAGGTGGACCCGAGTCTCCTGTTACACGCACAAG

c     W  G  P  W  S  E  C  N  I  H  L  G  S  E  D  N  V  R  V  R -

     GTGAGGACACCGCTTGCGGCGTGACGGAGTACGAGGAGTGCAGCAAGCCGGCGAACAACG
6241 ---------+---------+---------+---------+---------+---------+ 6300
     CACTCCTGTGGCGAACGCCGCACTGCCTCATGCTCCTCACGTCGTTCGGCCGCTTGTTGC

c     L  D  T  A  C  G  V  T  E  Y  E  E  C  S  K  P  A  N  N  A -

     CCTTTGTCTGCACACCTTGGAGTGAATGCTCGGACAAGAAGGAGCGGAGAACGTGCACCA
6301 ---------+---------+---------+---------+---------+---------+ 6360
     GGAAACAGACGTGTGGAACCTCACTTACGAGCCTGTTCTTCCTCGCCTCTTGCACGTGGT

c     F  V  C  T  P  W  S  E  C  S  D  K  K  E  R  R  T  C  T  I -

     TCCGCAAAAACGGTCTTGTTCAGACACGTCAAGAATTCAGAACATGCAGTGTAGACATCG
6361 ---------+---------+---------+---------+---------+---------+ 6420
     AGGCGTTTTTGCCAGAACAAGTCTGTGCAGTTCTTAAGTCTTGTACGTCACATCTGTAGC

c     R  K  N  G  L  V  Q  T  R  Q  E  F  R  T  C  S  V  D  I  A -

     CCACAACTTGCGGCGATTTCGGCGCATGGTCTGAATGCAACGCTGAGGGCTTGCATCAGC
6421 ---------+---------+---------+---------+---------+---------+ 6480
     GGTGTTGAACGCCGCTAAAGCCGCGTACCAGACTTACGTTGCGACTCCCGAACGTAGTCG

c     T  T  C  G  D  F  G  A  W  S  E  C  N  A  E  G  L  H  Q  R -

     GCAGTCTCGAGAAATGCCCCGACGTCATCGAGGTCGCAACTTGCGGCAGTGAGGATTGCC
6481 ---------+---------+---------+---------+---------+---------+ 6540
     CGTCAGAGCTCTTTACGGGGCTGCAGTAGCTCCAGCGTTGAACGCCGTCACTCCTAACGG

c     S  L  E  K  C  P  D  V  I  E  V  A  T  C  G  S  E  D  C  P -

     CGCCATTCGGCGAGTGGACTGAATGCGGCGTTCCAGAGGAGGGCATGCGTTCTCGCCAAC
6541 ---------+---------+---------+---------+---------+---------+ 6600
     GCGGTAAGCCGCTCACCTGACTTACGCCGCAAGGTCTCCTCCCGTACGCAAGAGCGGTTG

c     P  F  G  E  W  T  E  C  G  V  P  E  E  G  M  R  S  R  Q  R -

     GCATTGACTGCGTTGAATCTGCAGCCTGCCAGTGCACAGAAGTGGAGAGCTGCTTCGACA
6601 ---------+---------+---------+---------+---------+---------+ 6660
     CGTAACTGACGCAACTTAGACGTCGGACGGTCACGTGTCTTCACCTCTCGACGAAGCTGT

c     I  D  C  V  E  S  A  A  C  Q  C  T  E  V  E  S  C  F  D  T -

     CCGAATTGCACCCCATTCCAGCCCCCGGTACGGAAACAGGCGAAGGAGAGGGAGAGACCG
6661 ---------+---------+---------+---------+---------+---------+ 6720
     GGCTTAACGTGGGGTAAGGTCGGGGGCCATGCCTTTGTCCGCTTCCTCTCCCTCTCTGGC

c     E  L  H  P  I  P  A  P  G  T  E  T  G  E  G  E  G  E  T  E -

     AGACAGGCGAAGGCGAAACTGGTGAAGCAGGTGGCGAGGAAGGCGAGCAAACAGGAGAAG
6721 ---------+---------+---------+---------+---------+---------+ 6780
     TCTGTCCGCTTCCGCTTTGACCACTTCGTCCACCGCTCCTTCCGCTCGTTTGTCCTCTTC
```

```
c         T  G  E  G  E  T  G  E  A  G  G  E  E  G  E  Q  T  G  E  G -

          GCGAAGTGCAGCCCCCAGAAGAAGAGCTTCCTGGGGAGAGTGTAACTGAGCCTGAGGAGA
     6781 ---------+---------+---------+---------+---------+---------+ 6840
          CGCTTCACGTCGGGGGTCTTCTTCTCGAAGGACCCCTCTCACATTGACTCGGACTCCTCT

c         E  V  Q  P  P  E  E  E  L  P  G  E  S  V  T  E  P  E  E  K -

          AGCCTGAGGAGGAGCTACCTGAGGAGGAGGTTACTGAGCCTGAGGAGAAGCCTGAGGAGG
     6841 ---------+---------+---------+---------+---------+---------+ 6900
          TCGGACTCCTCCTCGATGGACTCCTCCTCCAATGACTCGGACTCCTCTTCGGACTCCTCC

c         P  E  E  E  L  P  E  E  E  V  T  E  P  E  E  K  P  E  E  G -

          GTGTGACTCAGCCTGAGGAGACACCTGAGCAGCCTGTTGAGGGTACCGAAGAAGAGGGCA
     6901 ---------+---------+---------+---------+---------+---------+ 6960
          CACACTGAGTCGGACTCCTCTGTGGACTCGTCGGACAACTCCCATGGCTTCTTCTCCCGT

c         V  T  Q  P  E  E  T  P  E  Q  P  V  E  G  T  E  E  E  G  K -

          AGCAGGAGTCTGAGGCTGCCCCCGAAACTCCTGCCGTCCAGCCAAAACCAGAGGAGGGTC
     6961 ---------+---------+---------+---------+---------+---------+ 7020
          TCGTCCTCAGACTCCGACGGGGGCTTTGAGGACGGCAGGTCGGTTTTGGTCTCCTCCCAG

c         Q  E  S  E  A  A  P  E  T  P  A  V  Q  P  K  P  E  E  G  H -

          ACGAACGCCCAGAACCCGAAGAGGAGGAGGACAAGAAGGAAGAAGGCGGCGGCTTCCCAA
     7021 ---------+---------+---------+---------+---------+---------+ 7080
          TGCTTGCGGGTCTTGGGCTTCTCCTCCTCCTGTTCTTCCTTCTTCCGCCGCCGAAGGGTT

c         E  R  P  E  P  E  E  E  E  E  K  K  E  E  G  G  G  F  P  T -

          CAGCTGCAGTGGCAGGAGGTGTTGGTGGTGTTGCTCATAGCTGCTGTAGGTGGTGCTG
     7081 ---------+---------+---------+---------+---------+---------+ 7140
          GTCGACGTCACCGTCCTCCACAACCACCACACAACGAGTATCGACGACATCCACCACCAC

c         A  A  V  A  G  G  V  G  G  V  L  L  I  A  A  V  G  G  G  V -

          TTGCAGCCTTCACTAGCGGCGGAGGTGGCGCTGGCGCACAGGAGGCAGAACAGGTCGAGT
     7141 ---------+---------+---------+---------+---------+---------+ 7200
          AACGTCGGAAGTGATCGCCGCCTCCACCGCGACCGCGTGTCCTCCGTCTTGTCCAGCTCA

c         A  A  F  T  S  G  G  G  G  A  G  A  Q  E  A  E  Q  V  E  F -

          TCGAAGGAGAAGATACCGGAGCAGCAACTGCCGAGACACCTGAAGCCGATACAGTTATCG
     7201 ---------+---------+---------+---------+---------+---------+ 7260
          AGCTTCCTCTTCTATGGCCTCGTCGTTGACGGCTCTGTGGACTTCGGCTATGTCAATAGC

c         E  G  E  D  T  G  A  A  T  A  E  T  P  E  A  D  T  V  I  D -

          ACATCACAGACGAAGACGACTACTGGGCCGACAGCGGCGACATTCAGTAAAGTTGAATGT
     7261 ---------+---------+---------+---------+---------+---------+ 7320
          TGTAGTGTCTGCTTCTGCTGATGACCCGGCTGTCGCCGCTGTAAGTCATTTCAACTTACA

c         I  T  D  E  D  D  Y  W  A  D  S  G  D  I  Q  *  S  *  H  S -

          CTGTTTTCTTCCAAGGAGAAGATACAAAACCAAAATCTTAACAAAACGAAGGATGCGAAG
```

*FIGURE 6 (CONT.)*

```
7321 ---------+---------+---------+---------+---------+---------+ 7380
     GACAAAAGAAGGTTCCTCTTCTATGTTTTGGTTTTAGAATTGTTTTGCTTCCTACGCTTC

c     V  F  F  Q  G  E  D  T  K  P  K  S  *  Q  N  E  G  C  E  G -

     GCGAAACAGGCCAAAGTCGACCTGTTTTCTCATTCAATCAATGGTTGCAGTCGTGAAGGA
7381 ---------+---------+---------+---------+---------+---------+ 7440
     CGCTTTGTCCGGTTTCAGCTGGACAAAAGAGTAAGTTAGTTACCAACGTCAGCACTTCCT

c     E  T  G  Q  S  R  P  V  F  S  F  N  Q  W  L  Q  S  *  R  S -

     GCTGGACTCAGTTGCATCTCCACCCCAAGAGCTCGCCGTTAGTGGGCAAGTTGGATAGGG
7441 ---------+---------+---------+---------+---------+---------+ 7500
     CGACCTGAGTCAACGTAGAGGTGGGGTTCTCGAGCGGCAATCACCCGTTCAACCTATCCC

c     W  T  Q  L  H  L  H  P  K  S  S  P  L  V  G  K  L  D  R  V -

     TGAATGCATTTTCATCTCCGCAGGCGAAAGTCACGACGAGGGCCTGTTCTTGTTTGTTTG
7501 ---------+---------+---------+---------+---------+---------+ 7560
     ACTTACGTAAAAGTAGAGGCGTCCGCTTTCAGTGCTGCTCCCGGACAAGAACAAACAAAC

c     N  A  F  S  S  P  Q  A  K  V  T  T  R  A  C  S  C  L  F  V -

     TTTGAATTGGTTGGTTGGTGCATCCTGCTGGATTTCAACGACGGCAATCATCACGCAGTG
7561 ---------+---------+---------+---------+---------+---------+ 7620
     AAACTTAACCAACCAACCACGTAGGACGACCTAAAGTTGCTGCCGTTAGTAGTGCGTCAC

c     *  I  G  W  L  V  H  P  A  G  F  Q  R  R  Q  S  S  R  S  E -

     AGACGGAGCAGCAGCGCATACTATTTTCTGAGCAAGTTCATCGTTTATTTTTCGCTGTAT
7621 ---------+---------+---------+---------+---------+---------+ 7680
     TCTGCCTCGTCGTCGCGTATGATAAAAGACTCGTTCAAGTAGCAAATAAAAAGCGACATA

c     T  E  Q  Q  R  I  L  F  S  E  Q  V  H  R  L  F  P  A  V  S -

     CTCGTAGCGCCGAGGAAGCAAACAAGCAAACGCCCACCAACTGACCAACCAATGAGAGAG
7681 ---------+---------+---------+---------+---------+---------+ 7740
     GAGCATCGCGGCTCCTTCGTTTGTTCGTTTGCGGGTGGTTGACTGGTTGGTTACTCTCTC

c     R  S  A  E  E  A  N  K  Q  T  P  T  N  *  P  T  N  E  R  A -

     CCGTCCTTTAATTTCCACCCCTCTTCTGTCTTCCGAAGATTCGGCGGGGTTTCGGATGGG
7741 ---------+---------+---------+---------+---------+---------+ 7800
     GGCAGGAAATTAAAGGTGGGGAGAAGACAGAAGGCTTCTAAGCCGCCCCAAAGCCTACCC

c     V  L  *  F  P  P  L  F  C  L  P  K  I  R  R  G  F  G  W  G -

     GGAGAAATTGTGGTTGGATTGGTCGGGTGTTTTCGTTTTCTTTGATTGATGCAACAATAT
7801 ---------+---------+---------+---------+---------+---------+ 7860
     CCTCTTTAACACCAACCTAACCAGCCCACAAAAGCAAAAGAAACTAACTACGTTGTTATA

c     R  N  C  G  W  I  G  R  V  F  S  F  S  L  I  D  A  T  I  S -

     CTGCTAGCCAGCGTACAAAGAATAGCTGCAGTTCAAATGAATGCATCTTAATTATTCCAC
7861 ---------+---------+---------+---------+---------+---------+ 7920
     GACGATCGGTCGCATGTTTCTTATCGACGTCAAGTTTACTTACGTAGAATTAATAAGGTG
```

Figure 6:
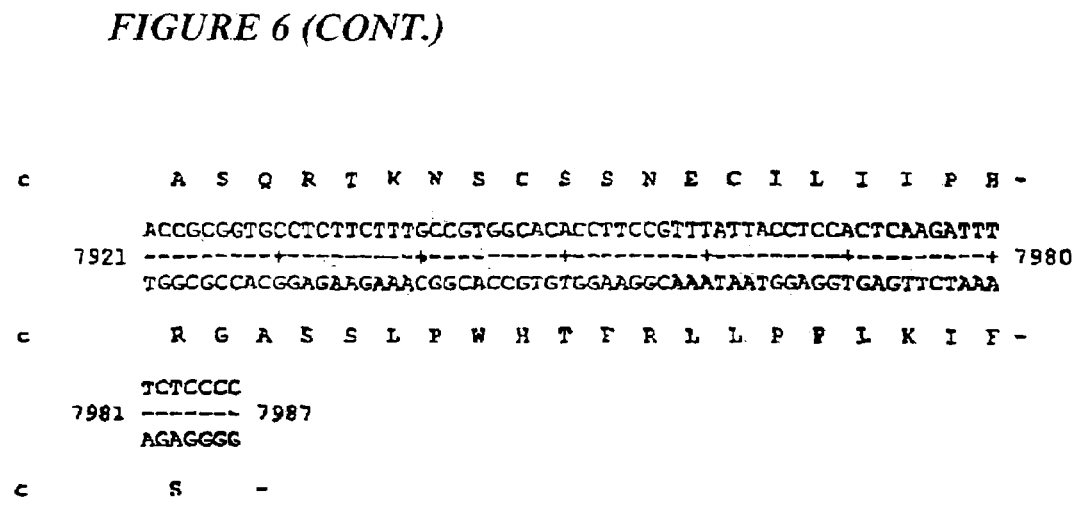

```
c          A  S  Q  R  T  K  N  S  C  S  S  N  E  C  I  L  I  I  P  H -

         ACCGCGGTGCCTCTTCTTTGCCGTGGCACACCTTCCGTTTATTACCTCCACTCAAGATTT
    7921 ---------+---------+---------+---------+---------+---------+ 7980
         TGGCGCCACGGAGAAGAAACGGCACCGTGTGGAAGGCAAATAATGGAGGTGAGTTCTAAA

c          R  G  A  S  S  L  P  W  H  T  F  R  L  L  P  P  L  K  I  F -

         TCTCCCC
    7981 ------- 7987
         AGAGGGG

c          S  -
```

*FIGURE 7A*

```
230      1 ATGCTGCATCGCAACCCGCGGTGGGCGCTTTGTGCAGCCCTCGCTGCACT   50
WO 9     1                                                      0

230     51 CTATGGCGGAACAGGAATCGCCAGCGCCGAAGTTAACAATGAATTGAGCA  100
WO 9     1                                                      0

230    101 AGTGCGAATCTGGGTGGACACCCTGGACTACCTGCAACCCGCAAACTGGT  150
WO 9     1                                                      0

230    151 CTGCGGGAGAGGCACAATGCACAGTGCGAGACATGGGTGGAGGTTGAGGA  200
WO 9     1                                                      0

230    201 ATGCCAGAAGCTGACAGGATGTGGCAACTGGACTCCTTGGTCTCCCGGCG  250
WO 9     1                                                      0

230    251 ATATGTCGTGTGTGGTGGGACAGTTTCAAACCCGCAACAGGGAGGGCTGC  300
WO 9     1                                                      0

230    301 CCAGAGGTGCAGGAAGTGAGGGCATGCAGGCCTGTACTTCTAGAATGCAA  350
WO 9     1                                                      0

230    351 CGATCAATGGACCCCCTGGACAATGTGCGACACCAACCGCGTCCAGGAAA  400
WO 9     1                                                      0

230    401 GATACAACTCAAAGTGCGGACCCGTCGAAGTCCGCGAGTGCAACATGGAC  450
WO 9     1                                                ATG   3
```

*FIGURE 7A (cont.)*

```
230    451 GACGCAGAGATCGAGAAATGCGGCGAGTTCGTGGAATGGGATGCCCCTAT  500
WO 9     4 GGTTTTTTCGTCTTCACAGGCGGTGATTTCGGCGACTGGAGCCCCCCTCT   53
           *         **   * * **** ** ****  ** ***   ****** *

230    501 GAATGGAGACTGCGTACGCGGGGGTACCCACACGCGTTACCGTCAAAACT  550
WO 9    54 CGCTGGTGACTGCGTGCCTGGCACTACTCACACACGCCAGAGGGCAAATT  103
              *** ******** *  **   *** ***** **  *  *   *** *

230    551 GCCCAGACCGCAAAGAGGTGCGGGTGTGCGGAGCCTTTGATTGCAGTAGC  600
WO 9   104 GCCCAAACCACAAGGAGGTGCGGGTTTGCGGCGCCTTCGATTGTAGCCAG  153
           ***** *** *** *********** ***** ***** ***** **

230    601 TGCTCTGTAAACGCCACTTGCGATCCCATTGGTGCATCCTGCGAATGCAA  650
WO 9   154 TGCTCAGTCAACGCTACCTGCGACCCCCTCGGAGCCACTTGTCAGTGCAA  203
           ***** ** ***** ** ***** *** * ** **  * **  * *****

230    651 GCCTGGTTTCCGCGGCAATGGAAGACCTGCGAGGCCTTCAACCCCTGCG  700
WO 9   204 ACCGGGTTTCCGAGGCGATGGACTCAGTGCGAGGCATTCAACCCTTGCG  253
            ** ******** *** ******     ******** ******** ****

230    701 AAGATACCCCTGCACCTTGCGACAGCAACGCCATCTGCACCCCAGACGCA  750
WO 9   254 AAGGGAGACGGCTCCTTGTGATGCGAACGCGACCTGCACGGCTGATGGA  303
           ***      * ** ***** **     ***** * ****** * ** * *

230    751 A-TGACGCCAAATGCCAGTGCAAGGCAGGCTGGACGCAGATTCCGGAGC  799
WO 9   304 AATGACGCCAAATGCCACTGCAACAAGGGCTGGAACGCAGACAGCAAGGC  353
           * **************** *****    ****** *******   *  **

230    800 AGGCAGCAGCAAGAAGCCTTGCGTTGAGGTCGACGAGTGCGCATCCAACA  849
WO 9   354 AGGTGCCAGCGGTCACGCATGCGTGGAGGAGGACGAATGCGCCAACAACA  403
           ***    ****    * * ****** ****  ***** *****  *****

230    850 CCCACCAGTGCCTCGGCACACTCCACATGCATCAACACCAAGGGCTCTTAT  899
WO 9   404 CGCACGAATGTCCCGCAGCACTCAACTTGCGTCAACACTGAGGGCTCCTAT  453
           * *** * ** ***   ***** ** *** ******** ******* ***

230    900 AAGTGCGACTGCAACCAGGGATACCGTCAAGGGAGAGGACGGACAGTGTC  949
WO 9   454 GAATGCAACTGCTTACCGGGTTATCAG-AAGGATCAGGATGGGAAATGCC  502
             * *** *****   * *** ** *   ****   **** ** * ** *

230    950 ATGACGTCGATGAATGCACCAACGGAGAGCACACCTGCCCCGCTCACTCC  999
WO 9   503 AGGACATAGACGAGTGCGCT---GGGGAACATGGTTGTCCCGCACACTCG  549
           * *** * ** ** *** *     ** ** **   ** ****** *****

230   1000 ACTTGTTTGAATACAGCTGGCAGCTACGAGTGCCGCTGCGACACTGGGTA 1049
WO 9   550 ACTTGCGTGAACACGGCAGGCAGCTTCGAGTGCAAGTGCGACGCCGGTTT  599
           *****  **** ** ** ******** *******   ****** * ** *

230   1050 CAGCGGAAATGCAACTGCAGACAGCCCTTGCAAGAACATTGACGAATGCG 1099
WO 9   600 CAGTGGCAGTGCTACTTCTGAGAGTCCTTGCTCGAATATAGACGAGTGCC  649
           *** ** * *** *** * ** ** ******  *** ** ***** ***

230   1100 CCAACCCCAACGCCTGCTCGGCCAACGCTATCTGCACAGACACCGACGGC 1149
WO 9   650 AAGACCCGGATGCCTGCTCAGCCAACGCAATCTGCGCAGACACTGAGGGC  699
             ****  * ********* ******** ****** ******* ** ***

230   1150 TCCTTCACCTGCAGCTGCCCCGAAGGGTACAGCGGCCAGGGAACCCATGA 1199
```

*FIGURE 7A (cont.)*

```
WO 9    700 TCTTTCACTTGCAGCTGCCCTGAGGGTTACAGCGGTGGGGGATCACACGA  749
            ** ***** *********** ** ** ********   **** * ** **

230    1200 CTCTCCCTGCTCCAAGATCGACTTCTGCGCATACCCCTCACTCAATACAT 1249
WO 9    750 CTCTCCTTGCTCGAAGATAGATTACTGCGCCGACCCCACACTGAACACCT  799
            ****** ***** ***** ** * ******  ***** **** ** ** *

230    1250 GCGGAGCCCACTCCACTTGC---AACACCCTCACATCTTTCAAGTGCATC 1296
WO 9    800 GCGGGGCCCACTCGACTTGTGTGAACACACTAACGACGTTCAAGTGCGTT  849
            **** ******** *****    ***** ** **  * ********* *

230    1297 TGCGATGCGGGATATGAAGGCGCCGGCACTCGCGAGAGCCCGTGCGTGGA 1346
WO 9    850 TGCGATGCCGGTTATGACGGCCGCGGAACGCACGAGAGCCCTTGTGTGGA  899
            ******** ** ***** ***  *** ** * ********* ** *****

230    1347 CGTGAACGAGTGCTCGAACGAGAAGCCCACAAACAACTGCAACAGAAACG 1396
WO 9    900 TATCGACGAGTGCTCCAAGGAGAAACCATCCAATGACTGCAACCGAAACG  949
              *  ********** ** ***** *** * **  ******** ******

230    1397 CAAACTGCACCAACACCGAGGGATCCTACACTTGCGAATGCAAGCCCGGT 1446
WO 9    950 CCGTTTGCACAAATACTGAGGGATCGTACACCTGCGCATGCAAGGAAGGC  999
            *    ***** ** ** ******** ***** **** *******   **

230    1447 TTCTCTGGCGACGGCATGGGTCCCAACGGGTGTACCGACATCGACGAGTG 1496
WO 9   1000 TTCTCTGGCGAGGGTTTCGGAGCTGCAGGGTGTGCAGATGTCGATGAGTG 1049
            *********** **  * **  *    ****** * **  **** *****

230    1497 CGCGGCGGAGCAGTCCCCCTGCGACCCTCACGCCTCCTGCAGCAACACTG 1546
WO 9   1050 CGCGA------ATTCGCCCTGCGACGCCCACGCCTCTTGTGCCAACACCG 1093
            ****       * ** ********* * ******** **   ****** *

230    1547 AGGGCTCGTATGTATGCACCTGCAACACCGGCTACGAGCCAGCTTCAACC 1596
WO 9   1094 AGGGTTCCTACGTTTGCACTTGCAACCCTGGCTATGAACCAGCCTCAAGC 1143
            **** ** ** ** ***** ****** * ***** ** ***** **** *

230    1597 GACGGGCATGCATGCAAAGATATCGACGAGTGCGCCACCGGTGCAGCTGG 1646
WO 9   1144 GACGGACATGCATGCAAGGACGTTGACGAGTGTGCAGCGGGCACGGCGGA 1193
            ***** *********** **  * ******** **  * **  * ** *

230    1647 GTGCCACGTGTCAGCACAGTGTCTGAACACGGACGGCAGCTACGAGTGCA 1696
WO 9   1194 ATGCCACGTCTCCGCACAGTGTGTGAACGTGGATGGCAGCTATGAATGCC 1243
             ******** ** ********* *****  *** ******** ** ***

230    1697 AGTGTCTTGAGGGCTTCGTCGGCGACGGAAAGACCTGCAACGACGTCGAT 1746
WO 9   1244 ACTGCTTGGAAGGTTTCATTGGCGACGGAAAGGTGTGCAGTGACGTTGAC 1293
            * **  * ** ** *** * ************   ****  ***** **

230    1747 GAGTGCGCTGCGGCGACATCTCCTTGCGGTGACAACACTCACTGCCAGAA 1796
WO 9   1294 GAGTGTGCGGCTGAGGCTTCGCCCTGTGGCGCAAACACGCATTGCCTGAA 1343
            ***** ** ** * * * ** ** ** ** *  ***** ** **** ***

230    1797 CACAATTGGCAGCTACGAGTGCGAGTGCAAGGCTGGCTATGGCAACATGC 1846
WO 9   1344 CACCATCGGCAGCTACGAGTGCGAGTGCAAGGACGGATATGGCCACATGG 1393
            *** ** *************************  ** ****** *****

230    1847 AAGACAACGCATGCAGCGACATTGACGAGTGCAAGGATGCGAACACCAAG 1896
WO 9   1394 AGGGCAACGCGTGCAGCGACATCGATGAGTGCTCAGAGGCGTCTACAGAG 1443
```

```
                * * ****** *********** ** ******   ** *** . **  **

230   1897 ATCCCTGACAACTGTCTTTGCGTGAACAATGATGGCAGCTACTCCCTTGA 1946
WO 9  1444 ATCCCAGAGAACTGCAACTGTGTCAACACCGAGGGGAGCTTCTCCCTTGA 1493
           ***** ** *****    ** ** ****  ** ** **** **********

230   1947 GGCGAAGGCTGGATACGAATTGGTGAACGGCGAGTGCATCAAGATCGACT 1996
WO 9  1494 GGCAAAGCCTGGGTACGAGCTCGTCGACGGCAAGTGCGTCAAGATCGACT 1543
           *** *** **** ***** . * **  ***** ***** *************

230   1997 TCTGCGCCCGCGGCGCATGCAACTCGCTGGCCTCCTGCAAGGAGAATGAA 2046
WO 9  1544 TCTGCGCCCGTGGTGCATGCAACTCGCTGGCGCACTGCAAGGAGAATCCC 1593
           ********** ** *****************   **************

230   2047 GAAGGCACAGCGGCGATCTGCACCTGCCTGCCAGGCTACAGCGGCGACGG 2096
WO 9  1594 GAGGGCACCGCGGCGATCTGCACTTGCATAGCTGGCTATTCAGGTGACGG 1643
           ** ***** ************** *** * * *****   ** *****

230   2097 CACTGCTGAAGGCCACTGCAACGACATTGACGAGTGTGCAGGTCAGAATG 2146
WO 9  1644 CACAGCTCAGGGCCACTGCGATGACATCGATGAGTGCTTGGCGGAGAATG 1693
           *** *** * ********* * ***** ** *****    *   ******

230   2147 ACTGTGCTCCTGCCGAGCAGGGAGGCATCTGCGAGAACACTGTCGGCTCG 2196
WO 9  1694 ACTGCACCCCTGCCGATCAAGGAGGGATTTGCGAGAACACTGTCGGCTCT 1743
           ****  * ******** ** ***** ** ********************

230   2197 TACACCTGCAAGTGCAAAGAGGGGTACAGGCAAGATGGAAACTCATGCAC 2246
WO 9  1744 TACACCTGCAAATGCGCAGCTGGGTACCAGCAAGACGGCAACTCATGCAC 1793
           *********** ***  **  ******  ****** ** ***********

230   2247 TGAGATCGACGAGTGCGCTGAGGGAACCCACAACTGCCACCCTTCCGCCA 2296
WO 9  1794 TGACATTGACGAGTGCGCCAACGGCACTCACAACTGCCATGCCTCCGCGA 1843
           *** ** ************ . * ** ** ***********  * ***** *

230   2297 CCTGCAGCAACACCCCCGGAAGCTTCACCTGCCAATGCAACAGTGGATTC 2346
WO 9  1844 CATGCACGAACACGCAAGGCTCCTTTGAGTGCGCCTGCAACGCAGGCTTC 1893
           * ****  ***** *  **  ***   ***  ******   ** ***

230   2347 ACTGGCAGCGGTGTGGAGTGCGAAGACATTGACGAGTGCTCAACTGAGGC 2396
WO 9  1894 AGCGGCAACGGGGTTGAATGCAACGACGTCGACGAGTGCTCGACTGACGC 1943
           *  **** *** ** ** *** * *** * *********** ***** **

230   2397 AGATGATTGTGGTGCAAACACCATCTGCAGCAACACCATTGGTGCTTTCG 2446
WO 9  1944 TGACGATTGCGGAGAGAACACACTGTGCAACAACACAGTTGGCAGCTTCG 1993
            ** ***** ** *  *****  * **** ******  ****    ****

230   2447 AGTGCAACTGCCGTGAAGGCTATGAACGCGCAGACGCAAAGACGTGCGTC 2496
WO 9  1994 AGTGCACATGCATGGCTGGCTTCGAGGCCGCGGACGCGAAGACCTGCAAA 2043
           ******  ***   *  ****  **   *** ***** ***** ***

230   2497 GACATCGACGAATGCGCGACAGGCACACACACTTGCTCGAACCACGCCAC 2546
WO 9  2044 GACATCGACGAATGTGCAAGCGGGACCCACACTTGCTCCACCCACGCGAC 2093
           ************** ** *  ** ** *********** * ****** **

230   2547 CTGCACCAATACCGATGGGTCATTCACATGCCAGTGCAACCCCGGCTTCG 2596
WO 9  2094 ATGCACCAACACTGCTGGGTCGTTCACATGTGAGTGCAACCCAGGCTTTG 2143
            ******** ** * ****** ********  ********** ***** *
```

*FIGURE 7A (cont.)*

```
230   2597 AAGGTGACGGCCACAAGTGCGAGGACATCGACTTCTGCGGTGCTGGACAG 2646
WO 9  2144 ACGGTGACGGCCACAAGTGCGAGGACGTGGACTTCTGCGGCCAGGGGCTG 2193
           * ************************ * ***********    ** * *

230   2647 CACGACTGCAATGTGCATGCCGAGTGCTCTGAGAGCGAGGACAACACCAC 2696
WO 9  2194 CACGACTGCAACGTGCATGCAGAGTGCTCGGAAAGCGACGACAACACCAC 2243
           *********** ******** ******** ** ***** ***********

230   2697 TTTCAAGTGCACCTGTATAACAGGGTACGCTGGAGACGGCCATGGCGAGG 2746
WO 9  2244 CTTCAAGTGCACCTGCGGCATTGGGTACAGCGGGGAAGGCCACGGGGAGA 2293
            **************     *  ******    ** ** ***** ** ***

230   2747 CAGGCTGCCAAGACATTGATGAGTGCGCAGAAGAAAACATCTGCGGAAGC 2796
WO 9  2294 ATGGTTGCCAAGACATTGATGAGTGCGCCCAAGATGCCATCTGTGGGGAG 2343
             ** *********************** ****   ****** **

230   2797 AACGCTGTCTGCACAAACACCGCAGGAAGCTACCAATGCGCATGCCGTGA 2846
WO 9  2344 AACACAGTGTGTACCAACACACCAGGTAGCTTTGAATGTGCGTGTGTGGA 2393
           *** * ** ** ** *****  **** ****    **** ** **    **

230   2847 GGGCTTCGTTGCATCAGCTGAACAGCAGCAGCAGGGAACCCCAGCACTGG 2896
WO 9  2394 AGGGTTCGTGG---CTGTGGAGCGAAGCTCAAGGGAGCAACTTCATTGA 2440
            ** ***** *    * *  * *  * ***   ***** *  *  ** **

230   2897 TTTGCGTGGACGTCGACGAGTGCAGCGACGCTTCGAAGAACACATGTGCC 2946
WO 9  2441 CCTGCATAGACATCGATGAATGCAACGACGCCTCGAAAAACACTTGCGCC 2490
             *** * *** **** ** **** ****** ***** ***** ** ***

230   2947 AAGCCAGCCGACGGAGGCATTTGCACAAACACTGAAGGCAGCTACGAATG 2996
WO 9  2491 ACGTCAGCTGACGGAGGCTCTTGCAAGAACACCGCAGGCAGCTATGAGTG 2540
           * * **** *********  *****   ***** * ********* ** **

230   2997 CGCTTGCAAGCCAGGCTACCAAGGTGACGGCCACAGCTGCGCAGACATCA 3046
WO 9  2541 CTCGTGTTTGCCTGGGTTCCAGGGCGACGGCCACAGCTGCACAGATATTG 2590
           * * **    *** ** * *** ** *************** **** **

230   3047 ACGAATGCACTGCACAGGGCACCTGCGGCGAACACACAACTTGCAAGAAC 3096
WO 9  2591 ATGAGTGCGCCACCCAAGGCGTATGCGGGGAACATGCGACCTGCGAAAAC 2640
           * ** *** *  * ** ***   ***** *****  * ** *** * ***

230   3097 ACACCCGGATCCTTCCAGTGCGACTGCGTTGAGGGATTCG---AGCGCGC 3143
WO 9  2641 ACTGCGGGTTCGTACAATTGCACCTGCGAGGCGGGTTACACTCAGCAAGA 2690
           **  * ** ** * * * ***  *****  * *** * *    *** *

230   3144 TGATGAACGCACCTGCCGTGACATCAACGAGTGCGAGACAGGAGCAGTCG 3193
WO 9  2691 TGGGGCCGTCGGCTGCATTGATATTGATGAGTGTGCAGCCTCCACAGCAG 2740
           **  *    * **** *** ** * ****** *   *     ***  *

230   3194 TGCTGCCACCGAACTCCACCTGCGTCAACACTGAAGGCAGCTACGACTTC 3243
WO 9  2741 TGTTACCCGCCAACGCCACTTGCGTGAACACTGAAGGCAGCTATACATTC 2790
           ** * **  * *** **** ***** *****************     ***

230   3244 GACTGCGTTGCTGGGTACCGCCGCACTGATGGAGCTTGTGTGAAGATCGA 3293
WO 9  2791 GAATGCGTGCCCGGCTACCGCCATACGGAGAATGGCTGTACCAAGATTGA 2840
           ** *****  * ** ********  ** **     * ***   ***** **
```

*FIGURE 7A (cont.)*

```
230   3294 CTTCTGCAAGGAGAAGGGATGCAACGCAAACGCCACATGCCGCGAAAACG 3343
WO 9  2841 TTTCTGCAGCGAAAAGGGATGCAATGCGAATGCCAGCTGCAAGGAGAACG 2890
             *******  ** ***********  **  **  ****  ***   ** ****

230   3344 ATGCCGGCACCGAGGCCATCTGCACTTGCAAGGAAGGCTATGAAGGCAGC 3393
WO 9  2891 ATGCGGGCACCGAAGCCATCTGCACCTGCCACAGCGGGTACGAGGGCAAT 2940
           **** ******** *********** *** *     ** ** ** ****

230   3394 GGAGAAGGCGAAGATGGTTGCCAGAACATCAATGAGTGCGAGAGAGGCGA 3443
WO 9  2941 GGCGAAGGAGAAGAAGGGTGCAAAAACATTGACGAGTGCTCCGTGGGAGA 2990
           ** ***** ***** ** *** * *****  * ******      ** **

230   3444 ACCCTGCAAGGACTTCGGCGAAGGCGGTGTTTGCGTCGACACACCAGGAT 3493
WO 9  2991 GCCATGCAAAGACTTCGGCGAGGGCGGCGTCTGTGTCGATTCTCCGGGAT 3040
            ** ***** *********** ***** ** ** ***** * ** ****

230   3494 CATTCACTTGCGAGTGCGCTGCTGGATTCATTCAACGCCGCTCCGTTTGC 3543
WO 9  3041 CCTTCAGCTGCTCTTGCGCCACCGGTTTTATCAAGAGGCGATCTACTTGC 3090
           * ****  ***   ***** * ** ** ** * * ** **   ****

230   3544 CAAGATGTTGACGAATGTCTCGACGGAAAGCTGAACACCTGCGCTGCCAC 3593
WO 9  3091 CAGGACATAGATGAGTGCCTCGACGGAAAGATGAACACTTGCGCCCCCGT 3140
           ** **  * ** ** ** ************ ******* *****  **

230   3594 CGGAGGCGTCTGCTCCAACACCGTCGGTTCCTTCACCTGCTCGTGCGCCA 3643
WO 9  3141 CGGGGGTATCTGCACGAACACCGTCGGCTCCTTCACCTGCTCTTGCGCTG 3190
           *** **  ***** * *********** ************** *****

230   3644 GCGGCTTCGAAGGCGATGGCCACACCTGCAATGATGTCGACGAATGCGCA 3693
WO 9  3191 CTGGCTTCACGGGTGACGGCCTTACTTGCGAGGACATCGACGAATGTGCT 3240
             ******  ** ** ****  ** *** * **  ********* **

230   3694 ACAGCACAGCACACCTGTGACCCGAATGCCACTTGCGTCAACACCGAAGG 3743
WO 9  3241 ACGGCGGCACACACGTGCGACCCCAACGCCACCTGTGTCAACACTGTCGG 3290
           ** **    ***** ** ***** ** ***** ** ********  *  **

230   3744 CAGCTTCGAGTGCCGCTGCAATGCCGGATTCGAGGGCGACGGACACACCT 3793
WO 9  3291 CAGCTTCGAATGCGGATGCAAGGAGGGATTCTCTGGTGACGGCCACACAT 3340
           ********* *** * ***** *  ******   ** ***** ***** *

230   3794 GCGCAGACATCGACGAATGCGCAGACCCAGCCAAAAACACATGCGATACA 3843
WO 9  3341 GCACCGATATCGACGAATGCGCTGACCCTAACCTTAACAAATGCGACACA 3390
           ** * ** ************** *****   *   **** ****** ***

230   3844 CACAAGGGTGTATGCCAAAACACCACAGGGTCCTACACCTGCGGCTGCAA 3893
WO 9  3391 CACAAGGGCATCTGCCAGAACGGCACTGGATCCTACACTTGCGGATGCAG 3440
           ********  * ***** ***  *** ** ********* ***** ****

230   3894 GACCGGATTCAGTCTTGCAGCTGACGGAAGCACATGCGAAAACGTCGACG 3943
WO 9  3441 GCCTGGATACAGTCTGGCGGCGGACGGCTTCACTTGCGACAATGTCGATG 3490
           * * **** ****** ** ** *****    *** ***** ** ***** *

230   3944 AGTGCGGCGGCGGGAACTGCAAACTGCAACGAGCGAAGCTTCTGTAAGGAC 3993
WO 9  3491 AGTGCGCTGCCGGGGACGGCCACTTGCGGAGAGCGCAGCTTCTGCGTGGAC 3540
           ******* ***** ** ** * ***    ***** *********    ****

230   3994 ACAGAGGGTTCCTACCAATGCGAGTGCAAGAACGGCTACAAGGCTGCAGC 4043
```

*FIGURE 7A (cont.)*

```
WO 9 3541 ACGCAAGGGTCATACAAGTGCGAGTGCAAGAACGGCTACCGCCAGTCTGG 3590
          **  * ** ** *** * *********************       * **

230  4044 AGAGGACTGTGTGGACGTTGACGAGTGCGAGGCTGGCGTGCATGGATGCA 4093
WO 9 3591 GGAGGACTGCGTGGACGTTGACGAGTGCGAGGCTCATGTGCACACATGCA 3640
           ******** ************************   *****   *****

230  4094 GCGAGCACGCAATCTGCACAAATACAGACGGCAGCTACTCCTGCGAATGC 4143
WO 9 3641 GCGAGCACGCTACGTGCACGAACACTGAGGGGAGCCACACCTGCACCTGC 3690
          ********** *  ***** ** ** ** ** *** ** *****   ***

230  4144 ATGGAGGGATACCAGGGAGACGGCAAGGCTTGCGAGAAGACAGTCGGCGT 4193
WO 9 3691 AATGAAGGGTACCAGGGAGACGGAAAGAAGTGCGAGAAGACAGTGGGCCC 3740
          *  ** ** ************** ***   ************** ***

230  4194 CTGCGACTCCGCTCCCTGCGGTGCCCACGCCACCTGCGAGCCTGCAGGGG 4243
WO 9 3741 TTGCGACAACTCGCCATGCGGCAACAACGCCATGTGTGAAGCTACTGCCG 3790
           ******  * * ** *****   * ******  ** **  ** * *  *

230  4244 ACAACTACACTTGCACATGCCACCCAGGCTACGAGATGCGCGAAGGAGCC 4293
WO 9 3791 ATAGCTACAACTGCACTTGCAAAGCTGGCTACGAGATGAAGGACGGGGCC 3840
          * * *****  ***** *** *  * ************   ** ** ***

230  4294 TGCGTTGACATCGATGAGTGCACAGCAGGCAGCCTCAACTGCGACCCTCA 4343
WO 9 3841 TGTGTCGACATCGATGAGTGCCAGTCGGGCACCCACAACTGCGACCCGCA 3890
          ** ** ***************    * **** ** ************ **

230  4344 TGCCATTTGCACAAACACCGACGGCTCCTTCACTTGCGTCTGTGGCAGCG 4393
WO 9 3891 TGCTGACTGCAGCAACACCGATGGATCCTTCACGTGCACGTGCGGTTCTG 3940
          ***    ****  ******** ** ******** ***   ** **    *

230  4394 GCTATACCGGCCTTGGCACATCCTGCGAAGACATCGACGAGTGCGCGGGT 4443
WO 9 3941 GCTACACTGGTGTGGGTACCCTTTGCGAGGATGTGGACGAGTGCGCGGGC 3990
          **** ** **  * ** **    ***** **  ****************

230  4444 AACGCAGCAGGCTGCGACATCCACGCCGTCTGCACGAACACTCCCGGATC 4493
WO 9 3991 AACCATGCGGGCTGTGACATCAACGCTGTTTGCACTAACGTCCCTGGCTC 4040
          ***   ** ***** ****** **** ** ***** ***   ** ** **

230  4494 GTTCAAGTGCGAGTGCAAGAGCGGCTTCGAAGGCGATGGCACGCAATGCA 4543
WO 9 4041 GTTCACTTGCGAGTGCAAGAGTGGCTTCGAAGGCGATGGGCACGAGTGTA 4090
          *****  ************** *****************     * ** *

230  4544 CGGAGAAGGTGTTGCTCCCCGGACAGATTCACTGCGAAGCCTGGACTGCA 4593
WO 9 4091 CGGAGAAAGTGCTGCTCCCTGGCCAGATTCACTGCGATTCGTGGACTGCA 4140
          ******* *** ******* ** **************  * *********

230  4594 TGGACAGAGTGTACCGACGGCGCCAAAACCAGCACACGCAGCTGCCTTGC 4643
WO 9 4141 TGGACCGAATGTACAGCTGAAACTAAGCAGAGCACCCGCAAGTGCGTGGC 4190
          ***** ** ***** *  *   * **    ***** ****  *** * **

230  4644 ACTGCCGCTTAAGAAGGAGATGCGCGCCTGCCCTGCAGCTGACTTCTCCC 4693
WO 9 4191 TCTTCCTCTCAAGGTCGAGGTGAAGCTTTGCCCCGATGCTGACATTTCAG 4240
           ** ** ** ***   *** **      ***** *  ****** * **

230  4694 AGTGCGGAGAGTTCACTGAATGGACTGCCTGCCCTGGAACCAACAATAAC 4743
WO 9 4241 CCTGCGGTGAACTCGGCGAGTGGTCATCATGCCCAGGAGTTGACAACAAC 4290
```

```
               ***** **  **   ** *** *  * ***** ***    **** ***

230   4744 CTGTCTCATAGGCGCACTGAAAGATTCGGAGAACCCGGATGCGAAGATGC 4793
WO 9  4291 CTGTCGCACCGCAGAGCAGAGAAGTTCGGGGAGCCGGGCTGTGAGCACGC 4340
           ***** **  *  *  * ** *  ***** ** ** ** ** **  * **

230   4794 AGAGGAAGTCCGCGAATGCCCAGATGAAGAGACCGAGCAGAAATGCGGCG 4843
WO 9  4341 TGAGGAGGTCAGGGAGTGCCCAGATGAAGAAGTTGAGGAGCGCTGTGGTG 4390
            ***** *** * ** **************    *** **   ** ** *

230   4844 CCTGGGGTGAGTGGACCGCCTGCGGCGACCCATCCCCTGGCCTGAGAACT 4893
WO 9  4391 CCTTTGGCGAGTGGACTGCATGCGGCGATCCTTCTGAGGGCTTGAGGACC 4440
           ***  ** ********* ** ********* ** **    *** **** **

230   4894 CGCGCACGCGAGAACTGCCCCGATGTGGTAGAGTTCGAGCGTTGCACTAT 4943
WO 9  4441 AGGACGCGCCAGAACTGCCCAGAAGAGGCAGAATTCGAGCACTGCACAAT 4490
            *  * *** *********** ** * ** *** ******** ***** **

230   4944 GCCCAGTGAGCCTGAGGCTGGCGAAGTGACTGAGCCTCACACAGAAGGAG 4993
WO 9  4491 GCCCTCTGCACCATCCGTTCCCGAGGGCGGCAGCAGCTGCACAGAGTTCG 4540
           ****  ** ** ** * * *** *              ******    *

230   4994 GAGCCGGAGTTGGTGGCGAAGTGACTGAGCCTGACACGGAAGAAGGAGCC 5043
WO 9  4541 GGGCCTGGAGTGAATGCG---TGGCTGACGCT--CATGGGATCAAGATGC 4585
           * *** *   **   ***  ** **** **  ** ** *  * **   *

230   5044 GGAGTTGGTGGTGAAGTGCAGCCCGGTACAGAAGAAGGAGCAGGAGTTGG 5093
WO 9  4586 AGCACAGAACGTGC-GTACACAATGAAGCTGTGCAGGAACACAGAATCTG 4634
            *    *   *** ** **    *   * *  * * *    ** *   *

230   5094 TGGTGAAGTGCAGCCCGGTACAGAAGAAGGAGCCGGAGTTGGTGGTGAAG 5143
WO 9  4635 CACCGTGGAAGA-TCCACAACAGTGCGGGGAGTGGTCGCAGTGGTCAGAG 4683
                * *  *  **  ****    **** *  *  *  *   **

230   5144 TGCA-GCCCGGTACAGAAGAAGGAGCCGGAGTTGGTGGTGAAGTGCAGCC 5192
WO 9  4684 TGCAAGAATGGCAAGCAGTACAGAGGCGCCGCCGG-----ATGCGCGTCT 4728
           **** *   ** *  *  *  *** **  *  **     * * ** *

230   5193 CGGTACGGAAGAAGGAGCCGGCATTGGTGGCGAAGTGACTGAGCCTGACA 5242
WO 9  4729 GTGTACG-AAGTCAGAGCCTGCAGCGGCG---------------CTAGCG 4762
             ***** ***  ***** ***  ** *                ** *

230   5243 CCGAAGGAGGAGCCGGAGTTAGTG-GCGAACCGACCGAAGAAGAGGGCAC 5291
WO 9  4763 ATGCGAAAGAATGCTCTTTTGGTGCGTGGAGCGGCTGCGTGGTGGAGTTT 4812
             *   ** *  *    ** *** * * * ** * *      * *

230   5292 CGAAAGCACCGGTCCATGCAAAGAGTTCGGACCCTGGACGGCCTGCAAGG 5341
WO 9  4813 GGCGGTCAC------ACTTACAAAGTGCGAAACTCAATCGAC-TGCGAGC 4855
            *    ***      *    * * *** ** * *     ** * *** **

230   5342 AGGACGAGAACGGAGTCGGCATCCAACGCCGTATGTGCGCCGGCAGAGAA 5391
WO 9  4856 TCAGTGAGCT----GCAGGCTTGCAA-GCC----GAGCGCCGCCACCGAG 4896
               ***     * *** * *** ***    * ******* **  **

230   5392 GACATCATCGAATCCAGAATTTGCACTGTCACGGATGACTGCGGAGAATG 5441
WO 9  4897 GGCGAGGGCAAGTGCGCTGCTTGGAGCCCCTGGACGATCTGCAGGGA--C 4944
           * *    * * * *    *** *    *  *      **** * **
```

*FIGURE 7A (cont.)*

```
230    5442 GACCCCCTGGTCAACTTGCACTAACGGCAGCCAGGCCAGAAACAAACGCT 5491
WO 9   4945 GGCATGCAGACTCGCGACTGCAAAAGCCTGGGTGTTCAGGAGTCC-CGCC 4993
             * *  * *    *    * ** * * *  *  *** *     ***

230    5492 TCTGCACCAACGTTAGGGAAGTCCGTCTCTGCGGAGCTGACATTCCAGTT 5541
WO 9   4994 CATGCTCAGCTGAAGGAGAGACCGATTCTTGCGGAGCCTTTGGACCC-TT 5042
              *** *    *   * **   *  *   ********       **  **

230    5542 ACAGACGGATGCACGTGGAGCGAGTGGACTTCTTGCAGTCTAGTCAATGA 5591
WO 9   5043 CGAGCCGGCAGCTTGCAAGGCTGGCGAGATGGTCACGA---GGACGCGGG 5089
              ** *** **  *   **  * *   *  *  *      * *   *

230    5592 GGAGGGCGGCTACTTCCGCACGCGCACATCCTCTGACTGCAACATGAATG 5641
WO 9   5090 AGTGCAACGGTGCT-CAGCAGAAGGAAACC---AGACTGTGCAATCC-TG 5134
             * *     * * ** * ***  * * * *    *****   **   **

230    5642 AAGTGCAGGCCTGCTCTCCCAGCAGCAGCACAACCGCAGACAGCGAAACA 5691
WO 9   5135 AGGGCAATGACAACTGCAACAACTGGGGTGCTTGGACAGAGTGCTCGCTA 5184
            * *  * * * **    ** * *  *  *     ****  **     *

230    5692 GAAGGCACCTGCTCTGCATGGAACCCCTGGACGGAGTGCTCGAACGGCCA 5741
WO 9   5185 ATTGTGGGCGGCTCTGCCCTGCGGTCTCGCGAGGAGTCCACTTGCGGCTA 5234
               *    * ******** . *     *  *   ***** * *   **** *

230    5742 CCAGACACGCAAGTGTGCCACAATGGAAGCAGAAGAATCGCGCACTTGCG 5791
WO 9   5235 TGTGGA--GTTAGAGGAGTGCAGTGGCAGCAGCAGCAGCGGCGACCAGAC 5282
               *    *  ** *      ** *** ***** ** * **   **  *

230    5792 GAGAGACTCCAGAGAACTGCGGAGAATTCGGCCCCTTCGAACCCGCAAAC 5841
WO 9   5283 CGTCCACTGCGGC-AGCTGGTCGGAGT---GCTCCATGAGAAAAACGGAG 5328
                  *** * *  * ***    ** *  ** ** *   *    *  *

230    5842 TGCACGGCCGGCCAAATGGTCACCAGGACGCGCACCTGCGGAGAAACCGA 5891
WO 9   5329 CGCACCTGTGATGTCCTCTCTGACGGATCCCACACCAGCGTTACTGAAGT 5378
             ****    *      *     * *  * * **** ***         *

230    5892 GCAGAAGGAAACCAAACTGTGCCGACGTCAGCTCCACCGAAGAAGGAAAAC 5941
WO 9   5379 GCTCACCTGCGACGACGTGCTGCCTGACTCTTGCGGTGAATTTGGCGAGT 5428
            **  *      * *  **    * *   * *   ***   ** *

230    5942 AATGCGGTCAGTGGGGCCCATGGAGCGAATGCAACATCCACCTGGGCTCA 5991
WO 9   5429 GGTCCGAAT-GTAGCGCTGACGGCTTGCACTCGAGGTCCCTGTCAGGCTG 5477
              * **    ** * **  * **  * *  * *  ***    *  *

230    5992 GAGGACAATGTGCGTGTTCGTGAGG-ACACCGCTTGCGGCGTGACGGAGT 6040
WO 9   5478 CCCAGACGTAACTGAAGTGATGACTTGCGGCAGCGAAAACTGCCCGGCTT 5527
                  *    *   *  ***    *   *         *   ***  *

230    6041 ACGAGGAGTGCAGCAAGC-CGGCGAACAACGCCTTTGTCTGCACACCTTG 6089
WO 9   5528 TCGGCGAGTGGAGCGAGTGCGGCAGCCCAGAGGACGGCCTACGGTCGCGT 5577
             **  ***** *** **  ****   * *        * ** *   *

230    6090 GAGTGAATGCTCGGACAAGAAGGAGCGGAGAACGTGCACCATCGGCAAAA 6139
WO 9   5578 CAGCGAACGAACTGCGAAGAGGGATCCGGCTGCATTTGC--TCCGAGAGA 5625
             ** *** *  * *  **** *** * *    * *   * ****  * *
```

*FIGURE 7A (cont.)*

```
230  6140 ACGGTCT-TGTTCAGACACGTCAAGAATTCAGAACATGCAGTGTAGACAT 6188
WO 9 5626 GAAGCCTGTGTTAACACTGAGCTCCACCCCATCCCATTGCCAGTTCCTGG 5675
             * ** **** * **    *   *   **   ***     **

230  6189 CGCCACAACTTGCGGCGATTTCGGCGCA--TGGTCTGAATGCAACGCTGA 6236
WO 9 5676 CGGCGGCGAGGGCAGCGAGAACGCCGAGGGTGGCCAAACCGGAGAGGAGG 5725
          ** *       ** ****   *****    *** *  *  * *  *  *

230  6237 GGGCTTGCATCAGCGCAGTCT-CGAGAAATGCCCCGACGTCATCGAGGTC 6285
WO 9 5726 GAACGGAGGGAGGCGCAGGCGGTGCTGGAGGATCCGGTGGTGCTGAGGA- 5774
          *  *        ****** *   *    * *  ***  *     ****

230  6286 GCAACTTGCGGCAGTGAGGATTGCCCGCCATTCGGCGAGTGGACTGAATG 6335
WO 9 5775 GCTGCC--CGGAGAAGAGGGTGGCGCAGGTGCCGGCGGAGAAGGAGGCTC 5822
          **  *   ***    **** * ** *      *****        *  *

230  6336 CGGCGTTCCAGAGGAGGGCATGCGTTCTCGCCAACGCATTGACTGCGTTG 6385
WO 9 5823 TGGCGGTAATGCTGAGGAGCTGC---CCGGAGAAGGGGGTGCTGGCG--- 5866
           **** *   *  ****   ***   *  *  ** *   **   ***

230  6386 AATCTGCAGCCTGCCAGTGCACAGAAGTGGAGAGCTGCTTCGACACCGAA 6435
WO 9 5867 AAGCTGGAGGCT-CTGGCG-GTAGTGCTGAGGAGCTGC-------CCGGA 5907
          ** *** ** ** *  * *   **   **  *******       *** *

230  6436 TTGCACCCCATTCCAGCCCCCGGTACGGAAACAGGCGAAGGAGAGGGAGA 6485
WO 9 5908 GAAGAGGGCGGCGCAGGTGCCGGCGGAGGAGGAGGCTCTGGCGGTAGTGC 5957
              *   *    ***   ****    * *  ****   ** *   * *

230  6486 GACCGAGACAGGCGAAGGCGAAACTGGTGAAGCAGGTGGCGAGGAAGGCG 6535
WO 9 5958 TGAGGAGCTGCCTGGAGAAGAGGGCGGCGCAGGTGCCGGCGGAGAAGGAG 6007
              ***      * **  **    ** * **  *  ****  ***** *

230  6536 AGCAAACAGGAGAAGGCGAAGTGCAGCCCCCAGAAGAAGAGCTTCCTGGG 6585
WO 9 6008 GCTCTGGCGGCAATGCTGAGGAGCTGCCCGGAGAAGAGGGCGGCGCAGGT 6057
                  **  * *  ** * **  ****  ****** *      * **

230  6586 GAGAGTGTAACTGAGCCTGAG---GAGAAGCCTGAGGAGGAGCTACCTGA 6632
WO 9 6058 GCTGGAGGAGCCGAAGGCGAGACAGGGAAACCTGGCGGCGAAGAGGGTGG 6107
          *   * * * * **    ***   * *** ****  *   **     **

230  6633 GGAGGAGGTTACTGAGCCTGAGGAGAAGCCTGAGGAGGGTGTGACTCAGC 6682
WO 9 6108 CGCAGGCGGCGCTGGTGAGGGTGCTGGCGGTGAAGGTGGTGAGGTCCAGC 6157
           *  *  *   ***     *  *       *** *  **** *   ****

230  6683 CTGAGGAGACACCTGAGCAGCCTGTTGAGGGTACCGAAGAAGAGGGCAAG 6732
WO 9 6158 CTGGAGAGGGAGAACGGGCGAGTGAAGGAGGCGAGCAAGTGCCGGAAACC 6207
          ***  ***  *   * *  *  **  *  **     ***    **  *

230  6733 CAGGAG---TCTGAGGCTG---CCCCCGAAACT------CCTGCCGTCCA 6770
WO 9 6208 CCTGAGACACCCGAACCGGAAACACCTGAAGCTGAGAGACCTGAAGAGCA 6257
          *  ***    * **  *  *   * ** *** **      ****  *  **

230  6771 GCCAAAACCAGAGGA---GGGTCACGAACGCCCAGAACCCGAAGAGGAGG 6817
WO 9 6258 ACCCTCGACGGAAACTCCAGCAGAGGAGCCCACCGAAGGCGGTGCAGAAG 6307
           **     * **       *   * ** * * * ***  **  *  ** *

230  6818 AGGAGAAGAAGGAAGAAGGCGGCGGCTTCCCAACAGCTGCAGTGGCAGGA 6867
```

*FIGURE 7A (cont.)*

```
WO 9 6308 AAGAGGAGAAGGAGGAGGGCAGCGGCTTCCCCACGGCAGCTGTTGCCGGA 6357
          * *** ******** ** *** *********** ** ** ** ** ** ***

230  6868 GGTGTTGGTGGTGTGTTGCTCATAGCTGCTGTAGGTGGTGGTGTTGCAGC 6917
WO 9 6358 GGTGTAGGTGGTGTACTACTGCTGGCAGCAGTGGGTGGTGGCGTTGCCGC 6407
          ***** *********    * **   * ** ** ** ********* ****** **

230  6918 CTTCACTAGCGGCGGAGGTGGCGCTGGCGCACAGGAGGCAGAACAGGTCG 6967
WO 9 6408 GTACTCCGGTGGTGGTGGAGGTGGCGGTGCCGAGGAGGCTGAGCAAGTTG 6457
            * * *  * ** ** ** ** *  ** **  ******* ** ** ** *

230  6968 AGTTCGAAGGAGAAGATACCGGAGCAGCAACTGCCGAGACACCTGAAGCC 7017
WO 9 6458 AGTTTGAAGGTGAAGAGTCGGGTGGTGCGTCTGCCGAAACACCTGAGGCT 6507
          **** ***** *****   * ** *  **  ******* ******** **

230  7018 GATACAGTTATCGACATCACAGACGAAGACGACTACTGGGCCGACAGCGG 7067
WO 9 6508 GATACTGTGATTGACATCACTGACGAAGACGACTACTGGGCAGACAGTGG 6557
          ***** ** ** ********* ******************** ***** **

230  7068 CGACATTCAG 7077
WO 9 6558 TGACATCCAG 6567
           ***** ***
```

*FIGURE 7B*

```
230 Tran     1 MLHRNPRWALCAALAALYGGTGIASAEVNNELSKCESGWTPWTTCNPQTG  50
WO 900040    1                                                     0

230 Tran    51 LRERHNAQCETWVEVTEECQKLTGCGNWTPWSPGDMSCVVGQFQTRNREGC 100
WO 900040    1                                       MGFFVFTG----   8
                                                     .* *    .

230 Tran   101 FEVQEVRACRPVLLECNDQWTPWIMCDINRVQERYNSKCGPVEVRECNMD 150
WO 900040    9 --------------------------------------------------   8

230 Tran   151 DAEIEKCGEFVEWDPPMNGDCVRGGIHTRYRQNCPDRKEVRVCGAFDCSS 200
WO 900040    9 -------GDFGDWSPPLAGDCVPGTIETRQRANCPNHKEVRVCGAFDCSQ  51
                      *.* .* **. **** * **** * ***. .************

230 Tran   201 CSVNATCDPIGASCECKPGFRGNGKICEAFNPCEDTPAPCDSNAICTPDA 250
WO 900040   52 CSVNATCDPLGATCQCKPGFRGDGTQCEAFNPCEGETAPCDANATCTADG 101
               *********.**.*.******* * ********  ****.** ** *

230 Tran   251 MTPNASARQAGTQIPEQAAARSLALR-STSAHPTPTSARHTPHASTPRAL 299
WO 900040  102 NDAKCHCNKGWNADSKAGASGHACVEEDECANNTHECPQHSTCVNTEGSY 151
                 . . . .       *.   ..   .*. *  . .*.    *  .

230 Tran   300 ISATATRDTVKGEDGQCHDVDECTNGEHTCPAHSTCLNTAGSYECRCDTG 349
WO 900040  152 ECNCLPGYQKD-QDGKCQDIDECA-GEHGCPAHSTCVNTAGSFECKCDAG 199
               . .        .**.*.*.***. *** *******.*****.**.**.*

230 Tran   350 YSGNATADSPCKNIDECANPNACSANAICTDTDGSFTCSCPEGYSGQGTH 399
WO 900040  200 FSGSATSESPCSNIDECQDPDACSANAICADTEGSFTCSCPEGYSGGGSH 249
               .** **..*** *****  * *********.**.**************.*

230 Tran   400 DSPCSKIDFCAYPSLNTCGAHSTCN-TLTSFKCICDAGYEGAGTRESPCV 448
WO 900040  250 DSPCSKIDYCADPTLNTCGAHSTCVNTLTTFKCVCDAGYDGAGTHESPCV 299
```

```
                     ********_** *_**********  ***_***_*****,****_*****

230 Tran     449 DVNECSNEKPTNNCNRNANCTNTEGSYTCECKPGFSGDGMGPNGCTDIDE  498
WO 900040    300 DIDECSKEKPSNDCNRNAVCTNTEGSYTCACKEGFSGEGFGAAGCADVDE  349
                 *. *** ***.* ***** ********** ** ****.* *  **,*,**

230 Tran     499 CAAEQSPCDPHASCSNTEGSYVCTCNTGYEPASTDGHACKDIDECATGAA  548
WO 900040    350 CAN--SPCDAHASCANTEGSYVCTCNPGYEPASSDGHACKDVDECAAGTA  397
                 **   **** ****_*********** ******_*******.****.*.*

230 Tran     549 GCHVSAQCLNTDGSYECKCLEGFVGDGKTCNDVDECAAATSPCGDNTHCQ  598
WO 900040    398 ECHVSAQCVNVDGSYECHCLEGFIGDGKVCSDVDECAAEASPCGANTHCL  447
                  *******.* ******.*****.**** * *******  _**** ****

230 Tran     599 NTIGSYECECKAGYGNMQDNACSDIDECKDANTKIPDNCLCVNNDGSYSL  648
WO 900040    448 NTIGSYECECKDGYGHKEGNACSDIDECSEASTEIPENCNCVNTEGSFSL  497
                 *********** ***_*. ********* .* * **_** ***..**,**

230 Tran     649 EAKAGYELVNGECIKIDFCARGACNSLASCKENEEGTAAICTCLPGYSGD  698
WO 900040    498 EAKPGYELVDGKCVKIDFCARGACNSLAHCKENPEGTAAICTCIAGYSGD  547
                 *** ***** * *.************** **** *********, *****

230 Tran     699 GTAEGHCNDIDECAGQNDCAPAEQGGICENTVGSYTCKCKEGYRQDGNSC  748
WO 900040    548 GTAQGHCDDIDECLAENDCTPADQGGICENTVGSYTCKCAAGYQQDGNSC  597
                 ***.*** *****  _***_**.****************   **.******

230 Tran     749 TEIDECAEGTHNCHPSATCSNTPGSFTCQCNSGFTGSGVECEDIDECSTE  798
WO 900040    598 TDIDECANGTHNCHASATCTNTQGSFECACNAGFSGNGVECNDVDECSTD  647
                 *.***** ****** ****_** *** * **_**_* **** *.*****.

230 Tran     799 ADDCGANTICSNTIGAFECNCREGYERADAKTCVDIDECATGTHTCSNHA  848
WO 900040    648 ADDCGENTLCNNTVGSFECTCMAGFEAADAKTCKDIDECASGTHTCSTHA  697
                 ***** **.* **_*.***.*  *.* ****** ******_******.**

230 Tran     849 TCTNTDGSFTCQCNPGFEGDGHKCEDIDECGAGQHDCNVHAECSESEDNT  898
WO 900040    698 TCTNTAGSFTCECNPGFDGDGHKCEDVDECGQGLHDCNVHAECSESDDNT  747
                 ***** *****_*****_********_**** * ************_***

230 Tran     899 TFKCTCITGYAGDGHGEAGCQDIDECAEENICGSNAVCTNTAGSYQCACR  948
WO 900040    748 TFKCTCGIGYSGEGHGENGCQDIDECAQDAICGENTVCTNTPGSFECACV  797
                 ****** ** *.**** *********..  *** *.***** **..***

230 Tran     949 EGFVASAEQQQQGTPALVCVDVDECSDASKNTCAKPADGGICTNTEGSYE  998
WO 900040    798 EGFVAVG-AKLKGATSLTCIDIDECNDASKNTCATSADGGSCKNTAGSYE  846
                 *****    _ .*. .* *.*.***.********  **** *.** ****

230 Tran     999 CACKPGYQGDGHSCADINECTAQGTCGERTTCKNTPGSFQCDCVEGFERA 1048
WO 900040    847 CSCLPGFQGDGHSCTDIDECATQGVCGEHATCENTAGSYNCTCEAGYTQQ  896
                 *.* **.*******_** **_.** ****.** ** **..* *  *. .

230 Tran    1049 D-ERTCRDINECETGAVVLPPNSTCVNTEGSYDFDCVAGYRRTDGACVKI 1097
WO 900040    897 DGAVGCIDIDECAASTAVLPANATCVNTEGSYTFECVPGYRHTENGCIKI  946
                 *    * ** **  . . *** *_********** *.** ***_*.. * **

230 Tran    1098 DFCKEKGCNANATCRENDAGTEAICTCKEGYEGSGEGEDGCQNINECERG 1147
WO 900040    947 DFCSEKGCNANASCKENDAGTEAICTCHSGYEGNGEGEEGCKNIDECSVG  996
                 *** ******** * ************ **** **** ** ** **  *
```

*FIGURE 7B (cont.)*

```
230 Tran   1148 EPCKDFGEGGVCVDTPGSFTCECAAGFIQRRSVCQDVDECLDGKLNTCAA 1197
WO 900040   997 EPCKDFGEGGVCVDSPGSFSCSCATGFIKRRSTCQDIDECLDGKMNTCAP 1046
                **************.****.* **.***.*** ***.*******.****

230 Tran   1198 TGGVCSNTVGSFTCSCASGFEGDGHTCNDVDECATAQHTCDPNATCVNTE 1247
WO 900040  1047 VGGICTNTVGSFTCSCAAGFTGDGLTCSDIDECATAAHTCDPNATCVNTV 1096
                 **.*.***********.** *** ** *.****** ************

230 Tran   1248 GSFECRCNAGFEGDGHTCADIDECADPARNTCDTHKGVCQNTTGSYTCGC 1297
WO 900040  1097 GSFECGCKEGFSGDGHTCTDIDECADPNLNKCDTHKGICQNGTGSYTCGC 1146
                ***** *  ** ******.********* * ******.*** ********

230 Tran   1298 KTGFSLAADGSTCENVDECAAGTANCNERSFCKDTEGSYQCECKNGYKAA 1347
WO 900040  1147 RPGYSLAADGFTCDNVDECAAGTATCGERSPCVDTQGSYKCECKNGYRQS 1196
                . *.****** **.**********.*.***** **.***.*******. .

230 Tran   1348 GEDCVDVDECEAGVHGCSEHAICTNTDGSYSCECMEGYQGDGKACEKTVG 1397
WO 900040  1197 GEDCVDVDECEADVHTCSEHATCTNTEGSFTCTCNEGYQGDGKKCEKTVG 1246
                ************ ** ***** ****.** .* * ********* ******

230 Tran   1398 VCDSAPCGAHATCEPAGINYTCTCHPGYEMREGACVDIDECTAGSLNCDP 1447
WO 900040  1247 PCDNSPCGNNAMCEATADSYNCTCKAGYEMKDGACVQIDECQSGTHNCDP 1296
                 ** .*** .* ** .  * *.***. ****..********* .*. ****

230 Tran   1448 HAICTNTDGSFTCVCGSGYTGLGTSCEDIDECAGNAAGCDIHAVCINTPG 1497
WO 900040  1297 HADCSNTDGSFTCTCGSGYTGVGTLCEDVDECAGNHAGCDINAVCINVPG 1346
                ** *.******** *******.** ***.****** *****.***** **

230 Tran   1498 SFKCECKSGFEGDGTQCTEKVLLPGQIHCEAWTAWTECTDGAKTSTRSCL 1547
WO 900040  1347 SFTCECKSGFEGDGHECTEKVLLPGQIHCDSWTAWTECTAETKQSTRKCV 1396
                ** ***********  .**************.. ********  .* *** *.

230 Tran   1548 ALPLKKEMRACPAADFSQCGEFTEWTACPGTNNNLSHRRTERFGEPGCED 1597
WO 900040  1397 ALPLKVEVKLCPDADISACGELGEWSSCPGVDNNLSHRRAEKFGEPGCEH 1446
                ***** *..  ** ** * *** ** ..*** ********.*.*******

230 Tran   1598 AEEVRECPDEETEQKCGAWGEWTACGDPSPGLRTRAREKCPDVVEFERCT 1647
WO 900040  1447 AEEVRECPDEEVEERCGAFGEWTACGDPSEGLRTRTRQNCPEEAEFEHCT 1496
                *********** *..*** ********** *****.*.***.  ***.**

230 Tran   1648 MPSEPEAGEVTEPHTEGGAGVGGEVTEPDTEEGAGVGGEVQPGTEEGAGV 1697
WO 900040  1497 MPSAP--------------------------------------------- 1501
                *** *

230 Tran   1698 GGEVQPGTEEGAGVGGEVQPGTEEGAGVGGEVQPGTEEGAGIGGEVTEPD 1747
WO 900040  1502 ------------------------------------------SVP- 1504
                                                         .*

230 Tran   1748 TEGGAGVSGEPTEEEGTESTGPCKEFGPWTACKEDENGVGIQRRMCAGRE 1797
WO 900040  1505 -EGGS---------------S--CTEFGAWSECVADAEGIKMQFRTCVHNE 1537
                 ***.              .   * *** *. *  * .*..*.*.* *   *

230 Tran   1798 DIIESRICTVTD--DCGEWTPWSTCTNGSQARNKRPCINVREVRLCGADI 1845
WO 900040  1538 AVQEHRICTVEDPQQCGEWSQWSECRNGKQYRGAAGCASVYEVRACSGAS 1587
                . * ***** *   ****. ** * *.*.*.   *. * *** *
```

*FIGURE 7B (cont.)*

```
230 Tran   1846 FVTDGCTWSEWTSCSLVNEEGGYFRTRTSSDCNMNEVQACSPSSSTTADS 1895
WO 900040  1588 DAKE-CSFGAWSGCVVEFG-GHTYKVRNSIDCELSELQACKPS----AAT 1631
                  . *.   *. * .    *  .. *.* ** . *.*** **    * .

230 Tran   1896 ETEGTCSAWNPWTECSNGHQTRKCATMEAEESRTCGETPEN--CGEFGPF 1943
WO 900040  1632 EGEGKCAAWSPWTTCRDGMQTRDCKSLGVQESRPCSAEGETDSCGAFGPF 1681
                * ** *.** *** *  * *** * ..  .*** *     *.  ** ****

230 Tran   1944 EPANCTAGQMVTRTRTCGETEQKETKLCDVSSTEEGKQCGQWGPWSECNI 1993
WO 900040  1682 EPAACKAGEMVTRTRECNGAQQKETRLCNPEGND---NCNNWGAWTECSL 1728
                *** * **.****** *. ..****.**     ..   .*..** *.** .

230 Tran   1994 HLGSEDNVRVREDTACGVTEYEECS---KPANNAFVCTPWSECSDKKERR 2040
WO 900040  1729 IVGG-SALRSREESTCGYVELEECSGSSSSGDQTVHCGSWSECSMRKTER 1777
                 .*    .* **...** * ****      ..  *  ***** .*  *

230 Tran   2041 TCTIRKNGLVQTRQEFRTCSVDIATTCGDFGAWSECNAEGLEQRSLEKCP 2090
WO 900040  1778 TCDVLSDGSHTSVTEVLTCDDVLPDSCGEPGEWSECSADGLHSRSLSGCP 1827
                ** .   *    . .* **   .  .**.** ****.*.*** ***  **

230 Tran   2091 DVIEVATCGSEDCPPFGEWTECGVPEEGMRSRQRIDCVESAACQCTEVES 2140
WO 900040  1828 DVTEVMTCGSENCPAPGEWSECGSPEDGLRSRQRINCKEGSGCICSETEA 1877
                ** ** ***** ** ****.*** **.*.*****  * *  . * *.* *.

230 Tran   2141 CPDTELHPIPAPG------TETGEG--EGE--TETGEGETGEAG------ 2174
WO 900040  1878 CVNTELHPIPLPVPGGGEGSENGEGGQTGEEGTEGGAGGAGGSGGAEELP 1927
                *  ******* *          .*.***  **  ** * * .* .*

230 Tran   2175 GEEG--EQTGEGEVQPPKEELPGE--------SVTEPEEKP-EE------ 2207
WO 900040  1928 GEEGGAGAGGEGGSGGNAEELPGEGGAGEAGGSGGSAEELPGKEGGAGAG 1977
                ****      ***       ******          *   ** * **

230 Tran   2208 -----------ELPEEE------VTEP------EEKP-EEG---------V 2225
WO 900040  1978 GGGGSGGSAEELPGEEGGAGAGGEGGSGGNAEELPGEEGGAGAGGAEGET 2027
                           *** **        *        ** * ***

230 Tran   2226 TQP--EE------TPEQP------VEGTEEEGKQES-EAAPETPAVQ---- 2257
WO 900040  2028 GKPGGEEGGAGGAGEGAGGEGGEVQPGEGEGASEGGEQVPETPETPEPET 2077
                 .*  **     . *        *.  * **  *  *  ****

230 Tran   2258 PKPEEGHERP--------EPEE---EEEKKEEGGGFPTAAVAGGVGGVLLI 2297
WO 900040  2078 PEAERPEEQPSTETPAEEPTEGGAEEEEEKEEGSGFPTAAVAGGVGGVLLL 2127
                *  *   *.*   .   ** *   *** **** ****************.

230 Tran   2298 AAVGGGVAAFTEGGGGAGAQEAEQVEPEGEDTGAATAETPEADTVIDITD 2347
WO 900040  2128 AAVGGGVAAYSGGGGGGAEEAEQVEPEGEESGGASAETPEADTVIDITD 2177
                *********.. **** **.**********..* *.**************

230 Tran   2348 EDDYWADSGDIQ 2359
WO 900040  2178 EDDYWADSGDIQ 2189
                ************
```

FIGURE 8A

```
                10                            30                             50
5' GTG GTG ATT GAA TCT GCT CCA GCC AAG ATG GCT CAC CCT CCT GTG GTG ATT GAG TCT GCT
   Val Val Ile Glu Ser Ala Pro Ala Lys Met Ala His Pro Pro Val Val Ile Glu Ser Ala

                70                            90                            110
   CCG GTC GAG GTG GTC CAT CCT CCT ATG GTG ATT GAA TCT GCT CCA CCC AAG ATG GCT CAA
   Pro Val Glu Val Val His Pro Pro Met Val Ile Glu Ser Ala Pro Pro Lys Met Ala Gln

               130                           150                            170
   CCT CCG ATG GTG ATT GAG TCT GCT CCA CCC AAG ATG GCT CAA CCA CCT ATG GTG ATT GAG
   Pro Pro Met Val Ile Glu Ser Ala Pro Pro Lys Met Ala Gln Pro Pro Met Val Ile Glu

               190                           210                            230
   TCG GCT CCC GTC GAG GTG GTC CAT CCT CCT ATG GTG ATG GAA GCC GCT CCC ACC GTG AAG
   Ser Ala Pro Val Glu Val Val His Pro Pro Met Val Met Glu Ala Ala Pro Thr Val Lys

   GGA AGA TAC CTC GCT GCT GAG GAT GAG GTG GAA GAG CAG TTT GAA TCG AAC AG 3'
   Gly Arg Tyr Leu Ala Ala Glu Asp Glu Val Glu Glu Gln Phe Glu Ser Asn
```

Nucleic acid sequence of the first 293 nucleotides of clone pEM 250/14.
Note the presence of a 14 amino acid repetitive sequence in the single translated open reading frame.

FIGURE 8B

```
                  10                            30                            50
5' C CTG CAG GTT GTA CTA AGA GCG CTT TAT GAC TAT CGG GAG CTC AAA TGC GGC TCA GCA TGC
     Leu Gln Val Val Leu Arg Ala Leu Tyr Asp Tyr Arg Glu Leu Lys Cys Gly Ser Ala Cys

                  70                            90                           110
   CGG AAC GTG GGC ATT TTG GTA CAC GGA GGT ATC ACC TCG AGC GAA TGG GCG GGG GTC TTT
   Arg Asn Val Gly Ile Leu Val Hys Gly Gly Ile Thr Ser Ser Glu Trp Ala Gly Val Phe

                 130                           150                           170
   CCG CAA ACA AGC GTT CCA CCA AAA CCT AAG GTG GAA AAC TGT TCA GTT GCA TTT AAT TAC
   Pro Gln Thr Ser Val Pro Pro Lys Pro Lys Val Glu Asn Cys Ser Val Ala Phe Asn Tyr

                 190
   GCT TTT GTA AAT ACC 3'
   Ala Phe Val Asn Thr
```

Nucleic Acid sequence of the last 196 nucleotides of clone pEM 250/14.
The single open reading frame is translated into the amino acid sequence shown below the nucleotide sequence. A potential N-linked glycosylation site (Asn-Cys-Ser) is underlined.

NaCl (M) →

EmIP tryptic peptide #1: QWTAWTE

EtMIC4/5401 antigen motifs: SWTAWTEC: 1377 - 1384;

EFGAWSEC: 1512 - 1519;

EWSQWSEC: 1555 - 1562;

AWSPWTEC: 1639 - 1646;

NWGAWTEC: 1719 - 1726

FIGURE 22

```
Query = (445 letters)

Database: All non-redundant GenBank CDS
translations+PDB+SwissProt+PIR+PRF
907,641 sequences; 284,333,007 total letters


                                                                Score    E
Sequences producing significant alignments:                     (bits) Value

gi|13399179|emb|CAC34726.1|  (AJ306453) microneme protein 4 ...    74   6e-13
gi|6017001|gb|AAF01565.1|AF061273_1  (AF061273) thrombospond...    37   5e-04
gi|1923217|gb|AAB63303.1|  (U62660) micronemal protein MIC2 ...    34   0.001
gi|18030184|gb|AAA83600.2|  (U42846) Hypothetical protein T1...    39   0.020
gi|17569855|ref|NP_508681.1|  (NM_076280) T19D2.1.p [Caenorh...    39   0.020
gi|18859415|ref|NP_571592.1|  (NM_131517) spondin 1b [Danio ...    39   0.020
[LocusLink info]
gi|5281383|gb|AAD41495.1|AF149302_1  (AF149302) F-spondin pr...    39   0.020
gi|1147634|gb|AAC48313.1|  (U42213) micronemal TRAP-C1 prote...    38   0.026
gi|16805235|ref|NP_473263.1|  (NC_000521) predicted using he...    37   0.058
gi|2388718|gb|AAC48311.1|  (AF017267) thrombospondin related...    37   0.058


>gi|13399179|emb|CAC34726.1|  (AJ306453) microneme protein 4 [Eimeria tenella]
          Length = 2189

 Score = 73.6 bits (179), Expect = 6e-13
 Identities = 35/88 (39%), Positives = 51/88 (57%), Gaps = 3/88 (3%)
 Frame = +3

Query: 3    EQKETKLCDVSSTEEGKQCGQWGPWSECNIYLGSEDNVRVREDTACGVTECEECSKPANN 182
             +QKET+LC+     E     C  WG W+EC++ +G     +R RE++ CG  E EECS   +++
Sbjct: 1702 QQKETRLCN---PEGNDNCNNWGAWTECSLIVGGSA-LRSREESTCGYVELEECSGSSSS 1757

Query: 183  A---FVCTPWSECSDKKERRTCTIRKNG 257
                   C  WSECS +K   RTC +   +G
Sbjct: 1758 GDQTVHCGSWSECSMRKTERTCDVLSDG 1785
```

FIGURE 25

```
    ACCTTGGCCCATGTGCCACATGGTCATTTTTCTTCAGTTTGTTCATGAGAAGAGCTGCTA
121 ---------+---------+---------+---------+---------+---------+ 180
    TGGAACCGGGTACACGGTGTACCAGTAAAAAGAAGTCAAACAAGTACTCTTCTCGACGAT

    CAGTGTAGCTCGAACTCAACTTTAAACGCAGCCGTTTCAGCGGCGACAATATGCTGCATC
181 ---------+---------+---------+---------+---------+---------+ 240
    GTCACATCGAGCTTGAGTTGAAATTTGCGTCGGCAAAGTCGCCGCTGTTATACGACGTAG

      *  L  E  L  N  F  K  R  S  R  F  S  G  D  N  M  L  H  R

    GCAACCCGCGGTGGGCGCTTTGTGCAGCCCTCGCTGCACTCTATGGCGGAACAGGAATCG
241 ---------+---------+---------+---------+---------+---------+ 300
    CGTTGGGCGCCACCCGCGAAACACGTCGGGAGCGACGTGAGATACCGCCTTGTCCTTAGC

     N  P  R  W  A  L  C  A  A  L  A  A  L  Y  G  G  T  G  I  A

    CCAGCGCCGAAGTTAACAATGAATTGAGCAAGTGCGAATCTGGGTGGACACCCTGGACTA
301 ---------+---------+---------+---------+---------+---------+ 360
    GGTCGCGGCTTCAATTGTTACTTAACTCGTTCACGCTTAGACCCACCTGTGGGACCTGAT

     S  A [E  V  N  N  E  L  S  K  C  E  S  G  W  T  P  W] T  T

    CCTGCAACCCGCAAACTGGTCTGCGGGAGAGGCACAATGCACAGTGCGAGACATGGGTGG
361 ---------+---------+---------+---------+---------+---------+ 420
    GGACGTTGGGCGTTTGACCAGACGCCCTCTCCGTGTTACGTGTCACGCTCTGTACCCACC

     C  N  P  Q  T  G  L  R  E  R  H  N  A  Q  C  E  T  W  V  E
```

```
Query = (7077 letters)

Database: All GenBank+EMBL+DDBJ+PDB sequences (but no EST, STS,
GSS, or phase 0, 1 or 2 HTGS sequences)
1,205,903 sequences; 5,297,768,116 total letters


                                                                  Score    E
Sequences producing significant alignments:                       (bits) Value

gi|13399178|emb|AJ306453.1|ETE306453  Eimeria tenella mRNA f...    157   2e-34
gi|19807793|gb|AC097586.3|  Sus scrofa clone RP44-394E19, co...     52   0.008
gi|15920130|gb|AC019084.9|  Homo sapiens BAC clone RP11-354O...     52   0.008
gi|17542491|ref|NM_068212.1|  Caenorhabditis elegans                52   0.008
gi|2736374|gb|AF039040.1|AF039040  Caenorhabditis elegans co...     52   0.008

>gi|13399178|emb|AJ306453.1|ETE306453  Eimeria tenella mRNA for microneme protein
4 (mic4 gene)
          Length = 7053

 Score =  157 bits (79), Expect = 2e-34
 Identities = 181/215 (84%)
 Strand = Plus / Plus


Query: 2497 gacatcgacgaatgcgcgacaggcacacacacttgctcgaaccacgccacctgcaccaat 2556
            |||||||||||||| || |  || || ||||||||||| | |||||| || |||||||| 
Sbjct: 2044 gacatcgacgaatgtgcaagcgggacccacacttgctccacccacgcgacatgcaccaac 2103


Query: 2557 accgatgggtcattcacatgccagtgcaaccccggcttcgaaggtgacggccacaagtgc 2616
            || | |||||| ||||||||  ||||||||||  |||| || ||||||||||||||||||
Sbjct: 2104 actgctgggtcgttcacatgtgagtgcaacccaagctttgacggtgacggccacaagtgc 2163


Query: 2617 gaggacatcgacttctgcggtgctggacagcacgactgcaatgtgcatgccgagtgctct 2676
            |||||| | |||||||||||    || | ||||||||||||| |||||||| |||||||| 
Sbjct: 2164 gaggacgtggacttctgcggccaggggctgcacgactgcaacgtgcatgcagagtgctcg 2223


Query: 2677 gagagcgaggacaacaccactttcaagtgcacctg 2711
            || ||||| |||||||||||| ||||||||||||||
Sbjct: 2224 gaaagcgacgacaacaccaccttcaagtgcacctg 2258
```

FIGURE 29A

```
CAACATTTCTTCTTCCTTTTTCTTCTTCGAGCTTCTTTAGCTCGATTTTCTGGCCCTTGCAGCTCTCCGCGGGTGCAGGGCGCAGCCAGC  90

TCACTACTGCCTTTCACAGCGTCGTTCCCCACCTTGGCCCATGTGCCACATGGTCATTTTTCTTCAGTTTGTTCATGAGAAGAGCTGCTA  180

CAGTGTAGCTCGAACTCAACTTTAAACGCAGCCGTTTCAGCGGCGACAATATGCTGCATCGCAACCCGCGGTGGGCGCTTTGTGCAGCCC  270
                                                  M  L  H  R  N  P  R  W  A  L  C  A  A   16

TCGCTGCACTCTATGGCGGAACAGGAATCGCCAGCGCCGAAGTTAACAATGAATTGAGCAAGTGCGAATCTGGGTGGACACCCTGGACTA  360
L  A  A  L  Y  G  G  T  G  I  A  S  A [E  V  N  N  E  L  S  K  C  E  S  G  W  T  P  W] T   43

CCTGCAACCCGCAAACTGGTCTGCGGGAGAGGCACAATGCACAGTGCGAGACATGGGTGGAGGTTGAGGAATGCCAGAAGCTGACAGGAT  450
T  C  N  P  Q  T  G  L  R  E  R  H  N  A  Q  C  E  T  W  V  E  V  E  E  C  Q  K  L  T  G   73

GTGGCAACTGGACTCCTTGGTCTCCCGGCGATATGTCGTGTGTGGTGGGACAGTTTCAAACCCGCAACAGGGAGGGCTGCCCAGAGGTGC  540
C  G  N  W  T  P  W  S  P  G  D  M  S  C  V  V  G  Q  F  Q  T  R  N  R  E  G  C  P  E  V   103

AGGAAGTGAGGGCATGCAGGCCTGTACTTCTAGAATGCAACGATCAATGGACCCCCTGGACAATGTGCGACACCAACCGCGTCCAGGAAA  630
Q  E  V  R  A  C  R  P  V  L  L  E  C  N  D  Q  W  T  P  W  T  M  C  D  T  N  R  V  Q  E   133

GATACAACTCAAAGTGCGGACCCGTCGAAGTCCGCGAGTGCAACATGGACGACGCAGAGATCGAGAAATGCGGCGAGTTCGTGGAATGGG  720
R  Y  N  S  K  C  G  P  V  E  V  R  E  C  N  M  D  D  A  E  I  E  K  C  G  E  F  V  E  W   163

ATCCCCCTATGAATGGAGACTGCGTACGCGGGGGTACCCACACGCGTTACCGTCAAAACTGCCCAGACCGCAAAGAGGTGCGGGTGTGCG  810
D  P  P  M  N  G  D  C  V  R  G  G  T  H  T  R  Y  R  Q  N  C  P  D  R  K  E  V  R  V  C   193

GAGCCTTTGATTGCAGTAGCTGCTCTGTAAACGCCACTTGCGATCCCATTGGTGCATCCTGCGAATGCAAGCCTGGTTTCCGCGGCAATG  900
G  A  F  D  C  S  S  C  S  V  N  A  T  C  D  P  I  G  A  S  C  E  C  K  P  G  F  R  G  N   223

GGAAGACCTGCGAGGCCTTCAACCCCTGCGAAGATACCCCTGCACCTTGCGACAGCAACGCCATCTGCACCCCAGACGGCAATGACGCCA  990
G  K  T  C  E  A  F  N  P  C  E  D  T  P  A  P  C  D  S  N  A  I  C  T  P  D  G  N  D  A   253

AATGCCAGTGCAAGGCAGGCTGGGACGCAGATTCCGGAGCAGGCAGCAGCAAGAAGCCTTGCGTTGAGGTCGACGAGTGCGCATCCAACA  1080
K  C  Q  C  K  A  G  W  D  A  D  S  G  A  G  S  S  K  K  P  C  V  E  V  D  E  C  A  S  N   283

CCCACCAGTGCCCGGCACACTCCACATGCATCAACACCAAGGGCTCTTATAAGTGCGACTGCAACCAGGGATACGTCAAGGGAGAGGACG  1170
T  H  Q  C  P  A  H  S  T  C  I  N  T  K  G  S  Y  K  C  D  C  N  Q  G  Y  V  K  G  E  D   313

GACAGTGTCATGACGTCGATGAATGCACCAACGGAGAGCACACCTGCCCCGCTCACTCCACTTGTTTGAATACAGCTGGCAGCTACGAGT  1260
G  Q  C  H  D  V  D  E  C  T  N  G  E  H  T  C  P  A  H  S  T  C  L  N  T  A  G  S  Y  E   343

GCCGCTGCGACACTGGGTACAGCGGAAATGCAACTGCAGACAGCCCTTGCAAGAACATTGACGAATGCGCCAACCCCAACGCCTGCTCGG  1350
C  R  C  D  T  G  Y  S  G  N  A  T  A  D  S  P  C  K  N  I  D  E  C  A  N  P  N  A  C  S   373

CCAACGCTATCTGCACAGACACCGACGGCTCCTTCACCTGCAGCTGCCCCGAAGGGTACAGCGGCCAGGGAACCCATGACTCTCCCTGCT  1440
A  N  A  I  C  T  D  T  D  G  S  F  T  C  S  C  P  E  G  Y  S  G  Q  G  T  H  D  S  P  C   403

CCAAGATCGACTTCTGCGCAGACCCCTCACTCAATACATGCGGAGCCCACTCCACTTGCGTGAACACCCTCACATCTTTCAAGTGCATCT  1530
S  K  I  D  F  C  A  D  P  S  L  N  T  C  G  A  H  S  T  C  V  N  T  L  T  S  F  K  C  I   433

GCGATGCGGGATATGAAGGCGCCGGCACTCGCGAGAGCCCGTGCGTGGACGTGAACGAGTGCTCGAACGAGAAGCCCACAAACAACTGCA  1620
C  D  A  G  Y  E  G  A  G  T  R  E  S  P  C  V  D  V  N  E  C  S  N  E  K  P  T  N  N  C   463

ACAGAAACGCAAACTGCACCAACACCGAGGGATCCTACACTTGCGAATGCAAGCCCGGTTTCTCTGGCGACGGCATGGGTCCCAACGGGT  1710
N  R  N  A  N  C  T  N  T  E  G  S  Y  T  C  E  C  K  P  G  F  S  G  D  G  M  G  P  N  G   493

GTACCGACATCGACGAGTGCGCGGCGGAGCAGTCCCCCTGCGACCCTCACGCCTCCTGCAGCAACACTGAGGGCTCGTATGTATGCACCT  1800
C  T  D  I  D  E  C  A  A  E  Q  S  P  C  D  P  H  A  S  C  S  N  T  E  G  S  Y  V  C  T   523

GCAACACCGGCTACGAGCCAGCTTCAACCGACGGGCATGCATGCAAAGATATCGACGAGTGCGCCACCGGTGCAGCTGGGTGCCACGTGT  1890
C  N  T  G  Y  E  P  A  S  T  D  G  H  A  C  K  D  I  D  E  C  A  T  G  A  A  G  C  H  V   553

CAGCACAGTGTCTGAACACGGACGGCAGCTACGAGTGCAAGTGTCTTGAGGGCTTCGTCGGCGACGGAAAGACCTGCAACGACGTCGATG  1980
S  A  Q  C  L  N  T  D  G  S  Y  E  C  K  C  L  E  G  F  V  G  D  G  K  T  C  N  D  V  D   583

AGTGCGCTGCGGCGACATCTCCTTGCGGTGACAACACTCACTGCCAGAACACAATTGGCAGCTACGAGTGCGAGTGCAAGGCTGGCTATG  2070
E  C  A  A  A  T  S  P  C  G  D  N  T  H  C  Q  N  T  I  G  S  Y  E  C  E  C  K  A  G  Y   613
```

FIGURE 29B

GCAACATGCAAGACAACGCATCCAGCGACATTGACGAGTGCAAGGATGCGAACACCAAGATCCCTGACAACTGTCTTTGCGTGAACAATG 2160
G N M Q D N A C S D I D E C K D A N T K I P D N C L C V N N 643

ATGGCAGCTACTCCCTTGAGGCGAAGGCTGGATACGAATTGGTGAACGGCGAGTGCATCAAGATCGACTTCTGCGCCCGCGGCGCATGCA 2250
D G S Y S L E A K A G Y E L V N G E C I K I D F C A R G A C 673

ACTCGCTGGCCTCCTGCAAGGAGAATGAAGAAGGCACAGCGGCGATCTGCACCTGCCTGCCAGGCTACAGCGGCGACGGCACTGCTGAAG 2340
N S L A S C K E N E E G T A A I C T C L P G Y S G D G T A E 703

GCCACTGCAACGACATTGACGAGTGTGCAGGTCAGAATGACTGTGCTCCTGCCGAGCAGGGAGGCATCTGCGAGAACACTGTCGGCTCGT 2430
G H C N D I D E C A G Q N D C A P A E Q G G I C E N T V G S 733

ACACCTGCAAGTGCAAAGAGGGGTACAGGCAAGATGGAAACTCATGCACTGAGATCGACGAGTGCGCTGAGGGAACCCACAACTGCCACC 2520
Y T C K C K E G Y R Q D G N S C T E I D E C A E G T H N C H 763

CTTCCGCCACCTGCAGCAACACCCCCGGAAGCTTCACCTGCCAATGCAACAGTGGATTCACTGGCAGCGGTGTGGAGTGCGAAGACATTG 2610
P S A T C S N T P G S F T C Q C N S G F T G S G V E C E D I 793

ACGAGTGCTCAACTGAGGCAGATGATTGTGGTGCAAACACCATCTGCAGCAACACCATTGGTGCTTTCGAGTGCAACTGCCGTGAAGGCT 2700
D E C S T E A D D C G A N T I C S N T I G A F E C N C R E G 823

ATGAACCGCAGACGCAAAGACGTGCGTCGACATCGACGAATGCGCGACAGGCACACACACTTGCTCGAACCACGCCACCTGCACCAATA 2790
Y E R A D A K T C V D I D E C A T G T H T C S N H A T C T N 853

CCGATGGGTCATTCACATGCCAGTGCAACCCCGGCTTCGAAGGTGACGGCCACAAGTGCGAGGACATCGACTTCTGCGGTGCTGGACAGC 2880
T D G S F T C Q C N P G F E G D G H K C E D I D F C G A G Q 883

ACGACTGCAATGTGCATGCCGAGTGCTCTGAGAGCGAGGACAACACCACTTTCAAGTGCACCTGTATAACAGGGTACGCTGGAGACGGCC 2970
H D C N V H A E C S E S E D N T T F K C T C I T G Y A G D G 913

ATGGCGAGGCAGGCTGCCAAGACATTGATGAGTGCGCAGAAGAAAACATCTGCGGAAGCAACGCTGTCTGCACAAACACCGCAGGAAGCT 3060
H G E A G C Q D I D E C A E E N I C G S N A V C T N T A G S 943

ACCAATGCGCATGCCGTGAGGGCTTCGTTGCATCAGCTGAACAGCAGCAGCAGGGAACCCCAGCACTGGTTTGCGTGGACGTCGACGAGT 3150
Y Q C A C R E G F V A S A E Q Q Q Q G T P A L V C V D V D E 973

GCAGCGACGCTTCGAAGAACACATGTGCCAAGCCAGCCGACGGAGGCATTTGCACAAACACTGAAGGCAGCTACGAATGCGCTTGCAAGC 3240
C S D A S K N T C A K P A D G G I C T N T E G S Y E C A C K 1003

CAGGCTACCAAGGTGACGGCCACAGCTGCGCAGACATCAACGAATGCACTGCACAGGGCACCTGCGGCGAACACACAACTTGCAAGAACA 3330
P G Y Q G D G H S C A D I N E C T A Q G T C G E H T T C K N 1033

CACCCGGATCCTTCCAGTGCGACTGCGTTGAGGGATTCGAGCGCGCTGATGAACGCACCTGCCGTGACATCAACGAGTGCGAGACAGGAG 3420
T P G S F Q C D C V E G F E R A D E R T C R D I N E C E T G 1063

CAGTCGTGCTGCCACCGAACTCCACCTGCGTCAACACTGAAGGCAGCTACGACTTCGACTGCGTTGCTGGGTACCGCCGCACTGATGGAG 3510
A V V L P P N S T C V N T E G S Y D F D C V A G Y R R T D G 1093

CTTGTGTGAAGATCGACTTCTGCAAGGAGAAGGGATGCAACGCAAACGCCACATGCCGCGAAAACGATGCCGGCACCGAGGCCATCTGCA 3600
A C V K I D F C K E K G C N A N A T C R E N D A G T E A I C 1123

CTTGCAAGGAAGGCTATGAAGGCAGCGGAGAAGGCGAAGATGGTTGCCAGAACATCAATGAGTGCGAGAGAGGCGAACCCTGCAAGGACT 3690
T C K E G Y E G S G E G E D G C Q N I N E C E R G E P C K D 1153

TCGGCGAAGGCGGTGTTTGCGTCGACACACCAGGATCATTCACTTGCGAGTGCGCTGCTGGATTCATTCAACGCCGCTCCGTTTGCCAAG 3780
F G E G G V C V D T P G S F T C E C A A G F I Q R R S V C Q 1183

ATGTTGACGAATGTCTCGACGGAAAGCTGAACACCTGCGCTGCCACCGGAGGCGTCTGCTCCAACACCGTCGGTTCCTTCACCTGCTCGT 3870
D V D E C L D G K L N T C A A T G G V C S N T V G S F T C S 1213

GCGCCAGCGGCTTCGAAGGCGATGGCCACACCTGCAATGATGTCGACGAATGCGCAACAGCACAGCACACCTGTGACCCGAATGCCACTT 3960
C A S G F E G D G H T C N D V D E C A T A Q H T C D P N A T 1243

GCGTCAACACCGAAGGCAGCTTCGAGTGCCGCTGCAATGCCGGATTCGAGGGCGACGGACACACCTGCGCAGACATCGACGAATGCGCAG 4050
C V N T E G S F E C R C N A G F E G D G H T C A D I D E C A 1273

ACCCAGCCAAAAACACATGCGATACACACAAGGGTGTATGCCAAAACACCACAGGGTCCTACACCTGCGGCTGCAAGACCGGATTCAGTC 4140
D P A K N T C D T H K G V C Q N T T G S Y T C G C K T G F S 1303

TTGCAGCTGACGGAAGCACATGCGAAAACGTCGACGAGTGCGCGGCGGGAACTGCAAACTGCAACGAGCGAAGCTTCTGTAAGGACACAG 4230
L A A D G S T C E N V D E C A A G T A N C N E R S F C K D T 1333

FIGURE 29C

```
AGGGTTCCTACCAATGCGAGTGCAAGAACGGCTACAAGGCTGCAGGAGAGGACTGTGTGGACGTTGACGAGTGCGAGGCTGGCGTGCATG  4320
E  G  S  Y  Q  C  E  C  K  N  G  Y  K  A  A  G  E  D  C  V  D  V  D  E  C  E  A  G  V  H   1363

GATGCAGCGAGCACGCAATCTGCACAAATACAGACGGCAGCTACTCCTGCGAATGCATGGAGGGATACCAGGGAGACGGCAAGGCTTGCG  4410
G  C  S  E  H  A  I  C  T  N  T  D  G  S  Y  S  C  E  C  M  E  G  Y  Q  G  D  G  K  A  C   1393

AGAAGACAGTCGGCGTCTGCGACTCCGCTCCCTGCGGTGCCCACGCCACCTGCGAGCCTGCAGGGGACAACTACACTTGCACATGCCACC  4500
E  K  T  V  G  V  C  D  S  A  P  C  G  A  H  A  T  C  E  P  A  G  D  N  Y  T  C  T  C  H   1423

CAGGCTACGAGATGCGCGAAGGAGCCTGCGTTGACATCGATGAGTGCACAGCAGGCAGCCTCAACTGCGACCCTCATGCCATTTGCACAA  4590
P  G  Y  E  M  R  E  G  A  C  V  D  I  D  E  C  T  A  G  S  L  N  C  D  P  H  A  I  C  T   1453

ACACCGACGGCTCCTTCACTTGCGTCTGTGGCAGCGGCTATACCGGCCTTGGCACATCCTGCGAAGACATCGACGAGTGCGCGGGTAACG  4680
N  T  D  G  S  F  T  C  V  C  G  S  G  Y  T  G  L  G  T  S  C  E  D  I  D  E  C  A  G  N   1483

CAGCAGGCTGCGACATCCACGCCGTCTGCACGAACACTCCCGGATCGTTCAAGTGCGAGTGCAAGAGCGGCTTCGAAGGCGATGGCACGC  4770
A  A  G  C  D  I  H  A  V  C  T  N  T  P  G  S  F  K  C  E  C  K  S  G  F  E  G  D  G  T   1513

AATGCACGGAGAAGGTGTTGCTCCCCGGACAGATTCACTGCGAAGCCTGGACTGCATGGACAGAGTGTACCGACGGCGCCAAAACCAGCA  4860
Q  C  T  E  K  V  L  L  P  G  Q  I  H  C  E  A  W  T  A  W  T  E  C  T  D  G  A  K  T  S   1543

CACGCAGCTGCCTTGCACTGCCGCTTAAGAAGGAGATGCGCGCCTGCCCTGCAGCTGACTTCTCCCAGTGCGGAGAGTTCACTGAATGGA  4950
T  R  S  C  L  A  L  P  L  K  K  E  M  R  A  C  P  A  A  D  F  S  Q  C  G  E  F  T  E  W   1573

CTGCCTGCCCTGGAACCAACAATAACCTGTCTCATAGGCGCACTGAAAGATTCGGAGAACCCGGATGCGAAGATGCAGAGGAAGTCCGCG  5040
T  A  C  P  G  T  N  N  N  L  S  H  R  R  T  E  R  F  G  E  P  G  C  E  D  A  E  E  V  R   1603

AATGCCCAGATGAAGAGACCGAGCAGAAATGCGGCGCCTGGGGTGAGTGGACCGCCTGCGGCGACCCATCCCCTGGCCTGAGAACTCGCG  5130
E  C  P  D  E  E  T  E  Q  K  C  G  A  W  G  E  W  T  A  C  G  D  P  S  P  G  L  R  T  R   1633

CACGCGAGAACTGCCCCGATGTGGTAGAGTTCGAGCGTTGCACTATGCCCAGTGAGCCTGAGGCTGGCGAAGTGACTGAGCCTCACACAG  5220
A  R  E  N  C  P  D  V  V  E  F  E  R  C  T  M  P  S  E  P  E  A  G  E  V  T  E  P  H  T   1663

AAGGAGGAGCCGGAGTTGGTGGCGAAGTGACTGAGCCTGACACGGAAGAAGGAGCCGGAGTTGGTGGTGAAGTGCAGCCCGGTACAGAAG  5310
E  G  G  A  G  V  G  G  E  V  T  E  P  D  T  E  E  G  A  G  V  G  G  E  V  Q  P  G  T  E   1693

AAGGAGCAGGAGTTGGTGGTGAAGTGCAGCCCGGTACAGAAGAAGGAGCCGGAGTTGGTGGTGAAGTGCAGCCCGGTACAGAAGAAGGAG  5400
E  G  A  G  V  G  G  E  V  Q  P  G  T  E  E  G  A  G  V  G  G  E  V  Q  P  G  T  E  E  G   1723

CCGGAGTTGGTGGTGAAGTGCAGCCCGGTACGGAAGAAGGAGCCGGCATTGGTGGCGAAGTGACTGAGCCTGACACCGAAGGAGGAGCCG  5490
A  G  V  G  G  E  V  Q  P  G  T  E  E  G  A  G  I  G  G  E  V  T  E  P  D  T  E  G  G  A   1753

GAGTTAGTGGCGAACCGACCGAAGAAGAGGGCACCGAAAGCACCGGTCCATGCAAAGAGTTCGGACCCTGGACGGCCTGCAAGGAGGACG  5580
G  V  S  G  E  P  T  E  E  E  G  T  E  S  T  G  P  C  K  E  F  G  P  W  T  A  C  K  E  D   1783

AGAACGGAGTCGGCATCCAACGCCGTATGTGCGCCGGCAGAGAAGACATCATCGAATCCAGAATTTGCACTGTCACGGATGACTGCGGAG  5670
E  N  G  V  G  I  Q  R  R  M  C  A  G  R  E  D  I  I  E  S  R  I  C  T  V  T  D  D  C  G   1813

AATGGACCCCCTGGTCAACTTGCACTAACGGCAGCCAGGCCAGAAACAAACGCTTCTGCACCAACGTTAGGGAAGTCCGTCTCTGCGGAG  5760
E  W  T  P  W  S  T  C  T  N  G  S  Q  A  R  N  K  R  F  C  T  N  V  R  E  V  R  L  C  G   1843

CTGACATTCCAGTTACAGACGGATGCACGTGGAGCGAGTGGACTTCTTGCAGTCTAGTCAATGAGGAGGGCGGCTACTTCCGCACGCGCA  5850
A  D  I  P  V  T  D  G  C  T  W  S  E  W  T  S  C  S  L  V  N  E  E  G  G  Y  F  R  T  R   1873

CATCCTCTGACTGCAACATGAATGAAGTGCAGGCCTGCTCTCCCAGCAGCAGCACAACCGCAGACAGCGAAACAGAAGGCACCTGCTCTG  5940
T  S  S  D  C  N  M  N  E  V  Q  A  C  S  P  S  S  S  T  T  A  D  S  E  T  E  G  T  C  S   1903

CATGGAACCCCTGGACGGAGTGCTCGAACGGCCACCAGACACGCAAGTGTGCCACAATGGAAGCAGAAGAATCGCGCACTTGCGGAGAGA  6030
A  W  N  P  W  T  E  C  S  N  G  H  Q  T  R  K  C  A  T  M  E  A  E  E  S  R  T  C  G  E   1933

CTCCAGAGAACTGCGGAGAATTCGGCCCCTTCGAACCCGCAAACTGCACGGCCGGCCAAATGGTCACCAGGACGCGCACCTGCGGAGAAA  6120
T  P  E  N  C  G  E  F  G  P  F  E  P  A  N  C  T  A  G  Q  M  V  T  R  T  R  T  C  G  E   1963

CCGAGCAGAAGGAAACCAAACTGTGCGACGTCAGCTCCACCGAAGAAGGAAAACAATGCGGTCAGTGGGGCCCATGGAGCGAATGCAACA  6210
T  E  Q  K  E  T  K  L  C  D  V  S  S  T  E  E  G  K  Q  C  G  Q  W  G  P  W  S  E  C  N   1993

TCCACCTGGGCTCAGAGGACAATGTGCGTGTTCGTGAGGACACCGCTTGCGGCGTGACGGAGTACGAGGAGTGCAGCAAGCCGGCGAACA  6300
I  H  L  G  S  E  D  N  V  R  V  R  E  D  T  A  C  G  V  T  E  Y  E  E  C  S  K  P  A  N   2023

ACGCCTTTGTCTGCACACCTTGGAGTGAATGCTCGGACAAGAAGGAGCGGAGAACGTGCACCATCCGCAAAAACGGTCTTGTTCAGACAC  6390
N  A  F  V  C  T  P  W  S  E  C  S  D  K  K  E  R  R  T  C  T  I  R  K  N  G  L  V  Q  T   2053
```

FIGURE 29D

```
GTCAAGAATTCAGAACATGCAGTGTAGACATCGCCACAACTTGCGGCGATTTCGGCGCATGGTCTGAATGCAACGCTGAGGGCTTGCATC   6480
R  Q  E  F  R  T  C  S  V  D  I  A  T  T  C  G  D  F  G  A  W  S  E  C  N  A  E  G  L  H    2083

AGCGCAGTCTCGAGAAATGCCCCGACGTCATCGAGGTCGCAACTTGCGGCAGTGAGGATTGCCCGCCATTCGGCGAGTGGACTGAATGCG   6570
Q  R  S  L  E  K  C  P  D  V  I  E  V  A  T  C  G  S  E  D  C  P  P  F  G  E  W  T  E  C    2113

GCGTTCCAGAGGAGGGCATGCGTTCTCGCCAACGCATTGACTGCGTTGAATCTGCAGCCTGCCAGTGCACAGAAGTGGAGAGCTGCTTCG   6660
G  V  P  E  E  G  M  R  S  R  Q  R  I  D  C  V  E  S  A  A  C  Q  C  T  E  V  E  S  C  F    2143

ACACCGAATTGCACCCCATTCCAGCCCCCGGTACGGAAACAGGCGAAGGAGAGGGAGAGACCGAGACAGGCGAAGGCGAAACTGGTGAAG   6750
D  T  E  L  H  P  I  P  A  P  G  T  E  T  G  E  G  E  G  E  T  E  T  G  E  G  E  T  G  E    2173

CAGGTGGCGAGGAAGGCGAGCAAACAGGAGAAGGCGAAGTGCAGCCCCCAGAAGAAGAGCTTCCTGGGGAGAGTGTAACTGAGCCTGAGG   6840
A  G  G  E  E  G  E  Q  T  G  E  G  E  V  Q  P  P  E  E  E  L  P  G  E  S  V  T  E  P  E    2203

AGAAGCCTGAGGAGGAGCTACCTGAGGAGGAGGTTACTGAGCCTGAGGAGAAGCCTGAGGAGGGTGTGACTCAGCCTCAGGAGACACCTG   6930
E  K  P  E  E  E  L  P  E  E  E  V  T  E  P  E  E  K  P  E  E  G  V  T  Q  P  E  E  T  P    2233

AGCAGCCTGTTGAGGGTACCGAAGAAGAGGGCAAGCAGGAGTCTGAGGCTGCCCCCGAAACTCCTGCCGTCCAGCCAAAACCAGAGGAGG   7020
E  Q  P  V  E  G  T  E  E  E  G  K  Q  E  S  E  A  A  P  E  T  P  A  V  Q  P  K  P  E  E    2263

GTCACGAACGCCCAGAACCCGAAGAGGAGGAGGAGAAGAAGGAAGAAGGCGGCGGCTTCCCAACAGCTGCAGTGGCAGGAGGTGTTGGTG   7110
G  H  E  R  P  E  P  E  E  E  E  E  K  K  E  E  G  G  G  F  P  T  A  A  V  A  G  G  V  G    2293

GTGTGTTGCTCATAGCTGCTGTAGGTGGTGGTGTTGCAGCCTTCACTAGCGGCGGAGGTGGCGCTGGCGCACAGGAGGCAGAACAGGTCG   7200
G  V  L  L  I  A  A  V  G  G  G  V  A  A  F  T  S  G  G  G  G  A  G  A  Q  E  A  E  Q  V    2323

AGTTCGAAGGAGAAGATACCGGAGCAGCAACTGCCGAGACACCTGAAGCCGATACAGTTATCGACATCACAGACGAAGACGACTACTGGG   7290
E  F  E  G  E  D  T  G  A  A  T  A  E  T  P  E  A  D  T  V  I  D  I  T  D  E  D  D  Y  W    2353

CCGACAGCGGCGACATTCAGTAAAGTTGAATGTCTGTTTTCTTCCAAGGAGAAGATACAAAACCAAAATCTTAACAAAACGAAGGATGCG   7380
A  D  S  G  D  I  Q                                                                          2360

AAGGCGAAACAGGCCAAAGTCGACCTGTTTTCTCATTCAATCAATGGTTGCAGTCGTGAAGGAGCTGGACTCAGTTGCATCTCCACCCCA   7470>

AGAGCTCGCCGTTAGTGGGCAAGTTGGATAGGGTGAATGCATTTTCATCTCCGCAGGCGAAAGTCACGACGAGGGCCTGTTCTTGTTTGT   7560

TTGTTTGAATTGGTTGGTTGGTGCATCCTGCTGGATTTCAACGACGGCAATCATCACGCAGTGAGACGGAGCAGCAGCGCATACTATTTT   7650

CTGAGCAAGTTCATCGTTTATTTTTCGCTGTATCTCGTAGCGCCGAGGAAGCAAACAAGCAAACGCCCACCAACTGACCAACCAATGAGA   7740

GAGCCGTCCTTTAATTTCCACCCCTCTTCTGTCTTCCGAAGATTCGGCGGGGTTTCGGATGGGGGAGAAATTGTGGTTGGATTGGTCGGG   7830

TGTTTTCGTTTTCTTTGATTGATGCAACAATATCTGCTAGCCAGCGTACAAAGAATAGCTGCAGTTCAAATGAATGCATCTTAATTATTC   7920

CACACCGCGGTGCCTCTTCTTTGCCGTGGCACACCTTCCGTTTATTACCTCCACTCAAGATTTTCTCCCC                         7990
```

FIGURE 30

```
27 - 69       -----EVNNELSKCESGWTPWT-----TCNPQTG----LRERHN--A-QCETWVEVEECQ
70 - 110      ----------KLTGCGNWTPWSP-GDMSCVVGQF---QTRNREG-----CPEVQEVRACR
111 - 148     --------PVLLECNDQWTPWT-----MCDTNR---VQERYNSK------CGPVEVRECN
149 - 194     ------MDDAEIEKCGEFVEWDPPMNGDCVRGGT---HTRYRQN-----CPDRKEVRVCG
1517 - 1560   ----EKVLLPGQIHCEAWTAWT-----ECTDGAKT--STRSCLA-----LPLKKEMRACP
1561 - 1606   --------AADFSQCGEFTEWT-----ACPGTNNNLSHRRTERFGEP-GCEDAEEVRECP
1607 - 1648   -------DEETEQKCGAWGEWT-----ACGDPSPGL-RTRAREN-----CPDVVEFERCT
1765 - 1807   --------TESTGPCKEFGPWT-----ACKEDENGVGIQRRMCAG----REDIIESRICT
1808 - 1843   ----------VTDDCGEWTPWS-----TCTNGS----QARNKRF-----CTNVREVRLCG
1844 - 1887   ------ADIPVTDGC-TWSEWT-----SCSLVNEEGGYFRTRTSS----DCNMNEVQACS
1888 - 1932   PSSSTTADSETEGTCSAWNPWT-----ECSNGH----QTRKCAT------MEAEESRTCG
1933 - 1973   ---------ETPENCGEFGPFEP---ANCTAGQM---VTRTRTCG----ETEQKETKLCD
1974 - 2019   -----VSSTEEGKQCGQWGPWS-----ECNIHLGSEDNVRVREDT----ACGVTEYEECS
2020 - 2061   ------KPANNAFVC---TPWS-----ECSDKK----ERRTCTIRKNGLVQTRQEFRTCS
2062 - 2100   --------VDIATTCGDFGAWS-----ECNAEG--L-HQRSLEK-----CPDVIEVATCG
2101 - 2143   -----------SEDCPPFGEWT-----ECGVPEEG-MRSRQRIDCVESAACQCTEVESCF

consensus                   CG W  WT      C           R R             EV  C
```

FIGURE 31

```
195 - 228     --AFDCS------SCS---VNATC-DPIG---ASCECKPGFR---------GNGKTCE
229 - 275     -AFNPCEDTP--APCD---SNAICTPDGN--DAKCQCKAGWDADSGAG---SSKKPCV
276 - 317     -EVDECASNTH--QCP---AHSTCINTKG--SYKCDCNQGYVK--------GEDGQCH
318 - 361     -DVDECTNGEH--TCP---AHSTCLNTAG--SYECRCDTGYSGN------ATADSPCK
362 - 404     -NIDECANP---NACS---ANAICTDTDG--SFTCSCPEGYSG------QGTHDSPCS
405 - 449     -KIDFCADPSLN-TCG---AHSTCVNTLT--SFKCICDAGYEG------AGTRESPCV
450 - 495     -DVNECSNEKPTNNCN---RNANCTNTEG--SYTCECKPGFSG------DGMGPNGCT
496 - 539     -DIDECAAEQS--PCD---PHASCSNTEG--SYVCTCNTGYEPA------STDGHACK
540 - 580     -DIDECATGAA--GCH---VSAQCLNTDG--SYECKCLEGFV---------GDGKTCN
581 - 622     -DVDECAAATS--PCG---DNTHCQNTIG--SYECECKAGYGN--------MQDNACS
623 - 663     -DIDECKDANT--KIP---DNCLCVNNDG--SYSLEAKAGYEL---------VNGECI
664 - 707     -KIDFCAR----GACN---SLASCKENEEGTAAICTCLPGYSGD------GTAEGHCN
708 - 750     -DIDEC--AG-QNDCAPAEQGGICENTVG--SYTCKCKEGYR---------QDGNSCT
751 - 791     -EIDECAEGTH--NCH---PSATCSNTPG--SFTCQCNSGFT---------GSGVECE
792 - 833     -DIDECSTEAD--DCG---ANTICSNTIG--AFECNCREGYER--------ADAKTCV
834 - 874     -DIDECATGTH--TCS---NHATCTNTDG--SFTCQCNPGFE---------GDGHKCE
875 - 920     -DIDFCGAGQ--HDCN---VHAECSESEDNTTFKCTCITGYAGD------GHGEAGCQ
921 - 969     -DIDECAEE---NICG---SNAVCTNTAG--SYQCACREGFVASAEQQQQGTPALVCV
970 - 1014    -DVDECSDAS-KNTCAKPADGGICTNTEG--SYECACKPGYQ---------GDGHSCA
1015 - 1055   -DINECTAQG---TCG---EHTTCKNTPG--SFQCDCVEGFER--------ADERTCR
1056 - 1096   -DINECETGAV--VLP---PNSTCVNTEG--SYDFDCVAGYRR---------TDGACV
1097 - 1140   -KIDFCKE----KGCN---ANATCRENDAGTEAICTCKEGYEGS------GEGEDGCQ
1141 - 1183   -NINECERGE---PCKDFGEGGVCVDTPG--SFTCECAAGFIQ---------RRSVCQ
1184 - 1226   -DVDECLDGK-LNTCA--ATGGVCSNTVG--SFTCSCASGFE---------GDGHTCN
1227 - 1267   -DVDECATAQH--TCD---PNATCVNTEG--SFECRCNAGFE---------GDGHTCA
1268 - 1312   -DIDECADPA-KNTCD--THKGVCQNTTG--SYTCGCKTGFSL-------AADGSTCE
1313 - 1353   -NVDECAAGTA--NCN---ERSFCKDTEG--SYQCECKNGYKA--------AGEDCV-
1354 - 1394   -DVDECEAGVH--GCS---EHAICTNTDG--SYSCECMEGYQ---------GDGKACE
1395 - 1434   KTVGVCDSAP----CG---AHATCEPAGD--NYTCTCHPGYE---------MREGACV
1435 - 1475   -DIDECTAGSL--NCD---PHAICTNTDG--SFTCVCGSGYT---------GLGTSCE
1476 - 1516   -DIDECAGNAA--GCD---IHAVCTNTPG--SFKCECKSGFE---------GDGTQCT

consensus       D DEC        C         C NT G   S  C C  G                C
```

FIGURE 32A

```
1649 - 1670  MPSEPEAGEVTEPHTEGGAGVG
1671 - 1685         GEVTEPDTEEGAGVG
1686 - 1699         GEV-QPGTEEGAGVG
1700 - 1713         GEV-QPGTEEGAGVG
1714 - 1727         GEV-QPGTEEGAGVG
1728 - 1741         GEV-QPGTEEGAGIG
1742 - 1764         GEVTEPDTEGGAGVSGEPTEEEG

consensus           GEV .P TE GAG.
```

DTELHPIPAPGTETGEGEGETETGEGETGEAGGEEGEQTGEGEVQPPEEELPGESVTEPEE

KPEEELPEEEVTEPEEKPEEGVTQPEETPEQPVEGTEEEGKQESEAAPETPAVQPKPEEGH

ERPEPEEEEEKKEEGGGFPT

FIGURE 33

| | |
|---|---|
| EmIP | AAVAGGVGGVLLIAAVGGGVAAFTSGGGGAGAQEAEQVEFEGEDTGAATAETPEADTVIDITDEDDYWADSGDIQ |
| EtMIC4 | AAVAGGVGGVLLLAAVGGGVAAYSGGGGGGGAEEAEQVEFEGEESGGASAETPEADTVIDITDEDDYWADSGDIQ |
| Emp100 | AAVAGGVAGGVLAIAAGAGAFYGLSGGAASAAGGAAAEVMVESGTANPPEVEKESLITAGEQSEMWAS |
| EtMIC1 | AAVAGGVAGGVLAIAAGAGAFYGLSGGSAAAATEAGAEVMTEAGTSNAAEVEKESLISAGEQSEMWAS |
| CpTRAPC1 | LAIAVGLPVGILGLCIIAGSLFLIGGRSGDQEEDETNYQYFDQSSATLDQDSEYVQEIGPESQNWAS |
| CpGP900 | IAIQAAGGASAAVGLVAAVGAWYASRNRQEGEDDDDYQMDLKQNMKKKRKKRVMKQQMKLLLQLSVIHHSGTNLKRRKDFSNSKKFRI |
| NcTRAP | VAAIAGGIVGGLILLGAAGGGAYYYFGGGKANESLAEMDFDVDSGATKVVMEEEKETLVPVDDDSDMWMGADH |
| PfTRAP | IAGGIAGGLALLACAGLAYKFVVPGAATPYAGEPAPFDETLGEEDKDLDEPEQFRLPEENEWN |
| PfCTRP | LAAGVIGLVALAAGGLIYGYNTLNGGEPPHSSNMEFENVENNSGTEEEENEDFEVVDADDPMWN |
| PbTRAP | IAGGIIGGLAIIGCIGVGYNFIAGSSAAAMAGEAAPFEDVMADDEKGIVENEQFKLPEDNDWN |
| PrTRAP | IAGGIIGGLALLGCAGFAYKFLAHAPTPPMTSEGAPFNDVLGEGEKDIEENEQFK |
| PkDBP | IVYFATGGAFLIILLLFASWNAASNDYEEEATFDEFVEYSDDIHRTPLMPNDIEHMQQFTPLDYS |
| Sm70 | AAIAGGIVGGVLLLGAAGGGAAYMMKGGGGPGGEAEQVVFEGEGADTGAGEAPPESETVIEIEDDAWADT |
| TgMIC2 | IAGAIAGGVIGGLILLGAAGGASYHYYLSSSVGSPSAEIEYEADDGATKVVMEEEKETLVPVDDDSDMWME |
| TgMIC6 | AGAIAGGVIGGLLLLSAAGAGVAYMRKSGSGGGEEIEYERGIEAAEASEVEVLVDLDSKTWD |
| TgMIC7 | TPLWLWCCVALAAVIFVGAVVYGVRYFLKKWKKTNESEDDALLRYGYDYGAAHSFRG |
| TgMIC8 | IALVVVGCVALLGIIAGGISYARNRGGERDDEDLAPPPRSTRERRLSSMGEGFENASWASSVSMIPSAPAPPPSGGI |
| TgMIC9 | MTQWYVAGGIGGCLCLFAVVYLTSSRQSPNSNDALYAHDFEGMY |
| TgAMA1 | ALIAGLAVGGVLLLALLGGGCYFAKRLDRNKGVQAAHHEHEFQSDRGARKKRPSDLMQEAEPSFWDEAEENIEQDGETHVMVEGDY |

FIGURE 34
1
2360
A
B
C
B
D
B
D
A
A Leader peptide, transmembrane regions
B TSP type 1 repeats
C EGF-like repeats
D Hydrophilic regions
E Cytoplasmic tail

FIGURE 35

Query = (2360 letters)

Database: All non-redundant GenBank CDS
translations+PDB+SwissProt+PIR+PRF
946,396 sequences; 296,505,930 total letters

| Sequences producing significant alignments: | Score (bits) | E Value |
|---|---|---|
| gi\|13399179\|emb\|CAC34726.1\| (AJ306453) microneme protein 4 ... | 1764 | 0.0 |
| gi\|1706768\|sp\|P98133\|FBN1_BOVIN Fibrillin 1 precursor (MP34... | 392 | e-107 |
| gi\|1335064\|emb\|CAA45118.1\| (X63556) fibrillin [Homo sapiens] | 391 | e-107 |
| gi\|7459676\|pir\|\|A47221 fibrillin 1 precursor - human (fragm... | 391 | e-107 |
| gi\|13626617\|sp\|Q9TV36\|FBN1_PIG Fibrillin 1 precursor >gi\|57... | 388 | e-106 |
| gi\|4557591\|ref\|NP_000129.1\| (NM_000138) fibrillin 1; Fibril... | 388 | e-106 |
| gi\|227918\|prf\|\|1713408A fibrillin [Homo sapiens] | 388 | e-106 |
| gi\|20549163\|ref\|XP_034890.4\| (XM_034890) fibrillin 1 [Homo ... | 387 | e-106 |
| gi\|3688648\|gb\|AAC62317.1\| (AF007248) mutant fibrillin-1 [Mu... | 386 | e-105 |
| gi\|627438\|pir\|\|A54105 fibrillin-2 precursor - human | 383 | e-104 |
| gi\|20546982\|ref\|XP_030164.4\| (XM_030164) similar to Fibrill... | 382 | e-104 |
| gi\|4503667\|ref\|NP_001990.1\| (NM_001999) fibrillin 2 [Homo s... | 381 | e-104 |
| gi\|13929180\|ref\|NP_114014.1\| (NM_031826) fibrillin-2 [Rattu... | 381 | e-104 |
| gi\|13929178\|ref\|NP_114013.1\| (NM_031825) fibrillin-1 [Rattu... | 375 | e-102 |
| gi\|6679759\|ref\|NP_032019.1\| (NM_007993) fibrillin 1 [Mus mu... | 372 | e-101 |
| gi\|2494284\|sp\|Q61554\|FBN1_MOUSE Fibrillin 1 precursor >gi\|1... | 372 | e-101 |
| gi\|6753826\|ref\|NP_034311.1\| (NM_010181) fibrillin 2 [Mus mu... | 371 | e-101 |
| gi\|15029514\|ref\|NP_115823.1\| (NM_032447) fibrillin3 [Homo s... | 369 | e-100 |
| gi\|13516889\|dbj\|BAB40596.1\| (AB041857) Ci-META1 [Ciona inte... | 330 | 2e-88 |
| gi\|1389670\|gb\|AAC36151.1\| (U58977) Notch homolog Scalloped ... | 321 | 7e-86 |

FIGURE 40

```
AAGGAGCGGAGAACGTGCACCATCCGCAAAAACGGTCTTGTTCAGACACGTCAA
 K  E  R  R  T  C  T  I  R  K  N  G  L  V  Q  T  R  Q   2055

GAATTCAGAACATGCAGTGTAGACATCGCCACAACTTGTAAGTATAACCGCGAA
 E  F  R  T  C  S  V  D  I  A  T  T  C                  2068

CGACTTTGAATTACGTGCAGCCAGAGTTTACTCATCAACCCTACACTAGTATGC

GCATAGTGGTTAGGGCTTGCTGGTACTTTTGGACGGTCTGTTTGTAGTTACATT

TGTCTGTGTGTGTGGTGTCATTTAGGCGGCGATTTCGGCGCATGGTCTGAATGC
                               G  D  F  G  A  W  S  E  C   2077

AACGCTGAGGGCTTGCATCAGCGCAGTCTCGAGAAATGCCCCGACGTCATCGAG
 N  A  E  G  L  H  Q  R  S  L  E  K  C  P  D  V  I  E   2095

GTCGCAACTTGCGGCAGTGAGTTTTGATGACGTTGCTGTCCGGCTTAGAATATT
 V  A  T  C  G  S  E                                    2102

GGCTTTGGTGTCGCTGGCAAGCAAGGGTAGAGAGGAATGGGGTACAGACGGAGG

AGACAGGNAACACGGGGTTCTTTCTGTTTGTGCTTGTGTTTAGGTGAGGATTGC
                                                 D  C   2104

CCGCCATTCGGCGAGTGGACTGAATGCGGCGTTCCAGAGGAGGGCATGCGTTCT
 P  P  F  G  E  W  T  E  C  G  V  P  E  E  G  M  R  S   2122
```

```
                    CP003

EmIP    1149 EPCKDFGEGGVCVDTPGSFTCECAAGFIQRRSVCQDVDECLDGKLNTCAA 1198
EtMIC4  997  EPCKDFGEGGVCVDSPGSFSCSCATGFIKRRSTCQDIDECLDGKMNTCAP 1046
             *************.****.* **.***.*** ***.*******.****

EmIP    1199 TGGVCSNTVGSFTCSCASGFEGDGHTCNDVDECATAQHTCDPNATCVNTE 1248
EtMIC4  1047 VGGICTNTVGSFTCSCAAGFTGDGLTCEDIDECATAAHTCDPNATCVNTV 1096
              **.*.***********.** *** ** *.****** ************

EmIP    1249 GSFECRCNAGFEGDGHTCADIDECADPAKNTCDTHKGVCQNTTGSYTCGC 1298
EtMIC4  1097 GSFECGCKEGFSGDGHTCTDIDECADPNLNKCDTHKGICQNGTGSYTCGC 1146
             ***** *   ** ******.********   * ******.*** ********

EmIP    1299 KTGFSLAADGSTCENVDECAAGTANCNERSFCKDTEGSYQCECKNGYKAA 1348
EtMIC4  1147 RPGYSLAADGFTCDNVDECAAGTATCGERSFCVDTQGSYKCECKNGYRQS 1196
             . *.****** **.**********.*.***** **.***.*******. .

EmIP    1349 GEDCVDVDECEAGVHGCSEHAICTNTDGSYSCECMEGYQGDGKACEKTVG 1398
EtMIC4  1197 GEDCVDVDECEADVHTCSEHATCTNTEGSHTCTCNEGYQGDGKKCEKTVG 1246
             ************ ** ***** ****.** .* * ******** ******
                    CP004
```

```
  CGAATTGCACCCCATTCCAGCCCCCGGTACGGAAACAGGCGAAGGAGAGGGAGAGACCGAGACAGGCGAAGGCGAAACTGGTGAAG  6750
   E  L  H  P  I  P  A  P  G  T  E  T  G  E  G  E  G  E  T  E  T  G  E  G  E  T  G  E   2173

CAGGTGGCGAGGAAGGCGAGCAAACAGGAGAAGGCGAAGTGCAGCCCCCAGAAGAAGAGCTTCCTGGGGAGAGTGTAACTGAGCCTGAGG  6840
A  G  G  E  E  G  E  Q  T  G  E  G  E  V  Q  P  P  E  E  E  L  P  G  E  S  V  T  E  P  E   2203

AGAAGCCTGAGGAGGAGCTACCTGAGGAGGAGGTTACTGAGCCTGAGGAGAAGCCTGAGGAGGGTGTGACTCAGCCTGAGGAGACACCTG  6930
E  K  P  E  E  E  L  P  E  E  E  V  T  E  P  E  E  K  P  E  E  G  V  T  Q  P  E  E  T  P   2233

AGCAGCCTGTTGAGGGTACCGAAGAAGAGGGCAAGCAGGAGTCTGAGGCTGCCCCCGAAACTCCTGCCGTCCAGCCAAAACCAGAGGAGG  7020
E  Q  P  V  E  G  T  E  E  E  G  K  Q  E  S  E  A  A  P  E  T  P  A  V  Q  P  K  P  E  E   2263

GTCACGAACGCCCAGAACCCGAAGAGGAGGAGGAGAAGAAGGAAGAAGGCGGCGGCTTCCCAACAGCTGCAGTGGCAGGAGGTGTTGGTG  7110
G  H  E  R  P  E  P  E  E  E  E  E  K  K  E  E  G  G  G  F  P  T  A  A  V  A  G  G  V  G   2293

GTGTGTTGCTCATAGCTGCTGTAGGTGGTGGTGTTGCAGCCTTCACTAGCGGCGGAGGTGGCGCTGGCGCACAGGAGGCAGAACAGGTCG  7200
G  V  L  L  I  A  A  V  G  G  G  V  A  A  F  T  S  G  G  G  G  A  G  A  Q  E  A  E  Q  V   2323

AGTTCGAAGGAGAAGATACCGGAGCAGCAACTGCCGAGACACCTGAAGCCGATACAGTTATCGACATCACAGACGAAGACGACTACTGGG  7290
E  F  E  G  E  D  T  G  A  A  T  A  E  T  P  E  A  D  T  V  I  D  I  T  D  E  D  D  Y  W   2353

CCGACAGCGGCGACATTCAG
A  D  S  G  D  I  Q
```

FIGURE 45

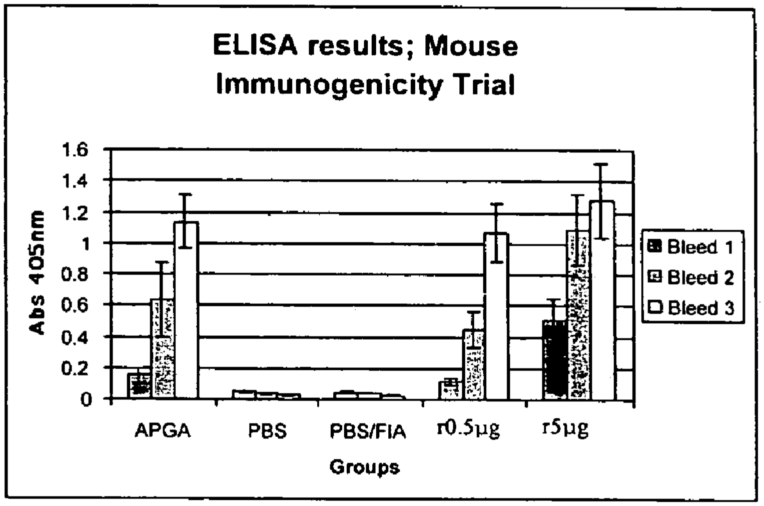

NUCLEIC ACIDS ENCODING A RECOMBINANT 250 KDA ANTIGEN FROM SPOROZOITES/MEROZOITES OF *EIMERIA MAXIMA* AND THEIR USES

This application is a §371 national stage of PCT International Application No. PCT/US02/21237, filed Jul. 3, 2002, designating the United States of America, which claims priority of U.S. Provisional Application No. 60/303,670, filed Jul. 6, 2001, the contents of which are hereby incorporated by reference.

Throughout this application various publications are referenced in parenthesis. Full citations for these publications may be found listed in alphabetical order at the end of the specification immediately preceding the claims. The disclosures of these publications in their entireties are hereby incorporated by reference into this application in order to more fully describe the state of the art to which this invention pertains.

BACKGROUND OF THE INVENTION

The organisms which cause the disease known as "coccidiosis" in chickens belong to the phylum Apicomplexa, class Sporozoa, subclass Coccidia, order Eucoccidia, suborder Eimeriorina, family Eimeriidae, genus *Eimeria*. Within the *Eimerian* genus there are many species, several of which are pathogenic in chickens. The species of major concern to the chicken industry are *Eimeria tenella, Eimeria maxima, Eimeria acervulina, Eimeria necatrix* and *Eimeria brunetti.*

Coccidiosis has become a major economic problem in the chicken industry over the past several decades, mainly due to the overcrowding of chicken houses and the development of drug resistance by the parasite. The rearing of chickens under crowded conditions on a litter floor provides optimal conditions for the growth and spread of *Eimeria* parasites. Under such circumstances, sanitary control is impossible and the farmer must rely on the effectiveness of coccidiostat drugs. However, drugs must be kept in the feed at all times, shuttle programs must be used to avoid the appearance of drug resistance strains of *Eimeria*, and certain drugs have costly side effects. Furthermore, these coccidiostats also have antibacterial effects and therefore are considered to be infeed antibiotics. Recently the European Union has decided to ban the use of all in-feed antibiotics in the chicken industry including anticoccidial drugs. Thus, the only viable approach to the control of coccidiosis in the future is by vaccine development.

The *Eimeria* parasite undergoes a complex life cycle in the mucosa of the intestinal tract. This life cycle is very similar to that of the other hemosporidian parasites (i.e. *plasmodium, babesia*, etc.) except for the lack of an arthropod vector. Oocysts sporulate on the litter floor producing four sporocysts, each containing two sporozoites (thus belonging to the class sporozoa). The oocysts are ingested by the chicken, and the sporocysts are released by the mechanical grinding of the gizzard. The sporozoites are then released from the sporocysts due to the digestion of the sporocyst wall by proteolytic enzymes in the intestine. Mobile sporozoites then invade lymphocytes and go on to invade epithelial cells where the asexual cycle begins. The parasite goes through 2-4 cycles of replication and division (each species having a defined number of divisions) leading to the production of large numbers of daughter merozoites. After the final cycle of merozoite production the sexual cycle begins with the production of the macrogametocyte (female) and microgametocyte. The macrogametocyte is characterized by the production of wall forming bodies, while microgametocytes contain the components involved in the formation of microgametes, which bud off from the surface of the intracellular parasite.

Microgametes are flagellated and are responsible for the fertilization of the macrogamete. A zygote is formed which matures into the oocyst by fusion of the wall forming bodies and condensation of the nucleus. Oocysts are secreted in the feces, thus completing the cycle.

Over the past several years, native antigens from the sexual (gametocyte) stages of *Eimeria maxima* have been used to immunize laying hens. Offspring chicks were consequently vaccinated via maternal immunity (protective maternal antibody). Three major protective antigens have previously been identified in *E. maxima* gametocytes having molecular weights of 250, 82 and 56 kDa (EP Patent No. 0 256 536, U.S. Pat. No. 5,496,550, and U.S. Pat. No. 5,932,225). EP Patent No. 0 256 536, U.S. Pat. No. 5,496,550, and U.S. Pat. No. 5,932,225 are hereby incorporated by reference into this application in order to more fully describe the state of the art to which this invention pertains. It was shown that these antigens are well conserved amongst *Eimeria* species (Wallach 1995) and can cross protect against the 3 major species that cause coccidiosis in broiler chickens, *E. maxima, E. tenella* and *E. acervulina*. More recently, it was shown that in floor pen trials, chicks from hens vaccinated with these native gametocyte antigens were protected against *Eimeria* under field conditions (Wallach 1996). This protection acts to lower the peak in oocyst shedding to a level which does not cause any damaging effect on the performance of the broiler chicken. Based on the above results it was concluded that these antigens are effective against coccidiosis in chickens and also have the potential for use against coccidiosis in other domestic animals including turkeys, geese, sheep, cattle, pigs and fish.

These three antigens were also characterized at the molecular level. Cell free translation experiments were carried out to identify the RNA molecules that encode them (Mencher er al.). cDNA molecules that encode these antigens were cloned by immunoscreening of a cDNA library made in the expression vector lambda zap (4, U.S. Pat. No. 5,932,225). By this approach, the gene encoding the 250 kDa antigen was cloned and partially sequenced. The clone pEM 250/14 was partially sequenced in U.S. Pat. Nos. 5,932,225 and 5,496,550. FIG. 8a of the subject application reproduces FIG. 11 of U.S. Pat. Nos. 5,932,225 and 5,496,550, which portrays the DNA sequence of the first 293 nucleotides of clone pEM 250/14. FIG. 8b of the subject application reproduces FIG. 12 of U.S. Pat. Nos. 5,932,225 and 5,496,550, which shows the DNA sequence of the last 196 nucleotides of clone pEM 250/14. Also, in U.S. Pat. Nos. 5,932,225 and 5,496,550, the putative genes encoding the 56 and 82 kDa antigens were cloned and sequenced.

Subsequently, Fried et al. sequenced the entire pEM 250/14 clone and found that the antigen had a molecular weight of 230 kDa rather than 250 kDa as had been previously thought. Fried et al. found that the 230 kDa gene contains highly repetitive motifs and that these repeats are contained throughout the entire gene (Fried et al.). This clone was expressed in bacteria using the pATH plasmid vector and it was shown that it is recognized by convalescent chicken sera taken 14 days post infection with *E. maxima*. Finally, it was shown that this gene is expressed only in the macrogametocyte stage and by immunofluorescence was found to be located in the wall forming bodies of the macrogamete (Fried et al.).

cDNA clones encoding the 56 and 82 kDa antigens were also obtained by screening the library with polyclonal antibodies as well as a monoclonal antibody against the 56 kDa antigen. This monoclonal antibody was previously shown to provide passive immunity to naive chicks (Wallach 1990). A few clones were obtained and analyzed. One of the clones was found to encode a small 10 kDa antigen and therefore was not the desired clone. Another clone was found to contain only a small part of the open reading frame (ORF) and by northern blotting was shown to hybridize with two mRNAs of about the expected size for the 56 and 82 kDa antigens. It was therefore concluded that this was the desired clone. Genomic libraries were then screened to obtain the full length clone. However, due to the highly repetitive GCA motifs in this clone, it was not possible to specifically isolate the full length clone. Attempts to clone the full length cDNA molecule were also not successful due to these repeats. Finally, attempts to express the partial cDNA clones in bacteria failed as well probably due to their unusual sequences and a reasonable level of gene expression was not obtained. It has previously been shown that the 56 and 82 kDa antigens are glycosylated (U.S. Pat. No. 5,932,225). This is based on their strong reactivity with Soybean lectin. Therefore, glycosylation may be required in order to obtain good expression of these genes and for proper conformation of the gene products.

In addition to the 56, 82 and 230 kDa antigens, a 14 kDa antigen obtained from highly purified fractions of oocyst walls has been proposed as a possible candidate for vaccines against coccidiosis (Eschenbacher et al.). However, this hypothesis has not been explored.

Several laboratories have been working on a subunit vaccine against coccidiosis. Most of these researchers have focused their efforts on the extracellular asexual stages of the life cycle, in particular the sporozoite and merozoite stages which are considered to be the most vulnerable to immune attack. In a previous study it was found that sporozoite extracts from *E. tenella* could induce in broilers protection against challenge infections against this parasite for up to 7 weeks of age (Karkhanis et al.). Work carried out using monoclonal antibodies against antigens from sporozoites of *E. tenella* led to the identification of a 25,000 molecular weight antigen which was cloned and sequenced (Eur. Patent publication No. 0 164 176, Dec. 11, 1985). Several other sporozoite genes were identified and their recombinant antigens or the transformed bacteria themselves were tested for protective immunity (Danforth et al.). The results indicated that these recombinants were only able to provide a relatively low level of protection against challenge infection with *Eimeria* and did not always prevent the appearance of significant lesions.

A vaccine using antigens from the merozoite stage has also been tested (European patent publication No. 0 135 073). Using these antigens to immunize young broiler chicks, it was once again found that the protection afforded was relatively low (Danforth et al.).

In 1993, it was found that there was a correlation between protective maternal immunity with the appearance of maternal antibodies against a 230 kDa merozoite (as opposed to gametocyte) antigen of *Eimeria maxima* (Smith et al.). This protection was often over 90% and was found to occur even when the maternal antibody level was relatively low (although reactivity with the 230 kDa protein remained strong). It was also found that a very small quantity of the native 230 kDa merozoite antigen cut out of an SDS-PAGE gel could induce a significant (60%) level of protective maternal immunity against infection with *E. maxima* in offspring chicks. Furthermore, Western blotting showed that this protein was expressed in both merozoites and sporozoites of *E. maxima* and is also well conserved between *Eimeria* species.

However, it is extremely difficult to isolate the *E. maxima* merozoite 230 kDa antigen on a large scale from the parasite itself. Therefore, there is a need to clone and express this antigen recombinantly. This will enable the production of the antigen for use in vaccination and to test its optimal concentration for inducing protective immunity.

SUMMARY OF THE INVENTION

The subject invention provides an isolated nucleic acid comprising a nucleotide sequence encoding a 250 kDa polypeptide from Sporozoites/Merozoites of *Eimeria maxima*, or encoding a homolog of the polypeptide, or a complement of the nucleic acid.

The subject invention further provides a method of producing a recombinant 250 kDa polypeptide from Sporozoites/Merozoites of *Eimeria maxima* comprising culturing a transformed cell comprising an isolated nucleic acid comprising a nucleotide sequence encoding a 250 kDa polypeptide from Sporozoites/Merozoites of *Eimeria maxima*, or encoding a homolog of the polypeptide, or a complement of the nucleic acid and isolating the recombinant 250 kDa polypeptide from Sporozoites/Merozoites of *Eimeria maxima.*

The subject invention also provides a vaccine against *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the isolated nucleic acid comprising a nucleotide sequence encoding a 250 kDa polypeptide from Sporozoites/Merozoites of *Eimeria maxima* or the immunodominant portion of a 250 kDa polypeptide from Sporozoites/Merozoites of *Eimeria maxima*, or encoding a homolog of the polypeptide, or a complement of the nucleic acid.

The subject invention also provides the above vaccine further comprising a 56 kDa, 82 kDa or 230 kDa protein isolated from the gametocytes of *Eimeria maxima* or a mixture thereof.

The subject invention also provides a vaccine against coccidiosis comprising the recombinant 250 kDa antigen.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject the any of the aforementioned vaccines.

The subject invention also provides an isolated nucleic acid comprising a nucleotide sequence encoding an immunodominant portion of a 250 kDa polypeptide from Sporozoites/Merozoites of *Eimeria maxima* having the amino acid sequence shown in SEQ. ID NO. 26, or encoding a homolog of the polypeptide, or a complement of the nucleic acid.

BRIEF DESCRIPTION OF THE FIGURES

FIG. 6 A complete DNA sequence of the 250 kDa cDNA clone. The coding sequence, its complement and amino acid sequences are shown (SEQ. ID. NOs. 1-3).

FIGS. 7A & 7B Multiple sequence alignment of the 250 kDa cDNA *E. maxima* clone with a homologous DNA sequence from patent WO 90/00403. 7A) DNA sequence alignment showing 60% homology (SEQ. ID. NOs. 4-5). 7B) Protein sequence alignment showing 59% homology (SEQ. ID. NOs. 6-7).

FIG. 8*a* depicts the DNA sequence of the first 293 nucleotides of clone pEM 250/14. The coding sequence and its amino acid sequences are shown (SEQ. ID. NOs. 11-12).

FIG. 8*b* depicts the DNA sequence of the last 196 nucleotides of clone pEM 250/14. The coding sequence and its amino acid sequences are shown (SEQ. ID. NOs. 13-14).

FIG. 20 Similarity between tryptic peptide #1 of the *E. maxima* immunodominant protein and selected motifs from EtMIC4 and surface antigen 5401 of *E tenella*. The conserved cysteine residue (shown in bold type) was considered in the design of degenerate PCR primers based on tryptic peptide #1 of EmIP. The numbers proceeding motifs refer to their respective positions within the EtMIC4/5401 amino acid sequence. (SEQ. ID NOS. 15-19)

FIG. 21 3' RACE amplification of sporulated oocyst cDNA of *E. maxima* using degenerate PCR primer FP008. The reaction sample and molecular weight markers were separated on a 1% agarose gel. Lane 1, 1 μg of Lambda DNA/EcoRI+HindIII Markers; Lane 2, 10 μL of 100 bp DNA ladder.

FIG. 22 Protein sequence sharing homology with translated sequence form a 3' RACE PCR product generated with primer FP008. A 445 bp query was submitted for BLASTX analysis against all non-redundant protein databases through NCBI. The ten highest scores are listed and the alignment for the most significant score displayed. (SEQ. ID NO. 20)

FIG. 25 Partial DNA sequence and predicted amino acid sequence of the 5' PCR product generated with primers AP2 and RP019. The putative initiating methionine is shown in bold type at position 231, with an upstream in-frame TAG codon at position 186. The N-terminus sequence of the mature protein as predicted by Edman sequencing is boxed. (SEQ. ID. NOS. 21-23)

FIG. 28 BLASTN similarity search with the putative cDNA coding region for the *E. maxima* immunodominant protein. The five highest scores are listed and the alignment with the most significant score-mRNA for EtMIC4—is displayed. (SEQ. ID NO. 24)

FIG. 29A-D Nucleotide and predicted amino acid sequence of the *E. maxima* immunodominant protein. (SEQ. ID NOS. 25-26) The sequence was derived from cDNA clones encoding the full mature protein and overlapping 5' and 3' RACE products. The predicted signal sequence is underlined and the N-terminus amino acid sequence of the mature protein is boxed.

FIG. 30 CLUSTALW (4.1) alignment showing the predicted TSP-1 like domains present within the *E. maxima* immunodominant protein. The consensus sequence was established with a 50% identity cut-off, showing the WXXW and RXR motifs (underlined). The highly conserved cysteine residues are shown in bold type.

FIG. 31 CLUSTALW (4.1) alignment of the predicted EGF-line like domains present within the *E. maxima* immunodominant protein. The consensus sequence was established with a 75% identity cut-off, showing the highly conserved cysteine residues in bold type.

FIG. 32 Regions of low complexity within the predicted polypeptide sequence of the *E. maxima* immunodominant protein A: CLUSTALW (4.1) alignment highlighting the degenerate repetitive motif with low complex region 1. The consensus sequence shows conserved identities with similarity between residues indicated by '.'.B: Low complex region 2 showing the high frequency of glutamic acid, glycine and proline residues.

FIG. 33 Alignment of the transmembrane and cytoplasmic tail regions of EmIP and other proteins belonging to the TRAP family of apicomplexan microneme proteins. The putative transmembrane region is underlined and the conserved tyrosine and tryptophan residues shown in bold. Sequences are from the following organism: *Eimeria maxima* (EmIP, EmIP100); *Eimeria telnella* (EtMIC4, EtMIC1/Etp100); *Cryptosporidum parvum* (cpTRAPC1, CpGP900); *Neospara caninum* (NcTRAP); *Plasmodium falciparum* (PfTRAP PFCTRP); *Plasmodium berghei* (PbTRAP); *Plasmodium relictum* (PrTRAP); *Plasmodium knowlesi* (PkDBP); *Sarcocystis muris* (Sm70); *Toxoplasma gondii* (TgMIC2, TgMIC6, TgMIC7, TgMIC8, TgMIC9, TgAMA1). (SEQ. ID NOS. 27-41)

FIG. 35 Protein sequences sharing homology with the predicted amino acid sequence for the *E. maxima* immunodominant protein. The sequence representing the mature protein was submitted for BLASTP analysis against all non-redundant protein databases through NCBI. The twenty alignments with the highest significance are listed.

FIG. 40 Particial genomic DNA sequence generated by primers FP010 and RP023. The two introns detected within the amplified gene fragment are shown underlined.

FIG. 41 ClustalW (4.1) alignment of EmIP and EtMIC4 amino acid sequences showing the regions selected (in bold type) for the design of degenerate primers CP003 and CP004. Identical residues are identified by '*' and similar residues by '.'.

FIG. 44 DNA and encoded amino acid sequence of the expressed protein fragment from the 250 kDa asexual stage protein.

FIG. 45 Mouse immunogenicity trial of the recombinant fragment of the 250 kDa asexual stage protein. The average of each group for the three consecutive bleeds is shown, with standard error bars indicated. All serum samples were tested at 1:1000 dilution. Coating antigen was 100 ng of APGA for sera from the positive control APGA group, or 100 ng of the recombinant protein for the negative control PBS and PBS/FIA groups and the two recombinant protein doses (r0.5 µg and r5 µg)

DETAILED DESCRIPTION OF THE INVENTION

Figure 1:
FIG. 1 Western blot of a crude sporulated oocyst extract of *E. maxima* using sera and yolk from maternal immunization trials. Lane 1—Serum of 12 day old hatchlings of hens infected with *E. maxima*, which also were exposed to a challenge infection; Lane 2—serum from 3 day old hatchlings of hens infected with *E. maxima*; Lane 3—Yolk from hens immunized with the SDS-PAGE cutout 250 kDa merozoite protein band; Lane 4—serum from hens immunized with a crude merozoite extract. The 250 kDa band is shown with an arrow on the left of the figure.

The subject invention provides an isolated nucleic acid comprising a nucleotide sequence encoding a 250 kDa polypeptide from Sporozoites/Merozoites of *Eimeria maxima*, or encoding a homolog of the polypeptide, or a complement of the nucleic acid.

It was previously thought that the antigen from the sporozoites/merozoites of *E. maxima* was a 230 kDa antigen. However, our subsequent studies have revealed that the antigen actually is a 250 kDa antigen of the sporozoites/merozoites of *E. maxima*.

In one embodiment, the polypeptide has the amino acid sequence shown in FIG. 7*b* (SEQ. ID. NO. 6).

In another embodiment, the homolog of the polypeptide has greater than 59% identity to the polypeptide having the sequence shown as SEQ. ID. NO. 6.

In a further embodiment, the homolog of the polypeptide has at least 70% identity to the polypeptide having the sequence shown as SEQ. ID. NO. 6.

In an added embodiment, the homolog of the polypeptide has at least 75% identity to the polypeptide having the sequence shown as SEQ. ID. NO. 6.

In yet another embodiment, the homolog of the polypeptide has at least 80% identity to the polypeptide having the sequence shown as SEQ. ID. NO. 6.

In a further embodiment, the homolog of the polypeptide has at least 85% identity to the polypeptide having the sequence shown as SEQ. ID. NO. 6.

In one embodiment, the homolog of the polypeptide has at least 90% identity to the polypeptide having the sequence shown as SEQ. ID. NO. 6.

In another embodiment, the homolog of the polypeptide has at least 93% identity to the polypeptide having the sequence shown as SEQ. ID. NO. 6.

In a further embodiment, the homolog of the polypeptide has at least 95% identity to the polypeptide having the sequence shown as SEQ. ID. NO. 6.

In an additional embodiment, the homolog of the polypeptide has at least 97% identity to the polypeptide having the sequence shown as SEQ. ID. NO. 6.

In one embodiment, the homolog of the polypeptide has at least 99% identity to the polypeptide having the sequence shown as SEQ. ID. NO. 6.

In an additional embodiment, the nucleotide sequence has greater than 60% identity to the nucleotide sequence shown in FIG. 7*a* (SEQ. ID. NO. 4).

In a further embodiment, the nucleotide sequence has at least 70% identity to the nucleotide sequence shown as SEQ. ID. NO. 4.

In another embodiment, the nucleotide sequence has at least 75% identity to the nucleotide sequence shown as SEQ. ID. NO. 4.

In an additional embodiment, the nucleotide sequence has at least 80% identity to the nucleotide sequence shown as SEQ. ID. NO. 4.

In a further embodiment, the nucleotide sequence has at least 85% identity to the nucleotide sequence shown as SEQ. ID. NO. 4.

In one embodiment, the nucleotide sequence has at least 90% identity to the nucleotide sequence shown as SEQ. ID. NO. 4.

In yet another embodiment, the nucleotide sequence has at least 93% identity to the nucleotide sequence shown as SEQ. ID. NO. 4.

In an added embodiment, the nucleotide sequence has at least 95% identity to the nucleotide sequence shown as SEQ. ID. NO. 4.

In a further embodiment, the nucleotide sequence has at least 97% identity to the nucleotide sequence shown as SEQ. ID. NO. 4.

In one embodiment, the nucleotide sequence has at least 99% identity to the nucleotide sequence shown as SEQ. ID. NO. 4.

In a further embodiment, the nucleic acid is a DNA molecule.

In yet another embodiment, the DNA molecule is a cDNA molecule.

In an added embodiment, the nucleic acid has the nucleotide sequence shown in FIG. 7*a* (SEQ. ID. NO. 4).

In another embodiment, the nucleic acid is an RNA molecule.

In one embodiment, the isolated nucleic acid is operatively linked to a promoter of RNA transcription.

The subject invention also includes a vector comprising an isolated nucleic acid comprising a nucleotide sequence encoding a 250 kDa polypeptide from Sporozoites/Merozoites of *Eimeria maxima*, or encoding a homolog of the polypeptide, or a complement of the nucleic acid.

In one embodiment, the vector comprises the nucleic acid having the nucleotide sequence shown in FIG. 7*a* (SEQ. ID. NO. 4).

In another embodiment, the vector is a plasmid.

In a further embodiment, the plasmid comprises the nucleic acid having the nucleotide sequence shown in FIG. 7*a* (SEQ. ID. NO. 4).

In an additional embodiment, the plasmid comprises an isolated nucleic acid comprising a nucleotide sequence encoding a 250 kDa polypeptide from Sporozoites/Merozoites of *Eimeria maxima*, or encoding a homolog of the polypeptide, or a complement of the nucleic acid.

In yet another embodiment, the plasmid is the plasmid designated 230.1 plasmid (Australian Government Analytical Laboratories Accession No. NMO1/22396).

The subject invention also encompasses a host cell comprising a vector which comprises an isolated nucleic acid comprising a nucleotide sequence encoding a 250 kDa polypeptide from Sporozoites/Merozoites of *Eimeria maxima*, or encoding a homolog of the polypeptide, or a complement of the nucleic acid.

In one embodiment, the host cell comprises a vector comprising a nucleic acid having the nucleotide sequence shown in FIG. 7*a* (SEQ. ID. NO. 4).

In another embodiment, the host cell is selected from the group consisting of a bacterial cell; a plant cell; an insect cell; and a mammalian cell.

The subject invention additionally presents a transformed cell comprising an isolated nucleic acid comprising a nucleotide sequence encoding a 250 kDa polypeptide from Sporozoites/Merozoites of *Eimeria maxima*, or encoding a homolog of the polypeptide, or a complement of the nucleic acid.

In one embodiment, the transformed cell is the transformed cell designated 230.1 in bacteria (Australian Government Analytical Laboratories Accession No. NM01/22397).

The subject plasmid encoding the 250 kDa antigen was deposited with the Australian Government Analytical Laboratories, Pymble, Australia, on Jun. 26, 2001, under Accession No. NM01/22396. The bacterial cell transformed with the 250 kDa antigen was deposited with the Australian Government Analytical Laboratories, Pymble, Australia, on Jun. 26, 2001, under Accession No. NM01/22397. Both deposits were made according to the Budapest Treaty on the International Recognition of the Deposit of Microorganisms for the Purposes of patent Procedure.

In an added embodiment, the transformed cell further comprises a 250 kDa polypeptide from Sporozoites/Merozoites of *Eimeria maxima*, or a homolog of the polypeptide.

The subject invention further contains a method of producing a recombinant 250 kDa polypeptide from Sporozoites/Merozoites of *Eimeria maxima* comprising culturing a transformed cell comprising an isolated nucleic acid comprising a nucleotide sequence encoding a 250 kDa polypeptide from Sporozoites/Merozoites of *Eimeria maxima*, or encoding a homolog of the polypeptide, or a complement of the nucleic acid and isolating the recombinant 250 kDa polypeptide from Sporozoites/Merozoites of *Eimeria maxima*. The recombinant polypeptide produced by this method is also encompassed by the subject invention.

The subject invention also provides a vaccine against *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the isolated nucleic acid comprising a nucleotide sequence encoding a 250 kDa polypeptide from Sporozoites/Merozoites of *Eimeria maxima*, or encoding a homolog of the polypeptide, or a complement of the nucleic acid.

In one embodiment of the vaccine, the isolated nucleic acid is a plasmid.

In addition, the subject invention presents a vaccine against *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising a recombinant 250 kDa polypeptide from Sporozoites/Merozoites of *Eimeria maxima* produced by culturing a transformed cell comprising an isolated nucleic acid comprising a nucleotide sequence encoding a 250 kDa polypeptide from Sporozoites/Merozoites of *Eimeria maxima*, or encoding a homolog of the polypeptide, or a complement of the nucleic acid and isolating the recombinant 250 kDa polypeptide from Sporozoites/Merozoites of *Eimeria maxima*.

In another embodiment, the vaccine is comprised of a mixture of the isolated nucleic acid of the subject invention and the recombinant polypeptide of the subject invention.

In another embodiment, the vaccine is comprised of a mixture of the isolated nucleic acid of the subject invention, the recombinant polypeptide of the subject invention and a plasmid comprising the isolated nucleic acid of the subject invention.

In an added embodiment, the vaccine further comprises a second antigen.

In one embodiment, the second antigen is selected from the group consisting of a nucleic acid coding for an antigen from *Eimeria maxima*, a plasmid comprising such a nucleic acid, and a polypeptide coded by such a nucleic acid.

In one embodiment, the second antigen is a 56 kDa protein isolated from the gametocytes of *Eimeria maxima*.

In one embodiment, the second antigen is an 82 kDa protein isolated from the gametocytes of *Eimeria maxima*.

In one embodiment, the second antigen is a 230 kDa protein isolated from the gametocytes of *Eimeria maxima*.

In another embodiment, the vaccine further comprises a 56 kDa protein and an 82 kDa protein isolated from the gametocytes of *Eimeria maxima*.

In another embodiment, the vaccine further comprises a 56 kDa protein, an 82 kDa protein and a 230 kDa protein isolated from the gametocytes of *Eimeria maxima*.

The extraction and characterization of the *E. maxima* gametocyte proteins is described in examples 3 and 4 of U.S. Pat. Nos. 5,932,225 and 5,496,550 and the contents of these patents is hereby incorporated by reference into this application. Briefly, chickens were infected with 10,000 oocysts each and then sacrificed several days after infection. The intestines were removed and the gametocytes extracted by one of two methods as described in Example 1 of the above referenced patents. The proteins were then extracted from the gametocytes using various detergents and the extracted proteins were examined by SDS polyacrylamide gel electrophoresis (SDS-PAGE). The proteins had molecular weights between 10 and 300 kDa, with 5 major metabolically labeled proteins of molecular weights of about 82 kDa, 73 kDa, 56 kDa, and 35 kDa. The proteins were then analyzed by ELISA, immunofluoroscence, Western blotting and immune precipitation of cell-free translation products. Western blotting detected 3 major bands in chicken sera at 82, 56 and 43 kDa as well as minor bands at 250, 116, 78, 52 and 36 kDa. Parts of the 250 kDa protein were cloned and sequenced as well. Fried et al. subsequently cloned and sequenced the entire 250 kDa gametocyte protein.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject the vaccine of the subject invention.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In an additional embodiment, the avian species is chickens.

In one embodiment, the administering step comprises spraying the vaccine into the nostrils of the subject.

In a further embodiment, the administration comprises intravenous, intramuscular or intraperitoneal injection.

In another embodiment, the administration is performed in ovo.

In a further embodiment, the administration is to the air sac of an egg, thus contacting an embryo with the vaccine.

The subject invention also provides a method of conferring upon a newborn subject of an avian species maternal immunity (antibodies) against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the mother of the subject at a suitable time prior to the laying of a fertilized egg the vaccine of the subject invention in order to thereby confer protection via maternal immunity against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, in the newborn subject.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of reducing the output of *Eimeria* oocysts in feces from a newborn subject of an avian species which comprises the step of administering to the mother of the subject at a suitable time prior to the laying of a fertilized egg the vaccine of the subject invention in order induce an immune response and transmit maternal antibodies to the newborn so that the output of oocysts from the newborn is reduced.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject a live vaccine comprising a living non-virulent micro-organism or live virus that expresses a 250 kDa polypeptide from Sporozoites/Merozoites of *Eimeria maxima.*

In one embodiment, the live virus is the pox virus.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of feeding to the subject a plant whose cells express a 250 kDa polypeptide from Sporozoites/Merozoites of *Eimeria maxima.*

In one embodiment, the plant is wheat.

In another embodiment, the plant is corn.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject a plasmid comprising an isolated nucleic acid comprising a nucleotide sequence encoding a 250 kDa polypeptide from Sporozoites/Merozoites of *Eimeria maxima*, or encoding a homolog of the polypeptide, or a complement of the nucleic acid.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also contains a fertilized egg from an avian species having an air sac which is inoculated with the vaccine of the subject invention, which vaccine is capable of inducing before or immediately after hatching an immune response in the embryo against a virulent form of *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen.

In one embodiment, the avian species is selected from the group consisting of chickens, ducks, turkeys, geese, bantams, quail and pigeons.

In another embodiment, the avian species is chickens.

The subject invention also provides an isolated nucleic acid comprising a nucleotide sequence encoding an immunodominant portion of a 250 kDa polypeptide from Sporozoites/Merozoites of *Eimeria maxima* having the amino acid sequence shown as SEQ. ID NO. 26, or encoding a homolog of the polypeptide, or a complement of the nucleic acid.

In one embodiment, the homolog of the polypeptide has greater than 59% identity to the polypeptide having the sequence shown as SEQ. ID NO. 26.

In a further embodiment, the homolog of the polypeptide has at least 70% identity to the polypeptide having the sequence shown as SEQ. ID. NO. 26.

In an added embodiment, the homolog of the polypeptide has at least 75% identity to the polypeptide having the sequence shown as SEQ. ID. NO. 26.

In yet another embodiment, the homolog of the polypeptide has at least 80% identity to the polypeptide having the sequence shown as SEQ. ID. NO. 26.

In a further embodiment, the homolog of the polypeptide has at least 85% identity to the polypeptide having the sequence shown as SEQ. ID. NO. 26.

In one embodiment, the homolog of the polypeptide has at least 90% identity to the polypeptide having the sequence shown as SEQ. ID. NO. 26.

In another embodiment, the homolog of the polypeptide has at least 93% identity to the polypeptide having the sequence shown as SEQ. ID. NO. 26.

In a further embodiment, the homolog of the polypeptide has at least 95% identity to the polypeptide having the sequence shown as SEQ. ID. NO. 26.

In an additional embodiment, the homolog of the polypeptide has at least 97% identity to the polypeptide having the sequence shown as SEQ. ID. NO. 26.

In one embodiment, the homolog of the polypeptide has at least 99% identity to the polypeptide having the sequence shown as SEQ. ID. NO. 26.

In an additional embodiment, the nucleotide sequence has greater than 60% identity to the nucleotide sequence shown as SEQ. ID. NO. 25.

In a further embodiment, the nucleotide sequence has at least 70% identity to the nucleotide sequence shown as SEQ. ID. NO. 25.

In another embodiment, the nucleotide sequence has at least 75% identity to the nucleotide sequence shown as SEQ. ID. NO. 25.

In an additional embodiment, the nucleotide sequence has at least 80% identity to the nucleotide sequence shown as SEQ. ID. NO. 25.

In a further embodiment, the nucleotide sequence has at least 85% identity to the nucleotide sequence shown as SEQ. ID. NO. 25.

In one embodiment, the nucleotide sequence has at least 90% identity to the nucleotide sequence shown as SEQ. ID. NO. 25.

In yet another embodiment, the nucleotide sequence has at least 93% identity to the nucleotide sequence shown as SEQ. ID. NO. 25.

In an added embodiment, the nucleotide sequence has at least 95% identity to the nucleotide sequence shown as SEQ. ID. NO. 25.

In a further embodiment, the nucleotide sequence has at least 97% identity to the nucleotide sequence shown as SEQ. ID. NO. 25.

In one embodiment, the nucleotide sequence has at least 99% identity to the nucleotide sequence shown as SEQ. ID. NO. 25. In a further embodiment, the nucleic acid is a DNA molecule.

In yet another embodiment, the DNA molecule is a cDNA molecule.

In an added embodiment, the nucleic acid has the nucleotide sequence shown as SEQ. ID. NO. 25.

In another embodiment, the nucleic acid is an RNA molecule.

In one embodiment, the isolated nucleic acid is operatively linked to a promoter of RNA transcription.

The subject invention also includes a vector comprising an isolated nucleic acid comprising a nucleotide sequence encoding an immunodominant portion of a 250 kDa polypeptide from Sporozoites/Merozoites of *Eimeria maxima* having the amino acid sequence shown as SEQ. ID NO. 26, or encoding a homolog of the polypeptide, or a complement of the nucleic acid.

In one embodiment, the vector comprises the nucleic acid having the nucleotide sequence shown as SEQ. ID. NO. 25.

In another embodiment, the vector is a plasmid.

In a further embodiment, the plasmid comprises the nucleic acid having the nucleotide sequence shown as SEQ. ID. NO. 25.

In an additional embodiment, the plasmid comprises an isolated nucleic acid comprising a nucleotide sequence encoding an immunodominant portion of a 250 kDa polypeptide from Sporozoites/Merozoites of *Eimeria maxima* having the amino acid sequence shown as SEQ. ID NO. 26, or encoding a homolog of the polypeptide, or a complement of the nucleic acid.

The subject invention also encompasses a host cell comprising a vector which comprises an isolated nucleic acid comprising a nucleotide sequence encoding an immunodominant portion of a 250 kDa polypeptide from Sporozoites/Merozoites of *Eimeria maxima* having the amino acid sequence shown as SEQ. ID NO. 26, or encoding a homolog of the polypeptide, or a complement of the nucleic acid.

In one embodiment, the host cell comprises a vector comprising a nucleic acid having the nucleotide sequence shown as SEQ. ID. NO. 25.

In another embodiment, the host cell is selected from the group consisting of a bacterial cell; a plant cell; an insect cell; and a mammalian cell.

The subject invention additionally presents a transformed cell comprising an isolated nucleic acid comprising a nucleotide sequence encoding an immunodominant portion of a 250 kDa polypeptide from Sporozoites/Merozoites of *Eimeria maxima* having the amino acid sequence shown as SEQ. ID NO. 26, or encoding a homolog of the polypeptide, or a complement of the nucleic acid.

In an added embodiment, the transformed cell further comprises an immunodominant portion of a 250 kDa polypeptide from Sporozoites/Merozoites of *Eimeria maxima* having the amino acid sequence shown as SEQ. ID NO. 26 or encoding a homolog of the polypeptide.

The subject invention further provides a method of producing a recombinant polypeptide from Sporozoites/Merozoites of *Eimeria maxima* comprising culturing a transformed cell comprising an isolated nucleic acid comprising a nucleotide sequence encoding an immunodominant portion of a 250 kDa polypeptide from Sporozoites/Merozoites of *Eimeria maxima* having the amino acid sequence shown as SEQ. ID NO. 26, or encoding a homolog of the polypeptide and isolating the recombinant immunodominant portion of the 250 kDa polypeptide from Sporozoites/Merozoites of *Eimeria*

*maxima*. The recombinant polypeptide produced by this method is also encompassed by the subject invention.

The subject invention also provides a vaccine against *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the isolated nucleic acid comprising a nucleotide sequence encoding an immunodominant portion of a 250 kDa polypeptide from Sporozoites/Merozoites of *Eimeria maxima* having the amino acid sequence shown as SEQ. ID NO. 26, or encoding a homolog of the polypeptide, or a complement of the nucleic acid.

In one embodiment of the vaccine, the isolated nucleic acid is a plasmid.

In addition, the subject invention provides a vaccine against *Eimeria tenella, Eimeria maxima, Eimeria acervulina, Elmeria necatrix, Eimeria praecox, Eimeria mitis* or *Eimeria brunetti*, or a microorganism expressing an immunologically cross-reactive antigen, comprising a recombinant polypeptide from Sporozoites/Merozoites of *Eimeria maxima* produced by culturing a transformed cell comprising an isolated nucleic acid comprising a nucleotide sequence encoding an immunodominant portion of a 250 kDa polypeptide from Sporozoites/Merozoites of *Eimeria maxima* having the amino acid sequence shown as SEQ. ID NO. 26, or encoding a homolog of the polypeptide, or a complement of the nucleic acid and isolating the recombinant polypeptide from Sporozoites/Merozoites of *Eimeria maxima.*

In another embodiment, the vaccine is comprised of a mixture of the isolated nucleic acid of the subject invention and the recombinant polypeptide of the subject invention.

In an added embodiment, the vaccine further comprises a second antigen.

In one embodiment, the second antigen is selected from the group consisting of a nucleic acid coding for an antigen from *Eimeria maxima*, a plasmid comprising such a nucleic acid, and a polypeptide coded by such a nucleic acid.

The subject invention also provides a method of immunizing a subject against infection by *Eimeria tenella, Eimeria maxima, Eimeria acervulina, Eimeria necatrix, Eimeria praecox, Elmeria mitis* or *Eimeria brunetti*, or a microorganism expressing an immunologically cross-reactive antigen, comprising the step of administering to the subject the vaccine of the subject invention.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In an additional embodiment, the avian species is chickens.

In one embodiment, the administering step comprises spraying the vaccine into the nostrils of the subject.

In another embodiment, the administration comprises intravenous, intramuscular or intraperitoneal injection.

In another embodiment, the administration is performed in ovo.

In a further embodiment, the administration is to the air sac of an egg, thus contacting an embryo with the vaccine.

The subject invention also provides a method of conferring upon a newborn subject of an avian species maternal immunity (antibodies) against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the mother of the subject at a suitable time prior to the laying of a fertilized egg the vaccine of the subject invention in order to thereby confer protection via maternal immunity against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, in the newborn subject.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of reducing the output of *Eimeria* oocysts in feces from a newborn subject of an avian species which comprises the step of administering to the mother of the subject at a suitable time prior to the laying of a fertilized egg the vaccine of the subject invention in order induce an immune response and transmit maternal antibodies to the newborn so that the output of oocysts from the newborn is reduced.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject a live vaccine comprising a living non-virulent micro-organism or live virus that expresses the immunodominant portion of a 250 kDa polypeptide from Sporozoites/Merozoites of *Eimeria maxima* having the amino acid sequence shown as SEQ. ID NO. 26.

In one embodiment, the live virus is the pox virus.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of feeding to the subject a plant whose cells express the immunodominant portion of a 250 kDa polypeptide from Sporozoites/Merozoites of *Eimeria maxima.*

In one embodiment, the plant is wheat.

In another embodiment, the plant is corn.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject a plasmid comprising the nucleic acid having the nucleotide sequence shown as SEQ. ID. NO. 25.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also contains a fertilized egg from an avian species having an air sac which is inoculated with the vaccine of the subject invention, which vaccine is capable of inducing before or immediately after hatching an immune response in the embryo against a virulent form of *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen.

In one embodiment, the avian species is selected from the group consisting of chickens, ducks, turkeys, geese, bantams, quail and pigeons.

In another embodiment, the avian species is chickens.

The present invention provides the recombinant cloning and sequencing of the 250 kDa sporozoite/merozoite antigen from *E. maxima.*

The 250 kDa antigen was isolated from purified *E. maxima* sporozoites which are present in sporulated oocysts (see life cycle above). The isolation procedure involved extraction of proteins from the sporulated oocysts and separation of the extracted proteins on a DEAE-sephacel anion-exchange column. This was followed by SDS-PAGE of the peak fractions and Western blotting to identify the 250 kDa antigen. Furthermore, protective maternal antisera both from vaccinated hens and offspring chicks were used to confirm the identity of the purified antigen. Finally, the 250 kDa protein was isolated from a PVDF membrane filter for carrying out protein sequencing and cloning.

The amino terminal and tryptic peptide digest products of the 250 kDa antigen were sequenced. The sequences from the tryptic digest were used to design degenerate PCR oligonucleotide primers. The primers were used in RACE (rapid amplification of cDNA ends) PCR to amplify partial gene products. From the sequences of these products, gene specific primers were designed and used in RACE PCR to define the 3' and 5' ends of the mRNA. A full length 7 kilobase cDNA clone encoding the antigen was then amplified by PCR using gene specific primers designed to the 5' and 3' ends. This clone was fully sequenced and shown to contain the correct DNA sequence at its 5' end when compared to the amino acid sequence of the N-terminus of the native protein. Thus, this nucleic acid sequence encoded the protective 250 kDa sporozoite/merozoite antigen and could now be used to produce recombinant antigen for vaccination of chickens against coccidiosis.

A homolog of the nucleic acid of the invention is a nucleic acid that codes for a polypeptide which has substantially the same biological activity as the polypeptide encoded by the nucleic acid. The term “homology”, as used herein, refers to a degree of complementarity. There may be partial homology or complete homology (i.e., identity). A partially complementary sequence is one that at least partially inhibits an identical sequence from hybridizing to a target nucleic acid; it is referred to using the functional term “substantially homologous.” The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

It is an object of the present invention to provide nucleotide sequences encoding the 250 kDA antigens from Sporozoites/Merozoites of *Eimeria maxima* and the deduced amino acid sequence therefor. Specifically exemplified coding sequences are given in FIG. 6, together with the deduced amino acid sequence. All synonymous coding sequences for the exemplified amino acid sequences are within the scope of the present invention.

It is a further object of the present invention to provide functionally equivalent coding and protein sequences, including equivalent sequences from other *Eimeria* species. Functionally equivalent 250 kDa antigens from Sporozoites/Merozoites of *Eimeria maxima* coding sequences are desirably from about 50% to about 80% nucleotide sequence homology (identity) to the specifically identified coding sequence, from about 80% to about 95%, and desirably from about 95% to about 100% identical in coding sequence to the specifically exemplified coding sequence.

Hybridization conditions of particular stringency provide for the identification of homologs of the coding sequence from other species and the identification of variant sequences, where those homologs and/or variant sequences have at least (inclusively) 50 to 85%, 85 to 100% nucleotide sequence identity, 90 to 100%, or 95 to 100% nucleotide sequence identity. Each integer and each subset of each specified range is intended within the context of the present invention.

The coding sequence and methods of the present invention include the homologous coding sequences in species other than *Eimeria maxima*. Methods can be employed to isolate the corresponding coding sequences (for example, from cDNA) from other organisms, including but not limited to other species such as *Eimeria tenella, Elmeria acervulina, Eimeria necatrix, Eimeria praecox, Eimeria mitis* and *Eimeria brunetti* useful in the methods of this invention using the sequences disclosed herein and experimental techniques well known to the art.

Specifically included in this invention are sequences from other species than those exemplified herein, which sequences hybridize to the sequences disclosed under stringent conditions. Stringent conditions refer to conditions understood in the art for a given probe length and nucleotide composition and capable of hybridizing under stringent conditions means annealing to a subject nucleotide sequence, or its complementary strand, under standard conditions (i.e., high temperature and/or low salt content) which tend to disfavor annealing of unrelated sequences.

"Conditions of high stringency" means hybridization and wash conditions of 650-68° C., 0.1×SSC and 0.1% SDS (indicating about 95-100% nucleotide sequence identity/similarity). Hybridization assays and conditions are further described in Sambrook et al. (1989) Molecular Cloning, Second Edition, Cold Spring Harbor Laboratory, Plainview, N.Y. As used herein, conditions of moderate (medium) stringency are those with hybridization and wash conditions if 50-65° C., 1×SSC and 0.1% SDS (where a positive hybridization result reflects about 80-95% nucleotide sequence identity). Conditions of low stringency are typically those with hybridization and wash conditions of 40-50° C., 6×SSC and 0.1% SDS (reflecting about 50-80% nucleotide sequence identity).

A homolog of the polypeptide of the invention is a polypeptide which has substantially the same amino acid sequence and biological activity as the polypeptide. Thus, a homolog may differ from the polypeptide of the invention by the addition, deletion, or substitution of one or more non-essential amino acid residues, provided that the resulting polypeptide retains the biological activity of the polypeptide. Persons skilled in the art can readily determine which amino acids residues may be added, deleted, or substituted (including with which amino acids such substitutions may be made) using established and well known procedures, including, for example, conventional methods for the design and manufacture of DNA sequences coding for bacterial expression of polypeptide homologs of the subject polypeptide, the modification of cDNA and genomic sequences by site-directed mutagenesis techniques, the construction of recombinant polypeptides and expression vectors, the bacterial expression of the polypeptides, and the measurement of the biochemical activity of the polypeptides by means of conventional biochemical assays.

Examples of homologs are deletion homologs containing less than all the residues specified in the subject polypeptide, substitution homologs wherein one or more residues specified are replaced by other residues, and addition homologs wherein one or more amino acids residues are added to the polypeptide. All such homologs share the biological activity of the polypeptide of the invention.

"Substantially the same polypeptide" is herein defined as encompassing the deletion, addition or substitution of fewer than four amino acids at the N-terminus of the amino acid sequence of the polypeptide. Furthermore, there may be deletions, additions or substitutions in the sequence which do not eliminate the biological activity of the polypeptide. Such modifications are known to those skilled in the art. For example, substitutions may encompass up to 10 residues in accordance with the homologous or equivalent groups described by e.g. Lehninger, Biochemistry, 2nd ed. Worth Pub., New York. (1975); Creighton, Protein Structure, a Practical Approach, IRL Press at Oxford Univ. Press, Oxford, England (1989); and Dayhoff, Atlas of Protein Sequence and Structure 1972, National Biomedical Research Foundation, Maryland (1972).

The term "biologically active", as used herein, refers to a polypeptide having structural, regulatory, or biochemical functions of a naturally occurring molecule. Likewise, "immunologically active" refers to the capability of the natural, recombinant, or synthetic polypeptide, or any oligopeptide portion thereof, to induce a specific immune response in an animal or cells and to bind with specific antibodies.

"Substantially the same biological activity" refers to biological activity the same as that of the naturally occurring molecule possibly differing slightly in degree or level which would still be known by the skilled artisan to be the same biological activity.

The term "portion", as used herein, in connection with a polypeptide (as in "a portion of a given polypeptide") refers to fragments of that polypeptide. The fragments may range in size from four (4) amino acid residues to the entire amino acid sequence minus one amino acid.

The term "portion", as used herein, in connection with a nucleic acid (as in "a portion of a given nucleic acid") refers to fragments of that nucleic acid. The fragments may range in size from twelve (12) nucleotide residues to the entire nucleic acid sequence minus one nucleotide.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The present invention provides the recombinant cloning and sequencing of an immunodominant and highly protective 250 kDa antigen from sporulated oocysts of *Eimeria maxima*.

The antigen was shown to react with serum from protected hens and chicks and the sequence of the gene was based on the amino acid sequence of the protein recognized by the protective sera. The gene is strongly expressed in the sporozoite and merozoite stages of development and has been predicted to play a role in host cell invasion. Thus, this antigen can be used in a vaccine against coccidiosis.

The subject invention also provides a vaccine against coccidiosis comprising the recombinant 250 kDa antigen.

The subject invention also provides an isolated nucleic acid having the nucleotide sequence shown in SEQ. ID NO. 25.

The subject invention also provides a recombinant polypeptide, wherein the amino acid sequence is shown by SEQ. ID NO. 26.

The invention is further illustrated by the following examples which in no way should be construed as being further limiting. One skilled in the art will readily appreciate that the specific methods and results discussed are merely illustrative of the invention as described more fully in the claims which follow thereafter.

EXPERIMENTAL DETAILS

Example 1

Purification of the 250 kDa Sporozoite Antigen from Sporulated Oocysts

Sporulated oocysts of *E. maxima* were prepared as described previously (Wagenbach). 100×$10^6$ sporulated oocysts were thoroughly washed and then resuspended in an equal volume of 40 mM Tris.HCl pH 8.0, overlayed with glass beads and ruptured by vortexing for 5 minutes. The homogenate was then subjected to three cycles of freeze-thawing using liquid nitrogen/40° C. water bath, followed by centrifugation at 13,000×g for 10 minutes. The supernatant was removed, transferred to a microconcentrator (Centricon 100, Amicon) and concentrated by centrifugation at 9900×g for 30 minutes at 4° C. Protein concentration was determined by the Bradford method. A 5 microgram sample of the crude extract was analyzed by SDS-PAGE and Western blotting the results of which are shown in FIG. 1. As can be seen, sera from hens or their offspring chicks immunized by live infection with *E. maxima* or with a crude merozoite extract reacted with the 250 kDa protein band present in sporulated oocysts. In addition, as can be seen in lane 3, yolk from eggs of hens immunized with the merozoite 250 kDa cutout protein band (used previously in our maternal immunization trial (Smith et al.)), also reacted with the 250 kDa protein.

Figure 2:
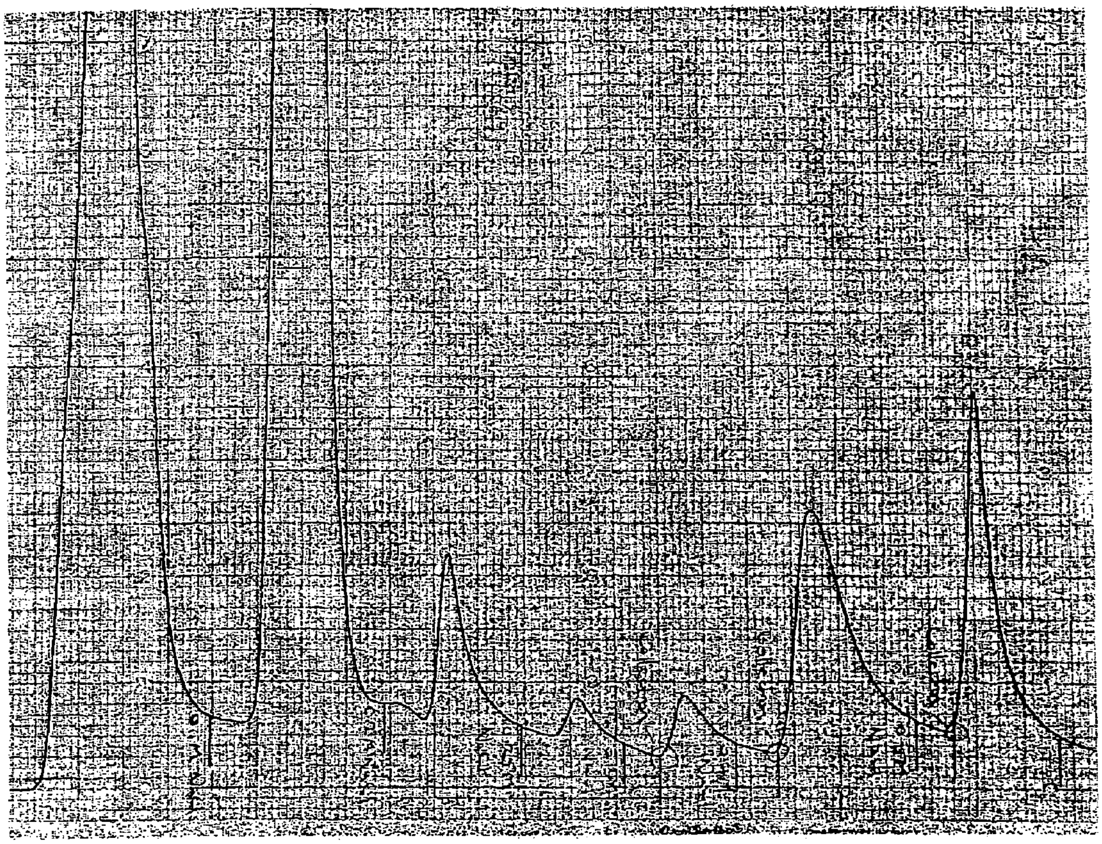
FIG. 2 Elution profile (OD 280) of sporulated oocyst proteins from the DEAE-sephacel column using various concentrations of NaCl.

DEAE-sephacel (Pharmacia, Sweden) anion-exchange resin was used to fill a 1 cm by 20 cm column and was equilibrated in 40 mM Tris.HCl pH 8.0 at a flow rate of 0.7 ml/min. 1.5 mg of crude sporulated oocyst protein extract was applied to the column and the proteins were subsequently eluted with a step gradient of 0-1M NaCl in 40 mM Tris pH 8.0. The eluate was monitored using a UV detector set at 280 nm and a chart recorder and the results are shown in FIG. 2. Fractions were collected and pooled according to the peaks found, concentrated and centrifuged as above.

Figure 3:
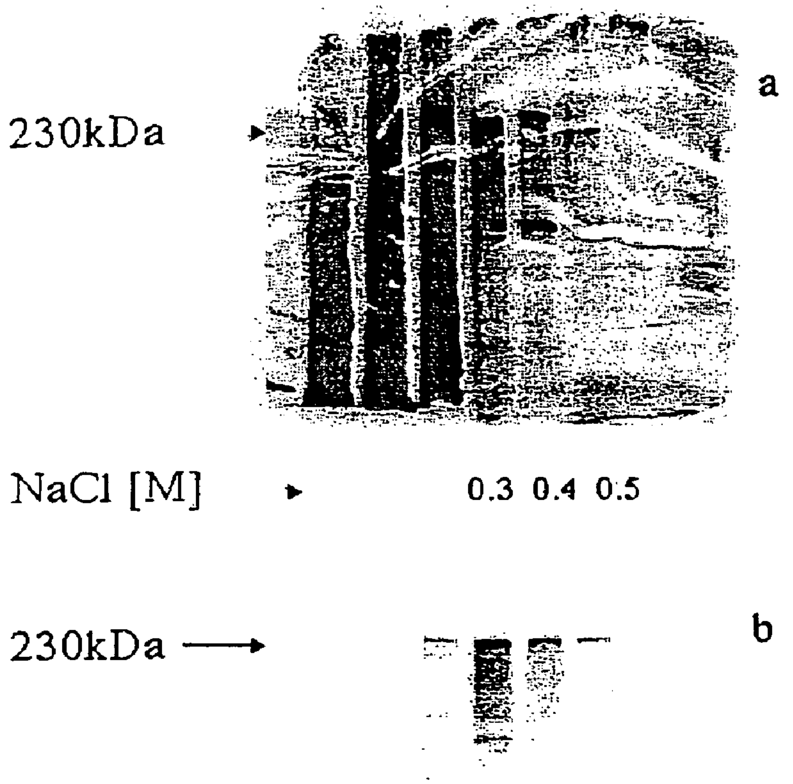
FIG. 3 Silver staining (3*a*) and Western blot (3*b*) analysis of ion exchange fractionated sporulated oocyst extract. The Western blot was performed using serum from hens immunized with a crude merozoite extract. The 250 kDa protein band is indicated on the left.

The pooled fractions obtained at the various NaCl concentrations used for elution, were analyzed by SDS PAGE and Western blotting (FIG. 3). As can be seen, both by silver staining of the gel or by reactivity with chicken antiserum raised against a crude merozoite extract, the 250 kDa antigen band appeared in the 0.3-0.5 M NaCl fractions. This same band was also recognized by antiserum from protected 3 day old offspring chicks of hens immunized by live infection.

Example 2

Figure 4:
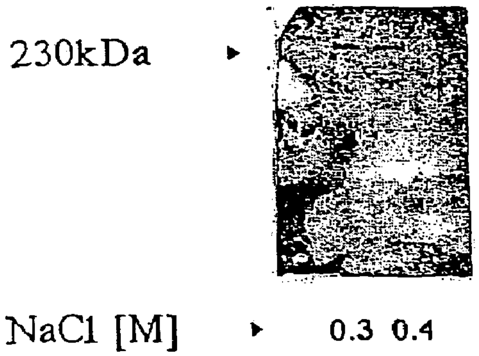
FIG. 4 Western blot analysis of sporulated oocyst extract fractions from the DEAE column detected with serum from a 3 day old offspring chick of hens immunized by live infection. The concentration of NaCl used for elution is indicated at the bottom of the blot and the 250 kDa protein band is shown with an arrow.

Amino Acid Sequencing of the N-Terminus as Well as Internal Tryptic Peptides from the 250 kDa Antigen Ion-exchange purified fractions eluted with 0.3 to 0.5 M NaCl were pooled and the proteins were separated by SDS-PAGE (FIG. 4). Following electrophoresis, the proteins were transferred to a PVDF membrane, which was then stained with Coomassie Blue. The band corresponding to the immunodominant 250 kDa protein was excised and the N-terminus was sequenced. For the sequencing of internal peptides, the 250 kDa protein band was subjected to tryptic digestion and subsequent sequence analysis of the generated peptides by mass spectrometry.

The results of the sequence analysis were as follows:

N-terminal: EVNNELSK(C)ESGWTPW (SEQ. ID. NO. 8)

Tryptic peptide 1 QWTAWTE (SEQ. ID. NO. 9)

Tryptic peptide 2 EL/IVNWF (SEQ. ID. NO. 10)

Example 3

RACE PCR Cloning and Sequencing of the Gene Encoding the 250 kDa Antigen

Figure 5:
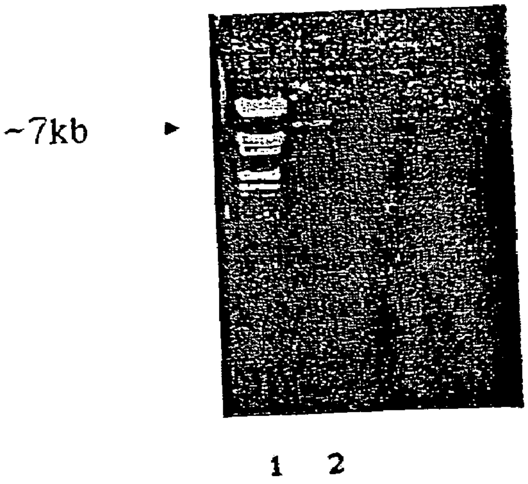
FIG. 5 The amplified cDNA product from PCR using gene specific primers specific to the 3' and 5' ends of the gene encoding for the 250 kDa antigen. Lane 1 shows the DNA marker bands and lane 2 the 7 KB PCR product band.

Total RNA was extracted from sporulated oocysts using TRIzol Reagent according to the manufacturer's protocol. mRNA was isolated from total RNA using a Dynal mRNA kit according to the manufacturer's instructions. The mRNA was then used for the construction of cDNA using a Marathon RACE kit (Clonetech). Degenerate PCR primers were designed from the N-terminal and tryptic peptide sequences and used in the 5' and 3' RACE PCR experiments. Bands generated were cloned and sequenced and the sequence obtained was used to design new gene-specific primers. Gene specific primers were then used together with the degenerate primers to precisely define the 5' and 3' ends of the cDNA. Gene specific primers were then designed to amplify the full length 7 kilobase cDNA. The result are shown in FIG. 5 where the 7 KB cDNA band can be visualized.

The DNA sequence data obtained from the 250 kDa cDNA clone is presented in FIG. 6. As can be seen, the sequence contains the amino terminus starting from base pair number 231 (ATG) and ending in the stop codon at base pair 7310. The total length of the sequence is 7987 bases. The sequence encodes for a protein of 2359 amino acids with a predicted molecular weight of 249 kDa.

The subject plasmid encoding the 250 kDa antigen was deposited with the Australian Government Analytical Laboratories, Pymble, Australia, on Jun. 26, 2001, under Accession No. NM01/22396. The bacterial cell transformed with the 250 kDa antigen was deposited with the Australian Government Analytical Laboratories, Pymble, Australia, on Jun. 26, 2001, under Accession No. NM01/22397. Both deposits were made according to the Budapest Treaty on the International Recognition of the Deposit of Microorganisms for the Purposes of patent Procedure.

As can be seen in FIG. 7, the sequence of the *E. maxima* 250 kDa gene was found to share homology with a gene sequence designated GX5401 and GX5401 FL from *E. tenella* (WO 90/00403). *E. tenella* clone GX5401 was selected from a cDNA library prepared from *E. tenella* sporulated oocysts using convalescent chicken serum for screening the library. The *E. tenella* full length gene GX5401FL was cloned from a genomic library using the GX5401 cDNA clone as a probe. This gene has an open reading frame of 6,567 bases and encodes a protein with a predicted molecular weight of about 250 kDa. In comparing the full length sequence of the *E. maxima* 250 kDa clone to the *E. tenella* sequence (FIGS. 7*a* and 7*b*), it was found that overall there was a homology of 60% and 59% for the DNA and amino acid sequences, respectively. This level of homology is relatively low and thus, this newly cloned *E. maxima* gene is significantly different from the *E. tenella* clone. Since the subject *E. maxima* clone is also strongly recognized by protective maternal antibodies, it therefore provides the basis for production of a new recombinant vaccine against coccidiosis in chickens.

Example 4

Purification and Western Blot Analysis of an Immunodominant Asexual Stage Protein from *Eimeria maxima*

Materials

For convenience, the chemical reagents, biological reagents and miscellaneous materials listed below are grouped with the names of suppliers.

Chemical Reagents

Unless otherwise stated all chemicals used throughout this study were of analytical grade.

Amresco (U.S.A); chloroform, citric acid (trisodium hydrate), acetic acid, citric acid EDTA, $NaHCO_3$, phenol, SDS, Tris Borate EDTA buffer (10× stock: 0.89M Tris, 0.89M borate, 0.02M EDTA)

British Drug Houses Chemicals (U.K); acetic acid, ethanol, glycine, HCl, isopropanol, KCl $KH_2PO_4$, methanol, $MgCl_2$, $MgSO_4$, NaCl, $Na_2HPO_4$, NaOH Progen Industries Ltd. (Australia); X-gal Sigma Chemical Company (U.S.A); 2-mercaptoethanol, BCIP/NBT Buffered Substrate Tablet, EtBr, glycerol, IPTG, HBS, isoamyl alcohol, PMSF, Tris Biological Reagents Biotech International Ltd. (Australia); 2 mM dNTP solution Clontech (U.S.A); Advantage® 2 Taq polymerase and 10× reaction buffer DIFCO Laboratories (U.S.A); bacteriological agar, trypsin, tryptone, yeast extract Fluka Chemical Corp (U.S.A); taurocholic acid ICN (U.S.A); penicillin 10,000 I.U./mL and streptomycin 10,000 |ig/mL antibiotic mixture New England Biolabs (U.S.A); restriction endonucleases and 10× reaction buffers PerkinElmer Life Sciences, Inc. (U.S.A); $^{32}$P-dCTP Pierce Chemical Company (U.S.A); BSA Progen Industries Ltd. (Australia); DNA grade agarose, ampicillin, proteinase K Promega (U.S.A); T4 DNA ligase and 2× ligation buffer Roche; DNase (Rnase free), RNase inhibitor Miscellaneous Materials BioRad; Econo-columns (low pressure chromatography columns)

Amersham Pharmacia Biotech (Sweden); DEAE sephacel, Hybond-N$^+$ nucleic acid transfer membrane, Percoll Pall corporation (U.S.A); PVDF protein transfer membrane Sigma Chemical Company (U.S.A); glass beads Solutions and Growth Media Denaturation solution; 0.5M NaCl, 0.5M NaOH Hybridisation solution; 0.263M $Na_2HPO_4$ pH 7.2, 1% BSA, 1 mM EDTA, 7% SDS LB medium; 1% NaCl, 1% tryptone, 0.5% yeast extract LB agar; LB medium with 0.24% $MgSO_4$, 1.5% agar Neutralisation solution; 0.5M Tris-Cl pH 7.4, 2.5M NaCl PBS 1×; 137 mM NaCl, 2.7 mM KCl, 4.3 mM $Na_2HPO_4$, 1.4 mM $KH_2PO_4$, pH 7.4

SDS electrophoresis buffer; 0.151% Tris, 7.2% glycine, 0.5% SDS

SOB media; 0.05% NaCl, 2% tryptone, 0.5% yeast extract

SOC media; SOB with 20 mM glucose, 10 mM $MgCl_2$, 10 mM $MgSO_4$

SSC 20×; 3M NaCl, 0.3M NaCltrate, pH 7.0

TBE electrophoresis buffer; 0.89M Tris, 0.89M borate, 0.02M EDTA

TE buffer; 10 mM Tris-Cl pH8.0, 1 mM EDTA

Transfer solution; 1M NaCl, 0.1M NaCitrate, pH 7.0 with 1M citric acid

Commercial Kits

Dynabeads® mRNA DIRECT kit (DYNAL, Norway)

GenElute™ Plasmid Miniprep Kit (Sigma, U.S.A.)

Marathon™ cDNA Amplification Kit (CLONTECH, U.S.A)

Omniscript™ RT Kit (QIAGEN, U.S.A.)

pGEM®-T Easy Vector System (Promega, U.S.A)

Protease Inhibitor Cocktail P8465 (Sigma, U.S.A.)

QIAquick® Gel Extraction Kit (QIAGEN, U.S.A.)

QIAquick PCR Purification Kit (QIAGEN, U.S.A.)

Random Primed DNA Labelling Kit (Roche)

Silver Staining Kit, PlusOne (Amersham Pharmacia Biotech, Sweden)

Parasites

The Houghton strain of *Eimeria maxima* was used throughout this study. Sporulated oocysts were initially supplied by the National Veterinary Institute, Uppsala, Sweden. Australian strains of *E. maxima* and *E. tenella* were used for comparative experiments and sporulated oocysts were supplied by Medichick Pty. Ltd., Victoria, Australia.

Host Strain

The Australorpe strain of domestic chicken was used throughout this study. Birds were supplied as day-old cockerels by Barter and Sons Pty. Ltd., N.S.W., Australia.

Methods

Parasite Preparation

Sporulated Oocysts

*E. maxima* was routinely passaged in the host strain every 3-4 months following a modified procedure of that described by Shirley (1995). At 3-4 weeks of age, birds were infected by oral inoculation with $5\times10^3$ sporulated oocysts and feces collected each day from day 6 to day 9 pi. On the day of collection, feces were transferred to a 4 L bucket and tap water added in the ratio 4 parts water to 1-part feces. The slurry was homogenized in an industrial strength blender and the resulting homogenate filtered through a 1 mm-gauge stainless steel laboratory sieve. The filtrate was centrifuged at 2000×g for 10 minutes and the supernatant discarded. Pellets containing the oocysts were resuspended in saturated NaCl solution by vigorous shaking and centrifuged at 750×g for 10 minutes. The supernatant containing floated oocysts was then filtered in succession through 17 μm and 10 μm polymon mesh and the oocysts collected with a sterile transfer pipette from the surface of the mesh. In order to maximize the yield, pellets that still contained oocysts were resuspended in fresh saturated NaCl solution and the procedure repeated up to 5 times. Oocysts collected in this manner were immediately washed free of NaCl by repeated dilution in water and centrifugation at 1500×g for 5 minutes. Oocysts were then resuspended in 2% potassium dichromate and sporulated by incubation at 28° C. in a shaking water bath for 72 hrs. Following sporulation, cultures were stored at 4° C.

The use of polymon mesh during the isolation procedure made advantage of the relatively large size of *E. maxima* oocysts (18 μm×30 μm). Oocysts were unable to pass through the 10 μm mesh and were recovered quickly and in a small volume easily manipulated in downstream steps.

Sodium Hypochlorite Treatment of Oocysts

Oocysts stored in potassium dichromate at 4° C. were cleaned with sodium hypochlorite in the preparation of infective doses and prior to crude antigen preparation. Potassium dichromate was removed from the oocyst culture by repeated water washes and centrifugation at 1500×g for 5 minutes. Pelleted oocysts were resuspended in water, an equal volume of 12.5% w/v sodium hypochlorite (final concentration 6.25% w/v) added and the suspension placed on ice for 10 minutes. Following centrifugation at 750×g for 10 minutes, the supernatant containing clean oocysts was filtered through 10 μm polymon mesh and the oocysts collected from the surface of the mesh with a sterile transfer pipette. Sodium hypochlorite was immediately removed by repeated washing with water and centrifugation at 1500×g for 5 minutes. Oocysts were resuspended in water if used for infection, or an appropriate buffer for crude antigen preparation.

Merozoites

Chickens were infected at 3-4 weeks of age by oral inoculation with $2\times10^5$ sporulated oocysts and killed at 93 hrs post infection. The intestines were removed, immediately rinsed in ice-cold PBS pH 7.4, then cut into pieces approximately 3 cm in length. The pieces were added to a solution of Hanks Balanced Salts solution (Sigma) pH 7.4 containing 0.025% trypsin, 1% Taurocholic acid (Fluka), 10 mM $MgCl_2$, 200 units/mL penicillin and 200 μg/mL streptomycin, and incubated at 40° C. for between 20-30 min. The release of merozoites was monitored microscopically throughout the incubation period. The solution was then filtered in succession through 1000 μm and 250 μm stainless steel laboratory sieves and finally through 17 μm polymon mesh, serving to remove larger intestinal debris. The resulting filtrate was centrifuged at 1000×g for 10 min, the supernatant discarded and pellets containing merozoites resuspended in an equal volume of ice-cold HBSS containing 10mM $MgCl_2$.

To remove smaller debris the merozoites were layered on a discontinuous Percoll (Pharmacia) gradient based on the method of Fernando et al (1984). The gradient was prepared by the addition of 2 ml each of an isotonic stock Percoll solution (9 parts Percoll to 1 part 10×PBS), followed by 70% stock (7 parts isotonic stock to 3 parts 1×PBS), then 50% stock (5 parts isotonic stock to 5 parts 1×PBS) and finally the merozoite suspension. The gradient was centrifuged at 10000×g for 10 min and merozoites pipetted from the 70%-50% boundary. The collected merozoites were washed with 1×PBS and pelleted by centrifugation at 1000×g for 10 min. Pellets were stored at −80° C.

SDS-Page

Proteins were separated on precast Tris-glycine polyacrylamide gels (Bio-Rad or Gradipore) using a Bio-Rad electrophoresis unit, according to the method of Laemmli (1970). All protein samples were diluted with 4× Sample buffer (1×=62 mM Tris-HCl pH 6.8, 10% glycerol, 2% SDS, 0.01% bromophenol blue) and for those samples analyzed under reducing conditions, (β-mercaptoethanol was added to a final concentration of 2.5% (unless otherwise indicated). The samples and molecular weight markers (Bio-Rad LMW) were heated at 100° C. for 4 min, immediately placed on ice to cool and then centrifuged at 13,000×g for 1 min to remove insoluble material. Samples and markers were then loaded onto gels submerged in 1× running buffer (25 mM Tris, 192 mM glycine, 0.1% SDS, pH 8.3) and electrophoresed at 125V for approximately 90 min.

Western Blotting

The transfer of protein from polyacrylamide gels to PVDF membrane was carried out using a Pharmacia NovaBlot electrophoretic transfer kit and Multiphor II electrophoresis unit. The system applied a semi-dry, discontinuous buffer technique using filter paper soaked in electrode buffer and stacked between graphite electrode plates.

In preparation for transfer both the anode and cathode plates were saturated with distilled water and excess water removed with paper towels. Each transfer unit was assembled by placing 6 filter papers soaked in Anode solution 1 (0.3M Tris pH 10.4, 20% v/v methanol) on the anode electrode, then 3 filter papers and the PVDF membrane soaked in Anode solution 2 (25 mM Tris pH 10.4, 20% v/v methanol). Following PAGE, the gel was placed onto the stack and overlaid with 9 filter papers soaked in Cathode solution (4 mM 6-Amino-n-hexanoic acid pH 7.6, 20% v/v methanol). All filter papers and PVDF membrane were pre-cut to gel size. The transfer unit was completed with the addition of the cathode plate and then placed into the Multiphor base. Transfer was performed at 0.8 $mA/cm^2$ gel surface area. Coloured molecular weight markers included on the gel served as a control to confirm successful transfer.

Immunodetection of Western Blots

Following the electrophoretic transfer of protein, PVDF membrane was blocked in PBS/5% SMP solution for 1 hr at RT with shaking. After blocking, the membrane was immersed in primary antibody diluted to an appropriate concentration in PBS/5% SMP and incubated for 2 hrs at RT with shaking. The membrane was then washed 3 times for 10 minutes each wash in PBS/0.03% TWEEN 20. The secondary antibody—alkaline phosphatase conjugated rabbit anti-chicken IgG—was then added at a concentration of 1/1000 in PBS/5% SMP and incubated for 1 hr at RT with shaking. Following secondary antibody incubation, the membrane was washed as previously and detected using BCIP/NET (SIGMA FAST BCIP/NBT tablets).

Preparation of Crude Antigens

Sporulated Oocysts

Potassium dichromate was removed from oocysts by repeated centrifugation at 1500×g for 5 min and water washes. The clean pellets were resuspended in an equal volume of 40 mM Tris.HCl pH 8.0 and protease inhibitors added (Sigma) according to the manufacturer's instructions. The suspension was overlayed with a saturating quantity of glass beads (Sigma) and ruptured by votexing for 5 min. Rupture of the oocysts was confirmed by microscopic examination. The homogenate was then subjected to three cycles of freeze thawing using liquid nitrogen and a 40° C. water bath, followed by centrifugation at 13000×g for 10 min at 4° C. The supernatant was removed, transferred to a microconcentrator (Centricon 100, Amicon) and concentrated by centrifugation at 900×g for 30 min at 4° C. The extract was stored at −80° C.

Merozoites and Gametocytes

Pellets of purified merozoites or gametocytes were resuspended in 40 mM Tris.HCl pH 8.0 containing 10 mM PMSF, and subjected to three cycles of freeze thawing as described above. The suspension was sonicated on ice using a Cole-Parmer Ultrasonic Homogeniser set at 25 W and 70% output for 20 sec, and the resulting homogenate centrifuged at 13000×g for 10 min at 4° C. The supernatant was retained and stored at −80° C.

Protein Concentration Determination

The protein concentrations of all crude antigen extracts and other protein samples used throughout this study were determined using the Bio-Rad Protein Assay kit, based on the Bradford dye-binding, method.

Protein Visualization

Proteins separated by electrophoresis on SDS-polyacrylamide gels were detected by Coomassie Blue or Silver staining. For Coomassie Blue staining, gels were immersed in a solution of 0.2% Coomassie Brilliant Blue R250 (Sigma), 50% methanol and 10% glacial acetic acid for 30 min with shaking. The gels were then destained in 12% Ethanol/7% glacial acetic acid with shaking until the protein bands became visible and the background was almost clear. Silver staining was performed using the Amersham Pharmacia Silver staining kit according to the manufacturer's instructions.

Proteins transferred to PVDF membrane for the purpose of N-termmal sequencing were detected by Coomassie Blue staining. Membranes were stained for 2 min as above and destained until protein bands were visible.

Protein Purification Procedures

Ion Exchange Chromatography

Proteins from crude extracts of sporulated oocysts were separated by DEAE-ion exchange chromatography. Approximately 5 ml of DEAE sephacel (Amersham Pharmacia Biotech) anion exchange resin was added to a lcm (internal diameter) by 20 cm (length), low pressure chromatography column (Econo-column, Bio-Rad), and equilibrated for 2 hrs in 40mM Tris.HCl pH 8.0 at a flow rate of 0.7 ml/min. Crude antigen prepared as described above was clarified by centrifugation at 13000×g for 10 min at 4° C., and applied to the column. Protein elution was subsequently performed with a step gradient of 0-1M NaCl in 40 mM Tris.HCl pH 8.0 at a flow rate of 0.7 ml/min. The eluate was monitored by a Gilson 112 UV/Vis in-line detector set at 280 nm and connected to an Activon Omniscribe series D5000 chart recorder. Fractions were collected manually, corresponding to increasing NaCl concentration. Following elution, all fractions were transferred to Centricon 100 microconcentrators (Amicon) and centrifuged at 900×g for 1 hr at 4° C., yielding retentate volumes of approximately 60 μL. To desalt the fractions, retentates were diluted to a volume of 2 ml with 40 mM Tris.HCl and centrifuged as above. Following concentration/buffer exchange the filtrate was discarded and the retentate stored at −20° C.

Size-Exclusion Chromatography

Following ion exchange chromatography, selected fractions containing the immunodominant protein were further separated by size-exclusion chromatography using a SMART HPLC system fitted with a Superdex 200 PC gel filtration column (Pharmacia Biotech). The column was equilibrated in 40 mM Tris.HCl pH 8.0 for 2 hrs at a flow rate of 50 μL/min. Protein fractions were injected onto the column and eluted at a flow rate as above. The eluate was monitored using the SMART system software at dual wavelengths of 280 nm and 214 nm, and 100 μL fractions were collected automatically over the course of the elution period.

N-Terminal Sequencing

Crude extracts of sporulated oocysts were purified by ion exchange chromatography as described, and fractions enriched for the immunodominant protein were pooled and concentrated by centrifugal ultrafiltration to a volume of 60 μL. Sample aliquots of 19 μL were applied to 3 adjacent wells of a 5% SDS-polyacrylamide gel, and a 3 μL aliquot applied to a 4th well. Following electrophoresis under reducing conditions, the separated proteins were transferred to PVDF by Western blotting. A strip of PVDF containing the protein from the 3 μL sample aliquot was then cut from the membrane and immunodetected with anti-crude merozoite serum to serve as a control for the visualisation of the immunodominant protein. The remaining membrane piece was stained with Coomassie Blue as described, and membrane bands containing the immunodominant protein were excised with a scalpel blade. Membrane pieces were stored at −20° C. prior to sequencing. Automated Edman degradation of protein, samples was subsequently carried out using an Applied Biosystems 494 Procise Protein Sequencing System at the Australian Proteome Analysis Facility (Sydney) and at Biotech Australia Pty. Ltd. (Sydney).

Tryptic Peptide Sequencing

Concentrated ion exchange chromatography fractions containing the immunodominant protein were separated under reducing conditions on a 5% SDS-polyacrylamide gel as above. Following electrophoresis the gel was stained with Coomassie Blue and the region of the gel containing the immunodominant protein excised with a scalpel blade. Gel pieces were immediately transported to the Australian Proteome Analysis Facility and the sample subjected to a 16 hr tryptic digest at 37° C., followed by concentration and desalting of the resulting peptides using a ZipTip. The sample peptides were then separated and selected peptides analysed by ESI-TOF MS/MS using a Micromass Q-TOF mass spectrometer.

Triton X-114 Fractionation

Purified merozoites were fractionated in the nonionic detergent Triton X-114 based on the method of Bordier (1981). Approximately $10^7$ purified merozoites were resuspended in 250 μL of a solution of 0.5% TX-114 in PBS containing 10 mM PMSF and 0.002% bromophenol blue. Following incubation on ice for 30 min, the suspension was centrifuged at 13000×g for 10 min, separating into a detergent insoluble pellet and a TX-114 supernatant. The supernatant fraction was transferred onto a sucrose cushion containing 6% sucrose and 0.06% TX-114 in PBS, and incubated at 37° C. for 3 min. The sample was then centrifuged at 13000×g for 3 min at RT, forcing separation into an upper aqueous phase and a lower, detergent rich phase. The aqueous phase was removed and the detergent phase diluted in ice cold PBS to the original lysate volume of 250 μL. The aqueous and detergent phases and the detergent insoluble pellet were kept on ice until separated by SDS-PAGE.

RNA Extraction

Total RNA was isolated from sporulated oocysts using TRIzol® Reagent (Life Technologies) following a procedure adapted from that described by Johnston et al (1998). Approximately $2.5\times10^7$ clean sporulated oocysts were pelleted in a 10 mL polypropylene tube by centrifugation at 1500×g for 5 min. An equal volume of glass beads (Sigma) and 1 mL of icecold PBS pH 7.4 were added to the pellet, and the mixture vortexed for 4×1 periods at 4° C., alternating with 1 min incubations on ice. The resulting homogenate was transferred to a sterile 10 mL tube and an equal volume (3.75 mL) of TRIzol reagent added. The solution was mixed by inversion and incubated at RT for 5 min to allow for the complete dissociation of nucleotide complexes. In order to remove insoluble material (i.e. sporocyst and oocyst shells) the suspension was then centrifuged at 11,000×g for 10 min at 4° C. The supernatant was removed, transferred to a sterile 10 mL tube and 0.75 mL of chloroform added (2 mL of chloroform per 1 mL of TRIzol® Reagent). Following vigorous shaking for 15 sec, the mixture was incubated at RT for 3 min and then centrifuged at 10,000×g for 15 min at 4° C. to force separation into a lower phenol-chloroform phase and an upper aqueous phase containing the purified RNA. The aqueous phase was transferred to a sterile 10 mL tube, 1.875 mL of isopropanol (0.5 mL per 1 mL of TRIzol® Reagent) added to precipitate the RNA, and the solution mixed by inversion. Following incubation for 10 min at RT, the RNA was pelleted by centrifugation at 11,000×g for 10 min at 4° C. The supernatant was removed and the pellet washed in 4 mL of 75% EtOH by briefly vortexing. The pellet was recovered by further centrifugation at 7,000×g for 5 min at 4° C., and, following removal of the 75% EtOH, was briefly dried in a vacuum hood for 10 min. The partially dried pellet was then resuspended in 200 μL of DEPC treated ddH2O, and stored at −80° C.

Poly(A)+ RNA was purified from total RNA of sporulated oocysts, or directly from merozoites and gametocytes using a Dynabeads® mRNA DIRECT kit (DYNAL Pty. Ltd.) with minor changes to the manufacturer's instructions. Briefly, total RNA from sporulated oocysts, or pellets of merozoites or gametocytes were mixed with Lysis/binding buffer (Dynal) and combined with Dynabeads® Oligo $(dT)_{25}$ magnetic polystyrene beads in a 1.5 mL sterile polypropylene tube. The suspension was mixed by gentle inversion for 4 min and the tube then placed in the Dynal magnetic particle concentrator (MPC) for 2 min. The supernatant was removed and the beads washed in Wash buffer A (Dynal) by repeated pipetting, before concentration in the MPC for 1 min. The wash procedure was repeated a second time with Wash buffer A and twice with Wash buffer B (Dynal). Following the final wash, mRNA was eluted from the beads by the addition of 10 mM Tris-HCl pH 8.0 and heating at 65° C. for 2 min. The tube was then transferred to the MPC for 1 min and the supernatant containing mRNA tranferred to a sterile 1.5 mL tube before storage at −80° C.

Nucleic Acid Concentration and Purity Determination

The concentrations of purified DNA or RNA samples used throughout this study were determined using a Pharmacia GeneQuant spectrophotometer to measure absorbance at 260 nm. The purity of samples was assessed by measurement of $A_{260/280}$ ratios, accepting samples with ratios between 1.6-2.0.

EtOH Precipitation of Nucleic Acids

Dilute solutions of DNA or RNA were routinely concentrated by EtOH precipitation. To each sample, 0.1 volume of 3M sodium acetate pH 5.2 and 2.5 volumes of EtOH were added and the solution mixed by inversion. Following incubation on ice for 30 min, the sample was centrifuged at 13,000×g for 45 min at 4° C. and the supernatant subsequently removed and discarded. The pellet was washed with 70% EtOH and recovered by further centrifugation at 13,000×g for 5 min. at 4° C. Pellets were dried in a vacuum hood and resuspended in a suitable volume of either $ddH_2O$ for DNA samples (non-genomic), or DEPC treated $ddH_2O$ for RNA samples.

cDNA Library Construction

Messenger RNA of sporulated oocysts of *E. maxima* was isolated from total RNA as described. An estimated 1 μg of mRNA was used with a Marathon™ cDNA Amplification Kit (CLONTECH), to prepare a library of adaptor-ligated, RACE PCR ready double-stranded cDNA. No changes in procedure were made to the manufacturer's instructions. The library was stored at −20° C.

PCR

PCR reactions were carried out using a PTC-200 Peltier Thermal Cycler DNA Engine (MJ Research). All reactions were of 50 μL volume using 1 μL of 50× Advantage 2 Polymerase Mix (CLONTECH)—a high fidelity polymerase mixture recommended for use with the Marathon™ cDNA Amplification Kit (CLONTECH). Oligonucleotide primers were synthesised by Sigma Genosys Australia Pty. Ltd., and 10 μM working stocks were prepared and used at a concentration of 0.2 μM for gene-specefic primers, or 0.4 μM for degenerate primers. For reactions employing cDNA as template, 5 μL of cDNA equivalent to approximately 0.5 ng was used per reaction, and with genomic DNA template, 5 μL of a 10 ng/μL working stock. Second round or nested PCR experiments employed 1 μL of a first round PCR reaction or gel-purified PCR product as template, while reactions involving amplification from plasmid DNA used 1 μL of a standard Miniprep (SIGMA) preparation equivalent to approximately 5-10 ng. For the amplification of products with an expected size less than 5 kb, 5 μL of 2 mM dNTP solution (Biotech International Ltd.) was added per reaction, and increased to 10 μL for the amplification of products larger than 5 kb. All reactions contained 5 μL of 10× Advantage 2 PCR Buffer (CLONTECH) and sterile $ddH_2O$ to 50 μL. Cycling parameters using both touchdown and conventional PCR were modified for optimal amplification from programmes recommended in the Marathon™ cDNA Amplification Kit User Manual (CLONTECH).

PCR Purification

Prior to direct sequencing or ligation into sequencing or expression vectors, PCR products were cleaned using a QIAquick PCR Purification Kit (QIAGEN, U.S.A.) according to the manufacturer's instructions. Clean DNA was routinely recovered in 30 μL of sterile $ddH_2O$ and stored at −20° C.

Gel Extraction

PCR products were regularly gel-purified to provide template for second round or nested PCR reactions, or in some instances prior to direct sequencing. Products were separated by agarose gel electrophoresis and appropriate DNA fragments were excised with a clean scalpel blade. DNA was purified from gel slices using a QIAquick® Gel Extraction Kit (QIAGEN) according to the manufacturer's instructions, and routinely recovered in 30 μL of sterile $ddH_2O$. The purified DNA was stored at −20° C.

Ligation

For purposes of sequencing, PCR products were cloned into the PGEM®-T Easy vector (Promega). Amplified DNA was purified as described and 8.5 μL added to a ligation mix containing 0.5 μL of pGEM®-T Easy vector, 10 μL of 2× Ligation buffer, and 1 μL of T4 Ligase. The solution was mixed by pipetting and incubated O/N at 4° C. prior to transformation into competent cells.

The vector pTrcHis B (Invitrogen®) was used for expression studies and the development of expression constructs is described in detail below. Purified insert DNA (7 μL) encoding the polypeptide to be expressed was added to a ligation mix containing 2 μL of digested pTrcHis B vector, 10 μL of 2× Ligation buffer and 1 μL of T4 Ligase (Promega). Vector only control ligations were also prepared as above, but with $ddH_2O$ replacing insert DNA. The ligation reactions were mixed by pipetting and incubated at 4° C. O/N.

Competent Cell Preparation

From frozen glycerol stocks of either DH5-α or TOP10 *E. coli* strains, a small portion was streaked on a LB media plate and incubated O/N at 4° C. The next day, a single colony was selected, transferred to 100 mL of SOB media and incubated at 37° C. in a rotary shaker set to 200 rpm. After the culture reached an $OD_{600}$ of approximately 0.5, the cells were collected by centrifugation at 2,500×g for 10 min at 4° C. and resuspended in 10 mL of ice-cold 50 mM $CaCl_2$. The cells were kept on ice for 30 min, centrifuged at 2,500×g for 5 min at 4° C., and gently resupended in 4 mL of ice-cold 50 mM $CaCl_2$. Following incubation on ice for 1 hr, the competent cells were divided into 90 μL aliquots and stored at −80° C.

Transformation

Aliquots of competent cells (90 μL) were routinely transformed with either 10 μL of a 20 μL ligation reaction, or 1 μL (approximately 5-10 ng) of plasmid from a standard Miniprep (Sigma) plasmid preparation. Following gentle mixing, the solution was incubated on ice for 20 min, heat shocked in a water bath at 42° C. for 90 sec and returned to ice for 1 min. SOC media (900 μL) was then added and the solution mixed by inversion before incubation at 37° C. for 1 hr in a rotary shaker set at 200 rpm. Appropriate amounts of the mixture were then plated onto LB plates containing 100 μg/mL ampicillin, and incubated O/N at 37° C. For the transformation of recombinant plasmids derived from the pGEM®-T Easy vector, plates were pre-spread with 20 μL of 50 mg/ml Xgal and 100 μL of 100 mM IPTG to allow for the direct identification of recombinant clones by colour screening. Following O/N incubation, a minimum of three bacterial colonies putatively containing recombinant plasmids were selected, cultured O/N and used for plasmid preparation as described below. The presence and size of DNA inserts was determined by PCR amplification using 1 μL of the plasmid as template with vector or insert specific primers, and subsequent analysis of the products by agarose gel electrophoresis.

Plasmid Preparation

A single bacterial colony was used to inoculate 4 mL of LB media with 100 μg/mL ampicillin, and the culture incubated with shaking (200 rpm) in a rotary shaker at 37° C. O/N. The next day plasmid was harvested from 1.5 mL of the O/N culture using a GenElute™ Plasmid Miniprep Kit (Sigma) according to the manufacturers instructions. Purified plasmid was recovered in 100 μL of sterile $ddH_2O$ and stored at −20° C.

DNA Sequencing

DNA sequencing was carried out at the Sydney University Prince Alfred Macromolecular Analysis Centre (SUPAMAC, Sydney) using dideoxy dye-terminator chemistry and ABI automated sequencers. Approximately 10 ng per 300 bp of purified PCR product, or 3 μg of plasmid were provided per reaction in a cocktail with 20 μmol of the appropriate primer and $ddH_2O$ to a final volume of 16 μL.

DNA for sequencing was regularly generated by PCR using plasmid template with vector or gene-specific primers. For the amplification of PCR products cloned into the pGEM®-T Easy vector, M13 forward and reverse primers were used with the following programme: 1 min at 94° C.; 30 cycles of 30 s at 94° C., 1 min at 55° C. and 3 min at 72° C. Gene-specific primers were designed with high $T_m$s (>72° C.) and were used in amplification with a more stringent programe, similar to the above but employing an annealing temperature of 68° C.

PCR Generation of cDNA Encoding the Immunodominant Protein

3' RACE PCR was carried out using adaptor-ligated double-stranded cDNA with the Marathon™ cDNA Amplification Kit (CLONTECH) Adaptor Primer 1 (AP1), and degenerate primers designed from the protein sequences for the N-terminus and tryptic peptides of the immunodominant protein. RACE products were generated with the following touchdown program: 1 min at 94° C.; 5 cycles of 30 s at 94° C. and 3 min at 65° C.; 5 cycles of 30 s at 94° C., 30 s at 60° C. and 3 min at 72° C.; 35 cycles of 30 s at 94° C., 1 min at 55° C. and 3 min at 72° C. Aliquots (10 μL) of the reactions were separated by agarose gel electrophoresis and appropriate bands were excised, purified and cloned into pGEM®-T Easy as described.

From the sequences of 3' RACE products, gene-specific primers were designed and used with degenerate primers based on the N-terminus protein sequence, to amplify an intermediate DNA fragment (between 5' and 3' ends) from cDNA template. PCR products were generated with the following touchdown programme: 1 min at 94° C.; 5 cycles of 30 s at 94° C., 30 s at 65° C. and 7 min at 72° C.; 5 cycles of 30 s at 94° C., 30 s at 60° C. and 7 min at 72° C.; 35 cycles of 30 s at 94° C., 1 min at 55° C. and 7 min at 72° C. Aliquots (10 μL) of the reactions were separated by agarose gel electrophoresis and appropriate bands were excised and gel-purified. The purified first round DNA was then used as template with nested primers for amplification with the following programme: 1 min at 94° C.; 30 cycles of 30 s at 94° C., 1 min at 55° C. and 8 min at 72° C. Following agarose gel electrophoresis, appropriate PCR products were gel-purified, cloned into pGEM®-T Easy and subsequently sequenced.

5' RACE was carried out using cDNA as template with AP1 and gene-specific primers designed from the 5' region of sequences of putative intermediate DNA fragments. PCR products were generated with the following touchdown programme: 1 min at 94° C.; 5 cycles of 30 s at 94° C. and 4 min at 72° C.; 5 cycles of 30 s at 94° C. and 4 min at 70° C.; 30 cycles of 20 s at 94° C. and 4 min at 68° C. In order to characterise products, 1 μL samples from the 5' RACE reactions were used as template with Nested Adaptor Primer 2 (AP2, CLONTECH) and nested gene-specific primers for amplification with the following programme: 1 min at 94° C.; 30 cycles of 30 s at 94° C., 1 min at 65° C. and 4 min at 72° C. Appropriate PCR products were gel-purified, cloned as described and sequenced.

From the sequence obtained from the 5' and 3' RACE products, gene-specific primers were designed and used with cDNA template to generate a full-length cDNA with the following programme: 1 min at 94° C.; 30 cycles of 20 s at 94° C. and 10 min at 72° C. The DNA product was gel-purified and cloned as above.

Sequencing of Clones Encoding the Immunodominant Protein

Clones containing the cDNA encoding the full mature immunodominant protein were sequenced using a primer-walking strategy, moving downstream from the 5' end and upstream from the 3' end of the cDNA. A minimum of three clones was used to generate a consensus sequence in both forward and reverse directions. The sequence of the extreme 5' and 3' ends of the cDNA was obtained by sequencing the 5' and 3' RACE products.

RT-PCR

Messenger RNAs from purified merozoites and gametocytes were isolated from cell pellets containing approximately $10^6$ parasites and were recovered in 10 μL of 10 mM Tris-HCl pH 8.0. Reverse transcriptions were performed using an Omniscript™ RT Kit (QIAGEN) with 1 μL of each mRNA preparation and primers specific for EmTFP250 and constitutively expressed *E. maxima* HSP70. Sham RT reactions serving as a negative control were also carried out in the absence of reverse transcriptase. All RT reactions were amplified at 37° C. for 1 hr and subsequently used as templates for standard PCR. Gene-specific primers for EmTFP250 were used with 1 μl from each RT reaction and negative controls in amplification with the following programme: 1 min at 94° C.; 30 cycles of 30 s at 94° C. and 4 min at 72° C. In addition the EmTFP250 primers were also used in PCR with 1 μL of a plasmid preparation containing the sporulated oocyst cDNA encoding EmTFP250, and with a no template control using the programme described above. Primers specific for HSP70 were designed with lower $T_m$s and were used with 1 μL from each RT reaction and the following programme: 1 min at 94° C.; 30 cycles of 30 s at 94° C., 1 min at 55° C. and 3 min at 72° C.

Genomic DNA Purification

Cell pellets containing approximately $5\times10^5$ purified gametocytes were gently resuspended in 2 mL of PBS and 40 μL of 10% N-lauryl sarcosine, and incubated at 37° C. for 20 min. DNAse free RNAse (20 μL) was added and the solution incubated for a further 20 min at 37° C., followed by the addition of 20 μL of 20 mg/mL proteinase K and incubation at 37° C. for 30 min. An equal volume of phenol/chloroform/isoamyl-alcohol (25:24:1) was then added and the solution mixed by inversion before centrifugation at 5,000×g for 5 min to force separation into organic and aqueous soluble phases. The aqueous phase containing genomic DNA was removed and the extraction procedure repeated once with phenol/chloroform/isoamyl alcohol as above and once with chloroform/isoamyl-alcohol (24:1). Following the final extraction, the aqueous phase was removed and the DNA EtOH precipitated as described. Pellets of genomic DNA were dried in a vacuum hood for approximately 1 hr and allowed to resuspend in 75 μL T.E. buffer O/N at 4° C. Samples were stored at 4° C.

Restriction Digestion

For the purpose of Southern blotting, genomic DNA from *E. maxima* was digested with a number of restriction enzymes prior to separation by agarose gel electrophoresis. Approximately 2.5 μg of genomic DNA was added to each digestion mix containing 40 U of restriction enzyme (2-4 μL), 10 μL of the appropriate 10× enzyme buffer, and $ddH_2O$ to a final volume of 100 μL. The mixtures were incubated at 37° C. for 2 hr, then EtOH precipitated O/N as described. The following day the dried pellets were resuspended in 20 μL of TE buffer, heated for 5 min at 65° C. and briefly vortexed. A further 10 U of the appropriate restriction enzyme (0.5-1 μL), 5 μL of 10× enzyme buffer and TE buffer to 25 μL were added, and the mixtures incubated for 1 hr at 37° C. To assess the degree of digestion, 2 μL of each sample was separated on a 0.8% agarose gel. Samples that produced a visibly uniform smear from approximately 23 kb to 1 kb were accepted for further analysis.

In the development of expression constructs, PCR amplified insert DNA and vector DNA were double digested with Bam HI and Eco RI restriction enzymes. The mixtures were incubated at 37° C. for 1 hr prior to analysis by agarose gel electrophoresis and subsequent gel purification.

Southern Blotting

Restriction enzyme-digested genomic DNA or PCR products were separated by agarose gel electrophoresis as described. Following staining with EtBr and subsequent photography, gels were submerged in a solution of 0.5M NaCl and 0.5M NaOH for 20 min to denature the DNA, then rinsed in $ddH_2O$ before neutralisation for 20 min in a solution of 2.5M NaCl and 0.5M Tris-Cl pH 7.4. After rinsing the gels in $ddH_2O$, the DNA was tranferred by capilliary action to Hybond-$N^+$ nucleic acid transfer membrane (Amersham) using standard procedures (Sambrook). Following O/N transfer, each membrane was allowed to air dry for 10 min and then baked in a vacuum oven at 80° C. for 1 hr. Membranes were stored in heat-sealed plastic bags prior to hybridisation with radio-labelled DNA probes.

DNA Probe Preparation

A 1590 bp DNA fragment from the 5' region of the cDNA encoding EmTFP250 was used to generate a probe for the detection of restriction enzyme-digested *E. maxima* genomic DNA. Probe DNA was amplified with EmTFP250 gene-specific primers and EmTFP250 plasmid using the following programme: 1 min at 94° C.; 30 cycles of 30 s at 94° C., 1 min at 68° C. and 3 min at 72° C. Degenerate PCR primers designed on EmTFP250/EtMIC4 DNA sequence homology were used to generate a 622 bp probe for the detection of PCR products amplified from genomic DNA from Australian *Eimeria* strains. The probe DNA was amplified from *E. maxima* genomic DNA using the following touchdown programme: 1 min at 94° C.; 5 cycles of 30 s at 94° C., 30 s at 70° C. and 3 min at 72° C.; 5 cycles of 30 s at 94° C., 30 s at 65° C. and 3 min at 72° C.; 30 cycles of 30 s at 94° C., 1 min at 60° C. and 3 min at 72° C.

The PCR amplified probe DNA was purified as described and approximately 25 ng was labelled with $^{32}P$-dCTP using a Random Primed DNA Labelling Kit (Roche) according to the manufacturer's instructions. The specific activity of probes was determined by TCA precipitation following the method of Sambrook, and probes with an incorporation greater than 75% were accepted for use.

Hybridisation

Each nylon membrane was placed in an appropriate size hybridisation tube (Hybaid) and hybridisation solution preheated to 65° C. was added. Following prehybridisation for 2 hr at 65° C. the solution was replaced with fresh hybridisation solution pre-heated to 65° C. The radiolabelled DNA probe was denatured by heating at 100° C. for 10 min then added to the hybridisation tube and allowed to hybridise for between 16-20 hr at 65° C. After hybridisation the membrane was removed and subjected to 2×30 min washes in 2×SSC and 0.1% SDS at 65° C., followed by 2×30 min washes in 0.1% SSC and 0.1% SDS at 65° C. The membrane was then blotted with 3 mM paper to remove excess moisture, covered in plastic wrap and placed in a film cassette containing intensifying screens on both sides. Following exposure to x-ray film for a suitable period the film was developed using standard procedures.

Examination of Genomic Organisation by PCR

A series of primer pairs specific for the cDNA encoding EmTFP250 were used to amplify the corresponding fragments from plasmid containing EmTFP250 cDNA and from *E. maxima* genomic DNA. The following high stringency programme was employed: 1 min at 94° C.; 30 cycles of 20 s at 94° C. and 4 min at 72° C. PCR products were analysed by agarose gel electrophoresis and appropriate bands were sequenced in order to confirm the presence of introns.

Detection of EmTFP250 Homologues in Australian Strains of *Eimeria* by PCR and Southern Hybridisation A pair of degenerate PCR primers designed on sequence homology between EmTFP250 and EtMIC4 were used in amplification with genomic DNA isolated from Australian strains of the seven species of *Eimeria* parasitic in chickens. Approximately 50 ng of DNA from each strain was used with the following touchdown PCR programme: 1 min at 94° C.; 5 cycles of 30 s at 94° C., 30 s at 70° C. and 3 min at 72° C.; 5 cycles of 30 s at 94° C., 30 s at 65° C. and 3 min at 72° C.; 30 cycles of 30 s at 94° C., 1 min at 60° C. and 3 min at 72° C. A 10 μL sample from each reaction was separated on a 0.8% agarose gel, subsequently stained and photographed and then transferred to nylon membrane by Southern blotting. A DNA probe was generated from *E. maxima* Houghton strain genomic DNA as described using the degenerate primer pair as above, and hybridised to the transferred DNA. Following hybridisation and washing procedures, the membrane was exposed to x-ray film for periods of 10 and 30 min.

Protective maternal antibodies induced by the deliberate infection of hens with *Eimeria maxima* were shown by Western blot analyses to consistently recognise a high molecular weight, asexual stage protein in crude extracts of *E. maxima*. Furthermore, immunization with an emulsified SDS-PAGE cutout of the immunodominant protein was found to induce significant protection in chicks subsequently challenged with *E. maxima*. (Smith et al, 1994).

In light of the preliminary investigations suggesting a protective potential for the imuunodominant protein, the aims of the work presented below were two-fold: (1) to partially purify the immunodominant protein in order to obtain N-terminal and peptide sequence data for downstream application in cDNA cloning and; (2) to use antisera recognising the protein to provide fundamental information on its biochemistry, as well as an insight into its stage development and conservation across various strains and species of *Eimeria*.

Results

Immunodetection of Crude Antigens

Approximately 5 μg samples of crude sporulated oocyst extract were loaded onto separate wells of a 5% resolving polyacrylamide gel (Bio-Rad), electrophoresed and transferred to PVDF. Following transfer the PVDF was cut into strips and individual strips detected with a range of chicken sera and yolk collected during previous maternal immunisation trials (Smith et al, 1995). Sera were used at a dilution of 1/100 and yolk at 1/500.

Figure 9:
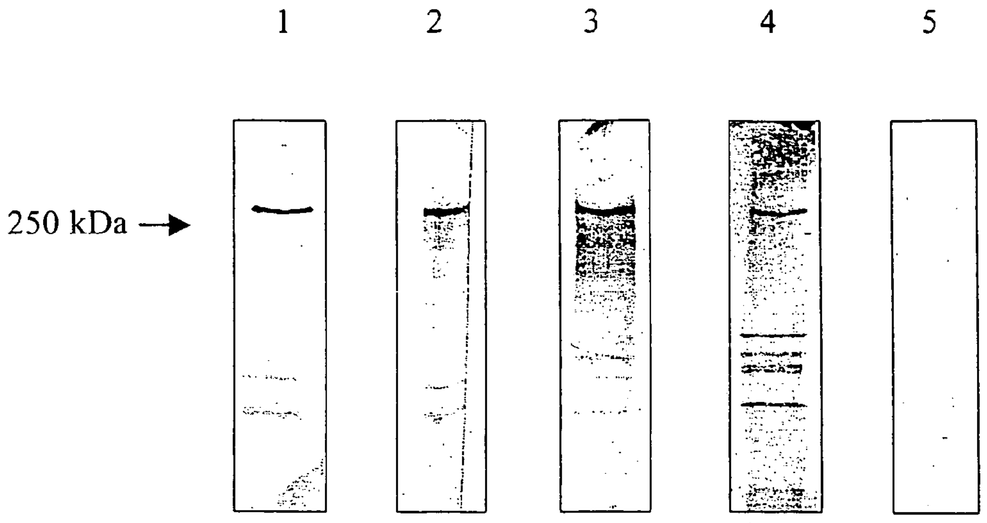
FIG. 9 Western blot analysis of crude sporulated oocyst extract of *E. maxima* separated on a 5% polyacrylamide gel, using selected sera and yolk from maternal immunisation trials (Smith et al, 1995). Lane 1, serum from 3-day-old hatchlingts of hens infected with *E. maxima*; Lane 2, serum from 12-day-old hatchlings of hens infected with *E. maxima* following infection of hatchlings with *E. maxima*; Lane 3, serum from hens immunised with crude merozoite extract; Lane 4, yolk from hens immunised with SDS-PAGE cutout of the 250 kDa merozoite protein band; Lane 5, serum from uninfected control group.

The selected immune sera used to analyze the strips shown in FIG. 9, were harvested from 3-day-old hatchlings of hens infected with *E. maxima* (lane 1), like 12-day-old hatchlings challenged with *E. maxima* (lane 2), and hens immunized with crude merozoite extract of *E. maxima* (lane 3). All predominantly detected a protein band with an apparent molecular weight greater then 230 kDa. Analysis with a yolk sample derived from the 230 kDa band merozoite cutout experiment also reacted with a band of the same size although not as strongly (lane 4). Control chicken serum from uninfected birds did not react with the extract (lane 5).

Purification of the Immunodominant Protein

Ion Exchange Chromatography

Figure 10:
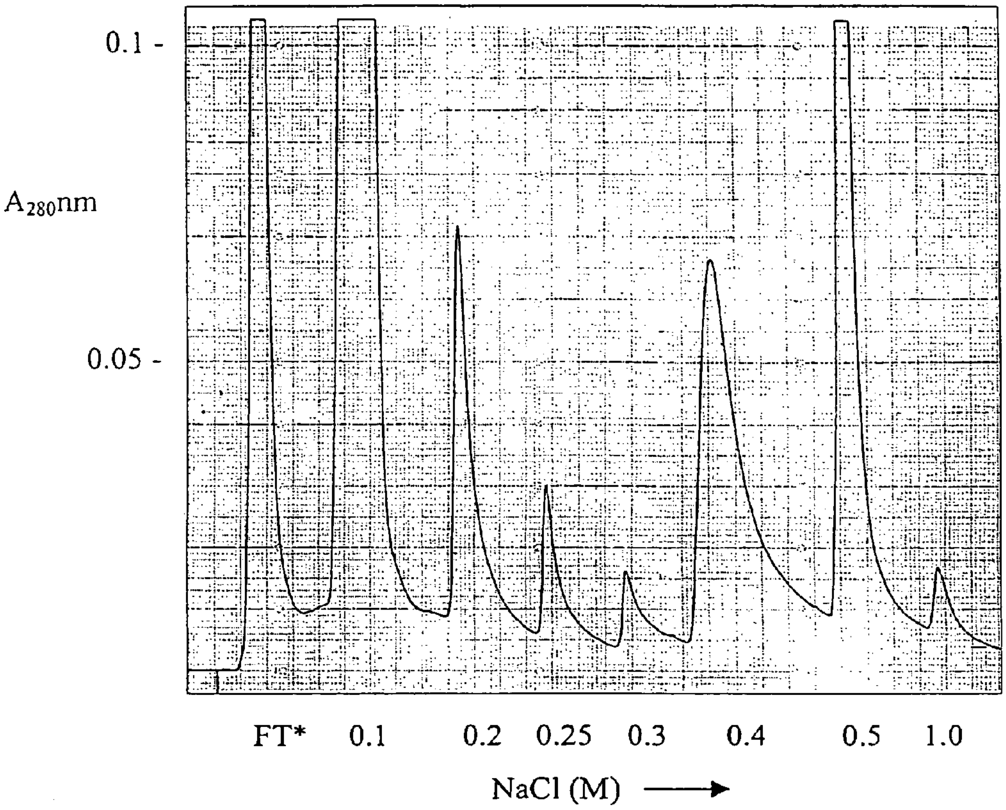
FIG. 10 DEAE-ion exchange chromatography of crude sporulated oocyst extract of *E. maxima*. Approximately 11.0 mg of extract was added to the column and eluted with a step gradient of 0.0-1 M NaCL in 40 mM Tris. HCL pH 8.0, at a flow rate of 0.7 mL/min. Fractions were collected manually and fraction sizes were between 10-15 mL.

Approximately 1.5 mg of crude sporulated oocysts antigen was applied to a DEAE sephacel ion exchange column as described. Fractions were collected manually corresponding to $A_{280}$ nm absorbtion peaks representing elution with increasing NaCl concentration (FIG. 10).

Figure 11A:
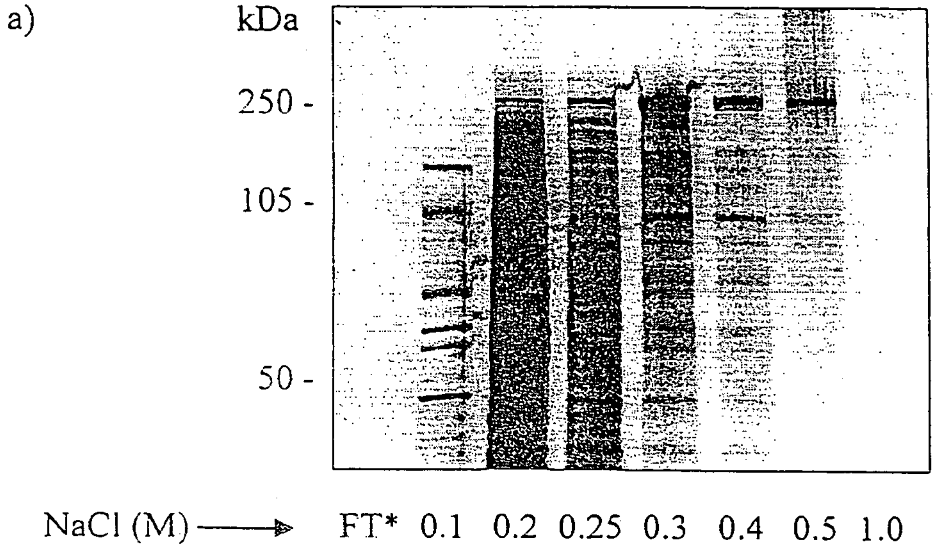
FIG. 11 Silver staining (a) and Western blot analysis (b) of ion exchange fractionated sporulated oocyst extract of *E. maxima*. 15 μL of each fraction was loaded onto parallel 7.5% SDS-PAGE gels and electrophoresed under reducing conditions. The western blot was immunodetected with serum from hens immunised with crude merozoite extract. (*Column flow-through (unbound protein fraction).)
Figure 11B:
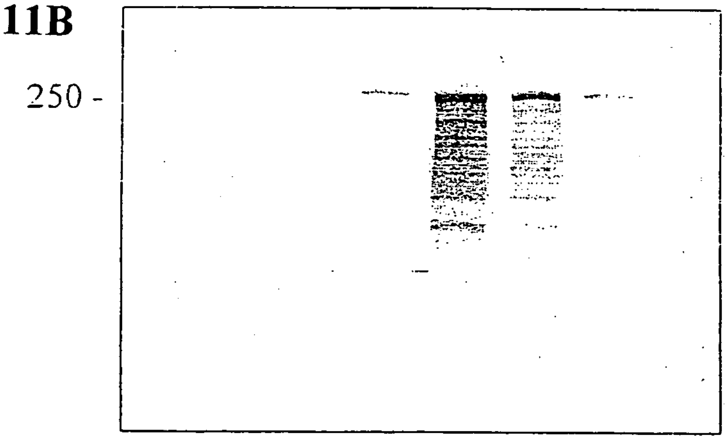

All fractions were concentrated by centrifugal ultrafiltration yielding a retentate volume for each of approximately 60 μL. From each fraction, 15 μL of retentate was loaded onto parallel 7.5% SDS-PAGE gels (Bio-Rad) and electrophoresed under reducing conditions. Following electrophoresis, one of the gels was subjected to silver staining (FIG. 11.A) while the second gel was Western blotted and the transferred protein detected with serum from hens infected with crude merozoite extract (FIG. 11.B). The serum sample was used at a dilution of 1/100 in PBS.

As can be seen both by silver staining and immunoblotting, the immunodominant protein migrating with an apparent molecular weight greater than 230 kDa, appeared predominantly in those fractions eluted with 0.3-0.5M NaCl. The majority of contaminating, smaller molecular weight proteins were eluted in the preceding fractions as visualised by silver staining, or presumably removed during the course of ultrafitration.

Figure 12A:
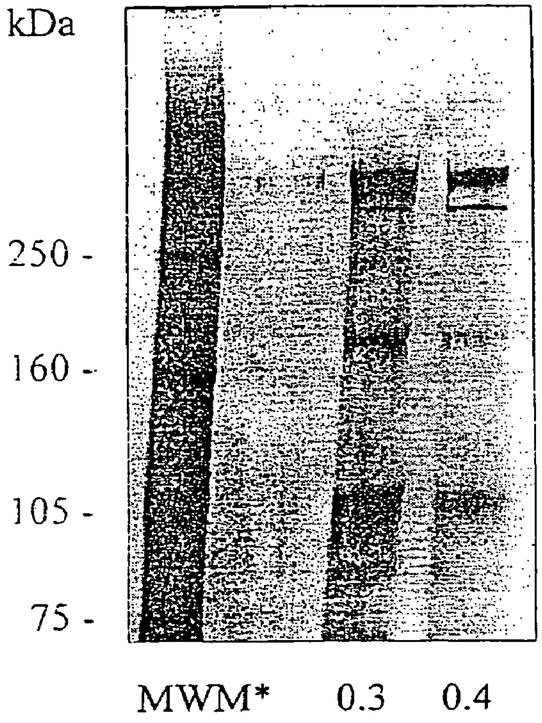
FIG. 12 Silver staining (a) and Western blot analysis (b) of ion exchange chromatography fractions enriched for the immunodominant protein and electrophoresed on 5% SDS-PAGE gels under reducing conditions. The Western blot was immunodetected with protective maternal antiserum harvested from 12-day-old hatchlings of hens infected with *E. maxima* following infection of hatchlings with *E. maxima* following infection of hatchlings with *E. maxima*. (*Molecular weight markers (2 μL))
Figure 12B:
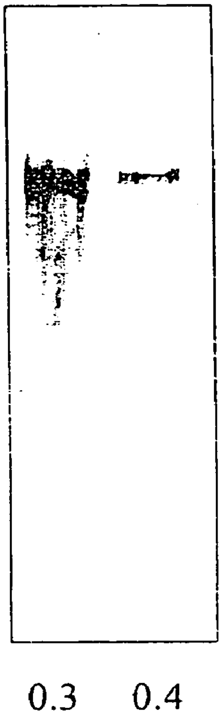

In order to further resolve the partially purified fractions containing the immunodominant protein, 15 μL each of those fractions eluted with 0.3-0.4M NaCl was loaded onto parallel 5% SDS-PAGE gels (Bio-Rad). Following electrophoresis one of the gels was silver stained (FIG. 12 A) and the other Western blotted (FIG. 12 B). The transferred protein was immonodetected with serum harvested from 12-day-old hatchlings of hens infected with *E. maxima*, following challenge of the hatchlings with *E. maxima*. Serum was used at a dilution of 1/100.

In those fractions enriched for the immunodominant protein and separated by 5% SDS-PAGE, the protein appears as an individual band migrating above 250 kDa and resolved from contaminating, co-migrating proteins (FIG. 12 A). Serum associated with maternal immunity reacted strongly with the high molecular weight protein band (FIG. 12 B).

Size-Exclusion Chromatography

Figure 13:
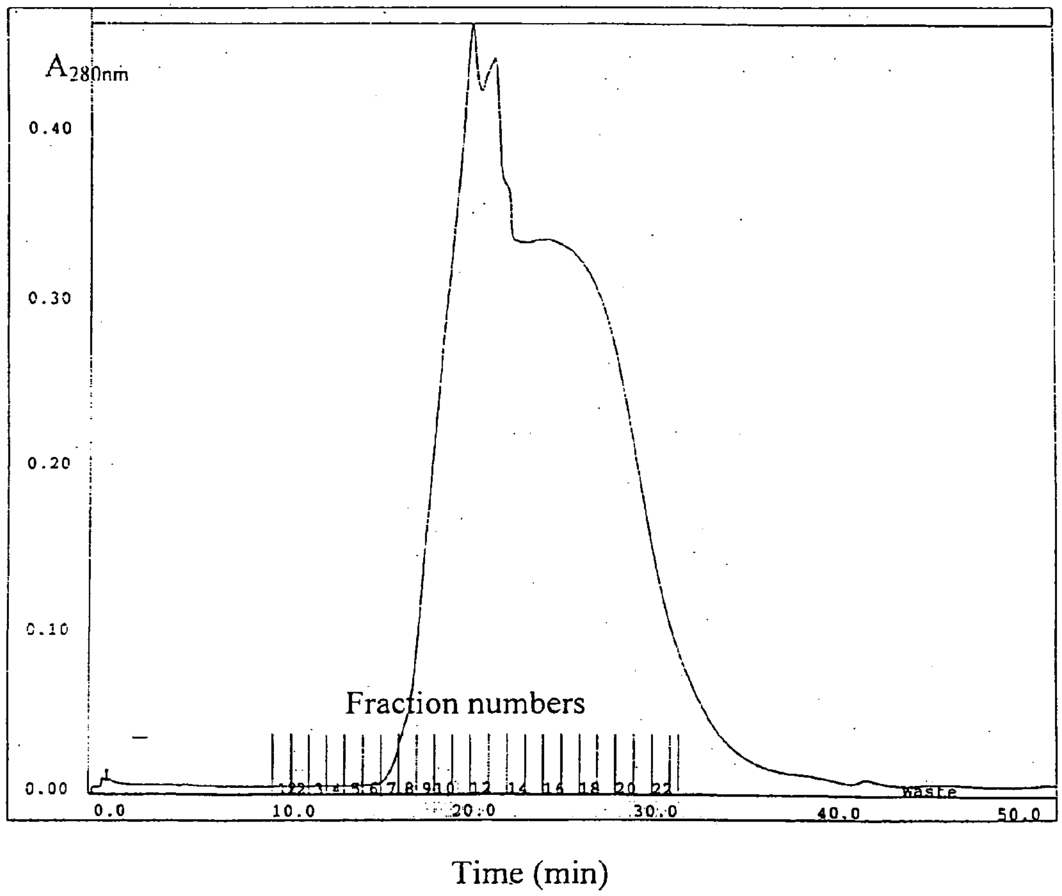
FIG. 13 Superdex 200 gel filtration chromatography of ion exchange chromatography fractions enriched for the immunodominant protein. IEX fractions eluted with 0.3-0.4M NaCL from 10 mg of crude sporulated oocyst extract were pooled and concentrated to a sample volume of 15 mL. The sample was applied to the column and eluded at a flow rate of 50 μL/min. Fractions of size 50 μL were collected automatically as indicated.

Approximately 10 mg of crude sporulated oocyst extract was separated by IEX chromatography and the collected fractions concentrated as above. Fractions eluted with 0.3-0.4M NaCl were pooled and the sample volume reduced to 15 μL by vacuum centrifugation for 2 hrs. The concentrated sample was injected onto a Superdex 200 PC gel filtration column and protein fractions eluted and collected as described. FIG. 13 shows the $A_{280}$ nm elution profile obtained. From each of fractions 7-15, 5 μL was loaded onto separate wells of a 7.5% SDS-PAGE gel (Bio-Rad) and electrophoresed under reducing conditions. Fractions eluted after fraction 15 were not expected to contain the high molecular weight immunodominant protein and were not analysed. Following electrophoresis the gel was subjected to silver staining (FIG. 14).

Figure 14:
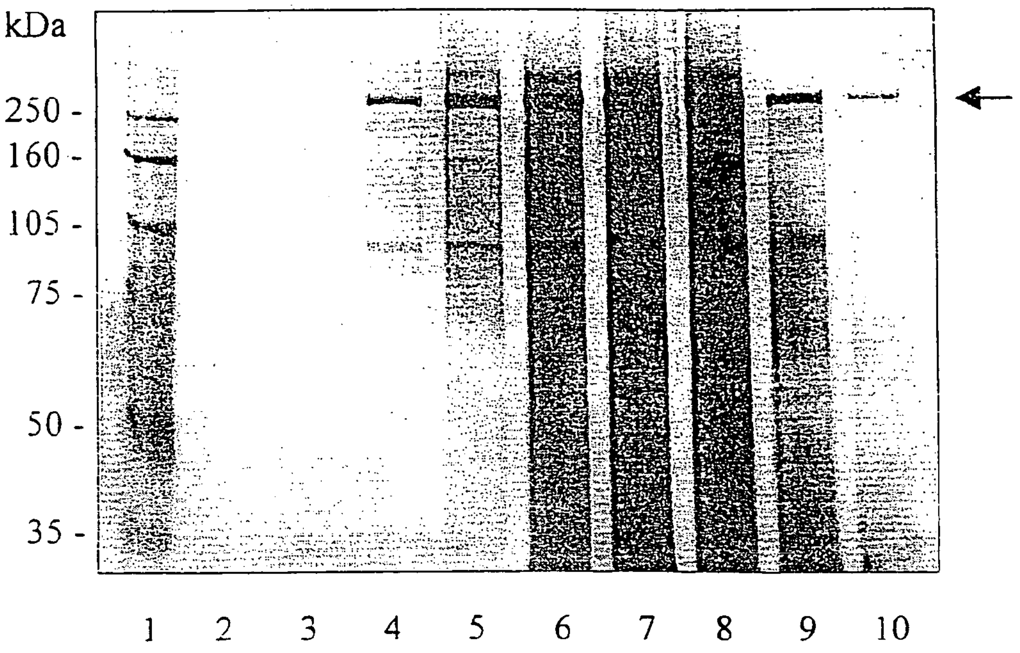
FIG. 14 Silver staining of gel filtration chromatography fractions separated on a 7.5% SDS-polyacrylamide gel. A 10 μL sample from each of fractions 7-15 was electrophoresed under reducing conditions. Lane 1, molecular weight markers (Amersham Rainbow MWM, 2 μL); Lane 2, fraction 7; Lane 3, fraction 8; Lane 4, fraction 9; Lane 5, fraction 10; Lane 6, fraction 11; Lane 7, fraction 12; Lane 8, fraction 13; Lane 9, fraction 14; Lane 10, fraction 15. The arrow indicates the immunodominant protein.

From FIG. 14 it can be seen that the immunodominant protein migrating at above 250 kDa eluted through fractions 7-15. While all fractions appear visibly cleaner than the IEX purified precursor fractions, some lower molecular weight contaminating proteins remained.

Protein Sequencing

N-Terminal Sequencing

Approximately 10 mg of crude sporulated oocyst extract from the Houghton strain of *E. maxima* was purified by ion exchange chromatography, and concentrated fractions enriched for the immunodominant protein were further separated by SDS-PAGE as described. Following transfer of the protein to PVDF and detection by Coomassie Blue staining, membrane pieces containing the immunodominant protein were excised, and the protein sample subsequently sequenced by Edman degradation at the Australian Proteome Analysis Facility. In addition, a protein sample prepared as above and derived from approximately 1.0 mg of crude sporulated extract from an Australian strain of *E. maxima*, was sequenced at Biotech Australia Pty. Ltd.

The results of N-terminal sequencing shown in table 1 indicate that the methods of IEX chromatography, centrifugal ultrafiltration and gel electrophoresis sufficiently purified the immunodominant protein for the purpose of amino terminal analysis. From the Houghton strain sample approximately 13 pmole of protein was available for sequencing, while approximately 1 pmole of the Australian strain sample was present. The sequence for the Houghton strain sample was called to 16 cycles, with a blank at cycle 9 probably indicating a Cysteine residue or a modified amino acid (eg glycosylated) at that cycle. The sequence for the Australian strain was called to 8 cycles, matching identically the first 8 residues predicted for the Houghton strain sequence.

TABLE 1

N-terminal sequencing results for the immunodominant protein isolated from Houghton and Australian strains of *E. maxima*. Sequences are represented using single-letter amino acid symbols, with the N-terminus on the left.

| *E. maxima* strain | N-terminal sequence | SEQ. ID NO. |
|---|---|---|
| Houghton | E V N N E L S K - E S G W T P W | 8 |
| Australian | E V N N E L S K | 42 |

Tryptic Peptide Sequencing

Approximately 10 mg of crude sporulated oocyst extract was purified by IEX chromatography and fractions enriched for the immunodomiant protein were pooled, concentrated by centrifugal ultrafiltration and separated by SDS-PAGE as described. Gel pieces containing the immunodominant protein were then excised from the gel and delivered to the Australian Proteome Analysis Facility for tryptic digestion and subsequent sequence analysis of resulting peptides by mass spectrometry. The procedure was repeated for a second protein sample, similarly derived from approximately 10 mg of crude sporulated oocyst extract.

Predicted sequences were generated for 2 tryptic peptides and are shown in Table 2, however limited confidence was given to the sequences called. Probably due to the structure of the protein, many of the peptides generated were of similar mass making it difficult to separate them and ensure that only single peptides were subjected to MS/MS analysis (Hains, APAF, personal communication). Additionally the technique does not distinguish between Leucine and Isoleucine (shown as [L/I]) due to their identical molecular mass.

TABLE 2

Tryptic peptide sequencing results for the immunodominant protein isolated from the Houghton strain of *E. maxima*. Sequences are represented using single-letter amino acid symbols, with the N-terminus of each peptide on the left.

| Protein sample # | Peptide sequence | SEQ. ID NO. |
|---|---|---|
| 1 | Q W T A W T E | 9 |
| 2 | E [L/I] V N W F | 10 |

Sequence Analysis

The sequences generated for the N-terminus and tryptic peptides of the immunodominant protein were submitted for BLASTP analysis against all non-redundant databases accessed through NCBI. No significant alignments were obtained for the sequences using the Basic BLAST parameters, however an Advanced BLAST search selecting a PAM-30 matrix and E value of 100 for tryptic peptide #1, produced an alignment with microneme protein 4 from *Eimeria tenella* (EtMIC4). Applying the same search against the patent database generated a single alignment with surface antigen 5401 from *E. tenella*—a protein almost identical to EtMIC4. Neither the N-terminal sequence nor tryptic peptide #2 sequence could be aligned to either EtMIC4 or surface antigen 5401 sequences.

Triton X-114 Fractionation

To determine whether the immunodominant asexual stage protein exists largely as a soluble protein within the parasite, or as an integral membrane protein, merozoites of *E. maxima* were fractionated in the detergent TX-114. Approximately $10^7$ merozoites were solubilised and partitioned as described, and aqueous and detergent soluble fractions and a detergent insoluble fraction retained. All fractions were diluted to a volume of 250 μL (equal to the initial cell lysate volume) with $ddH_2O$ and 4×SDS-PAGE reducing sample buffer to a 1× concentration. From each sample, 20 μL was loaded onto separate wells of a 7.5% SDS-PAGE gel (Bio-Rad) and electrophoresed as described. The separated proteins were then transferred to PVDF by Western blotting and detected with anti-crude merozoite serum used at a dilution of 1/100.

Figure 15:
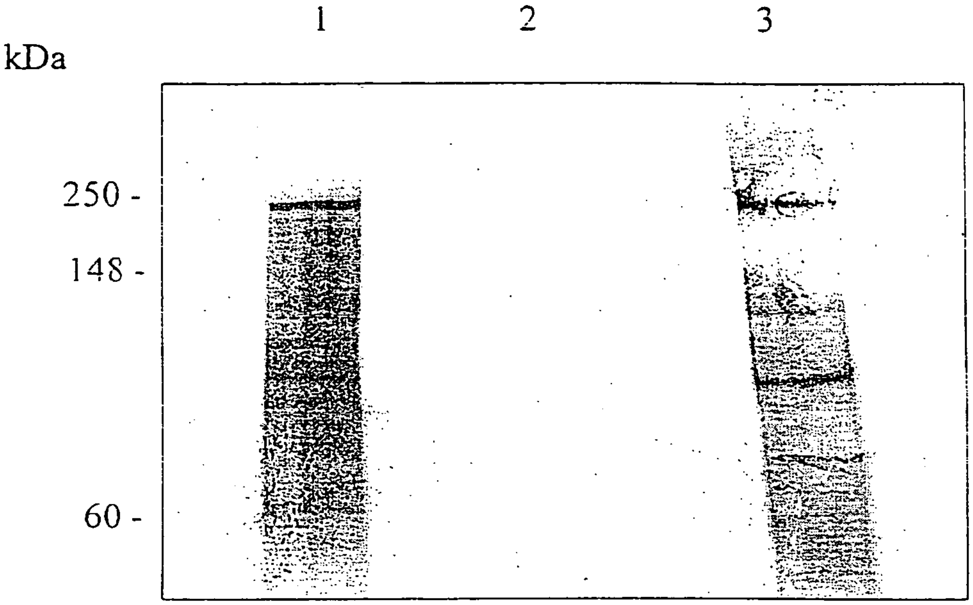
FIG. 15 Western blot analysis of Triton X-114 fractionated merozoites immunodetected with serum from hens immunised with crude *E. maxima* merozoite extract. Purified merozoites were partitioned in the nonionic detergent TX-114 as described. Lane 1, TX-114 aqueous soluble fraction; Lane 2, TX-114 detergent soluble fraction; Lane 3, TX-114 detergent insoluble fraction. (*Column flow-through (unbound protein fraction).)

From FIG. 15, it can be seen that the high molecular weight immunodominant protein partitioned predominantly into the aqueous soluble fraction (lane 1), however a protein band migrating at the same apparent molecular weight is faintly visible in the TX-114 detergent soluble phase (lane 2). Additionally a protein band of the same size is visible in the detergent insoluble fraction (lane 3).

Detection of the Immunodominant Protein Across Developmental Stages

Protein extracts from asexual and sexual stages of development were prepared as described and compared by Western analysis. Approximately 10 μg samples from crude extracts of sporulated oocysts, merozoites and gametocytes were loaded onto adjacent wells of a 7.5% SDS-polyacrylamide gel, electrophoresed under reducing conditions and transferred to PVDF. Following transfer the membrane was immunodetected with serum from hens infected with crude merozoite extract.

Figure 16:
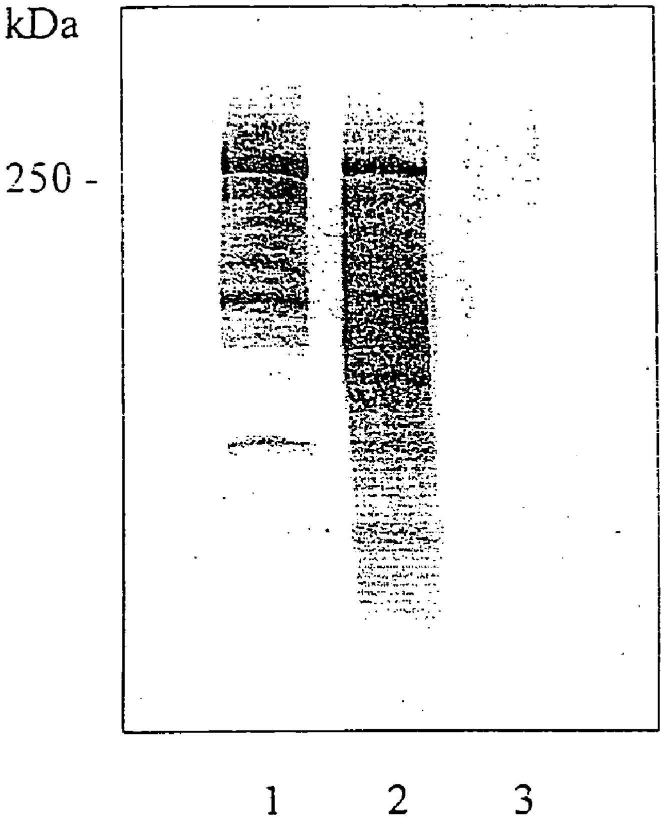
FIG. 16 Western blot analysis of crude antigen extracts of *E. maxima* derived from asexual and sexual developmental stages. A 10 μg sample of each extract prepared as described was eletcrophoresed on a 7.5% SDS-polyacrylamide gel under reducing conditions. Lane 1, sporulated oocyst extract; Lane 2, merozoite extract; Lane 3, gametocyte extract. The Western blot was immunodetected using serum from hens infected with crude merozoite extract.

As can be seen in FIG. 16, the immunodominant protein was detected in the sporulated oocyst and merozoite extracts (lanes 1 and 2), but was not visible in the crude gametocyte extract (lane 3). The results are consistent with earlier findings (Smith, 1994) and indicate that the immunodominant protein is confined to the asexual stages of development.

Detection of the Immunodominant Protein Across Strains and Species of *Eimeria*

In order to examine conservation of the immunodominant protein, crude sporulated oocyst extracts from the Houghton and Australian strains of *E. maxima*, and from an Australian strain of *E. tenella* were compared by immunoblot analysis using serum from hens infected with crude merozoite extract. Approximately 10 μg of each extract was separated on 7.5% SDS-polyacrylamide gels under reducing conditions, tranferred to PVDF and immunodetected as described.

Figure 17A:
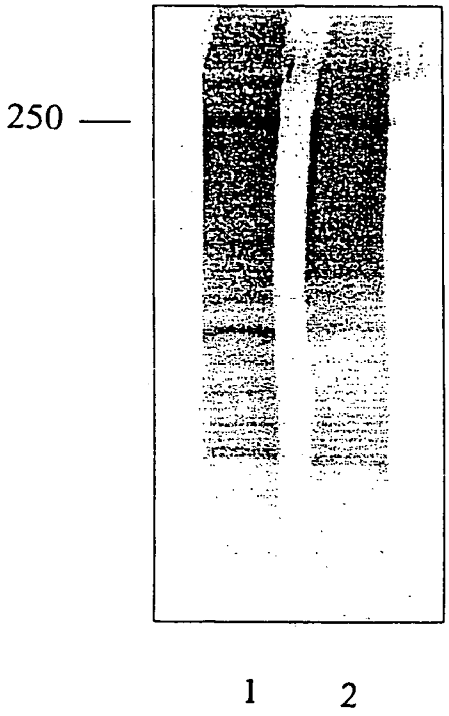
FIG. 17 Western blot analysis of crude sporulated oocyst extracts of the Houghton strain of *E. maxima* and Australian strains of *E. maxima* and *E. tenella*, immunodetected with serum from hens infected with crude merozoite extract from the Houghton strain of *E. maxima*. A 10 μg sample of each extract was applied to 7.5% SDS-polyacrylamide gels and eletrophoresed under reducing conditions. A, Lane 1, Houghton *E. maxima*; Lane 2, Australian *E. maxima*. B, Lane 1, Australian *E. maxima*; Lane 2, Australian *E. tenella.*
Figure 17B:
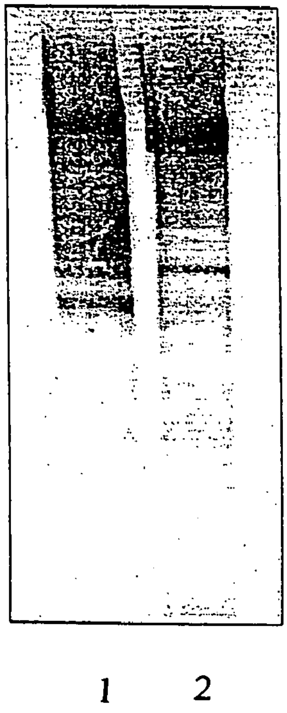

From FIG. 17, the immunodominant protein migrating at approximately 250 kDa was observed in the Houghton strain (A, lane 1) and Australian strain (A, lane 2; B, lane 1) of extracts from *E. maxima*. Additionally the serum predominantly detected a high molecular weight protein band in the Australian *E. tenella* strain extract (B, lane 2), migrating slightly faster than the immunodominant protein band visible in the *E. maxima* extracts. The results suggest a degree of conservation for the immunodominant protein across strains and species of *Eimeria* and imply a functional significance.

SDS-PAGE Characterisation

Samples of protein enriched for the high molecular weight immunodominant protein were analysed by SDS-PAGE under reducing and non-reducing conditions. Approximately 1.2 mg of crude sporulated oocyst antigen was purified by ion-exchange chromatography as described and fractions containing the immunodominant protein (0.3 and 0.4M NaCl fractions) were pooled and concentrated to a volume of 60 μL. Aliquots (8 μL) from those fractions were loaded onto 7.5% (FIG. 18.A) and 5% (FIG. 18.B) PAGE gels (Bio-Rad) and electrophoresed with and without 2-β-mercaptoethanol present in the sample buffer. Following electrophoresis gels were western blotted and immunodetected with anti-crude merozoite serum used at a dilution of 1/100.

Figure 18A:
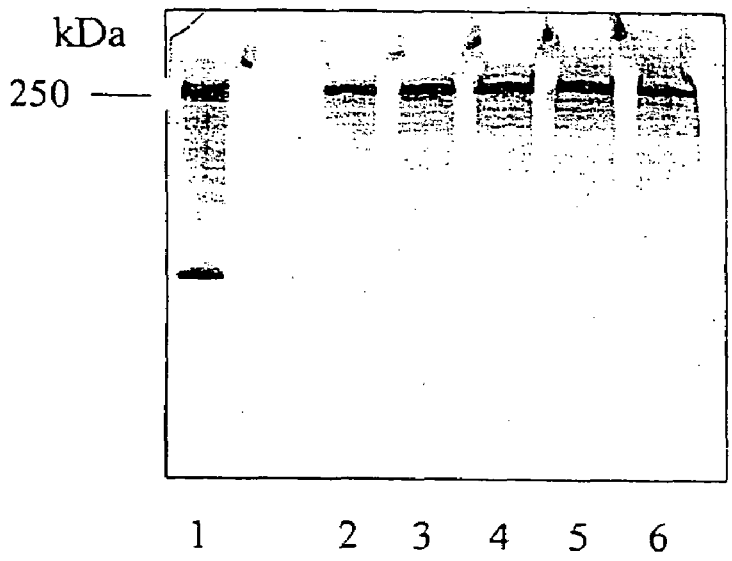
FIG. 18 Western blot analysis of the immunodominant protein separated on 7.5% (A) and 5% (B)SDS-plyacrylamide gels under reducing and non-reducing conditions. Ion exchange chromatography fractions enriched for the immunodominant protein were electrophoresed with and without 2-β-Mercaptoethanol in the sample buffer. A: Lane 1, without β-ME; Lane 2, 2.5% β-ME; Lane 3, 3.75% β-ME; Lane 4, 5% β-ME; Lane 5.7.5% β-ME; Lane 6, 10% β-ME. B: Lane 1, without β-ME; Lane 2, 2.5% β-ME. Western blots were immunodetected with antiserum from hens infected with crude merozoite extract.
Figure 18B:
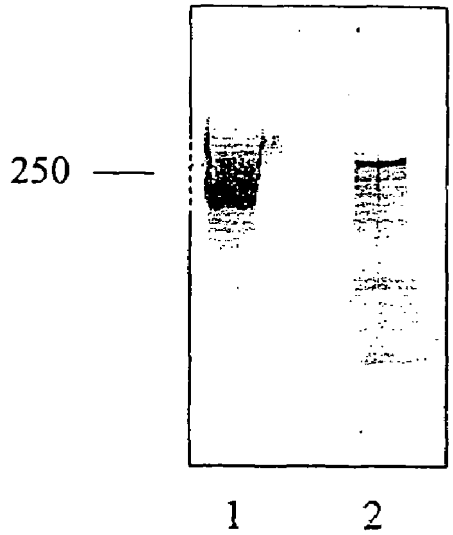

As can be seen in FIG. 18.A, when samples enriched for the immunodominant protein were analysed on a 7.5% gel in the presence of 2-β-mercaptoethanol within the concentration range 2.5-10% v/v (Lanes 2-6), a single predominant band was detected migrating at approximately 250 kDa. Under non-reducing conditions however, the serum detected a high molecular weight doublet band migrating slightly faster than the immunodominant band visible in the reduced samples. In addition, a second immunodominant band was detected migrating with an apparent molecular weight of approximately 75 kDa, which was not visible in the reduced samples.

When compared to separation on a 5% gel (FIG. 18.B), the immunodominant band was detected in the reduced sample (lane 2) migrating with an apparent molecular weight considerably higher than 250 kDa. Under non-reducing conditions the doublet band was more apparent and seen to migrate substantially faster than the immunodominant band in the reduced sample. The 75 kDa band detected in the non-reduced sample when separated on a 7.5% gel was not detected following separation on 5% polyacylamide, presumably because it had migrated off the bottom of the gel. It is likely that it is not visible in samples analysed under reducing conditions either because epitopes present in the native protein are lost after reduction, or the native form is an oligomer of smaller dusulphide-bonded polypeptides that migrate off the gel.

The results suggest that the high molecular weight immunodominant protein is monomeric and that intra-chain disulphide bonding stabilizes the native protein. The doublet band detected under non-reducing conditions might indicate the presence of isomeric forms of the protein.

Discussion

The purification of a high molecular weight, immunodominant protein for the purposes of protein sequencing has been described. Extracts of sporulated oocysts of *E. maxima* were fractionated by ion exchange chromatography, concentrated by centrifugal ultrafiltration and further separated by SDS-PAGE to provide protein of sufficient purity and quantity for N-terminal and tryptic peptide sequencing.

In order to examine the migration of the protein on polyacrylamide gels with higher resolving power, and to select suitable antibodies for detection, extracts of sporulated oocysts were initially separated on 5% polyacrylamide gels under reducing conditions, and immunoblotted with a range of sera and yolk harvested during previous maternal immunisation trials (Smith et al, 1994). The serum and yolk samples predominantly detected a single protein band with an apparent molecular weight significantly greater than 250 kDa, somewhat larger than the previous estimation of 230 kDa from SDS-PAGE using 11% gels (Smith et al, 1994). The estimates can only be considered approximate however, as proteins in some instances can migrate with disproportionate increases in apparent molecular weight, for example glycosylated and phosphorylated proteins (Smith, 1997; Dunn, 1993).

From the serum and yolk samples used in the initial immunodetection experiment, serum from hens infected with crude merozoite extract of *E. maxima* was selected for immunoblotting in many of the subsequent experiments. Although ideally, maternal protective antibodies derived from the deliberate infection of hens with viable oocysts would have been used throughout the study, such antibodies were available in extremely limited quantity and were conserved where possible. Repeating maternal immunisation trials to obtain antibodies was considered too time consuming, and the possibility that antisera raised in such an experiment would not detect the same immunodominant protein could not be excluded. The antisera derived from hens infected with crude merozoite extract were available in relatively large quantity and proved to be strongly reactive. While it can be argued that the different antibodies might have predominantly detected different proteins, results suggest that this is unlikely. Proteins of such high molecular weight are relatively rare in the proteome (Shirley et al, 1992) and silver staining of the protein detected by antisera from both sources did not suggest the presence of co-migrating proteins.

In selecting and developing a method for the purification of the immunodominant protein a number of issues were considered, the first being the protein source. Previous work had detected the protein in extracts of sporulated oocysts and merozoites, and the SDS-PAGE cutout protection experiment used protein extracts prepared from merozoites. Although in terms of association with the previous study it might have been preferable to source the protein from merozoites, the large numbers of merozoites required for method development and sequencing proved difficult to obtain. It was estimated that for a 250 kDa protein and requiring a suggested 10 pmol minimum for N-terminal sequencing (McInerny, Biotech Australia and APAF, personal communication), approximately 10 µg of purified protein would be needed. Conservatively, if the immunodominant protein represented ¹⁄₁₀₀₀th of the *E. maxima* proteome, then 10 mg of crude extract would be required for N-terminal sequencing alone, not allowing for method development. In routine infections of chickens for harvesting merozoites, approximately $10^8$ merozoites per bird were obtained from 20 birds, yielding a total protein extract less than 0.5 mg. In comparison, approximately $1\times10^8$ oocysts were obtained from infection of 20 birds giving approximately 10 mg of crude extract (results not shown). In addition merozoites are difficult to purify and preparations invariably contain some degree of host tissue and debris contamination, while the more robust oocysts are relatively easily cleaned and sterilized by sodium hypochlorite treatment. Furthermore, large supplementary numbers of sporulated oocysts were available through collaboration with the National Veterinary Institute, Uppsala, Sweden.

Although it cannot be excluded that the immunodominant band detected in sporulated oocyst and merozoite extracts does not represent the same protein, it appears unlikely. Anti-crude merozoite antibodies predominantly detected a protein of approximately 250 kDa in both sporulated oocyst and merozoite extracts and, as stated above, proteins of such high molecular weight are relatively rare within the proteome. In addition yolk sample from the SDS-PAGE cutout experiment and sera from hens infected with crude merozoite extract both detected a protein band of the same apparent molecular weight in extracts of crude sporulated oocysts.

The quantity of protein required for N-terminal sequencing necessitated the development of procedures that would produce protein fractions enriched for the immunodominant protein. Although 2-D electrophoresisis has a great capacity to separate complex protein mixtures, it was not considered a suitable technique for N-terminal sequencing in this application, due to its inherently low protein loading capacity (Dunn, 1997). In addition, hydrophobic and high molecular weight proteins are poorly absorbed onto IEF gels in the first dimension (personal communication, APAF). Ion exchange chromatography was selected for separation, being a widely used technique suitable for aqueous soluble proteins, having a high binding capacity and preserving the biological activity of proteins (Scopes, 1994).

Following IEX chromatography it was necessary to desalt and concentrate fractions before further analysis. Centrifugal concentrators with a molecular weight cut-off of 100 kDa were selected for the application, giving the additional benefit of removing some small molecular weight proteins. Gel filtration chromatography was then trialed in an endeavor to take advantage of the high molecular weight of the immunodominant protein and remove remaining lower molecular weight proteins. The technique is best suited as a final polishing step in purification however, and not as a separation tool for relatively complex protein mixtures (Scopes, 1994). Subsequent analysis of fractions by SDS-PAGE and silver staining did not suggest a significant further separation of IEX fractions enriched for the immunodominant protein, and the method was not further developed.

The results obtained for N-terminal and tryptic peptide sequencing indicated that the techniques employed for concentration and separation of the immunodominant protein were adequate for the purpose of protein sequencing. The N-terminal and tryptic peptide sequences were subjected to Basic BLAST searches, however no significant alignments were produced. An Advanced BLAST search was then conducted in order to generate short sequence alignments, using an appropriate search matrix (PAM-30) and increased Expect (E) value. An alignment was produced with tryptic peptide #1 and microneme protein 4 from *E. tenella*, a high molecular weight, acidic protein that is expressed within micronemes and on the parasite surface (Tomley et al, 2001). Although interesting, the result could not be considered statistically significant. The greatest indicator of significance in BLAST searches is the E value that represents the number of expected chance matches from the database with the same score (Wolfsberg and Madden, 1999). The E value of 43 produced for the EtMIC4 alignment suggested a strong probability that the match was due to chance.

During anion exchange chromatography the immunodominant protein was eluted under relatively high NaCl concentrations and over a wide concentration range, indicating that the protein is acidic and suggesting a degree of charge heterogeneity. Such microheterogeneity can be attributed to a number of factors, including the presence of stable alternative conformers, different oligomeric subunit combinations, or varying degrees of glycosylation, phosphorylation, methylation or acetylation (Righetti, 1983). Results from SDS-PAGE analysis under reducing conditions indicated that the immunodominant protein is a monomer consisting of one polypeptide chain, and therefore excluded the possibility of different oligomers contributing to charge heterogeneity. When analyzed under non-reducing conditions however, the high molecular weight immunodominant protein appeared as a doublet band, possibly suggesting the presence of stable conformers, or isomeric forms due to differential post-translation modification. In the presence of 2-β-mercaptoethanol the impact of conformers or varying modification on the apparent molecular weight might then be lessened, explaining the single protein band detected following analysis under reducing conditions.

Example 5

Cloning of the cDNA and Characterization of the Gene Encoding an Immunodominant Asexual Stage Protein from *Eimeria maxima*

In the development of a recombinant subunit vaccine the cloning of cDNAs encoding proteins of interest is of critical importance. The success of cDNA cloning depends largely on the preparation of a high quality cDNA library, and the selection of a suitable screening procedure that is determined by the available materials and information.

A large number of recombinant cDNA clones encoding putatively protective antigens have been reported, most having been identified by screening cDNA expression libraries with antibodies raised against crude parasite extracts or selected surface or internal proteins. The technique is reliant upon the availability of relatively large amounts of quality antibody able to strongly recognize the protein of interest under denaturing conditions (Sambrook). Primarily because such antisera were available only in very limited quantity, the method was not considered suitable for cloning the cDNA encoding the *E. maxima* asexual stage immunodominant protein. As an alternative, a RACE PCR-based strategy was considered, initially employing degenerate primers designed on the protein sequence generated for the N-terminus and tryptic peptides of the immunodominant protein (Example 5). The generation and sequencing of RACE products would then facilitate the amplification and cloning of a full-length cDNA via the use of 5' and 3' gene-specific primers.

The aim of the work presented is to clone and sequence the cDNA encoding the high molecular weight immunodominant protein discussed in Example 5 using a PCR-based approach. In addition, subsequent characterisation of the cDNA and corresponding gene can give an increased understanding of the structure and function of the protein, and further illustrate its potential as a target for a recombinant vaccine.

Results

RNA Isolation and cDNA Library Construction

Figure 19:
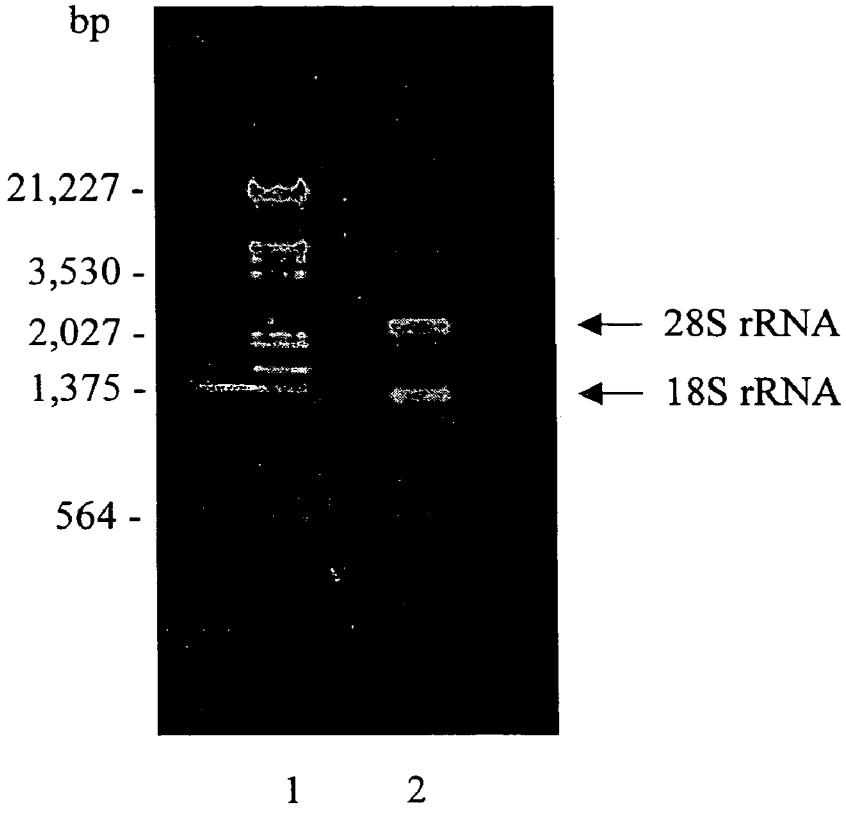
FIG. 19 Total RNA isolated from sporulated oocysts of *Eimeria maxima* and separated by electrophoresis on a 1% non-denaturing agarose gel, Lane 1, 1 μg Lambda DNA/EcoRI+HindIII Markers; Lane 2, 2.5 μg sporulated oocyst RNA. The 28S and 18S ribosomal RNA bands are indicated.

The disruption of oocysts with glass beads and treatment of the resulting homogenate with TRIzol Reagent proved to be a suitable method for isolating high-quality total RNA from sporulated oocysts of *E. maxima*. RNA was isolated from approximately $2.5\times10^7$ sporulated oocysts as described, giving a yield of 184 μg of RNA equivalent to 7.36 pg/oocyst. In order to assess the integrity of the RNA preparation, a 2.5 μg sample was separated on a 1% non-denaturing agarose gel. As shown in FIG. 19, the discrete rRNA bands and the greater intensity of the 28S rRNA band in comparison to the 18S rRNA band indicated a high-quality sample. In addition the purity of the preparation was assessed by measurement of the $A_{260/280}$ ratio, giving a value of 1.983 falling within the accepted range of 1.7-2.0.

The entire total RNA sample was used in the preparation of mRNA as described, and the mRNA recovered in 8 μL of DEPC treated $ddH_2O$. Assuming 100% recovery and a relative mRNA distribution between 1-5% of total RNA, a yield of between 1.84-9.2 μg of mRNA was estimated. Requiring 1 μg of mRNA for cDNA library construction, one half of the mRNA sample was used for first strand cDNA synthesis. A positive control cDNA synthesis was also carried out using 1 μg of Human Placental Poly A+ RNA included in the Marathon™ cDNA Amplification Kit, reported to typically produce approximately 1 μg of ds cDNA.

In order to monitor the synthesis and purification of the cDNA during construction of the library, $[\alpha\text{-}^{32}P]$dCTP was included in the first-strand reaction mixture. Following second-strand synthesis the experimental ds cDNA yield was checked with a series 900 radiation mini-monitor (Mini Instruments Ltd., England) and estimated to be approximately 1/10th the yield of the positive control ds cDNA. Because the sample yield was considerably less than expected, the integrity of the sporulated oocyst ds cDNA was not assessed by agarose gel electrophoresis. The entire ds cDNA sample was used in adaptor ligation and diluted accordingly to a concentration suitable for PCR.

To ensure that cDNA adaptor ligation was successful and that the Marathon RACE protocol was suitable for use with the PTC-200 Peltier Thermal Cycler, a control PCR experiment was carried out using the control ds cDNA with control primers and recommended PCR programme. Following amplification the samples were analysed on a 1% agarose gel. The 5' and 3' RACE and internal control reactions all generated DNA bands of the expected size (results not shown).

Cloning of a DNA Encoding the Immunodominant Protein

Note: For convenience the sequences of the degenerate and gene-specific primers referred to throughout this section are presented in Table 3

Figures 20, 21:
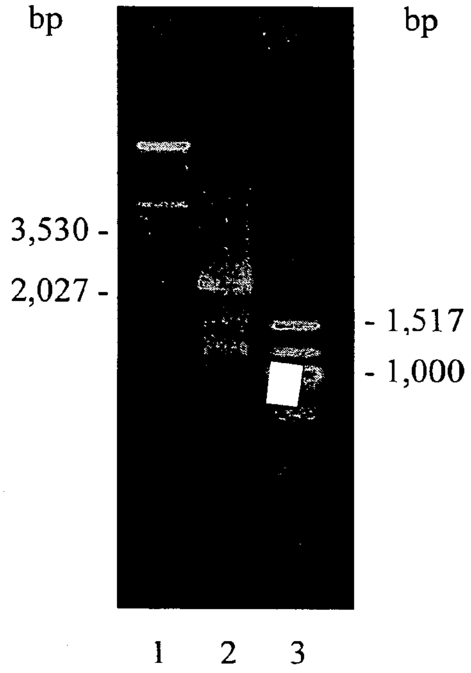

A number of degenerate PCR primers were designed based on the sequences generated from the N-terminus and tryptic peptides of the immunodominant protein. In addition, further examination of the EtMIC4 and 5401 *E. tenella* surface antigen sequences revealed a number of short peptide motifs similar to tryptic peptide #1 from the *E. maxima* immunodominant protein. As shown in FIG. 20, the *E. tenella* motifs all contain a conserved cysteine residue at the carboxy end. The information was used to design further degenerate primers based on tryptic peptide #1 and incorporating a C-terminal cysteine. The level of degeneracy within primers was reduced by consideration of codon usage reported in gene sequences of *Eimeria tenella* (Ellis et al, 1993).

Degenerate primers based on tryptic peptide #1 were used in 3'RACE PCR and as shown in FIG. 21 amplified a number of products. A predominant band of approximately 2.2 kb was generated with primers AP1 and FP008—designed with a 3' TG pertaining to a C-terminal cysteine residue. The band was cloned and partially sequenced, and the sequence submitted for BLASTX analysis against all non-redundant databases accessed through NCBI. The analysis revealed a high level of homology with a region of the predicted amino acid sequence of EtMIC4 (FIG. 22).

Figures 23A, 23B:
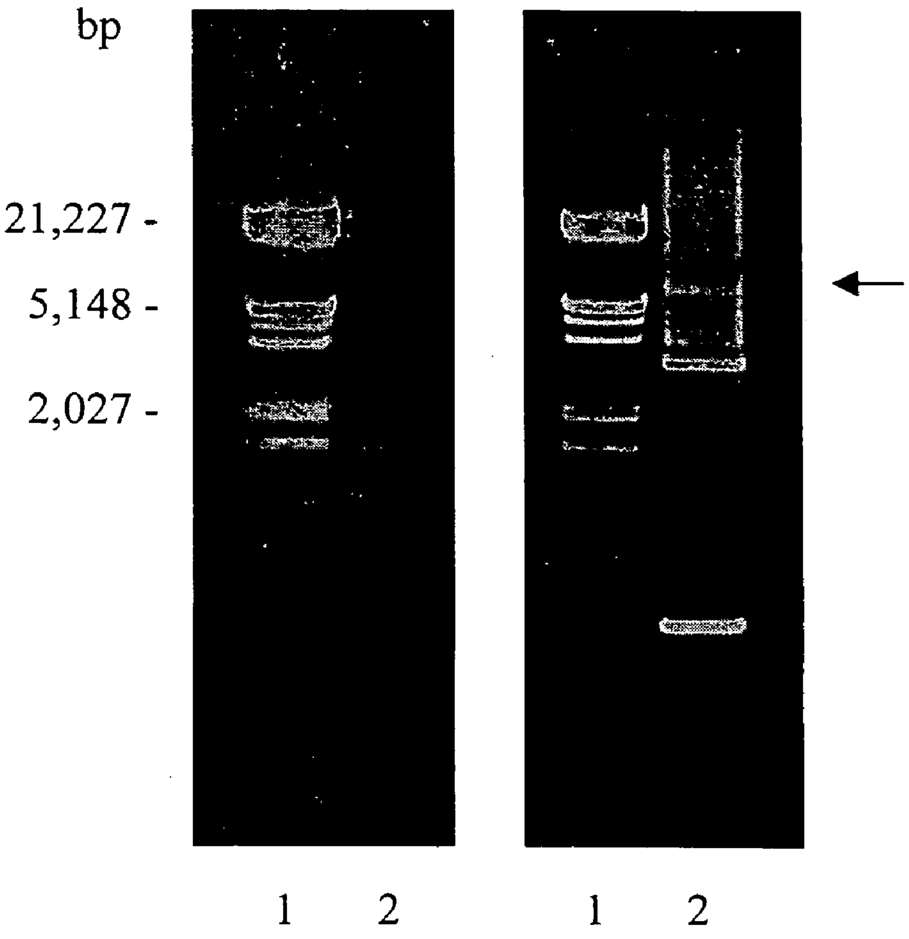
FIG. 23 Generation of intermediate cDNA products encoding EmIP and separated on 0.8% agarose gels. Amplification with degenerate primer FP004 and gene-specific primer RP016 produced a faintly visible, appropriate size band of approximately 6 kb (A, Lane 2). The band was gel-purified and characterised by nested PCR with degenerate primer FP006 and gene-specific primer RP015. A band of the expected size of approximately 6 kb was amplified (B, Lane 2) and is indicated by the arrow. A:Lane 1 and B:Lane 1, 1 μg of Lambda DNA/EcoRI+HidIII Markers; A:Lane 2 and B:Lane 1, 1 μg of Lambda DNA/EcoRI+HidIII Markers; A:Lane 2 and B:Lane 2, 10 μL of PCR reaction as indicated.

Forward and reverse gene-specific primers were designed from the 3' DNA band sequence and used in PCR with degenerate primers based on the N-terminus protein sequence. FP004 (degenerate) and RP016 (gene-specific) primers amplified a number of products and a band of approximately 6 kb was selected for gel-purification (FIG. 23 A). In order to further characterise the band, 1 μL of the purified product was used as template in a nested PCR reaction with FP006 (degenerate) and RP015 (gene-specific) primers. An amplified band of approximately 6 kb (FIG. 23 B) was gel-purified, cloned and partially sequenced.

Figure 24:
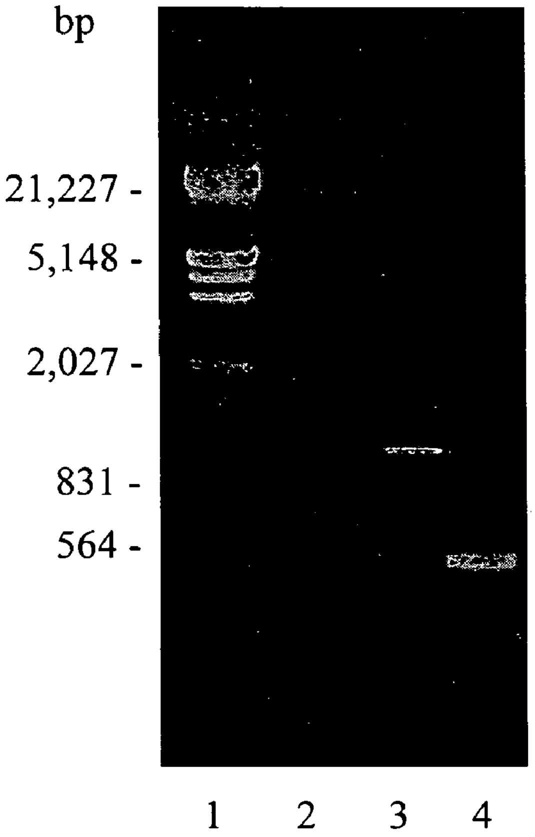
FIG. 24 Amplification of the 5' end of the cDNA encoding EmIP. Gene-specific primers RP019 and RP020 were used in 5' RACE reactions with AP1 (Lanes 2 and 3 respectively). A product between 500-600 bp visible in Lane 3 was further characterized by nested PCR with primers RP019 and AP2 (Lane 4). Lane 1, 1 μg of Lambda DNA/EcoRI+HidIII Markers; Lanes 2, 3 and 4, 10 μL of PCR reaction as indicated. The samples were analysed on a 0.8% agarose gel.

From the 5' region of the sequence obtained above, gene-specific reverse primers were designed to amplify the 5' end of the cDNA. Separate 5' RACE reactions were carried out using primers RP019 and RP020 (situated 31 bp 3' of RP019) and as shown in FIG. 24, Lanes 2 and 3, both reactions amplified a similar size band of between 500-600 bp. To further characterize the amplification products, 1 μL of the RP020 RACE reaction was used as template in a nested PCR reaction with AP2 and RP019 primers. The reaction generated a single product of the expected size of between 500-600 bp (FIG. 24, Lane 4). The band was cloned and a translation of the sequence revealed the N-terminus protein sequence of the mature immunodominant protein as determined by Edman degradation (FIG. 25).

Figure 26:
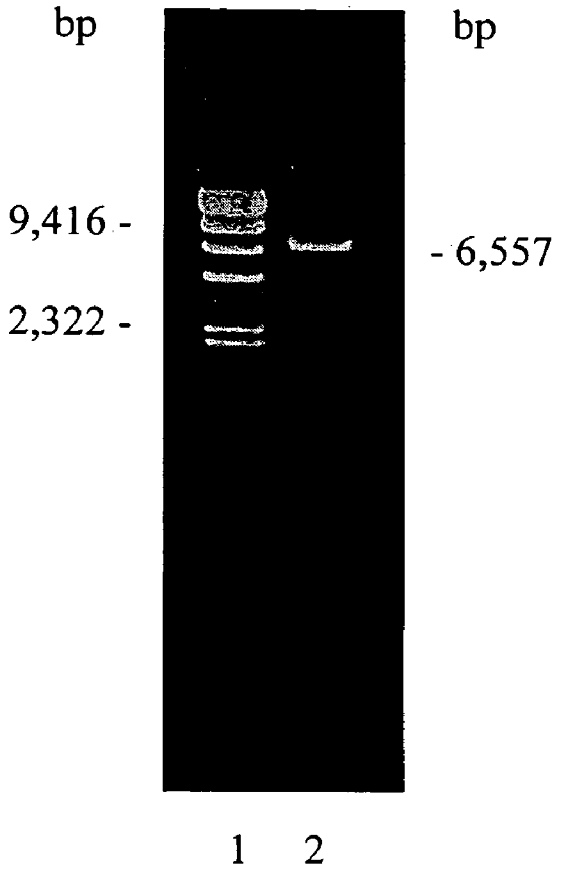
FIG. 26 Generation of a cDNA encoding the full, mature *E. maxima* immunodominant protein. Gene-specific primers FP015 and RP023 designed from 5' and 3' RACE sequence respectively, amplified a single PCR product of approximately 7 kb (Lane 2). Lane 1, 1 μg of Lambda DNA/Hind III Markers; Lane 2, 10 μL of PCR reaction as indicated. Samples were separated on a 0.8% agarose gel.
Figure 27:
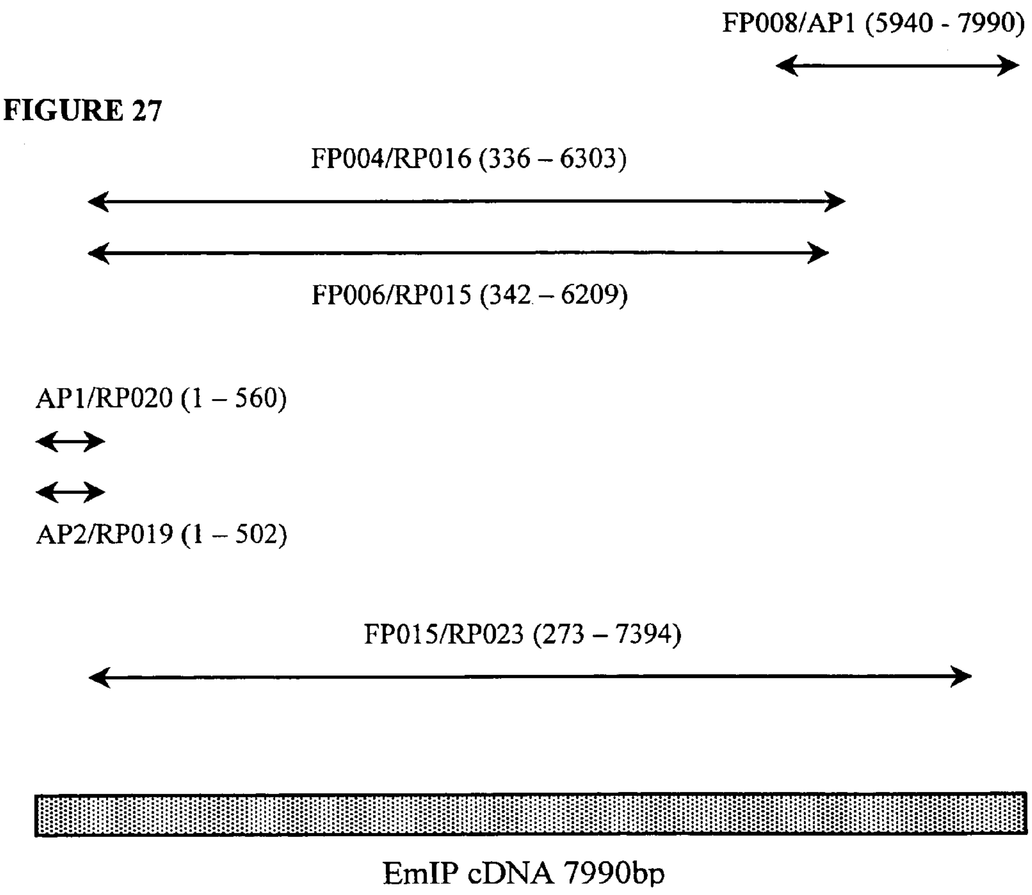
FIG. 27 Schematic overview of the PCR strategy used to clone the cDNA for the *E. maxima* immunodominant protein. The figure depicts the order in which the different cDNA fragments were generated. The bottom horizontal bar represents the full-length cDNA. Lines with arrowheads represent the overlapping cDNA regions amplified by the indicated primer pairs (also shown by corresponding bp numbers in parentheses).

Gene-specific primers were designed from the sequences of the 5' and 3' RACE products to amplify a cDNA putatively encoding the entire, mature immunodominant protein. A single band estimated to be approximately 7 kb was generated with primers FP015 and RP023 (FIG. 26) and cloned as described. A schematic overview of the PCR cloning strategy is presented in FIG. 27.

TABLE 3

Oligonucleotide primers used in the cloning of the cDNA for the *E. maxima* immunodominant protein.

| Primer | Sequence (5'-3') |
|---|---|
| AP1 | CCATCCTAATACGACTCACTATAGGGC |
| FP008 | TGGACNGCNTGGACNGARTG |
| FP004 | AARTGYGARTCNGGNTGGAC |
| RP016 | CGTTGTTCGCCGGCTTGCTGCACTCCTC |
| FP006 | GARTCNGGNTGGACNCC |
| RP015 | GTTGCATTCGCTCCATGGGCCCCACTG |
| RP019 | CTGTCCCACCACACACGACATATCGCC |
| RP020 | CCTGCATGCCCTCACTTCCTGCACCTC |
| AP2 | AGTCACTATAGGGCTCGAGCGGC |
| FP015 | GCTGCACTCTATGGCGGAACAGGAATCG |
| RP023 | GCCTGTTTCGCCTTCGCATCCTTCG |

Sequence Analysis of the Full-Length cDNA

The full-length cDNA sequence was generated by sequencing the clone putatively encoding the entire mature protein, and the 5' and 3' RACE PCR products overlapping this. All but a region of approximately 50 bp at the extreme 5' end of the cDNA was sequenced, with repeated attempts to sequence this T rich area unsuccessful. The cDNA predicts an open reading frame of 7122 bp and indicates a coding region of 7080 bp, a 3' untranslated region of 680 bp and a 5' untranslated region of approximately 280 bp. BLASTN analysis of the putative coding sequence against all non-redundant databases accessed through NCBI revealed a high level of homology with the mRNA sequence for EtMIC4 (FIG. 28). A Clustal W (1.4) sequence alignment pairing the EmIP and EtMIC4 cDNA coding sequences produced an identity score of 60% (alignment not shown).

Predicted Primary Structure of the Immunodominant Protein

The full cDNA putatively encoding EmIP and the predicted translation are presented in FIG. 29. The first in-frame ATG appears 43 bp downstream from the beginning of the predicted ORF, and is likely to represent the initiating methionine given that it encodes the only in-frame methionine occurring upstream of the mature N-terminus as determined by Edman degradation. Furthermore the translated sequence was submitted to the SignalP V1.1 WWW server through ExPASY, and revealed a typical signal peptide of 26 amino acids, starting with the putative initiating methionine and with a cleavage site immediately preceding the mature N-terminus.

The mature polypeptide predicted by the ORF consists of 2334 amino acids with a predicted molecular mass of approximately 246 kDa and a theoretical pI of 4.2 as determined by the program ProtParam. The polypeptide has a high frequency of glutamic acid residues representing 12.3% of the amino acid content, and a total of 440 negatively charged residues (glutamic acid and aspartic acid) compared to 147 positively charged residues (arginine and lysine), accounting for the predicted negative charge. The protein is also particularly rich in glycine and cysteine residues representing 11.8% and 10.6% of the amino acid composition respectively.

In order to search for conserved domains within the protein, the polypeptide sequence was submitted for analysis to the SMART, ScanProsite and PROSCAN programs through the ExPASY server. The majority of the protein is predicted to comprise repeats of two different cysteine rich adhesive domains, known to be associated with important binding interactions both between cells and between cells and the extracellular matrix. The first group consists of 16 repeats of a truncated form of the type 1 repeat of human platelet thrombospondin (TSP-1), occurring between residues 27-194 (4 copies), 1517-1648 (3 copies) and 1765-2143 (9 copies) (FIG. 30). Nine of the 16 repeats feature a WXXW motif, similar to the TSP-1 WSXW motif directly associated with binding to proteoglycans and sulfated glycolipids (Guo eta al, 1992). Downstream of the WXXW motif, eight of the repeats contain a basic residue motif RXR, associated with glycosaminoglycan-mediated cell binding activities (Gantt et al., 1997).

The second adhesive domain group constitutes approximately 57% of the mature protein and comprises 31 tandem repeats of a family of epidermal growth factor-like (EGF-like) domains, occurring between residues 195-1516 (FIG. 31). The domains have been identified in a large number of membrane-bound and extracellular proteins in eukaryotes and are believed to be involved primarily in ligand-receptor interactions. A characteristic feature of the domains is the presence of six highly conserved cysteine residues. All of the EGF-like repeats present in the immunodominant protein suggest a pattern typical of the EGF-CA calcium binding domain subset that require calcium for their biological function.

Between TSP-1 repeats 7 and 8 (residues 1649-1764) the polypeptide contains the first of two low complex, highly negatively charged regions abundant in glutamic acid and glycine residues. The first region features 7 repeats of a degenerate form of the motif GEVQPGTEEGAGVG SEQ. ID NO. (FIG. 32 A). The second region occurs following the final TSP-1 repeat between residues 2144-2285 and is additionally rich in proline residues (FIG. 32 B). Immediately downstream of the second region of low complexity is a predicted transmembrane region (TM) and cytoplasmic tail (CT), found highly conserved in the apicomplexa within members of the TRAP family of microneme proteins (FIG. 33). The cytoplasmic tail region is usually characterised by the presence of conserved tyrosine residues within close proximity to the TM and conserved tryptophan residues near the C-terminus.

Figure 34:
FIG. 34 Schematic representation of the *E. maxima* immunodominant protein showing the major structural features.
Figure 36:
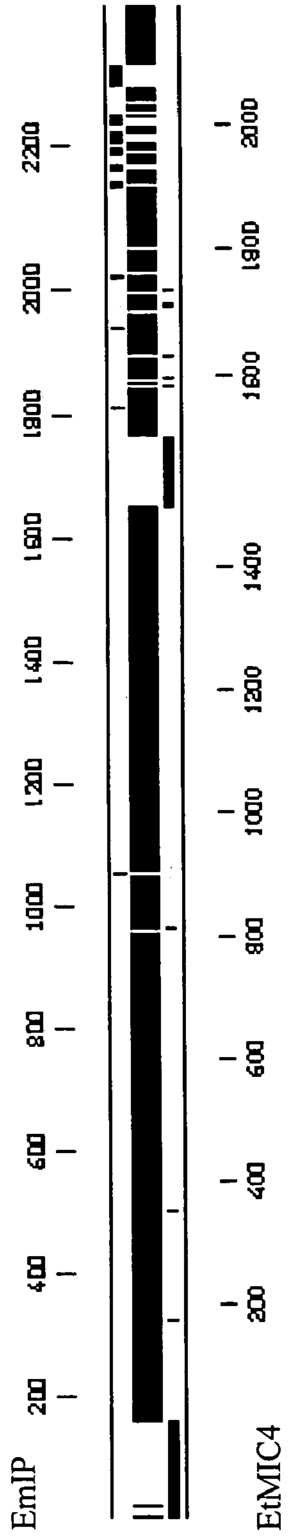
FIG. 36 GAPSHOW graph showing the similarity between EmIP and EtMIC4 amino acid sequences following alignment with the GAP program. The top unbroken line represents EmIP (2360 residues) and the bottom unbroken line EtMIC4 (2189 residues). Similarity is shown by the central vertical lines. The smaller vertical lines (below EmIP and above EtMIC4) represent gaps inserted during alignment.

The structural features of the protein are shown schematically in FIG. 34. BLASTP analysis of the predicted polypeptide sequence against all non-redundant databases accessed through NCBI revealed a highest score alignment with EtMIC4, and significant scores with members of the fibrillin family of proteins (FIG. 35). A ClustalW (1.1) alignment with EtMIC4 revealed an amino acid identity score of 61% with an additional 10% similarity (full alignment not shown). The overall similarity between EmIP and EtMIC4 at the amino acid level is represented diagrammatically in FIG. 36 by analysis with the GAP and GAPSHOW programs, showing a particularly high degree of conservation over the region spanned by the EGF-like repeats. The two proteins are most dissimilar at the N-termini.

Expression of the Immunodominant Protein Across Developmental Stages

Note: For convenience the sequences of the gene-specific primers referred to throughout this section are presented in Table 4

To substantiate earlier findings indicating that EmIP is confined to the asexual stages of development, mRNA was isolated from merozoites and gametocytes and subjected to RT-PCR primed with EmIP gene-specific primer RP022. In addition, primer CRP6 (specific for constitutively expressed *E. maxima* HSP70) was included in all RT. reactions to act as a positive control. Duplicate reactions were also carried out in the absence of reverse transcriptase to confirm that PCR bands generated were not amplified from genomic DNA potentially contaminating the mRNA samples. Standard PCR reactions were performed with 1 μl of each RT reaction, using EmIP specific primers FP010 and RP023 to generate a product with an expected size of 1211bp, and HSP70 specific primers CFP1 and CRP3 to produce a band with a predicted size of 336 bp. To verify the identity of products amplified with EMIP primers, 1 μL of plasmid DNA containing sporulated oocyst cDNA encoding EmIP was also used in amplification with FP010 and RP023 as described. A no template control was included to ensure that PCR reagents were uncontaminated.

Figure 37:
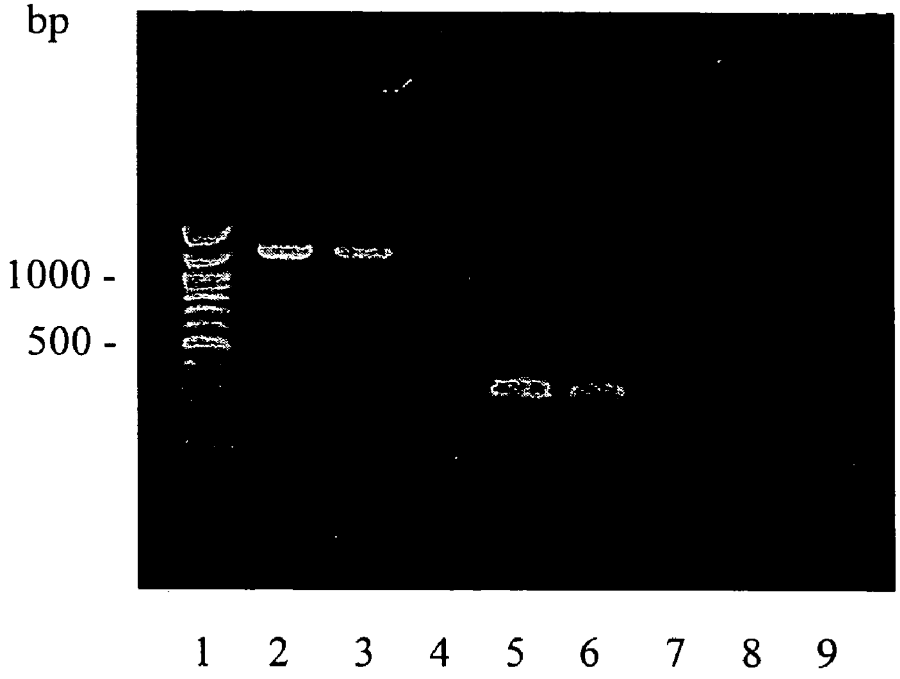
FIG. 37 Detection of the immunodominant protein across developmental stages of *E. maxima*. Messenger RNAs for merozoites or gametocytes were subjected to RT-PCR using primers specific to EmIP and HSP70. Standard PCR reactions werre subsequently performed using the RT reactions as template with gene-specific primers for EmIP or HSP70. Lane 1,100 bp DNA ladder (1 μg); Lane 2, sporulated oocyst cDNA amplified with EmIP primers (positive control, 2 μL); Lane 3, merozoite RT reaction amplified with EmIP primers (10 μL), Lane 5, merozoite RT reaction amplified with HSP70 primers (positive control, 10 μL); Lane 6, gametocyte RT reaction amplified with HSP70 primers (positive control, 10 μL); Lane 7, merozoite no RT reaction amplified with EmIP primers (negative control, 10 μL); Lane 8, gametocyte no RT reaction amplified with EmIP primers (negative control, 10 μL); Lane 9, no template reaction amplified with EmIP primers (negative control, 10 μL).

Following PCR, samples from all reactions were analyzed by electrophoresis on a 0.8% agarose gel. As can be seen in FIG. 37, primers specific for EmIP amplified a band of the expected size from sporulated oocyst cDNA (Lane 2) and detected messenger RNA specific for EmIP in merozoites (Lane 3). A PCR product specific for EmIP was not generated from gametocyte mRNA template (Lane 4), however HSP70 positive control primers amplified a band of the expected size from both merozoite (Lane 5) and gametocyte (Lane 6) mRNA. No amplification products were generated in the RT negative controls (Lanes 7 and 8), or in the no template control (Lane 9). The results confirm that the immunodominant protein is present in the asexual stages of development but not expressed in gametocytes.

TABLE 4

Oligonucleotide primers used for the amplification of gene-specific products in RT-PCR analysis. The predicted size of PCR products is given where applicable.

| Gene | Primers | Sequence (5'-3') | Product size (bp) |
|---|---|---|---|
| EmIP | RP022 | CGAGCTCTTGGGGTGGAGATGCAACTG | N/A |
| EmHSP70 | CRP6 | TGTTTATTAGCCTCATCCTCTGCC | N/A |
| EmIP | FP010 | CAGTGGGGCCCATGGAGCGAATGCAAC | 1211 |
| | RP023 | GCCTGTTTCGCCTTCGCATCCTTCG | |
| EmHSP70 | CFP1 | AGGATTAGAGACAGCAGGAGGAG | 336 |
| | CRP3 | CCTTGACTAAGTCTACCCTTATC | |

Genomic Organisation

Restriction Enzyme Analysis

Figure 38:
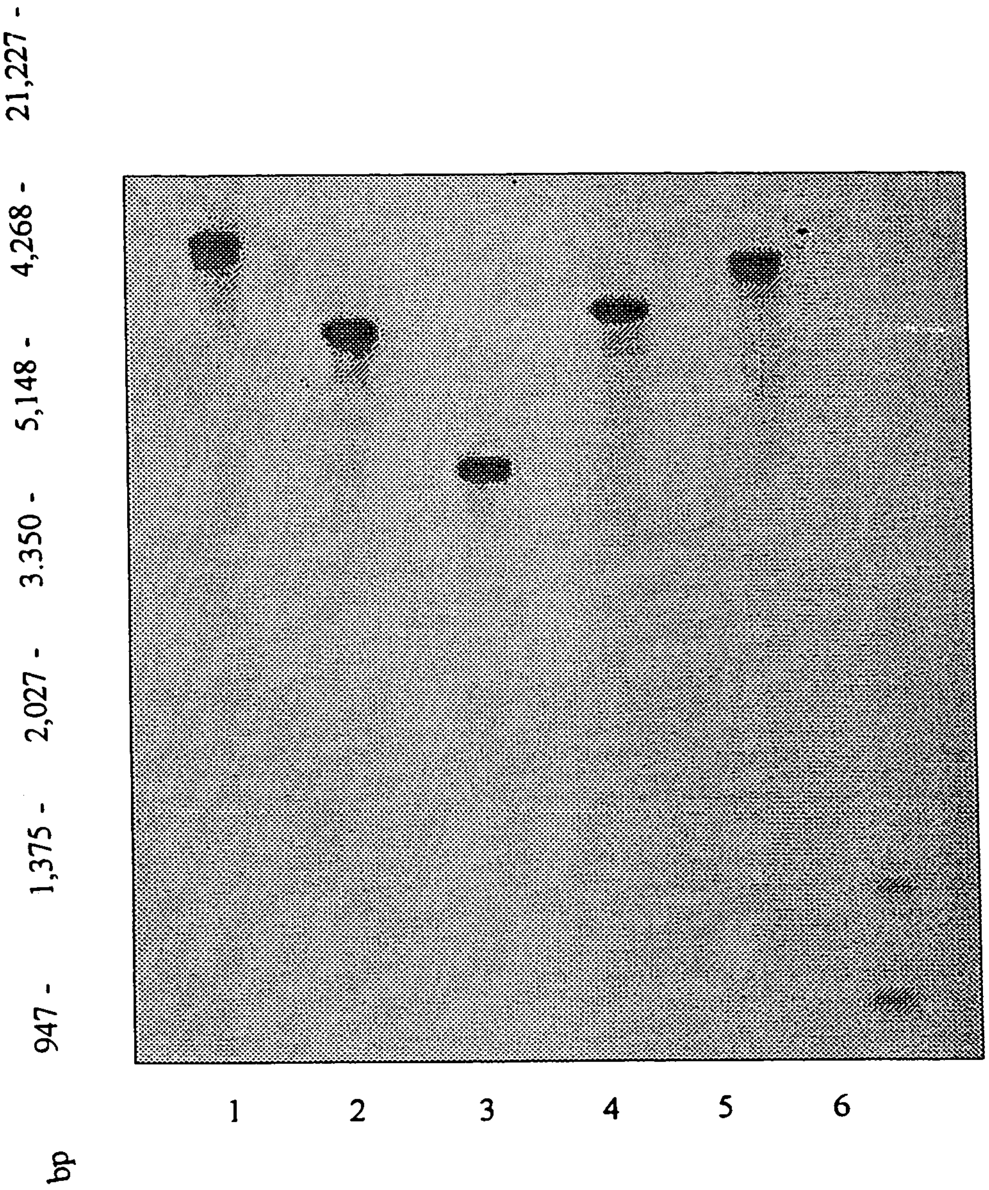
FIG. 38 Southern blot analysis of restriction digested *E. maxima* genomic DNA. Approximately 2.5 μg samples of DNA were digested with a range of restriction enzymes and separated on a 0.9% agarose as indicated. Lane 1, Bgl II; Lane 2, Eco RI; Lane 3, Hind III; Lane 4, Nco I; Lane 5, Nde I; Lane 6, Nsi I. Hybridisation was performed using a $^{32}P$ labeled 1590 bp cDNA fragment generated with EmIP gene-specific peimers FP015 and RP033.

Restriction digested genomic DNA of *E. maxima* was separated on a 0.9% agarose gel and transferred to nylon membrane as described. The membrane was hybridised using a 1590 bp cDNA fragment generated by PCR amplification with EmIP specific primers FP015 (5'-GCTGCACTCTATGGCGGAACAGGAATCG-3') and RP033 (5'-GGCGCACTCGTCG ATATC TTTGCATGC-3'). As can be seen in FIG. 38, digestion with Bgl II (Lane 1), Eco RI (Lane 2), Hind III (Lane 3), Nco I (Lane 4), and Nde I (Lane 5) produced a single hybridising band, while digestion with Nsi I (Lane 6) resulted in two bands due to the presence of a cleavage site within the probe sequence, and therefore the complementary genomic DNA. The Southern analyses suggest that the gene encoding EmTFP250 is present as a single copy within the *E. maxima* genome.

Intron-Exon Structure

Figure 39:
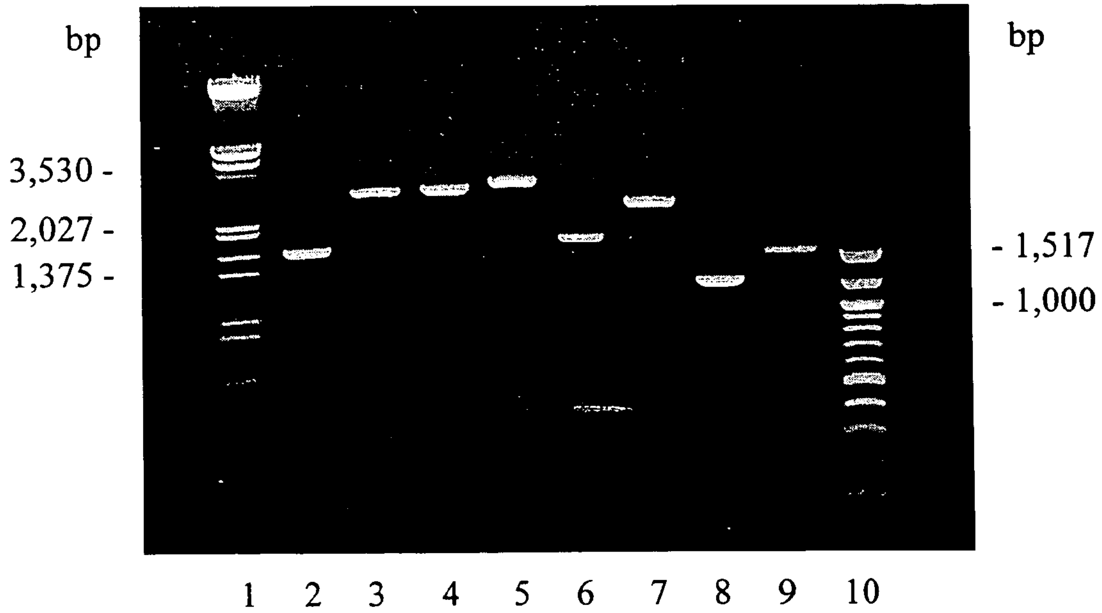
FIG. 39 PCR analysis of the intron-exon structure of the gene encoding the *E. maxima* immunodominant protein. Gene-specific primers pairs were used to amplify corresponding gene fragments from cDNA and genomic DNA. A 10 µL sample from each reaction was separated on a 0.8% agarose gel. Lane 1, 1 µg of Lambda DNA/EcoRI+HindIII Markers; Lane 2 and 3, cDNA and genomic DNA respectively amplified with primer pair FPA015/RP033; lanes 4 and 5, cDNA and genomic DNA respectively amplified with primer pair FP021/RP030; Lanes 6 and 7, cDNA and genomic DNA respectively amplified with primer pair FP010/RP023; Lane 10, 1 µg OF 100 bp DNA ladder.

A group of four gene-specific primer pairs were used in PCR amplification with EmIP cDNA to generate a series of DNA fragments covering the cDNA encoding the mature immunodominant protein (Table 5). In order to detect introns within the EmIP gene, the primer pairs were also used in amplification with *E. maxima* genomic DNA to generate DNA bands representing the corresponding gene fragments. Following separation of the PCR products by agarose gel electrophoresis, DNA bands putatively containing intron sequence were identified by an increase in size over the corresponding cDNA fragments. As shown in FIG. 39, all primers pairs predominantly amplified a single PCR product from genomic DNA, greater in size than the cDNA counterpart. No products were generated from single primer and no template negative controls performed for all primer pairs (results not shown).

To confirm the presence of introns, the genomic DNA fragment generated by amplification with primers FP010 and RP023 was purified and sequenced. Analysis of the sequence revealed two putative introns of 139 bp and 151 bp respectively, containing typical eukaryoytic donor/acceptor sites (FIG. 40). Genomic fragments amplified by primer pairs FP015/RP033, FP021/RP030 and FP026/RP015 were not sequenced.

Conservation of EmIP Across Strains and Species of *Eimeria*

The cDNA and protein sequences of EmIP and EtMIC4 were aligned using a Clustal W (1.4) multiple sequence alignment programme, and degenerate PCR primers were designed based on highly conserved regions (FIG. 41). Primer pair CP003 (5'-AAGACTTCGGCGARGGNGGNGTNTG-3') and CP004 (5'-GCCTCGCACTCRTCNACRT CNACRC was used with genomic DNA from the Houghton strain of *E. maxima* to amplify a DNAfragment with an expected size of 622 bp. A DNA product of appropriate size was generated and its identity confirmed by gel purification and sequencing.

TABLE 5

Oligonucleotide primer pairs used in intron-exon analysis for the amplification of gene-specific products from cDNA and genomic DNA. The region of cDNA amplified and predicted product size are shown.

| Primer Pair | Sequence (5'-3') | cDNA region amplified (bp) | cDNA product size (bp) |
|---|---|---|---|
| FP015 | GCTGCACTCTATGGCGGAACAGGAATCG | 273-1865 | 1593 |
| RP033 | GGCGCACTCGTCGATATCTTTGCATGC | | |
| FP021 | GCATGCAAAGATATCGACGAGTGCGCC | 1839-4554 | 2716 |
| RP030 | CTGCTGTGCACTCATCGATGTCAACG | | |
| FP026 | CGTTGACATCGATGAGTGCACAGCAG | 4529-6209 | 1681 |
| RP015 | GTTGCATTCGCTCCATGGGCCCCACTG | | |
| FP010 | CAGTGGGGCCCATGGAGCGAATGCAAC | 6183-7394 | 1212 |
| RP023 | GCCTGTTTCGCCTTCGCATCCTTCG | | |

In order to assess the degree of conservation of EmIP, genomic DNA from Australian isolates of all seven species of *Eimeria* parasitic in chickens was used in PCR amplification with degenerate primers CP003 and CP004. EtBr staining of PCR products separated on a 0.8% agarose gel revealed only faint bands of the appropriate size in samples generated using *E. acervulina, E. maxima, E. necatrix* and *E. tenella* DNA (results not shown). To examine the PCR products further, the DNA was transferred to nylon membrane by Southern blotting and hybridised with a Houghton strain, *E. maxima* genomic DNA probe generated with primers CP003 and CP004.

Figure 42A:
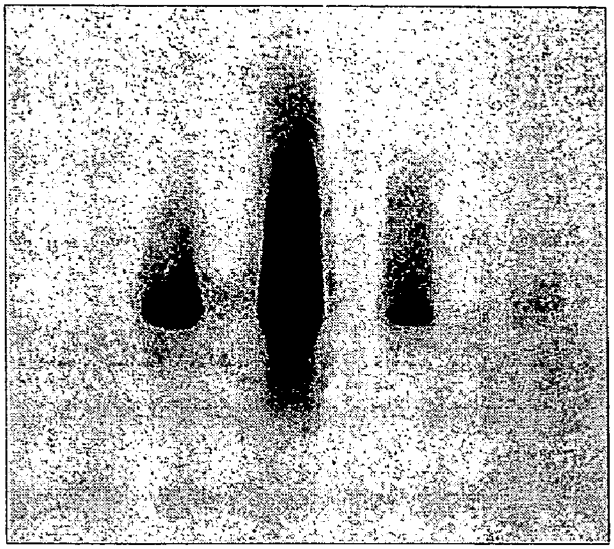
FIG. 42 Detection of EmIP homologues in Australian strains of *Eimeria* by PCR and Southern blot analysis. PCR products were generated from genomic DNA samples as indicated, using degenerate primers CP003 and CP004. Reaction samples (10 µL) were separated on a 0.8% agarose gel. Lane 2 *E. acervulina*; Lane 3, *E. brunetti*; Lane 4, *E. maxima*; Lane 5, *E. mittis*; Lane 6, *E. necatrix*; Lane 7, *E. praecox*; Lane 8, *E. tenella*. (Lane 1, 1 µg of 100 bp ladder). Products were detected by Southern hybridisation with a Houghton strain *E. maxima* genomic DNA probe generated with primers CP003 and CP004. The membrane was exposed to x-ray film for periods of 10 (A) and 30 (B) min.
Figure 42B:
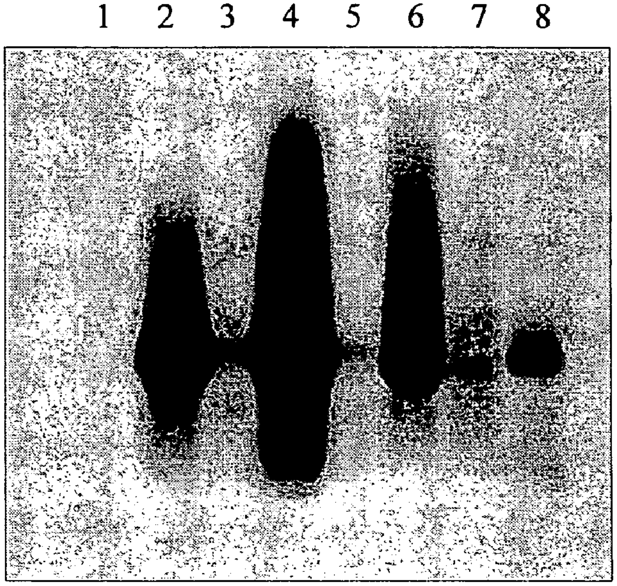

As shown in FIG. 42 A, following high stringeny washes and exposure of the membrane to x-ray film for 10 min, a hybridising band of appropriate size was detected in *E. acervulina, E. maxima, E. necatrix* and *E. tenella* samples (Lanes 2, 4, 6 and 8 respectively). After 30 min exposure (FIG. 42 B) a single hybridising band of similar size was also detected in *E. brunetti, E. mitis* and *E. praecox* PCR products (Lanes 3, 5 and 7 respectively). The results provide further evidence that the EmIP gene is highly conserved throughout strains and species of *Eimeria* causing coccidiosis in chickens.

Example 6

Immunization and Challenge Trial of the Recombinant 56 kDa (r56) and 82 kDa (r82) Gametocyte Antigens, and the 250 kDa (r250) Asexual Stage Antigen in Chickens Immunization Animals Chickens:

- 84 day old (~12 weeks) Australorp cockerels
- kept on medicated (robenidene) food
- all chickens were individually tagged and recorded Antigens Recombinant proteins in the pTRCHisb expression system were grown at 37° C. in 0.1 mg/ml ampicillin in 0.01 M $Mg^{2+}$ SOB and induced for 4 hours with 1 mM IPTG. Proteins were purified on a Ni-agarose column, concentrated, desalted, and lyophilized with stabilizers (3% lactose, 1% monosodium glutamate). Protein concentrations used for all antigens were measured using the Bradford assay. Affinity Purified Gametocyte Antigen (APGA) preparations provided by M. Wallach was used as a positive control for the trial.

Groups and Doses

- 9 chickens used per group; 9 groups in total; 81 chickens used in total.
- Chickens were immunized with 0.5 ml antigen/Freunds Incomplete Antigen (FIA) cocktail (0.25 ml antigen/0.25 ml FIA) per bird, intra-muscularly, on one side only of the chicken, with the following antigens:

| | |
|---|---|
| Group 1 | PBS only |
| Group 2 | Adjuvant (FIA)/PBS |
| Group 3 | APGA (2.5 g) |
| Group 4 | r250 protein (1.0 g) |
| Group 5 | r250 protein (10.0 g) |
| Group 6 | r56 protein (0.5 g) |
| Group 7 | r56 protein (5.0 g) |
| Group 8 | r82 protein (0.5 g) |
| Group 9 | r82 protein (5.0 g) |

Immunization Schedule

| | |
|---|---|
| Immunization 1: | week 1 |
| Immunization 2: | week 3 |
| Bleed: | week 6 |
| Bleed: | week 8 |
| Bleed/Kill: | week 9 |

Analyzes

Figure 43A:
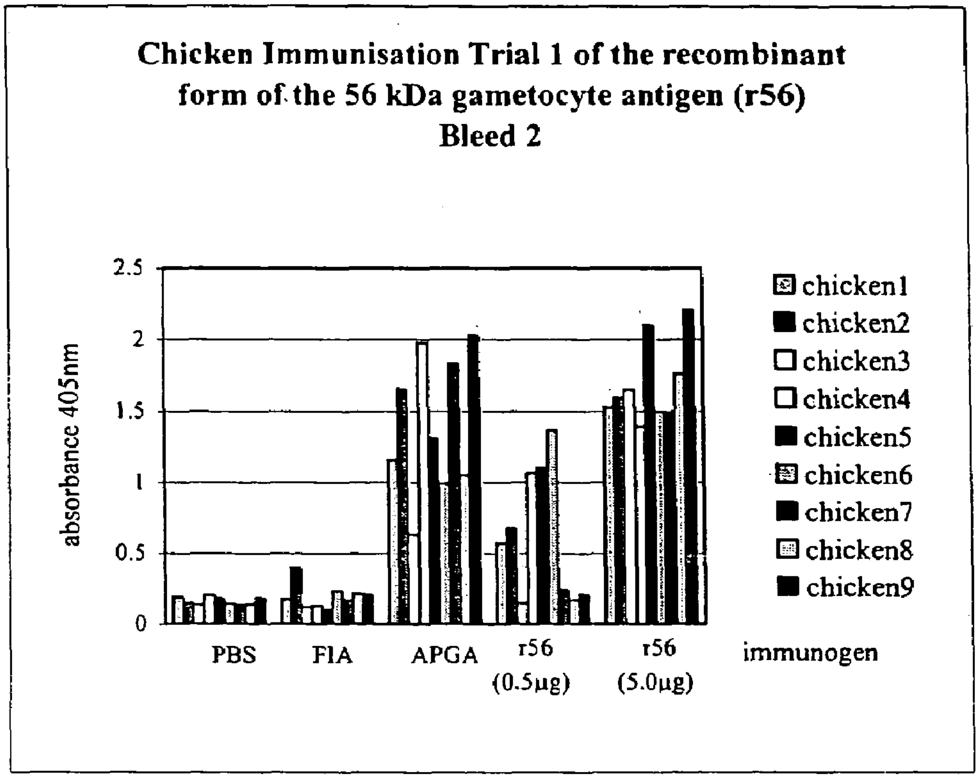
FIG. 43 A & B ELISA results for chicken immunogenicity trial of the recombinant form of the 56 kDa and 82 kDa gametocyte antigen. All serum samples were tested at 1:1000 dilution. A) Coating antigen: APGA to test sera against APGA; r56 purified to test sera taken from chickens immunized with PBS, FIA and the two doses of r56. B) Coating antigen: APGA to test sera against APGA; r82 purified protein to test sera taken from chickens immunized with PBS, FIA and the two doses of r82.
Figure 43B:
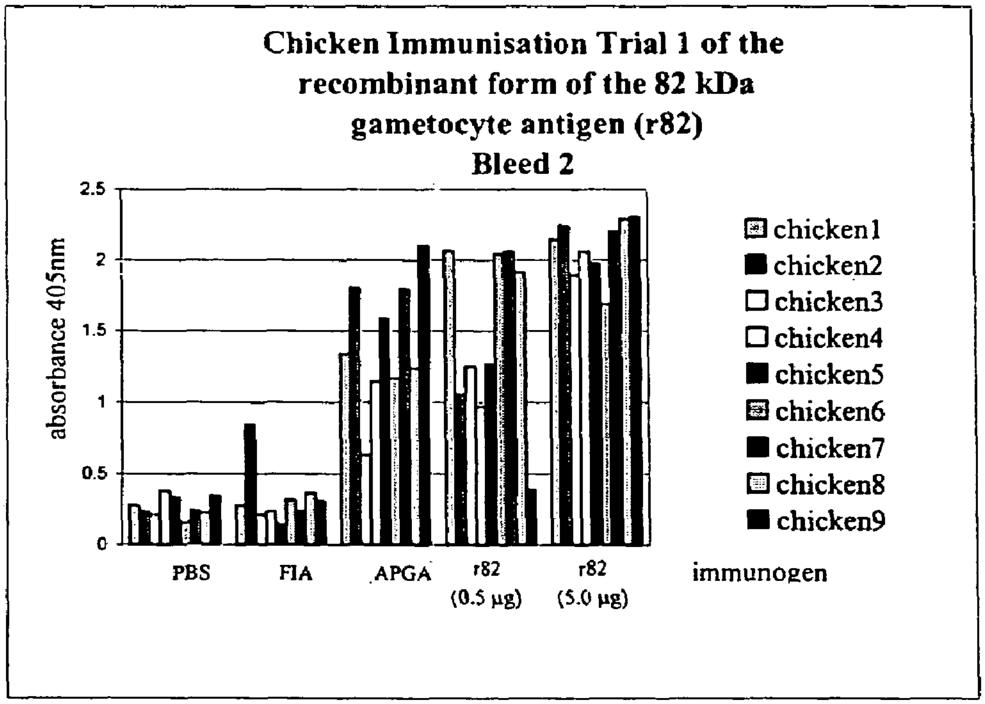

Bleeds were taken (~1.5-2 ml/bird), sera separated and tested by ELISA and immunoblotting Results Results of the bleeds are shown in FIG. 43.

Challenge

Animals and Parasites 5 chickens (148 days old; ~4.5 months) from each group which had the highest antibody titre based on the ELISA results of bleed 1 were used; in the case of the PBS and FIA controls, chickens with the lowest antibody titres were used

*E. maxima* (strain Houghton);

robenidene was removed from the feed one week prior to challenge

Groups

The following groups and chickens were taken from the immunization trial described above, and used in the challenge experiments

| | | |
|---|---|---|
| Group 1 | PBS only | chicken numbers 2, 3, 4, 6, 8 |
| Group 2 | Adjuvant (FIA)/PBS | chicken numbers 12-16 |
| Group 3 | APGA (2.5 g) | chicken numbers 20, 22, 23, 25, 27 |
| Group 5 | r250 protein (10.0 g) | chicken numbers 37, 39, 41, 44, 45 |
| Group 7 | r56 protein (5.0 g) | chicken numbers 57, 59, 60, 61, 63 |
| Group 9 | r82 protein (5.0 g) | chicken numbers 74, 75, 76, 79, 80 |

Challenge Schedule

Robenidene Removed

Challenged with 100 sporulated oocysts per bird Day 6

Oocyst Harvest and Count Schedule

Day 0 post-infection

Day 1 post-infection

Day 2 post-infection

Day 3 post-infection

Day 4 post-infection

Checked oocyst output for contamination of another species Replaced plastic sheet to start collections.

Day 5 post-infection Feces collected, and oocysts counted

Day 6 post-infection Feces collected, and oocysts counted

Day 7 post-infection Feces collected, and oocysts counted

Day 8 post-infection Feces collected, and oocysts counted

Day 9 post-infection Feces collected, and oocysts counted

Day 10 post-infection Feces collected, and oocysts counted

TABLE 6

| | Immunization and Challenge Trial I | | | | | | | | | | | | | | | |
|---|---|---|---|---|---|---|---|---|---|---|---|---|---|---|---|---|
| | Groups/ | Cumulative oocyst counts (× $10^6$) | | | | | Output (%) | | | | | % inhibition | | | | |
| | Day p.i. | 6 | 7 | 8 | 9 | 10 | 6 | 7 | 8 | 9 | 10 | 6 | 7 | 8 | 9 | 10 |
| 1. | PBS only | 6.67 | 17.00 | 26.40 | 27.33 | 27.43 | 100 | 100 | 100 | 100 | 100 | 0 | 0 | 0 | 0 | 0 |
| 2. | FIA only | 3.20 | 14.40 | 17.30 | 17.50 | 17.50 | 48 | 85 | 66 | 64 | 64 | 52 | 15 | 34 | 36 | 36 |
| | | | | | | | (100) | (100) | (100) | (100) | (100) | (0) | (0) | (0) | (0) | (0) |
| 3. | APGA | 2.77 | 9.35 | 13.48 | 13.58 | 13.61 | 42 | 55 | 51 | 50 | 50 | 58 | 45 | 49 | 50 | 50 |
| | (2.5 µg) | | | | | | (87) | (65) | (78) | (78) | (78) | (13) | (35) | (22) | (22) | (22) |
| 5. | r250 | 0.83 | 8.35 | 13.72 | 14.72 | 14.72 | 12 | 49 | 52 | 54 | 54 | 88 | 51 | 48 | 46 | 46 |
| | (10 µg) | | | | | | (26) | (58) | (79) | (84) | (84) | (74) | (42) | (21) | (16) | (16) |
| 7. | r56 | 0.33 | 4.53 | 7.20 | 8.16 | 8.53 | 5 | 27 | 27 | 30 | 31 | 95 | 73 | 73 | 70 | 69 |
| | (5 µg) | | | | | | (10) | (32) | (42) | (47) | (49) | (90) | (68) | (58) | (53) | (51) |
| 9. | r82 | 4.23 | 10.33 | 14.73 | 14.93 | 15.06 | 63 | 61 | 56 | 55 | 55 | 37 | 39 | 44 | 45 | 45 |
| | (5 µg) | | | | | | (132) | (72) | (85) | (85) | (86) | (0) | (28) | (15) | (15) | (14) |

Example 7

Expression of a Recombinant Fragment of the 250 kDa Asexual Stage Protein

The region of the 250 kDa protein encoding the predicted transmembrane domain/cytosolic tail and upstream hydrophilic domain was selected for expression studies (FIG. 44). The area was chosen for a number of reasons and are as follows: 1) similar 3' hydrophilic tail regions have been identified in a number of apicomplexan microneme proteins and appear unique to this family of proteins; 2) such regions have been identified in other microneme proteins also recognised as immunodominant, primarily *Eimeria tenella* microneme protein 1 (EtMICl) and surface antigen 5401 (EtMIC4); 3) a similar region was expressed from the *E. tenella* 5401 antigen (EtMIC4) and was found to afford significant protection against challenge with *E. tenella* (Danforth et al, 1988); 4) other regions of the protein consist primarily of the EGF-like and TSP-1-like domains. These domain types are found highly conserved within eukaryotes and therefore the possiblility of their inducing auto-immunity must be considered. Furthermore because of the prevalence of such domain types it seems unlikely that they would be responsible for inducing a strong immune response.

PCR primers EP006 (5'-TTGGATCCCGAATTGCAC-CCCA TTCC-3') and EP007 (5'-TTGAATTCTGRAT-GTCGCCGCTGTCG-3') were designed to amplify the selected DNA region from a cDNA clone encoding the 250 kDa protein. The primers incorporated BamHI (EP006) and EcoRI (EP007) restriction sites to facilitate cloning into the selected expression vector. The PCR product subsequently generated using the primers was gel-purified and its identity confirmed by sequencing.

The bacterial expression vector pTrcHisB (Invitrogen) was selected for expression studies. Plasmid vector DNA and gel purified cDNA. insert were digested with the restriction enzymes BamHI and EcoRI, and the digested DNA fragments gel purified and ligated. The ligation mixture was transformed into *E. coli* strain DH5-a and following plating and incubation, resulting colonies were selected, cultured and used for plasmid preparation. The identity of the selected recombinants was confirmed by DNA sequencing.

In preparation for expression, plasmid DNA containing the expression construct was transformed into the *E. coli* host expression strain TOP10. Following plating and incubation, a single bacterial colony was selected and used to establish an O/N culture in LB media. A vector only negative control culture was also established. Aliquots of each culture were then transferred to fresh LB media and incubated until the cells reached mid-log phase, at which stage expression was induced with the addition of 1 mM IPTG. Samples from the expression culture and negative control culture were taken at 0, 1, 2, 5 and 24 hrs post induction, and centrifuged to pellet the bacterial cells. All pellets were subsequently resuspended in TE buffer, sonicated and centrifuged to separate the aqueous soluble fraction (supernatant) from the insoluble fraction (pellet). All fractions were analysed under reducing conditions on SDS-PAGE gels and subsequently stained with Coomassie Blue. When compared to the negative control samples, an over-expressed protein was detected in the soluble fractions, migrating at just below the 45 kDa marker. Western analyis of the soluble fractions using an antibody reactive with the 6× Histidine tag of pTrcHis expression products, detected a protein band of the same apparent molecular weight. The predicted size of the expressed protein is approximately 30 kDa, somewhat less than that observed on SDS-PAGE gels. The size difference might be explained by the high frequency of proline residues in the expressed protein, known to cause proteins to migrate with apparently high molecular weight.

In preparation for immunogenicity trials, the expressed protein was purified using Ni-NTA Agarose nickel-charged resin (QIAGEN), with minor modifications to the manufacturer's recommended protocol. Expressed proteins containing the 6× His tag bind to the resin and are displaced by an increased concentration of imidazole in the elution buffer. Briefly, cell pellets were resuspended in Lysis buffer (50 mM $NaH_2PO_4$, 300 mM NaCl, 10 rM imidazole, pH 8.0), containing 1 mg/ml lysozyme. The suspension was sonicated on ice and centrifuged to pellet insoluble material. The supernatant containing the soluble expressed protein was then mixed with Ni-NTA resin and added to a disposable elution column. The slurry was allowed to settle then washed with Wash buffer (50 mM $NaH_2PO_4$, 300 mM NaCl, 20 mM imidazole, pH 8.0), before elution with Elution buffer (50 mM $NaH_2PO_4$, 300 mM NaCl, 250 mM imidazole, pH 8.0). The purity of eluted fractions was analysed by reducing SDS-PAGE and Coomassie Blue staining.

Figure 46:
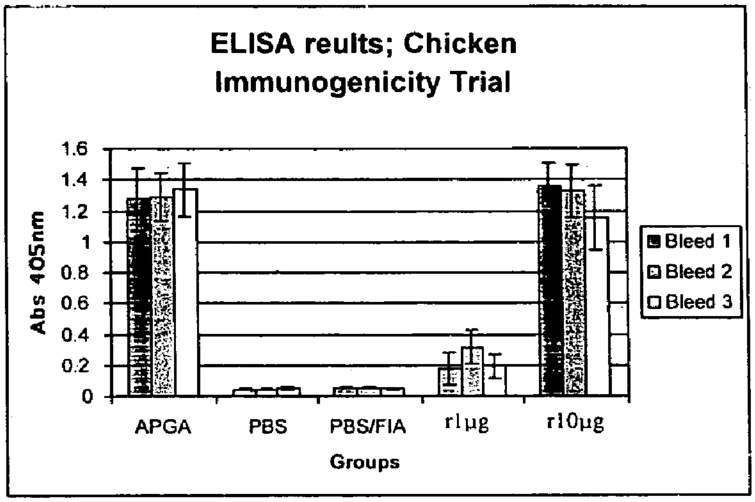
FIG. 46 Chicken immunogenicity trial of the recombinant fragment of the 250 kDa asexual stage protein. The average of each group for the three consecutive bleeds is shown, with standard error bars indicated. All serum samples were tested at 1:1000 dilution. Coating antigen was 100 ng of APGA for sera from the positive control APGA group, or 100 ng of the recombinant protein for the negative control PBS and PBS/FIA groups and the two recombinant protein doses (1 µg and r10 µg)

Details for the immunogenicity trials are as for the 56 kDa and 82 kDa trials. For the mouse trial, 0.5 μg and 5 μg doses of the recombinant protein per mouse were used (6 mice/group). For the chicken trial, 1 g and 10 μg doses per bird were used (9 chickens/group). ELISA results for the collected serum samples from the mouse and chicken trials are presented in FIGS. 45 and 46 respectively.

REFERENCES

Danforth, H. D., Augustine, P. C. and Jenkins, M. C. (1993) A Review of Progress in Coccidial Vaccine Development. pp. 49-60. In Vith International Coccidiosis Conference, Guelph, Ontario, Canada, Barta, J. R. and Fernando, M. A. (ed.)

Dunn, M. J., 1993. Sodium dodecyl sulfate-polyacrylamide gel electrophoresis (SDS-PAGE). In: Gel electrophoresis: proteins. Ch. 6, pp 51-64. BIOS Scientific Publishers Limited, Oxford.

Dunn, M. J., 1997. Two-dimensional polyacrylamide gel electrophoresis for the separation of proteins for chemical characterization. In; Smith, B. J., ed. Protein sequencing protocols. Ch. 3, pp 25-36. Humana Press, Totowa, N.J.

Gantt, S. M., Clavijo, P., Bai, X., Esko, J. D., Sinnis, P., 1997. Cell adhesion to a motif shared by the malaria circumsporozoite protein and thrombospondin is mediated by its glycosaminoglycan-binding region and not by CSVTCG. Journal of Biological Chemistry, 272: 19205-19213.

Guo, N. H., Krutzsch, H. C., Negre, E., Zabrenetsky, V. S., Roberts, D. D, 1992. Heparin-binding peptides from the type I repeats of thrombospondin. Structural requirements for heparin binding and promotion of melanoma cell adhesion and chemotaxis. Journal of Biological Chemistry. 267: 19349-19355.

Karkhanis, Y. D., Nollstadt, K. A., Bhogal, B. S., Ravino, O., Pellegrino, R., Crane, M. S., Murray, P. K., Turner, M. J. (1991) Purification and characterization of a protective antigen for *Eimeria tenella*. Infect. & Immun. 59: 983-989.

Righetti, P. G., 1983. Isoelectric focusing: theory, methodology and applications. In: Laboratory techniques in biochemistry and molecular biology. Ch. 4, pp 305-313. Elsevier Biomedical Press.

Scopes, R. K., 1994. Separation by adsorption II: ion exchangers and nonspecific adsorbents, Separation in solution. In: Protein purification. Ch. 6, pp 146-171, Ch. 8, pp 238-249. Springer-Verlag, New York.

Smith, N. C., Wallach, M., Miller, C. M. D., Morgenstern, R., Braun, R. and Eckert J., 1994. Maternal transmission of immunity to *Eimeria maxima*: western blot analysis of protective antibodies induced by infection. Infection and Immunity, 62(11): 4811-4817.

Smith, B. J., 1997. SDS polyacrylamide gel electrophoresis for N-terminal sequencing In; Smith, B. J., ed. Protein sequencing protocols. Ch. 2, pp 17-24. Humana Press, Totowa, N.J.

Sutton C. A., Shirley, M. W. and Wisher, M, 1989. Characterisation of coccidial proteins by two-dimensional sodium dodecyl sulphate-polyacrylamide gel electrophoresis. Parasitology, 1989(99): 175-187.

Tomley, F. M., Billington, K. J., Bumstead, J. M., Clark, J. D., Monaghan, P., 2001. EtMIC4: a microneme protein from Rimeria tenella that contains tandem arrays of epidermal growth factor-like repeats and thrombospondin type-I repeats. International Journal for Parasitology, 2001(31): 1303-1310.

Wagenbach, G. E. (1969) Purification of *Eimeria tenella* sporozoites with glass bead columns. J. Parasitol. 55: 833-838.

Wolfsberg and Madden, 1999. Bioinformatics. In: Auubel, F. M., Brent, R., Kingston, R. E., Moore, D. D., Seidman, J. G., Smith, J. A., Struhl, K., eds. Short protocols in molecular biology. Ch. 18, pp 18.1-18.23.

What is claimed is:

1. An isolated nucleic acid comprising a nucleotide sequence encoding a 250 kDa polypeptide present in sporozoites/merozoites of *Eimeria maxima*, wherein the 250 kDa polypeptide has the amino acid sequence shown as SEQ. ID. NO. 6, or a full complement of the nucleic acid.

2. The isolated nucleic acid of claim 1, wherein the nucleic acid has the nucleotide sequence shown as SEQ. ID. NO. 4.

3. An isolated vector comprising a nucleotide sequence encoding a 250 kDa polypeptide present in sporozoites/merozoites of *Eimeria maxima*, wherein the 250 kDa polypeptide has the amino acid sequence shown as SEQ. ID. NO. 6, or the full complement of the nucleic acid.

4. An isolated host cell comprising a-vector comprising a nucleotide sequence encoding a 250 kDa polypeptide present in sporozoites/merozoites of *Eimeria maxima*, which has the amino acid sequence shown as SEQ. ID. NO. 6, the full complement of the nucleic acid.

5. The vector of claim 3, wherein the vector is a plasmid.

6. The vector of claim 3, wherein the nucleic acid has the nucleotide sequence shown as SEQ. ID. NO. 4.

7. The nucleic acid of claim 1, wherein the nucleic acid is a DNA molecule or an RNA molecule.

8. The nucleic acid of claim 7, wherein the DNA molecule is a cDNA molecule.

9. The nucleic acid of claim 1 operatively linked to a promoter of RNA transcription.

10. An isolated plasmid comprising a nucleotide sequence encoding a 250 kDa polypeptide present in sporozoites/merozoites of *Eimeria maxima*, wherein the 250 kDa polypeptide has the amino acid sequence shown as SEQ. ID. NO. 6, or the full complement of the nucleic acid.

11. The plasmid of claim 10, designated 230.1 plasmid deposited under Australian Government Analytical Laboratories Accession No. NM01/22396.

12. The host cell of claim 4, wherein the cell is a bacterial cell, a plant cell, an insect cell, or a mammalian cell.

13. An isolated transformed cell comprising a nucleotide sequence encoding a 250 kDa polypeptide present in sporozoites/merozoites of *Eimeria maxima*, wherein the 250 kDa polypeptide has the amino acid sequence shown as SEQ. ID. NO. 6, or a the full complement of the nucleic acid.

14. The transformed cell of claim 13, designated 230.1 bacteria deposited under Australian Government Analytical Laboratories Accession No. NM01/22397.

15. A method of producing a 250 kDa polypeptide present in sporozoites/merozoites of *Eimeria maxima* comprising culturing host cells of claim 4 and isolating the 250 kDa polypeptide from the cells so cultured.

16. A vaccine for immunizing a subject against infection by an *Eimeria maxima* species comprising an isolated nucleic acid comprising a nucleotide sequence encoding a 250 kDa polypeptide present in gametocytes of *Eimeria maxima* having the amino acid sequence set forth in SEQ. ID. NO. 6 or the full complement of the nucleic acid, an isolated vector comprising such nucleic acid, or a polypeptide encoded by such nucleic acid.

17. The vaccine of claim 16, further comprising a second nucleic acid encoding for an antigen of *Eimeria maxima*, an isolated vector comprising such nucleic acid, or a polypeptide encoded by such nucleic acid.

18. The vaccine of claim 17, wherein the second nucleic acid encodes for a 56 kDa antigen of *Eimeria maxima*, the vector comprises a nucleic acid which encodes for a 56 kDa antigen of *Eimeria maxima*, and the polypeptide is a 56 kDa antigen of *Eimeria maxima.*

19. The vaccine of claim 17, wherein the second nucleic acid encodes for an 82 kDa antigen of *Eimeria maxima*, the vector comprises a nucleic acid which encodes for an 82 kDa antigen of *Eimeria maxima*, and the polypeptide is an 82 kDa antigen of *Eimeria maxima.*

20. The vaccine of claim 17, wherein the second nucleic acid encodes for a 230 kDa antigen of *Eimeria maxima*, the vector comprises a nucleic acid which encodes for a 230 kDa antigen of *Eimeria maxima*, and the polypeptide is a 230 kDa antigen of *Eimeria maxima.*

21. The vaccine of claim 16, wherein the subject is an avian species.

22. The vaccine of claim 21 wherein avian species is chickens, ducks, turkeys, geese, bantams, quail, or pigeons.

23. The vaccine of claim 16, wherein the vaccine is designed to be administered by intravenous, intramuscular or intraperitoneal injection; or by spraying said vaccine into the nostrils of the subject.

24. The vaccine of claim 22, wherein the vaccine is designed to be administered in ovo.

25. The vaccine of claim 24, wherein the vaccine is designed to be administered to an air sac of an egg.

26. A method of immunizing a subject against infection by an *Eimeria maxima* comprising the step of administering to the subject the vaccine of claim 16.

* * * * *

SEQUENCE LISTING

<160> NUMBER OF SEQ ID NOS: 46

<210> SEQ ID NO 1
<211> LENGTH: 7987
<212> TYPE: DNA
<213> ORGANISM: Chicken

<400> SEQUENCE: 1
caacatttct tcttcctttt tcttcttcga gcttctttag ctcgattttc tggcccttgc 60
agctctccgc gggtgcaggg cgcagccagc tcactactgc ctttcacagc gtcgttcccc 120
accttggccc atgtgccaca tggtcatttt tcttcagttt gttcatgaga agagctgcta 180
cagtgtagct cgaactcaac tttaaacgca gccgtttcag cggcgacaat atgctgcatc 240
gcaacccgcg gtgggcgctt tgtgcagccc tcgctgcact ctatggcgga acaggaatcg 300
ccagcgccga agttaacaat gaattgagca agtgcgaatc tgggtggaca ccctggacta 360
cctgcaaccc gcaaactggt ctgcgggaga ggcacaatgc acagtgcgag acatgggtgg 420
aggttgagga atgccagaag ctgacaggat gtggcaactg gactccttgg tctcccggcg 480
atatgtcgtg tgtggtggga cagtttcaaa cccgcaacag ggagggctgc ccagaggtgc 540
aggaagtcag ggcatgcagg cctgtacttc tagaatgcaa cgatcaatgg accccctgga 600
caatgtgcga caccaaccgc gtccaggaaa gatacaactc aaagtgcgga cccgtcgaag 660
tccgcgagtg caacatggac gacgcagaga tcgagaaatg cggcgagttc gtggaatggg 720
atccccctat gaatggagac tgcgtacgcg ggggtaccca cacgcgttac cgtcaaaact 780
gcccagaccg caaagaggtg cgggtgtgcg gagcctttga ttgcagtagc tgctctgtaa 840
acgccacttg cgatcccatt ggtgcatcct gcgaatgcaa gcctggtttc cgcggcaatg 900
ggaagacctg cgaggccttc aacccctgcg aagatacccc tgcaccttgc gacagcaacg 960
ccatctgcac cccagacgca atgacgccaa atgccagtgc aaggcaggct gggacgcaga 1020
ttccggagca ggcagcagca agaagccttg cgttgaggtc gacgagtgcg catccaacac 1080
ccaccagtgc ccggcacact ccacatgcat caacaccaag ggctcttata agtgcgactg 1140
caaccaggga taccgtcaag ggagaggacg gacagtgtca tgacgtcgat gaatgcacca 1200
acggagagca cacctgcccc gctcactcca cttgtttgaa tacagctggc agctacgagt 1260
gccgctgcga cactgggtac agcggaaatg caactgcaga cagcccttgc aagaacattg 1320
acgaatgcgc caaccccaac gcctgctcgg ccaacgctat ctgcacagac accgacggct 1380
ccttcacctg cagctgcccc gaagggtaca gcggccaggg aacccatgac tctccctgct 1440
ccaagatcga cttctgcgca taccccctcac tcaatacatg cggagcccac tccacttgca 1500
acaccctcac atctttcaag tgcatctgcg atgcgggata tgaaggcgcc ggcactcgcg 1560
agagcccgtg cgtggacgtg aacgagtgct cgaacgagaa gcccacaaac aactgcaaca 1620
gaaacgcaaa ctgcaccaac accgagggat cctacacttg cgaatgcaag cccggtttct 1680
ctggcgacgg catgggtccc aacgggtgta ccgacatcga cgagtgcgcg gcggagcagt 1740 cccccctgcga ccctcacgcc tcctgcagca acactgaggg ctcgtatgta tgcacctgca 1800
acaccggcta cgagccagct tcaaccgacg ggcatgcatg caaagatatc gacgagtgcg 1860
ccaccggtgc agctgggtgc cacgtgtcag cacagtgtct gaacacggac ggcagctacg 1920
agtgcaagtg tcttgagggc ttcgtcggcg acggaaagac ctgcaacgac gtcgatgagt 1980
gcgctgcggc gacatctcct tgcggtgaca acactcactg ccagaacaca attggcagct 2040

-continued

```
acgagtgcga gtgcaaggct ggctatggca acatgcaaga caacgcatgc agcgacattg   2100
acgagtgcaa ggatgcgaac accaagatcc ctgacaactg tctttgcgtg aacaatgatg   2160
gcagctactc ccttgaggcg aaggctggat acgaattggt gaacggcgag tgcatcaaga   2220
tcgacttctg cgcccgcggc gcatgcaact cgctggcctc ctgcaaggag aatgaagaag   2280
gcacagcggc gatctgcacc tgcctgccag gctacagcgg cgacggcact gctgaaggcc   2340
actgcaacga cattgacgag tgtgcaggtc agaatgactg tgctcctgcc gagcagggag   2400
gcatctgcga gaacactgtc ggctcgtaca cctgcaagtg caaagagggg tacaggcaag   2460
atggaaactc atgcactgag atcgacgagt gcgctgaggg aacccacaac tgccacccctt   2520
ccgccacctg cagcaacacc cccggaagct tcacctgcca atgcaacagt ggattcactg   2580
gcagcggtgt ggagtgcgaa gacattgacg agtgctcaac tgaggcagat gattgtggtg   2640
caaacaccat ctgcagcaac accattggtg ctttcgagtg caactgccgt gaaggctatg   2700
aacgcgcaga cgcaaagacg tgcgtcgaca tcgacgaatg cgcgacaggc acacacactt   2760
gctcgaacca cgccacctgc accaataccg atgggtcatt cacatgccag tgcaaccccg   2820
gcttcgaagg tgacggccac aagtgcgagg acatcgactt ctgcggtgct ggacagcacg   2880
actgcaatgt gcatgccgag tgctctgaga gcgaggacaa caccactttc aagtgcacct   2940
gtataacagg gtacgctgga gacggccatg gcgaggcagg ctgccaagac attgatgagt   3000
gcgcagaaga aaacatctgc ggaagcaacg ctgtctgcac aaacaccgca ggaagctacc   3060
aatgcgcatg ccgtgagggc ttcgttgcat cagctgaaca gcagcagcag ggaaccccag   3120
cactggtttg cgtggacgtc cacgagtgca gcgacgcttc gaagaacaca tgtgccaagc   3180
cagccgacgg aggcatttgc acaaacactg aaggcagcta cgaatgcgct tgcaagccag   3240
gctaccaagg tgacggccac agctgcgcag acatcaacga atgcactgca cagggcacct   3300
gcggcgaaca cacaacttgc aagaacacac ccggatcctt ccagtgcgac tgcgttgagg   3360
gattcgagcg cgctgatgaa cgcacctgcc gtgacatcaa cgagtgcgag acaggagcag   3420
tcgtgctgcc accgaactcc acctgcgtca acactgaagg cagctacgac ttcgactgcg   3480
ttgctgggta ccgccgcact gatggagctt gtgtgaagat cgacttctgc aaggagaagg   3540
gatgcaacgc aaacgccaca tgccgcgaaa acgatgccgg caccgaggcc atctgcactt   3600
gcaaggaagg ctatgaaggc agcggagaag gcgaagatgg ttgccagaac atcaatgagt   3660
gcgagagagg cgaaccctgc aaggacttcg gcgaaggcgg tgtttgcgtc gacacaccag   3720
gatcattcac ttgcgagtgc gctgctggat tcattcaacg ccgctccgtt tgccaagatg   3780
ttgacgaatg tctcgacgga aagctgaaca cctgcgctgc caccggaggc gtctgctcca   3840
acaccgtcgg ttccttcacc tgctcgtgcg ccagcggctt cgaaggcgat ggccacacct   3900
gcaatgatgt cgacgaatgc gcaacagcac agcacacctg tgacccgaat gccacttgcg   3960
tcaacaccga aggcagcttc gagtgccgct gcaatgccgg attcgagggc gacggacaca   4020
cctgcgcaga catcgacgaa tgcgcagacc cagccaaaaa cacatgcgat acacacaagg   4080
gtgtatgcca aaacaccaca gggtcctaca cctgcggctg caagaccgga ttcagtcttg   4140
cagctgacgg aagcacatgc gaaaacgtcg acgagtgcgc ggcgggaact gcaaactgca   4200
acgagcgaag cttctgtaag gacacagagg gttcctacca atgcgagtgc aagaacggct   4260
acaaggctgc aggagaggac tgtgtggacg ttgacgagtg cgaggctggc gtgcatggat   4320
gcagcgagca cgcaatctgc acaaatacag acggcagcta ctcctgcgaa tgcatggagg   4380
```

-continued

```
gataccaggg agacggcaag gcttgcgaga agacagtcgg cgtctgcgac tccgctccct   4440
gcggtgccca cgccacctgc gagcctgcag gggacaacta cacttgcaca tgccacccag   4500
gctacgagat gcgcgaagga gcctgcgttg acatcgatga gtgcacagca ggcagcctca   4560
actgcgaccc tcatgccatt tgcacaaaca ccgacggctc cttcacttgc gtctgtggca   4620
gcggctatac cggccttggc acatcctgcg aagacatcga cgagtgcgcg ggtaacgcag   4680
caggctgcga catccacgcc gtctgcacga acactcccgg atcgttcaag tgcgagtgca   4740
agagcggctt cgaaggcgat ggcacgcaat gcacggagaa ggtgttgctc cccggacaga   4800
ttcactgcga agcctggact gcatggacag agtgtaccga cggcgccaaa accagcacac   4860
gcagctgcct tgcactgccg cttaagaagg agatgcgcgc ctgccctgca gctgacttct   4920
cccagtgcgg agagttcact gaatggactg cctgccctgg aaccaacaat aacctgtctc   4980
ataggcgcac tgaaagattc ggagaacccg gatgcgaaga tgcagaggaa gtccgcgaat   5040
gcccagatga agagaccgag cagaaatgcg gcgcctgggg tgagtggacc gcctgcggcg   5100
acccatcccc tggcctgaga actcgcgcac gcgagaactg ccccgatgtg gtagagttcg   5160
agcgttgcac tatgcccagt gagcctgagg ctggcgaagt gactgagcct cacacagaag   5220
gaggagccgg agttggtggc gaagtgactg agcctgacac ggaagaagga gccggagttg   5280
gtggtgaagt gcagcccggt acagaagaag gagcaggagt tggtggtgaa gtgcagcccg   5340
gtacagaaga aggagccgga gttggtggtg aagtgcagcc cggtacagaa gaaggagccg   5400
gagttggtgg tgaagtgcag cccggtacgg aagaaggagc cggcattggt ggcgaagtga   5460
ctgagcctga caccgaagga ggagccggag ttagtggcga accgaccgaa gaagagggca   5520
ccgaaagcac cggtccatgc aaagagttcg gaccctggac ggcctgcaag gaggacgaga   5580
acggagtcgg catccaacgc cgtatgtgcg ccggcagaga agacatcatc gaatccagaa   5640
tttgcactgt cacggatcac tgcggagaat ggaccccctg gtcaacttgc actaacggca   5700
gccaggccag aaacaaacgc ttctgcacca acgttaggga agtccgtctc tgcggagctg   5760
acattccagt tacagacgga tgcacgtgga gcgagtggac ttcttgcagt ctagtcaatg   5820
aggagggcgg ctacttccgc acgcgcacat cctctgactg caacatgaat gaagtgcagg   5880
cctgctctcc cagcagcagc acaaccgcag acagcgaaac agaaggcacc tgctctgcat   5940
ggaacccctg gacggagtgc tcgaacggcc accagacacg caagtgtgcc acaatggaag   6000
cagaagaatc gcgcacttgc ggagagactc cagagaactg cggagaattc ggccccttcg   6060
aacccgcaaa ctgcacggcc ggccaaatgg tcaccaggac gcgcacctgc ggagaaaccg   6120
agcagaagga aaccaaactg tgcgacgtca gctccaccga agaaggaaaa caatgcggtc   6180
agtggggccc atggagcgaa tgcaacatcc acctgggctc agaggacaat gtgcgtgttc   6240
gtgaggacac cgcttgcggc gtgacggagt acgaggagtg cagcaagccg gcgaacaacg   6300
cctttgtctg cacaccttgg agtgaatgct cggacaagaa ggagcggaga acgtgcacca   6360
tccgcaaaaa cggtcttgtt cagacacgtc aagaattcag aacatgcagt gtagacatcg   6420
ccacaacttg cggcgatttc ggcgcatggt ctgaatgcaa cgctgagggc ttgcatcagc   6480
gcagtctcga gaaatgcccc gacgtcatcg aggtcgcaac ttgcggcagt gaggattgcc   6540
cgccattcgg cgagtggact gaatgcggcg ttccagagga gggcatgcgt tctcgccaac   6600
gcattgactg cgttgaatct gcagcctgcc agtgcacaga agtggagagc tgcttcgaca   6660
ccgaattgca ccccattcca gcccccggta cggaaacagg cgaaggagag ggagagaccg   6720
agacaggcga aggcgaaact ggtgaagcag gtggcgagga aggcgagcaa acaggagaag   6780
```

-continued

```
gcgaagtgca gcccccagaa gaagagcttc ctggggagag tgtaactgag cctgaggaga   6840

agcctgagga ggagctacct gaggaggagg ttactgagcc tgaggagaag cctgaggagg   6900

gtgtgactca gcctgaggag acacctgagc agcctgttga gggtaccgaa gaagagggca   6960

agcaggagtc tgaggctgcc cccgaaactc ctgccgtcca gccaaaacca gaggagggtc   7020

acgaacgccc agaacccgaa gaggaggagg agaagaagga agaaggcggc ggcttcccaa   7080

cagctgcagt ggcaggaggt gttggtggtg tgttgctcat agctgctgta ggtggtggtg   7140

ttgcagcctt cactagcggc ggaggtggcg ctggcgcaca ggaggcagaa caggtcgagt   7200

tcgaaggaga agataccgga gcagcaactg ccgagacacc tgaagccgat acagttatcg   7260

acatcacaga cgaagacgac tactgggccg acagcggcga cattcagtaa agttgaatgt   7320

ctgttttctt ccaaggagaa gatacaaaac caaaatctta acaaaacgaa ggatgcgaag   7380

gcgaaacagg ccaaagtcga cctgttttct cattcaatca atggttgcag tcgtgaagga   7440

gctggactca gttgcatctc caccccaaga gctcgccgtt agtgggcaag ttggataggg   7500

tgaatgcatt ttcatctccg caggcgaaag tcacgacgag ggcctgttct tgtttgtttg   7560

tttgaattgg ttggttggtg catcctgctg gatttcaacg acggcaatca tcacgcagtg   7620

agacggagca gcagcgcata ctattttctg agcaagttca tcgtttattt ttcgctgtat   7680

ctcgtagcgc cgaggaagca aacaagcaaa cgcccaccaa ctgaccaacc aatgagagag   7740

ccgtccttta atttccaccc ctcttctgtc ttccgaagat tcggcggggt ttcggatggg   7800

ggagaaattg tggttggatt ggtcgggtgt tttcgttttc tttgattgat gcaacaatat   7860

ctgctagcca gcgtacaaag aatagctgca gttcaaatga atgcatctta attattccac   7920

accgcggtgc ctcttctttg ccgtggcaca ccttccgttt attacctcca ctcaagattt   7980

tctcccc                                                             7987
```

<210> SEQ ID NO 2
<211> LENGTH: 7987
<212> TYPE: DNA
<213> ORGANISM: CHICKEN

<400> SEQUENCE: 2

```
gttgtaaaga agaaggaaaa agaagaagct cgaagaaatc gagctaaaag accgggaacg     60

tcgagaggcg cccacgtccc gcgtcggtcg agtgatgacg gaaagtgtcg cagcaagggg    120

tggaaccggg tacacggtgt accagtaaaa agaagtcaaa caagtactct tctcgacgat    180

gtcacatcga gcttgagttg aaatttgcgt cggcaaagtc gccgctgtta tacgacgtag    240

cgttgggcgc cacccgcgaa acacgtcggg agcgacgtga gataccgcct tgtccttagc    300

ggtcgcggct tcaattgtta cttaactcgt tcacgcttag acccacctgt gggacctgat    360

ggacgttggg cgtttgacca gacgccctct ccgtgttacg tgtcacgctc tgtacccacc    420

tccaactcct tacggtcttc gactgtccta caccgttgac ctgaggaacc agagggccgc    480

tatacagcac acaccaccct gtcaaagttt gggcgttgtc cctcccgacg ggtctccacg    540

tccttcactc ccgtacgtcc ggacatgaag atcttacgtt gctagttacc tgggggacct    600

gttacacgct gtggttggcg caggtccttt ctatgttgag tttcacgcct gggcagcttc    660

aggcgctcac gttgtacctg ctgcgtctct agctctttac gccgctcaag caccttaccc    720

tagggggata cttacctctg acgcatgcgc ccccatgggt gtgcgcaatg gcagttttga    780

cgggtctggc gtttctccac gcccacacgc ctcggaaact aacgtcatcg acgagacatt    840
```

-continued tgcggtgaac gctagggtaa ccacgtagga cgcttacgtt cggaccaaag gcgccgttac 900
ccttctggac gctccggaag ttggggacgc ttctatgggg acgtggaacg ctgtcgttgc 960
ggtagacgtg gggtctgcgt tactgcggtt tacggtcacg ttccgtccga ccctgcgtct 1020
aaggcctcgt ccgtcgtcgt tcttcggaac gcaactccag ctgctcacgc gtaggttgtg 1080
ggtggtcacg ggccgtgtga ggtgtacgta gttgtggttc ccgagaatat tcacgctgac 1140
gttggtccct atggcagttc cctctcctgc ctgtcacagt actgcagcta cttacgtggt 1200
tgcctctcgt gtggacgggg cgagtgaggt gaacaaactt atgtcgaccg tcgatgctca 1260
cggcgacgct gtgacccatg tcgcctttac gttgacgtct gtcgggaacg ttcttgtaac 1320
tgcttacgcg gttggggttg cggacgagcc ggttgcgata gacgtgtctg tggctgccga 1380
ggaagtggac gtcgacgggg cttcccatgt cgccggtccc ttgggtactg agagggacga 1440
ggttctagct gaagacgcgt atggggagtg agttatgtac gcctcgggtg aggtgaacgt 1500
tgtgggagtg tagaaagttc acgtagacgc tacgccctat acttccgcgg ccgtgagcgc 1560
tctcgggcac gcacctgcac ttgctcacga gcttgctctt cgggtgtttg ttgacgttgt 1620
ctttgcgttt gacgtggttg tggctcccta ggatgtgaac gcttacgttc gggccaaaga 1680
gaccgctgcc gtacccaggg ttgcccacat ggctgtagct gctcacgcgc cgcctcgtca 1740
gggggacgct gggagtgcgg aggacgtcgt tgtgactccc gagcatacat acgtggacgt 1800
tgtggccgat gctcggtcga agttggctgc ccgtacgtac gtttctatag ctgctcacgc 1860
ggtggccacg tcgacccacg gtgcacagtc gtgtcacaga cttgtgcctg ccgtcgatgc 1920
tcacgttcac agaactcccg aagcagccgc tgcctttctg gacgttgctg cagctactca 1980
cgcgacgccg ctgtagagga acgccactgt tgtgagtgac ggtcttgtgt taaccgtcga 2040
tgctcacgct cacgttccga ccgataccgt tgtacgttct gttgcgtacg tcgctgtaac 2100
tgctcacgtt cctacgcttg tggttctagg gactgttgac agaaacgcac ttgttactac 2160
cgtcgatgag ggaactccgc ttccgaccta tgcttaacca cttgccgctc acgtagttct 2220
agctgaagac gcgggcgccg cgtacgttga gcgaccggag gacgttcctc ttacttcttc 2280
cgtgtcgccg ctagacgtgg acggacggtc cgatgtcgcc gctgccgtga cgacttccgg 2340
tgacgttgct gtaactgctc acacgtccag tcttactgac acgaggacgg ctcgtccctc 2400
cgtagacgct cttgtgacag ccgagcatgt ggacgttcac gtttctcccc atgtccgttc 2460
tacctttgag tacgtgactc tagctgctca cgcgactccc ttgggtgttg acggtgggaa 2520
ggcggtggac gtcgttgtgg gggccttcga agtggacggt tacgttgtca cctaagtgac 2580
cgtcgccaca cctcacgctt ctgtaactgc tcacgagttg actccgtcta ctaacaccac 2640
gtttgtggta gacgtcgttg tggtaaccac gaaagctcac gttgacggca cttccgatac 2700
ttgcgcgtct gcgtttctgc acgcagctgt agctgcttac gcgctgtccg tgtgtgtgaa 2760
cgagcttggt gcggtggacg tggttatggc tacccagtaa gtgtacggtc acgttggggc 2820
cgaagcttcc actgccggtg ttcacgctcc tgtagctgaa gacgccacga cctgtcgtgc 2880
tgacgttaca cgtacggctc acgagactct cgctcctgtt gtggtgaaag ttcacgtgga 2940
catattgtcc catgcgacct ctgccggtac cgctccgtcc gacggttctg taactactca 3000
cgcgtcttct tttgtagacg ccttcgttgc gacagacgtg tttgtggcgt ccttcgatgg 3060
ttacgcgtac ggcactcccg aagcaacgta gtcgacttgt cgtcgtcgtc ccttggggtc 3120
gtgaccaaac gcacctgcag ctgctcacgt cgctgcgaag cttcttgtgt acacggttcg 3180
gtcggctgcc tccgtaaacg tgtttgtgac ttccgtcgat gcttacgcca acgttcggtc 3240

-continued

```
cgatggttcc actgccggtg tcgacgcgtc tgtagttgct tacgtgacgt gtcccgtgga   3300
cgccgcttgt gtgttgaacg ttcttgtgtg ggcctaggaa ggtcacgctg acgcaactcc   3360
ctaagctcgc gcgactactt gcgtggacgg cactgtagtt gctcacgctc tgtcctcgtc   3420
agcacgacgg tggcttgagg tggacgcagt tgtgacttcc gtcgatgctg aagctgacgc   3480
aacgacccat ggcggcgtga ctacctcgaa cacacttcta gctgaagacg ttcctcttcc   3540
ctacgttgcg tttgcggtgt acggcgcttt tgctacggcc gtggctccgg tagacgtgaa   3600
cgttccttcc gatacttccg tcgcctcttc cgcttctacc aacggtcttg tagttactca   3660
cgctctctcc gcttgggacg ttcctgaagc cgcttccgcc acaaacgcag ctgtgtggtc   3720
ctagtaagtg aacgctcacg cgacgaccta agtaagttgc ggcgaggcaa acggttctac   3780
aactgcttac agagctgcct ttcgacttgt ggacgcgacg gtggcctccg cagacgaggt   3840
tgtggcagcc aaggaagtgg acgagcacgc ggtcgccgaa gcttccgcta ccggtgtgga   3900
cgttactaca gctgcttacg cgttgtcgtg tcgtgtggac actgggctta cggtgaacgc   3960
agttgtggct tccgtcgaag ctcacggcga cgttacggcc taagctcccg ctgcctgtgt   4020
ggacgcgtct gtagctgctt acgcgtctgg gtcggttttt gtgtacgcta tgtgtgttcc   4080
cacatacggt tttgtggtgt cccaggatgt ggacgccgac gttctggcct aagtcagaac   4140
gtcgactgcc ttcgtgtacg cttttgcagc tgctcacgcg ccgcccttga cgtttgacgt   4200
tgctcgcttc gaagacattc ctgtgtctcc caaggatggt tacgctcacg ttcttgccga   4260
tgttccgacg tcctctcctg acacacctgc aactgctcac gctccgaccg cacgtaccta   4320
cgtcgctcgt gcgttagacg tgtttatgtc tgccgtcgat gaggacgctt acgtacctcc   4380
ctatggtccc tctgccgttc cgaacgctct tctgtcagcc gcagacgctg aggcgaggga   4440
cgccacgggt gcggtggacg ctcggacgtc ccctgttgat gtgaacgtgt acggtgggtc   4500
cgatgctcta cgcgcttcct cggacgcaac tgtagctact cacgtgtcgt ccgtcggagt   4560
tgacgctggg agtacggtaa acgtgtttgt ggctgccgag gaagtgaacg cagacaccgt   4620
cgccgatatg gccggaaccg tgtaggacgc ttctgtagct gctcacgcgc ccattgcgtc   4680
gtccgacgct gtaggtgcgg cagacgtgct tgtgagggcc tagcaagttc acgctcacgt   4740
tctcgccgaa gcttccgcta ccgtgcgtta cgtgcctctt ccacaacgag gggcctgtct   4800
aagtgacgct tcggacctga cgtacctgtc tcacatggct gccgcggttt tggtcgtgtg   4860
cgtcgacgga acgtgacggc gaattcttcc tctacgcgcg gacgggacgt cgactgaaga   4920
gggtcacgcc tctcaagtga cttacctgac ggacgggacc ttggttgtta ttggacagag   4980
tatccgcgtg actttctaag cctcttgggc ctacgcttct acgtctcctt caggcgctta   5040
cgggtctact tctctggctc gtctttacgc cgcggacccc actcacctgg cggacgccgc   5100
tgggtagggg accggactct tgagcgcgtg cgctcttgac ggggctacac catctcaagc   5160
tcgcaacgtg atacgggtca ctcggactcc gaccgcttca ctgactcgga gtgtgtcttc   5220
ctcctcggcc tcaaccaccg cttcactgac tccgactgtg ccttcttcct cggcctcaac   5280
caccacttca cgtcgggcca tgtcttcttc ctcgtcctca accaccactt cacgtcgggc   5340
catgtcttct tcctcggcct caaccaccac ttcacgtcgg gccatgtctt cttcctcggc   5400
ctcaaccacc acttcacgtc gggccatgcc ttcttcctcg gccgtaacca ccgcttcact   5460
gactcggact gtggcttcgt cctcggcctc aatcaccgct tggctggctt cttctcccgt   5520
ggctttcgtg gccaggtacg tttctcaagc ctgggacctg ccggacgttc ctcctgctct   5580
```

-continued

```
tgcctcagcc gtaggttgcg gcatacacgc ggccgtctct tctgtagtag cttaggtctt   5640
aaacgtgaca gtgcctactg acgcctctta cctgggggac cagttgaacg tgattgccgt   5700
cggtccggtc tttgtttgcg aagacgtggt tgcaatccct tcaggcagag acgcctcgac   5760
tgtaaggtca atgtctgcct acgtgcacct cgctcacctg aagaacgtca gatcagttac   5820
tcctcccgcc gatgaaggcg tgcgcgtgta ggagactgac gttgtactta cttcacgtcc   5880
ggacgagagg gtcgtcgtcg tgttggcgtc tgtcgctttg tcttccgtgg acgagacgta   5940
ccttggggac ctgcctcacg agcttgccgg tggtctgtgc gttcacacgg tgttaccttc   6000
gtcttcttag cgcgtgaacg cctctctgag gtctcttgac gcctcttaag ccggggaagc   6060
ttgggcgttt gacgtgccgg ccggtttacc agtggtcctg cgcgtggacg cctctttggc   6120
tcgtcttcct ttggtttgac acgctgcagt cgaggtggct tcttcctttt gttacgccag   6180
tcaccccggg tacctcgctt acgttgtagg tggacccgag tctcctgtta cacgcacaag   6240
cactcctgtg gcgaacgccg cactgcctca tgctcctcac gtcgttcggc cgcttgttgc   6300
ggaaacagac gtgtggaacc tcacttacga gcctgttctt cctcgcctct tgcacgtggt   6360
aggcgttttt gccagaacaa gtctgtgcag ttcttaagtc ttgtacgtca catctgtagc   6420
ggtgttgaac gccgctaaag ccgcgtacca gacttacgtt gcgactcccg aacgtagtcg   6480
cgtcagagct ctttacgggg ctgcagtagc tccagccttg aacgccgtca ctcctaacgg   6540
gcggtaagcc gctcacctga cttacgccgc aaggtctcct cccgtacgca agagcggttg   6600
cgtaactgac gcaacttaga cgtcggacgg tcacgtgtct tcacctctcg acgaagctgt   6660
ggcttaacgt ggggtaaggt cgggggccat gcctttgtcc gcttcctctc cctctctggc   6720
tctgtccgct tccgctttga ccacttcgtc caccgctcct tccgctcgtt tgtcctcttc   6780
cgcttcacgt cgggggtctt cttctcgaag gacccctctc acattgactc ggactcctct   6840
tcggactcct cctcgatgga ctcctcctcc aatgactcgg actcctcttc ggactcctcc   6900
cacactgagt cggactcctc tgtggactcg tcggacaact cccatggctt cttctcccgt   6960
tcgtcctcag actccgacgg gggctttgag gacggcaggt cggttttggt ctcctcccag   7020
tgcttgcggg tcttgggctt ctcctcctcc tcttcttcct tcttccgccg ccgaagggtt   7080
gtcgacgtca ccgtcctcca caaccaccac acaacgagta tcgacgacat ccaccaccac   7140
aacgtcggaa gtgatcgccg cctccaccgc gaccgcgtgt cctccgtctt gtccagctca   7200
agcttcctct tctatggcct cgtcgttgac ggctctgtgg acttcggcta tgtcaatagc   7260
tgtagtgtct gcttctgctg atgacccggc tgtcgccgct gtaagtcatt tcaacttaca   7320
gacaaaagaa ggttcctctt ctatgttttg gttttagaat tgttttgctt cctacgcttc   7380
cgctttgtcc ggtttcagct ggacaaaaga gtaagttagt taccaacgtc agcacttcct   7440
cgacctgagt caacgtagag gtggggttct cgagcggcaa tcacccgttc aacctatccc   7500
acttacgtaa aagtagaggc gtccgctttc agtgctgctc ccggacaaga acaaacaaac   7560
aaacttaacc aaccaaccac gtaggacgac ctaaagttgc tgccgttagt agtgcgtcac   7620
tctgcctcgt cgtcgcgtat gataaaagac tcgttcaagt agcaaataaa aagcgacata   7680
gagcatcgcg gctccttcgt ttgttcgttt gcgggtggtt gactggttgg ttactctctc   7740
ggcaggaaat taaaggtggg gagaagacag aaggcttcta agccgcccca aagcctaccc   7800
cctctttaac accaacctaa ccagcccaca aaagcaaaag aaactaacta cgttgttata   7860
gacgatcggt cgcatgtttc ttatcgacgt caagtttact tacgtagaat taataaggtg   7920
tggcgccacg gagaagaaac ggcaccgtgt ggaaggcaaa taatggaggt gagttctaaa   7980
```

-continued agagggg 7987

<210> SEQ ID NO 3
<211> LENGTH: 2653
<212> TYPE: PRT
<213> ORGANISM: Chicken

<400> SEQUENCE: 3

Thr Phe Leu Leu Pro Phe Ser Ser Ser Ser Phe Phe Ser Ser Ile Phe
1 5 10 15

Trp Pro Leu Gln Leu Ser Ala Gly Ala Gly Arg Ser Gln Leu Thr Thr
20 25 30

Ala Phe His Ser Val Val Pro His Leu Gly Pro Cys Ala Thr Trp Ser
35 40 45

Phe Phe Phe Ser Leu Phe Met Arg Arg Ala Ala Thr Val Leu Glu Leu
50 55 60

Asn Phe Lys Arg Ser Arg Phe Ser Gly Asp Asn Met Leu His Arg Asn
65 70 75 80

Pro Arg Trp Ala Leu Cys Ala Ala Leu Ala Ala Leu Tyr Gly Gly Thr
85 90 95

Gly Ile Ala Ser Ala Glu Val Asn Asn Glu Leu Ser Lys Cys Glu Ser
100 105 110

Gly Trp Thr Pro Trp Thr Thr Cys Asn Pro Gln Thr Gly Leu Arg Glu
115 120 125

Arg His Asn Ala Gln Cys Glu Thr Trp Val Glu Val Glu Glu Cys Gln
130 135 140

Lys Leu Thr Gly Cys Gly Asn Trp Thr Pro Trp Ser Pro Gly Asp Met
145 150 155 160

Ser Cys Val Val Gly Gln Phe Gln Thr Arg Asn Arg Glu Gly Cys Pro
165 170 175

Glu Val Gln Glu Val Arg Ala Cys Arg Pro Val Leu Leu Glu Cys Asn
180 185 190

Asp Gln Trp Thr Pro Trp Thr Met Cys Asp Thr Asn Arg Val Gln Glu
195 200 205

Arg Tyr Asn Ser Lys Cys Gly Pro Val Glu Val Arg Glu Cys Asn Met
210 215 220

Asp Asp Ala Glu Ile Glu Lys Cys Gly Glu Phe Val Glu Trp Asp Pro
225 230 235 240

Pro Met Asn Gly Asp Cys Val Arg Gly Gly Thr His Thr Arg Tyr Arg
245 250 255

Gln Asn Cys Pro Asp Arg Lys Glu Val Arg Val Cys Gly Ala Phe Asp
260 265 270

Cys Ser Ser Cys Ser Val Asn Ala Thr Cys Asp Pro Ile Gly Ala Ser
275 280 285

Cys Glu Cys Lys Pro Gly Phe Arg Gly Asn Gly Lys Thr Cys Glu Ala
290 295 300

Phe Asn Pro Cys Glu Asp Thr Pro Ala Pro Cys Asp Ser Asn Ala Ile
305 310 315 320

Cys Thr Pro Asp Ala Met Thr Pro Asn Ala Ser Ala Arg Gln Ala Gly
325 330 335

Thr Gln Ile Pro Glu Gln Ala Ala Ala Arg Ser Leu Ala Leu Arg Ser
340 345 350

Thr Ser Ala His Pro Thr Pro Thr Ser Ala Arg His Thr Pro His Ala
355 360 365

-continued

```
Ser Thr Pro Arg Ala Leu Ile Ser Ala Thr Ala Thr Arg Asp Thr Val
    370                 375                 380

Lys Gly Glu Asp Gly Gln Cys His Asp Val Asp Glu Cys Thr Asn Gly
385                 390                 395                 400

Glu His Thr Cys Pro Ala His Ser Thr Cys Leu Asn Thr Ala Gly Ser
                405                 410                 415

Tyr Glu Cys Arg Cys Asp Thr Gly Tyr Ser Gly Asn Ala Thr Ala Asp
            420                 425                 430

Ser Pro Cys Lys Asn Ile Asp Glu Cys Ala Asn Pro Asn Ala Cys Ser
        435                 440                 445

Ala Asn Ala Ile Cys Thr Asp Thr Asp Gly Ser Phe Thr Cys Ser Cys
    450                 455                 460

Pro Glu Gly Tyr Ser Gly Gln Gly Thr His Asp Ser Pro Cys Ser Lys
465                 470                 475                 480

Ile Asp Phe Cys Ala Tyr Pro Ser Leu Asn Thr Cys Gly Ala His Ser
                485                 490                 495

Thr Cys Asn Thr Leu Thr Ser Phe Lys Cys Ile Cys Asp Ala Gly Tyr
            500                 505                 510

Glu Gly Ala Gly Thr Arg Glu Ser Pro Cys Val Asp Val Asn Glu Cys
        515                 520                 525

Ser Asn Glu Lys Pro Thr Asn Asn Cys Asn Arg Asn Ala Asn Cys Thr
    530                 535                 540

Asn Thr Glu Gly Ser Tyr Thr Cys Glu Cys Lys Pro Gly Phe Ser Gly
545                 550                 555                 560

Asp Gly Met Gly Pro Asn Gly Cys Thr Asp Ile Asp Glu Cys Ala Ala
                565                 570                 575

Glu Gln Ser Pro Cys Asp Pro His Ala Ser Cys Ser Asn Thr Glu Gly
            580                 585                 590

Ser Tyr Val Cys Thr Cys Asn Thr Gly Tyr Glu Pro Ala Ser Thr Asp
        595                 600                 605

Gly His Ala Cys Lys Asp Ile Asp Glu Cys Ala Thr Gly Ala Ala Gly
    610                 615                 620

Cys His Val Ser Ala Gln Cys Leu Asn Thr Asp Gly Ser Tyr Glu Cys
625                 630                 635                 640

Lys Cys Leu Glu Gly Phe Val Gly Asp Gly Lys Thr Cys Asn Asp Val
                645                 650                 655

Asp Glu Cys Ala Ala Ala Thr Ser Pro Cys Gly Asp Asn Thr His Cys
            660                 665                 670

Gln Asn Thr Ile Gly Ser Tyr Glu Cys Glu Cys Lys Ala Gly Tyr Gly
        675                 680                 685

Asn Met Gln Asp Asn Ala Cys Ser Asp Ile Asp Glu Cys Lys Asp Ala
    690                 695                 700

Asn Thr Lys Ile Pro Asp Asn Cys Leu Cys Val Asn Asn Asp Gly Ser
705                 710                 715                 720

Tyr Ser Leu Arg Ala Lys Ala Gly Tyr Glu Leu Val Asn Gly Glu Cys
                725                 730                 735

Ile Lys Ile Asp Phe Cys Ala Arg Gly Ala Cys Asn Ser Leu Ala Ser
            740                 745                 750

Cys Lys Glu Asn Glu Glu Gly Thr Ala Ala Ile Cys Thr Cys Leu Pro
        755                 760                 765

Gly Tyr Ser Gly Asp Gly Thr Ala Glu Gly His Cys Asn Asp Ile Asp
    770                 775                 780
```

-continued

```
Glu Cys Ala Gly Gln Asn Asp Cys Ala Pro Ala Glu Gln Gly Gly Ile
785                 790                 795                 800

Cys Glu Asn Thr Val Gly Ser Tyr Thr Cys Lys Cys Lys Glu Gly Tyr
                805                 810                 815

Arg Gln Asp Gly Asn Ser Cys Thr Glu Ile Asp Glu Cys Ala Glu Gly
            820                 825                 830

Thr His Asn Cys His Pro Ser Ala Thr Cys Ser Asn Thr Pro Gly Ser
        835                 840                 845

Phe Thr Cys Gln Cys Asn Ser Gly Phe Thr Gly Ser Gly Val Glu Cys
    850                 855                 860

Glu Asp Ile Asp Glu Cys Ser Thr Glu Ala Asp Asp Cys Gly Ala Asn
865                 870                 875                 880

Thr Ile Cys Ser Asn Thr Ile Gly Ala Phe Glu Cys Asn Cys Arg Glu
                885                 890                 895

Gly Tyr Glu Arg Ala Asp Ala Lys Thr Cys Val Asp Ile Asp Glu Cys
            900                 905                 910

Ala Thr Gly Thr His Thr Cys Ser Asn His Ala Thr Cys Thr Asn Thr
        915                 920                 925

Asp Gly Ser Phe Thr Cys Gln Cys Asn Pro Gly Phe Glu Gly Asp Gly
    930                 935                 940

His Lys Cys Glu Asp Ile Asp Phe Cys Gly Ala Gly Gln His Asp Cys
945                 950                 955                 960

Asn Val His Ala Glu Cys Ser Glu Ser Glu Asp Asn Thr Thr Phe Lys
                965                 970                 975

Cys Thr Cys Ile Thr Gly Tyr Ala Gly Asp Gly His Gly Glu Ala Gly
            980                 985                 990

Cys Gln Asp Ile Asp Glu Cys Ala  Glu Glu Asn Ile Cys  Gly Ser Asn
        995                 1000                1005

Ala Val  Cys Thr Asn Thr Ala  Gly Ser Tyr Gln Cys  Ala Cys Arg
    1010                 1015                 1020

Glu Gly  Phe Val Ala Ser Ala  Glu Gln Gln Gln Gln  Gly Thr Pro
    1025                 1030                 1035

Ala Leu  Val Cys Val Asp Val  Asp Glu Cys Ser Asp  Ala Ser Lys
    1040                 1045                 1050

Asn Thr  Cys Ala Lys Pro Ala  Asp Gly Gly Ile Cys  Thr Asn Thr
    1055                 1060                 1065

Glu Gly  Ser Tyr Glu Cys Ala  Cys Lys Pro Gly Tyr  Gln Gly Asp
    1070                 1075                 1080

Gly His  Ser Cys Ala Asp Ile  Asn Glu Cys Thr Ala  Gln Gly Thr
    1085                 1090                 1095

Cys Gly  Glu His Thr Thr Cys  Lys Asn Thr Pro Gly  Ser Phe Gln
    1100                 1105                 1110

Cys Asp  Cys Val Glu Gly Phe  Glu Arg Ala Asp Glu  Arg Thr Cys
    1115                 1120                 1125

Arg Asp  Ile Asn Glu Cys Glu  Thr Gly Ala Val Val  Leu Pro Pro
    1130                 1135                 1140

Asn Ser  Thr Cys Val Asn Thr  Glu Gly Ser Tyr Asp  Phe Asp Cys
    1145                 1150                 1155

Val Ala  Gly Tyr Arg Arg Thr  Asp Gly Ala Cys Val  Lys Ile Asp
    1160                 1165                 1170

Phe Cys  Lys Glu Lys Gly Cys  Asn Ala Asn Ala Thr  Cys Arg Glu
    1175                 1180                 1185

Asn Asp  Ala Gly Thr Glu Ala  Ile Cys Thr Cys Lys  Glu Gly Tyr
```

-continued

```
    1190                1195                1200

Glu Gly  Ser Gly Glu Gly Glu  Asp Gly Cys Gln Asn  Ile Asn Glu
    1205                1210                1215

Cys Glu  Arg Gly Glu Pro Cys  Lys Asp Phe Gly Glu  Gly Gly Val
    1220                1225                1230

Cys Val  Asp Thr Pro Gly Ser  Phe Thr Cys Glu Cys  Ala Ala Gly
    1235                1240                1245

Phe Ile  Gln Arg Arg Ser Val  Cys Gln Asp Val Asp  Glu Cys Leu
    1250                1255                1260

Asp Gly  Lys Leu Asn Thr Cys  Ala Ala Thr Gly Gly  Val Cys Ser
    1265                1270                1275

Asn Thr  Val Gly Ser Phe Thr  Cys Ser Cys Ala Ser  Gly Phe Glu
    1280                1285                1290

Gly Asp  Gly His Thr Cys Asn  Asp Val Asp Glu Cys  Ala Thr Ala
    1295                1300                1305

Gln His  Thr Cys Asp Pro Asn  Ala Thr Cys Val Asn  Thr Glu Gly
    1310                1315                1320

Ser Phe  Glu Cys Arg Cys Asn  Ala Gly Phe Glu Gly  Asp Gly His
    1325                1330                1335

Thr Cys  Ala Asp Ile Asp Glu  Cys Ala Asp Pro Ala  Lys Asn Thr
    1340                1345                1350

Cys Asp  Thr His Lys Gly Val  Cys Gln Asn Thr Thr  Gly Ser Tyr
    1355                1360                1365

Thr Cys  Gly Cys Lys Thr Gly  Phe Ser Leu Ala Ala  Asp Gly Ser
    1370                1375                1380

Thr Cys  Glu Asn Val Asp Glu  Cys Ala Ala Gly Thr  Ala Asn Cys
    1385                1390                1395

Asn Glu  Arg Ser Phe Cys Lys  Asp Thr Glu Gly Ser  Tyr Gln Cys
    1400                1405                1410

Glu Cys  Lys Asn Gly Tyr Lys  Ala Ala Gly Glu Asp  Cys Val Asp
    1415                1420                1425

Val Asp  Glu Cys Glu Ala Gly  Val His Gly Cys Ser  Glu His Ala
    1430                1435                1440

Ile Cys  Thr Asn Thr Asp Gly  Ser Tyr Ser Cys Glu  Cys Met Glu
    1445                1450                1455

Gly Tyr  Gln Gly Asp Gly Lys  Ala Cys Glu Lys Thr  Val Gly Val
    1460                1465                1470

Cys Asp  Ser Ala Pro Cys Gly  Ala His Ala Thr Cys  Glu Pro Ala
    1475                1480                1485

Gly Asp  Asn Tyr Thr Cys Thr  Cys His Pro Gly Tyr  Glu Met Arg
    1490                1495                1500

Glu Gly  Ala Cys Val Asp Ile  Asp Glu Cys Thr Ala  Gly Ser Leu
    1505                1510                1515

Asn Cys  Asp Pro His Ala Ile  Cys Thr Asn Thr Asp  Gly Ser Phe
    1520                1525                1530

Thr Cys  Val Cys Gly Ser Gly  Tyr Thr Gly Leu Gly  Thr Ser Cys
    1535                1540                1545

Glu Asp  Ile Asp Glu Cys Ala  Gly Asn Ala Ala Gly  Cys Asp Ile
    1550                1555                1560

His Ala  Val Cys Thr Asn Thr  Pro Gly Ser Phe Lys  Cys Glu Cys
    1565                1570                1575

Lys Ser  Gly Phe Glu Gly Asp  Gly Thr Gln Cys Thr  Glu Lys Val
    1580                1585                1590
```

-continued

```
Leu Leu  Pro Gly Gln Ile His  Cys Glu Ala Trp Thr  Ala Trp Thr
    1595                 1600                 1605

Glu Cys  Thr Asp Gly Ala Lys  Thr Ser Thr Arg Ser  Cys Leu Ala
    1610                 1615                 1620

Leu Pro  Leu Lys Lys Glu Met  Arg Ala Cys Pro Ala  Ala Asp Phe
    1625                 1630                 1635

Ser Gln  Cys Gly Glu Phe Thr  Glu Trp Thr Ala Cys  Pro Gly Thr
    1640                 1645                 1650

Asn Asn  Asn Leu Ser His Arg  Arg Thr Glu Arg Phe  Gly Glu Pro
    1655                 1660                 1665

Gly Cys  Glu Asp Ala Glu Glu  Val Arg Glu Cys Pro  Asp Glu Glu
    1670                 1675                 1680

Thr Glu  Gln Lys Cys Gly Ala  Trp Gly Glu Trp Thr  Ala Cys Gly
    1685                 1690                 1695

Asp Pro  Ser Pro Gly Leu Arg  Thr Arg Ala Arg Glu  Asn Cys Pro
    1700                 1705                 1710

Asp Val  Val Glu Phe Glu Arg  Cys Thr Met Pro Ser  Glu Pro Glu
    1715                 1720                 1725

Ala Gly  Glu Val Thr Glu Pro  His Thr Glu Gly Gly  Ala Gly Val
    1730                 1735                 1740

Gly Gly  Glu Val Thr Glu Pro  Asp Thr Glu Glu Gly  Ala Gly Val
    1745                 1750                 1755

Gly Gly  Glu Val Gln Pro Gly  Thr Glu Glu Gly Ala  Gly Val Gly
    1760                 1765                 1770

Gly Glu  Val Gln Pro Gly Thr  Glu Glu Gly Ala Gly  Val Gly Gly
    1775                 1780                 1785

Glu Val  Gln Pro Gly Thr Glu  Glu Gly Ala Gly Val  Gly Gly Glu
    1790                 1795                 1800

Val Gln  Pro Gly Thr Glu Glu  Gly Ala Gly Ile Gly  Gly Glu Val
    1805                 1810                 1815

Thr Glu  Pro Asp Thr Glu Gly  Gly Ala Gly Val Ser  Gly Glu Pro
    1820                 1825                 1830

Thr Glu  Glu Glu Gly Thr Glu  Ser Thr Gly Pro Cys  Lys Glu Phe
    1835                 1840                 1845

Gly Pro  Trp Thr Ala Cys Lys  Glu Asp Glu Asn Gly  Val Gly Ile
    1850                 1855                 1860

Gln Arg  Arg Met Cys Ala Gly  Arg Glu Asp Ile Ile  Glu Ser Arg
    1865                 1870                 1875

Ile Cys  Thr Val Thr Asp Asp  Cys Gly Glu Trp Thr  Pro Trp Ser
    1880                 1885                 1890

Thr Cys  Thr Asn Gly Ser Gln  Ala Arg Asn Lys Arg  Phe Cys Thr
    1895                 1900                 1905

Asn Val  Arg Glu Val Arg Leu  Cys Gly Ala Asp Ile  Pro Val Thr
    1910                 1915                 1920

Asp Gly  Cys Thr Trp Ser Glu  Trp Thr Ser Cys Ser  Leu Val Asn
    1925                 1930                 1935

Glu Glu  Gly Gly Tyr Phe Arg  Thr Arg Thr Ser Ser  Asp Cys Asn
    1940                 1945                 1950

Met Asn  Glu Val Gln Ala Cys  Ser Pro Ser Ser Ser  Thr Thr Ala
    1955                 1960                 1965

Asp Ser  Glu Thr Glu Gly Thr  Cys Ser Ala Trp Asn  Pro Trp Thr
    1970                 1975                 1980
```

-continued

```
Glu Cys  Ser Asn Gly His Gln  Thr Arg Lys Cys Ala  Thr Met Glu
    1985                 1990                 1995

Ala Glu  Glu Ser Arg Thr Cys  Gly Glu Thr Pro Glu  Asn Cys Gly
    2000                 2005                 2010

Glu Phe  Gly Pro Phe Glu Pro  Ala Asn Cys Thr Ala  Gly Gln Met
    2015                 2020                 2025

Val Thr  Arg Thr Arg Thr Cys  Gly Glu Thr Glu Gln  Lys Glu Thr
    2030                 2035                 2040

Lys Leu  Cys Asp Val Ser Ser  Thr Glu Glu Gly Lys  Gln Cys Gly
    2045                 2050                 2055

Gln Trp  Gly Pro Trp Ser Glu  Cys Asn Ile His Leu  Gly Ser Glu
    2060                 2065                 2070

Asp Asn  Val Arg Val Arg Glu  Asp Thr Ala Cys Gly  Val Thr Glu
    2075                 2080                 2085

Tyr Glu  Glu Cys Ser Lys Pro  Ala Asn Asn Ala Phe  Val Cys Thr
    2090                 2095                 2100

Pro Trp  Ser Glu Cys Ser Asp  Lys Lys Glu Arg Arg  Thr Cys Thr
    2105                 2110                 2115

Ile Arg  Lys Asn Gly Leu Val  Gln Thr Arg Gln Glu  Phe Arg Thr
    2120                 2125                 2130

Cys Ser  Val Asp Ile Ala Thr  Thr Cys Gly Asp Phe  Gly Ala Trp
    2135                 2140                 2145

Ser Glu  Cys Asn Ala Glu Gly  Leu His Gln Arg Ser  Leu Glu Lys
    2150                 2155                 2160

Cys Pro  Asp Val Ile Glu Val  Ala Thr Cys Gly Ser  Glu Asp Cys
    2165                 2170                 2175

Pro Pro  Phe Gly Glu Trp Thr  Glu Cys Gly Val Pro  Glu Glu Gly
    2180                 2185                 2190

Met Arg  Ser Arg Gln Arg Ile  Asp Cys Val Glu Ser  Ala Ala Cys
    2195                 2200                 2205

Gln Cys  Thr Glu Val Glu Ser  Cys Phe Asp Thr Glu  Leu His Pro
    2210                 2215                 2220

Ile Pro  Ala Pro Gly Thr Glu  Thr Gly Glu Gly Glu  Gly Glu Thr
    2225                 2230                 2235

Glu Thr  Gly Glu Gly Glu Thr  Gly Glu Ala Gly Gly  Glu Glu Gly
    2240                 2245                 2250

Glu Gln  Thr Gly Glu Gly Glu  Val Gln Pro Pro Glu  Glu Glu Leu
    2255                 2260                 2265

Pro Gly  Glu Ser Val Thr Glu  Pro Glu Glu Lys Pro  Glu Glu Glu
    2270                 2275                 2280

Leu Pro  Glu Glu Glu Val Thr  Glu Pro Glu Glu Lys  Pro Glu Glu
    2285                 2290                 2295

Gly Val  Thr Gln Pro Glu Glu  Thr Pro Glu Gln Pro  Val Glu Gly
    2300                 2305                 2310

Thr Glu  Glu Glu Gly Lys Gln  Glu Ser Glu Ala Ala  Pro Glu Thr
    2315                 2320                 2325

Pro Ala  Val Gln Pro Lys Pro  Glu Glu Gly His Glu  Arg Pro Glu
    2330                 2335                 2340

Pro Glu  Glu Glu Glu Glu Lys  Lys Glu Glu Gly Gly  Gly Phe Pro
    2345                 2350                 2355

Thr Ala  Ala Val Ala Gly Gly  Val Gly Gly Val Leu  Leu Ile Ala
    2360                 2365                 2370

Ala Val  Gly Gly Gly Val Ala  Ala Phe Thr Ser Gly  Gly Gly Gly
```

-continued

```
    2375                2380                2385

Ala Gly  Ala Gln Glu Ala Glu  Gln Val Glu Phe Glu  Gly Glu Asp
    2390                2395                2400

Thr Gly  Ala Ala Thr Ala Glu  Thr Pro Glu Ala Asp  Thr Val Ile
    2405                2410                2415

Asp Ile  Thr Asp Glu Asp Asp  Tyr Trp Ala Asp Ser  Gly Asp Ile
    2420                2425                2430

Gln Ser  Met Ser Val Phe Phe  Gln Gly Glu Asp Thr  Lys Pro Lys
    2435                2440                2445

Ser Gln  Asn Glu Gly Cys Glu  Gly Glu Thr Gly Gln  Ser Arg Pro
    2450                2455                2460

Val Phe  Ser Phe Asn Gln Trp  Leu Gln Ser Arg Ser  Trp Thr Gln
    2465                2470                2475

Leu His  Leu His Pro Lys Ser  Ser Pro Leu Val Gly  Lys Leu Asp
    2480                2485                2490

Arg Val  Asn Ala Phe Ser Ser  Pro Gln Ala Lys Val  Thr Thr Arg
    2495                2500                2505

Ala Cys  Ser Cys Leu Phe Val  Ile Gly Trp Leu Val  His Pro Ala
    2510                2515                2520

Gly Phe  Gln Arg Arg Gln Ser  Ser Arg Ser Glu Thr  Glu Gln Gln
    2525                2530                2535

Arg Ile  Leu Phe Ser Glu Gln  Val His Arg Leu Phe  Phe Ala Val
    2540                2545                2550

Ser Arg  Ser Ala Glu Glu Ala  Asn Lys Gln Thr Pro  Thr Asn Pro
    2555                2560                2565

Thr Asn  Glu Arg Ala Val Leu  Phe Pro Pro Leu Phe  Cys Leu Pro
    2570                2575                2580

Lys Ile  Arg Arg Gly Phe Gly  Trp Gly Arg Asn Cys  Gly Trp Ile
    2585                2590                2595

Gly Arg  Val Phe Ser Phe Ser  Leu Ile Asp Ala Thr  Ile Ser Ala
    2600                2605                2610

Ser Gln  Arg Thr Lys Asn Ser  Cys Ser Ser Asn Glu  Cys Ile Leu
    2615                2620                2625

Ile Ile  Pro His Arg Gly Ala  Ser Ser Leu Pro Trp  His Thr Phe
    2630                2635                2640

Arg Leu  Leu Pro Pro Leu Lys  Ile Phe Ser
    2645                2650


<210> SEQ ID NO 4
<211> LENGTH: 7077
<212> TYPE: DNA
<213> ORGANISM: Chicken

<400> SEQUENCE: 4

atgctgcatc gcaacccgcg gtgggcgctt tgtgcagccc tcgctgcact ctatggcgga      60

acaggaatcg ccagcgccga agttaacaat gaattgagca agtgcgaatc tgggtggaca     120

ccctggacta cctgcaaccc gcaaactggt ctgcgggaga ggcacaatgc acagtgcgag     180

acatgggtgg aggttgagga atgccagaag ctgacaggat gtggcaactg gactccttgg     240

tctcccggcg atatgtcgtg tgtggtggga cagtttcaaa cccgcaacag ggagggctgc     300

ccagaggtgc aggaagtgag ggcatgcagg cctgtacttc tagaatgcaa cgatcaatgg     360

accccctgga caatgtgcga caccaaccgc gtccaggaaa gatacaactc aaagtgcgga     420

cccgtcgaag tccgcgagtg caacatggac gacgcagaga tcgagaaatg cggcgagttc     480
```

-continued

```
gtggaatggg atccccctat gaatggagac tgcgtacgcg ggggtaccca cacgcgttac    540
cgtcaaaact gcccagaccg caaagaggtg cgggtgtgcg gagcctttga ttgcagtagc    600
tgctctgtaa acgccacttg cgatcccatt ggtgcatcct gcgaatgcaa gcctggtttc    660
cgcggcaatg ggaagacctg cgaggccttc aacccctgcg aagatacccc tgcaccttgc    720
gacagcaacg ccatctgcac cccagacgca atgacgccaa atgccagtgc aaggcaggct    780
gggacgcaga ttccggagca ggcagcagca agaagccttg cgttgaggtc gacgagtgcg    840
catccaacac ccaccagtgc ccggcacact ccacatgcat caacaccaag ggctcttata    900
agtgcgactg caaccaggga taccgtcaag ggagaggacg gacagtgtca tgacgtcgat    960
gaatgcacca acggagagca cacctgcccc gctcactcca cttgtttgaa tacagctggc   1020
agctacgagt gccgctgcga cactgggtac agcggaaatg caactgcaga cagcccttgc   1080
aagaacattg acgaatgcgc caaccccaac gcctgctcgg ccaacgctat ctgcacagac   1140
accgacggct ccttcacctg cagctgcccc gaagggtaca gcggccaggg aacccatgac   1200
tctccctgct ccaagatcga cttctgcgca taccccctcac tcaatacatg cggagcccac   1260
tccacttgca acaccctcac atctttcaag tgcatctgcg atgcgggata tgaaggcgcc   1320
ggcactcgcg agagcccgtg cgtggacgtg aacgagtgct cgaacgagaa gcccacaaac   1380
aactgcaaca gaaacgcaaa ctgcaccaac accgagggat cctacacttg cgaatgcaag   1440
cccggtttct ctggcgacgg catgggtccc aacgggtgta ccgacatcga cgagtgcgcg   1500
gcggagcagt ccccctgcga ccctcacgcc tcctgcagca acactgaggg ctcgtatgta   1560
tgcacctgca acaccggcta cgagccagct tcaaccgacg ggcatgcatg caaagatatc   1620
gacgagtgcg ccaccggtgc agctgggtgc cacgtgtcag cacagtgtct gaacacggac   1680
ggcagctacg agtgcaagtg tcttgagggc ttcgtcggcg acggaaagac ctgcaacgac   1740
gtcgatgagt gcgctgcggc gacatctcct tgcggtgaca acactcactg ccagaacaca   1800
attggcagct acgagtgcga gtgcaaggct ggctatggca acatgcaaga caacgcatgc   1860
agcgacattg acgagtgcaa ggatgcgaac accaagatcc ctgacaactg tctttgcgtg   1920
aacaatgatg gcagctactc ccttgaggcg aaggctggat acgaattggt gaacggcgag   1980
tgcatcaaga tcgacttctg cgcccgcggc gcatgcaact cgctggcctc ctgcaaggag   2040
aatgaagaag gcacagcggc gatctgcacc tgcctgccag gctacagcgg cgacggcact   2100
gctgaaggcc actgcaacga cattgacgag tgtgcaggtc agaatgactg tgctcctgcc   2160
gagcagggag gcatctgcga gaacactgtc ggctcgtaca cctgcaagtg caaagagggg   2220
tacaggcaag atggaaactc atgcactgag atcgacgagt gcgctgaggg aacccacaac   2280
tgccaccctt ccgccacctg cagcaacacc cccggaagct tcacctgcca atgcaacagt   2340
ggattcactg gcagcggtgt ggagtgcgaa gacattgacg agtgctcaac tgaggcagat   2400
gattgtggtg caaacaccat ctgcagcaac accattggtg ctttcgagtg caactgccgt   2460
gaaggctatg aacgcgcaga cgcaaagacg tgcgtcgaca tcgacgaatg cgcgacaggc   2520
acacacactt gctcgaacca cgccacctgc accaataccg atgggtcatt cacatgccag   2580
tgcaaccccg gcttcgaagg tgacggccac aagtgcgagg acatcgactt ctgcggtgct   2640
ggacagcacg actgcaatgt gcatgccgag tgctctgaga gcgaggacaa caccactttc   2700
aagtgcacct gtataacagg gtacgctgga gacggccatg gcgaggcagg ctgccaagac   2760
attgatgagt gcgcagaaga aaacatctgc ggaagcaacg ctgtctgcac aaacaccgca   2820
```

-continued

```
ggaagctacc aatgcgcatg ccgtgagggc ttcgttgcat cagctgaaca gcagcagcag   2880
ggaaccccag cactggtttg cgtggacgtc gacgagtgca gcgacgcttc gaagaacaca   2940
tgtgccaagc cagccgacgg aggcatttgc acaaacactg aaggcagcta cgaatgcgct   3000
tgcaagccag gctaccaagg tgacggccac agctgcgcag acatcaacga atgcactgca   3060
cagggcacct gcggcgaaca cacaacttgc aagaacacac ccggatcctt ccagtgcgac   3120
tgcgttgagg gattcgagcg cgctgatgaa cgcacctgcc gtgacatcaa cgagtgcgag   3180
acaggagcag tcgtgctgcc accgaactcc acctgcgtca acactgaagg cagctacgac   3240
ttcgactgcg ttgctgggta ccgccgcact gatggagctt gtgtgaagat cgacttctgc   3300
aaggagaagg gatgcaacgc aaacgccaca tgccgcgaaa acgatgccgg caccgaggcc   3360
atctgcactt gcaaggaagg ctatgaaggc agcggagaag gcgaagatgg ttgccagaac   3420
atcaatgagt gcgagagagg cgaaccctgc aaggacttcg gcgaaggcgg tgtttgcgtc   3480
gacacaccag gatcattcac ttgcgagtgc gctgctggat tcattcaacg ccgctccgtt   3540
tgccaagatg ttgacgaatg tctcgacgga aagctgaaca cctgcgctgc caccggaggc   3600
gtctgctcca acaccgtcgg ttccttcacc tgctcgtgcg ccagcggctt cgaaggcgat   3660
ggccacacct gcaatgatgt cgacgaatgc gcaacagcac agcacacctg tgacccgaat   3720
gccacttgcg tcaacaccga aggcagcttc gagtgccgct gcaatgccgg attcgagggc   3780
gacggacaca cctgcgcaga catcgacgaa tgcgcagacc cagccaaaaa cacatgcgat   3840
acacacaagg gtgtatgcca aaacaccaca gggtcctaca cctgcggctg caagaccgga   3900
ttcagtcttg cagctgacgg aagcacatgc gaaaacgtcg acgagtgcgc ggcgggaact   3960
gcaaactgca acgagcgaag cttctgtaag gacacagagg gttcctacca atgcgagtgc   4020
aagaacggct acaaggctgc aggagaggac tgtgtggacg ttgacgagtg cgaggctggc   4080
gtgcatggat gcagcgagca cgcaatctgc acaaatacag acggcagcta ctcctgcgaa   4140
tgcatggagg gataccaggg agacggcaag gcttgcgaga agacagtcgg cgtctgcgac   4200
tccgctccct gcggtgccca cgccacctgc gagcctgcag ggacaacta cacttgcaca   4260
tgccacccag gctacgagat gcgcgaagga gcctgcgttg acatcgatga gtgcacagca   4320
ggcagcctca actgcgaccc tcatgccatt tgcacaaaca ccgacggctc cttcacttgc   4380
gtctgtggca gcggctatac cggccttggc acatcctgcg aagacatcga cgagtgcgcg   4440
ggtaacgcag caggctgcga catccacgcc gtctgcacga acactcccgg atcgttcaag   4500
tgcgagtgca agagcggctt cgaaggcgat ggcacgcaat gcacggagaa ggtgttgctc   4560
cccggacaga ttcactgcga agcctggact gcatggacag agtgtaccga cggcgccaaa   4620
accagcacac gcagctgcct tgcactgccg cttaagaagg agatgcgcgc ctgccctgca   4680
gctgacttct cccagtgcgg agagttcact gaatggactg cctgccctgg aaccaacaat   4740
aacctgtctc ataggcgcac tgaaagattc ggagaacccg gatgcgaaga tgcagaggaa   4800
gtccgcgaat gcccagatga agagaccgag cagaaatgcg gcgcctgggg tgagtggacc   4860
gcctgcggcg acccatcccc tggcctgaga actcgcgcac gcgagaactg ccccgatgtg   4920
gtagagttcg agcgttgcac tatgcccagt gagcctgagg ctggcgaagt gactgagcct   4980
cacacagaag gaggagccgg agttggtggc gaagtgactg agcctgacac ggaagaagga   5040
gccggagttg gtggtgaagt gcagcccggt acagaagaag gagcaggagt tggtggtgaa   5100
gtgcagcccg gtacagaaga aggagccgga gttggtggtg aagtgcagcc cggtacagaa   5160
gaaggagccg gagttggtgg tgaagtgcag cccggtacgg aagaaggagc cggcattggt   5220
```

-continued

```
ggcgaagtga ctgagcctga caccgaagga ggagccggag ttagtggcga accgaccgaa   5280
gaagagggca ccgaaagcac cggtccatgc aaagagttcg gaccctggac ggcctgcaag   5340
gaggacgaga acggagtcgg catccaacgc cgtatgtgcg ccggcagaga agacatcatc   5400
gaatccagaa tttgcactgt cacggatgac tgcggagaat ggaccccctg gtcaacttgc   5460
actaacggca gccaggccag aaacaaacgc ttctgcacca acgttaggga agtccgtctc   5520
tgcggagctg acattccagt tacagacgga tgcacgtgga gcgagtggac ttcttgcagt   5580
ctagtcaatg aggagggcgg ctacttccgc acgcgcacat cctctgactg caacatgaat   5640
gaagtgcagg cctgctctcc cagcagcagc acaaccgcag acagcgaaac agaaggcacc   5700
tgctctgcat ggaacccctg gacggagtgc tcgaacggcc accagacacg caagtgtgcc   5760
acaatggaag cagaagaatc gcgcacttgc ggagagactc cagagaactg cggagaattc   5820
ggccccttcg aacccgcaaa ctgcacggcc ggccaaatgg tcaccaggac gcgcacctgc   5880
ggagaaaccg agcagaagga aaccaaactg tgcgacgtca gctccaccga agaaggaaaa   5940
caatgcggtc agtggggccc atggagcgaa tgcaacatcc acctgggctc agaggacaat   6000
gtgcgtgttc gtgaggacac cgcttgcggc gtgacggagt acgaggagtg cagcaagccg   6060
gcgaacaacg cctttgtctg cacaccttgg agtgaatgct cggacaagaa ggagcggaga   6120
acgtgcacca tccgcaaaaa cggtcttgtt cagacacgtc aagaattcag aacatgcagt   6180
gtagacatcg ccacaacttg cggcgatttc ggcgcatggt ctgaatgcaa cgctgagggc   6240
ttgcatcagc gcagtctcga gaaatgcccc gacgtcatcg aggtcgcaac ttgcggcagt   6300
gaggattgcc cgccattcgg cgagtggact gaatgcggcg ttccagagga gggcatgcgt   6360
tctcgccaac gcattgactg cgttgaatct gcagcctgcc agtgcacaga agtggagagc   6420
tgcttcgaca ccgaattgca ccccattcca gcccccggta cggaaacagg cgaaggagag   6480
ggagagaccg agacaggcga aggcgaaact ggtgaagcag gtggcgagga aggcgagcaa   6540
acaggagaag gcgaagtgca gcccccagaa gaagagcttc ctggggagag tgtaactgag   6600
cctgaggaga agcctgagga ggagctacct gaggaggagg ttactgagcc tgaggagaag   6660
cctgaggagg gtgtgactca gcctgaggag acacctgagc agcctgttga gggtaccgaa   6720
gaagagggca agcaggagtc tgaggctgcc cccgaaactc ctgccgtcca gccaaaacca   6780
gaggagggtc acgaacgccc agaacccgaa gaggaggagg agaagaagga agaaggcggc   6840
ggcttcccaa cagctgcagt ggcaggaggt gttggtggtg tgttgctcat agctgctgta   6900
ggtggtggtg ttgcagcctt cactagcggc ggaggtggcg ctggcgcaca ggaggcagaa   6960
caggtcgagt tcgaaggaga agataccgga gcagcaactg ccgagacacc tgaagccgat   7020
acagttatcg acatcacaga cgaagacgac tactgggccg acagcggcga cattcag      7077
```

<210> SEQ ID NO 5
<211> LENGTH: 6567
<212> TYPE: DNA
<213> ORGANISM: Chicken

<400> SEQUENCE: 5

```
atgggttttt tcgtcttcac aggcggtgat ttcggcgact ggagcccccc tctcgctggt     60
gactgcgtgc ctggcactac tcacacacgc cagagggcaa attgcccaaa ccacaaggag    120
gtgcgggttt gcggcgcctt cgattgtagc cagtgctcag tcaacgctac ctgcgacccc    180
ctcggagcca cttgtcagtg caaaccgggt ttccgaggcg atgggactca gtgcgaggca    240
```

-continued

```
ttcaaccctt gcgaagggga gacggctcct tgtgatgcga acgcgacctg cacggctgat    300
ggaaatgacg ccaaatgcca ctgcaacaag ggctggaacg cagacagcaa ggcaggtgcc    360
agcggtcacg catgcgtgga ggaggacgaa tgcgccaaca acacgcacga atgtccgcag    420
cactcaactt gcgtcaacac tgagggctcc tatgaatgca actgcttacc gggttatcag    480
aaggatcagg atgggaaatg ccaggacata gacgagtgcg ctggggaaca tggttgtccc    540
gcacactcga cttgcgtgaa cacggcaggc agcttcgagt gcaagtgcga cgccggtttc    600
agtggcagtg ctacttctga gagtccttgc tcgaatatag acgagtgcca agacccggat    660
gcctgctcag ccaacgcaat ctgcgcagac actgagggct ctttcacttg cagctgccct    720
gagggttaca gcggtggggg atcacacgac tctccttgct cgaagataga ttactgcgcc    780
gaccccacac tgaacacctg cggggcccac tcgacttgtg tgaacacact aacgacgttc    840
aagtgcgttt gcgatgccgg ttatgacggc gcgggaacgc acgagagccc ttgtgtggat    900
atcgacgagt gctccaagga gaaaccatcc aatgactgca accgaaacgc cgtttgcaca    960
aatactgagg gatcgtacac ctgcgcatgc aaggaaggct tctctggcga gggtttcgga   1020
gctgcagggt gtgcagatgt cgatgagtgc gcgaattcgc cctgcgacgc ccacgcctct   1080
tgtgccaaca ccgagggttc ctacgtttgc acttgcaacc ctggctatga accagcctca   1140
agcgacggac atgcatgcaa ggacgttgac gagtgtgcag cgggcacggc ggaatgccac   1200
gtctccgcac agtgtgtgaa cgtggatggc agctatgaat gccactgctt ggaaggtttc   1260
attggcgacg gaaaggtgtg cagtgacgtt gacgagtgtg cggctgaggc ttcgccctgt   1320
ggcgcaaaca cgcattgcct gaacaccatc ggcagctacg agtgcgagtg caaggacgga   1380
tatggccaca tggagggcaa cgcgtgcagc gacatcgatg agtgctcaga ggcgtctaca   1440
gagatcccag agaactgcaa ctgtgtcaac accgagggga gcttctccct tgaggcaaag   1500
cctgggtacg agctcgtcga cggcaagtgc gtcaagatcg acttctgcgc ccgtggtgca   1560
tgcaactcgc tggcgcactg caaggagaat cccgagggca ccgcggcgat ctgcacttgc   1620
atagctggct attcaggtga cggcacagct cagggccact gcgatgacat cgatgagtgc   1680
ttggcggaga atgactgcac ccctgccgat caaggaggga tttgcgagaa cactgtcggc   1740
tcttacacct gcaaatgcgc agctgggtac cagcaagacg gcaactcatg cactgacatt   1800
gacgagtgcg ccaacggcac tcacaactgc catgcctccg cgacatgcac gaacacgcaa   1860
ggctcctttg agtgcgcctg caacgcaggc ttcagcggca acggggttga atgcaacgac   1920
gtcgacgagt gctcgactga cgctgacgat tgcggagaga acacactgtg caacaacaca   1980
gttggcagct tcgagtgcac atgcatggct ggcttcgagg ccgcggacgc gaagacctgc   2040
aaagacatcg acgaatgtgc aagcgggacc cacacttgct ccacccacgc gacatgcacc   2100
aacactgctg ggtcgttcac atgtgagtgc aacccaggct ttgacggtga cggccacaag   2160
tgcgaggacg tggacttctg cggccagggg ctgcacgact gcaacgtgca tgcagagtgc   2220
tcggaaagcg acgacaacac caccttcaag tgcacctgcg gcattgggta cagcggggaa   2280
ggccacgggg agaatggttg ccaagacatt gatgagtgcg cccaagatgc catctgtggg   2340
gagaacacag tgtgtaccaa cacaccaggt agctttgaat gtgcgtgtgt ggaagggttc   2400
gtggctgtgg gagcgaagct caagggagca acttcattga cctgcataga catcgatgaa   2460
tgcaacgacg cctcgaaaaa cacttgcgcc acgtcagctg acggaggctc ttgcaagaac   2520
accgcaggca gctatgagtg ctcgtgtttg cctgggttcc agggcgacgg ccacagctgc   2580
acagatattg atgagtgcgc cacccaaggc gtatgcgggg aacatgcgac ctgcgaaaac   2640
```

-continued actgcgggtt cgtacaattg cacctgcgag gcgggttaca ctcagcaaga tggggccgtc 2700
ggctgcattg atattgatga gtgtgcagcc tccacagcag tgttacccgc caacgccact 2760
tgcgtgaaca ctgaaggcag ctatacattc gaatgcgtgc ccggctaccg ccatacggag 2820
aatggctgta ccaagattga tttctgcagc gaaaagggat gcaatgcgaa tgccagctgc 2880
aaggagaacg atgcgggcac cgaagccatc tgcacctgcc acagcgggta cgagggcaat 2940
ggcgaaggag aagaagggtg caaaaacatt gacgagtgct ccgtgggaga gccatgcaaa 3000
gacttcggcg agggcggcgt ctgtgtcgat tctccgggat ccttcagctg ctcttgcgcc 3060
accggtttta tcaagaggcg atctacttgc caggacatag atgagtgcct cgacggaaag 3120
atgaacactt gcgccccgt cgggggtatc tgcacgaaca ccgtcggctc cttcacctgc 3180
tcttgcgctg ctggcttcac gggtgacggc cttacttgcg aggacatcga cgaatgtgct 3240
acggcggcac acacgtgcga ccccaacgcc acctgtgtca acactgtcgg cagcttcgaa 3300
tgcggatgca aggagggatt ctctggtgac ggccacacat gcaccgatat cgacgaatgc 3360
gctgacccta accttaacaa atgcgacaca cacaagggca tctgccagaa cggcactgga 3420
tcctacactt gcggatgcag gcctggatac agtctggcgg cggacggctt cacttgcgac 3480
aatgtcgatg agtgcgctgc ggggacggcc acttgcggag agcgcagctt ctgcgtggac 3540
acgcaagggt catacaagtg cgagtgcaag aacggctacc gccagtctgg ggaggactgc 3600
gtggacgttg acgagtgcga ggctgatgtg cacacatgca gcgagcacgc tacgtgcacg 3660
aacactgagg ggagccacac ctgcacctgc aatgaagggt accagggaga cggaaagaag 3720
tgcgagaaga cagtgggccc ttgcgacaac tcgccatgcg gcaacaacgc catgtgtgaa 3780
gctactgccg atagctacaa ctgcacttgc aaagctggct acgagatgaa ggacggggcc 3840
tgtgtcgaca tcgatgagtg ccagtcgggc acccacaact gcgacccgca tgctgactgc 3900
agcaacaccg atggatcctt cacgtgcacg tgcggttctg gctacactgg tgtgggtacc 3960
ctttgcgagg atgtggacga gtgcgcgggc aaccatgcgg gctgtgacat caacgctgtt 4020
tgcactaacg tccctggctc gttcacttgc gagtgcaaga gtggcttcga aggcgatggg 4080
cacgagtgta cggagaaagt gctgctccct ggccagattc actgcgattc gtggactgca 4140
tggaccgaat gtacagctga aactaagcag agcacccgca agtgcgtggc tcttcctctc 4200
aaggtcgagg tgaagctttg ccccgatgct gacatttcag cctgcggtga actcggcgag 4260
tggtcatcat gcccaggagt tgacaacaac ctgtcgcacc gcagagcaga gaagttcggg 4320
gagccgggct gtgagcacgc tgaggaggtc agggagtgcc cagatgaaga agttgaggag 4380
cgctgtggtg cctttggcga gtggactgca tgcggcgatc cttctgaggg cttgaggacc 4440
aggacgcgcc agaactgccc agaagaggca gaattcgagc actgcacaat gccctctgca 4500
ccatccgttc ccgagggcgg cagcagctgc acagagttcg gggcctggag tgaatgcgtg 4560
gctgacgctc atgggatcaa gatgcagcac agaacgtgcg tacacaatga agctgtgcag 4620
gaacacagaa tctgcaccgt ggaagatcca caacagtgcg gggagtggtc gcagtggtca 4680
gagtgcaaga atggcaagca gtacagaggc gccgccggat gcgcgtctgt gtacgaagtc 4740
agagcctgca gcggcgctag cgatgcgaaa gaatgctctt ttggtgcgtg gagcggctgc 4800
gtggtggagt ttggcggtca cacttacaaa gtgcgaaact caatcgactg cgagctcagt 4860
gagctgcagg cttgcaagcc gagcgccgcc accgagggcg agggcaagtg cgctgcttgg 4920
agcccctgga cgatctgcag ggacggcatg cagactcgcg actgcaaaag cctgggtgtt 4980

-continued caggagtccc gcccatgctc agctgaagga gagaccgatt cttgcggagc ctttggaccc 5040
ttcgagccgg cagcttgcaa ggctggcgag atggtcacga ggacgcggga gtgcaacggt 5100
gctcagcaga aggaaaccag actgtgcaat cctgagggca atgacaactg caacaactgg 5160
ggtgcttgga cagagtgctc gctaattgtg ggcggctctg ccctgcggtc tcgcgaggag 5220
tccacttgcg gctatgtgga gttagaggag tgcagtggca gcagcagcag cggcgaccag 5280
accgtccact gcggcagctg gtcggagtgc tccatgagaa aaacggagcg cacctgtgat 5340
gtcctctctg acggatccca caccagcgtt actgaagtgc tcacctgcga cgacgtgctg 5400
cctgactctt gcggtgaatt tggcgagtgg tccgaatgta gcgctgacgg cttgcactcg 5460
aggtccctgt caggctgccc agacgtaact gaagtgatga cttgcggcag cgaaaactgc 5520
ccggctttcg gcgagtggag cgagtgcggc agcccagagg acggcctacg gtcgcgtcag 5580
cgaacgaact gcgaagaggg atccggctgc atttgctccg agacagaagc ctgtgttaac 5640
actgagctcc accccatccc attgccagtt cctggcggcg gcgagggcag cgagaacggc 5700
gagggtggcc aaaccggaga ggagggaacg gagggaggcg caggcggtgc tggaggatcc 5760
ggtggtgctg aggagctgcc cggagaagag ggtggcgcag gtgccggcgg agaaggaggc 5820
tctggcggta atgctgagga gctgcccgga gaagggggtg ctggcgaagc tggaggctct 5880
ggcggtagtg ctgaggagct gcccggagaa gagggcggcg caggtgccgg cggaggagga 5940
ggctctggcg gtagtgctga ggagctgcct ggagaagagg gcggcgcagg tgccggcgga 6000
gaaggaggct ctggcggcaa tgctgaggag ctgcccggag aagagggcgg cgcaggtgct 6060
ggaggagccg aaggcgagac agggaaacct ggcggcgaag agggtggcgc aggcggcgct 6120
ggtgagggtg ctggcggtga aggtggtgag gtccagcctg gagagggaga aggggcgagt 6180
gaaggaggcg agcaagtgcc ggaaacccct gagacacccg aaccggaaac acctgaagct 6240
gagagacctg aagagcaacc ctcgacggaa actccagcag aggagcccac cgaaggcggt 6300
gcagaagaag aggagaagga ggagggcagc ggcttcccca cggcagctgt tgccggaggt 6360
gtaggtggtg tactactgct ggcagcagtg ggtggtggcg ttgccgcgta ctccggtggt 6420
ggtggaggtg gcggtgccga ggaggctgag caagttgagt ttgaaggtga agagtcgggt 6480
ggtgcgtctg ccgaaacacc tgaggctgat actgtgattg acatcactga cgaagacgac 6540
tactgggcag acagtggtga catccag 6567

<210> SEQ ID NO 6
<211> LENGTH: 2359
<212> TYPE: PRT
<213> ORGANISM: Chicken

<400> SEQUENCE: 6

Met Leu His Arg Asn Pro Arg Trp Ala Leu Cys Ala Ala Leu Ala Ala
1 5 10 15

Leu Tyr Gly Gly Thr Gly Ile Ala Ser Ala Glu Val Asn Asn Glu Leu
20 25 30

Ser Lys Cys Glu Ser Gly Trp Thr Pro Trp Thr Thr Cys Asn Pro Gln
35 40 45

Thr Gly Leu Arg Glu Arg His Asn Ala Gln Cys Glu Thr Trp Val Glu
50 55 60

Val Glu Glu Cys Gln Lys Leu Thr Gly Cys Gly Asn Trp Thr Pro Trp
65 70 75 80

Ser Pro Gly Asp Met Ser Cys Val Val Gly Gln Phe Gln Thr Arg Asn
85 90 95

-continued

```
Arg Glu Gly Cys Phe Glu Val Gln Glu Val Arg Ala Cys Arg Pro Val
            100                 105                 110

Leu Leu Glu Cys Asn Asp Gln Trp Thr Pro Trp Ile Met Cys Asp Thr
        115                 120                 125

Asn Arg Val Gln Glu Arg Tyr Asn Ser Lys Cys Gly Pro Val Glu Val
    130                 135                 140

Arg Glu Cys Asn Met Asp Asp Ala Glu Ile Glu Lys Cys Gly Glu Phe
145                 150                 155                 160

Val Glu Trp Asp Pro Pro Met Asn Gly Asp Cys Val Arg Gly Gly Thr
                165                 170                 175

His Thr Arg Tyr Arg Gln Asn Cys Pro Asp Arg Lys Glu Val Arg Val
            180                 185                 190

Cys Gly Ala Phe Asp Cys Ser Ser Cys Ser Val Asn Ala Thr Cys Asp
        195                 200                 205

Pro Ile Gly Ala Ser Cys Glu Cys Lys Pro Gly Phe Arg Gly Asn Gly
    210                 215                 220

Lys Thr Cys Glu Ala Phe Asn Pro Cys Glu Asp Thr Pro Ala Pro Cys
225                 230                 235                 240

Asp Ser Asn Ala Ile Cys Thr Pro Asp Ala Met Thr Pro Asn Ala Ser
                245                 250                 255

Ala Arg Gln Ala Gly Thr Gln Ile Pro Glu Gln Ala Ala Ala Arg Ser
            260                 265                 270

Leu Ala Leu Arg Ser Thr Ser Ala His Pro Thr Pro Thr Ser Ala Arg
        275                 280                 285

His Thr Pro His Ala Ser Thr Pro Arg Ala Leu Ile Ser Ala Thr Ala
    290                 295                 300

Thr Arg Asp Thr Val Lys Gly Glu Asp Gly Gln Cys His Asp Val Asp
305                 310                 315                 320

Glu Cys Thr Asn Gly Glu His Thr Cys Pro Ala His Ser Thr Cys Leu
                325                 330                 335

Asn Thr Ala Gly Ser Tyr Glu Cys Arg Cys Asp Thr Gly Tyr Ser Gly
            340                 345                 350

Asn Ala Thr Ala Asp Ser Pro Cys Lys Asn Ile Asp Glu Cys Ala Asn
        355                 360                 365

Pro Asn Ala Cys Ser Ala Asn Ala Ile Cys Thr Asp Thr Asp Gly Ser
    370                 375                 380

Phe Thr Cys Ser Cys Pro Glu Gly Tyr Ser Gly Gln Gly Thr His Asp
385                 390                 395                 400

Ser Pro Cys Ser Lys Ile Asp Phe Cys Ala Tyr Pro Ser Leu Asn Thr
                405                 410                 415

Cys Gly Ala His Ser Thr Cys Asn Thr Leu Thr Ser Phe Lys Cys Ile
            420                 425                 430

Cys Asp Ala Gly Tyr Glu Gly Ala Gly Thr Arg Glu Ser Pro Cys Val
        435                 440                 445

Asp Val Asn Glu Cys Ser Asn Glu Lys Pro Thr Asn Asn Cys Asn Arg
    450                 455                 460

Asn Ala Asn Cys Thr Asn Thr Glu Gly Ser Tyr Thr Cys Glu Cys Lys
465                 470                 475                 480

Pro Gly Pro Ser Gly Asp Gly Met Gly Pro Asn Gly Cys Thr Asp Ile
                485                 490                 495

Asp Glu Cys Ala Ala Glu Gln Ser Pro Cys Asp Pro His Ala Ser Cys
            500                 505                 510
```

-continued

```
Ser Asn Thr Glu Gly Ser Tyr Val Cys Thr Cys Asn Thr Gly Tyr Glu
        515                 520                 525

Pro Ala Ser Thr Asp Gly His Ala Cys Lys Asp Ile Asp Glu Cys Ala
    530                 535                 540

Thr Gly Ala Ala Gly Cys His Val Ser Ala Gln Cys Leu Asn Thr Asp
545                 550                 555                 560

Gly Ser Tyr Glu Cys Lys Cys Leu Glu Gly Phe Val Gly Asp Gly Lys
                565                 570                 575

Thr Cys Asn Asp Val Asp Glu Cys Ala Ala Ala Thr Ser Pro Cys Gly
            580                 585                 590

Asp Asn Thr His Cys Gln Asn Thr Ile Gly Ser Tyr Glu Cys Glu Cys
        595                 600                 605

Lys Ala Gly Tyr Gly Asn Met Gln Asp Asn Ala Cys Ser Asp Ile Asp
    610                 615                 620

Glu Cys Lys Asp Ala Asn Thr Lys Ile Pro Asp Asn Cys Leu Cys Val
625                 630                 635                 640

Asn Asn Asp Gly Ser Tyr Ser Leu Glu Ala Lys Ala Gly Tyr Glu Leu
                645                 650                 655

Val Asn Gly Glu Cys Ile Lys Ile Asp Phe Cys Ala Arg Gly Ala Cys
            660                 665                 670

Asn Ser Leu Ala Ser Cys Lys Glu Asn Glu Glu Gly Thr Ala Ala Ile
        675                 680                 685

Cys Thr Cys Leu Pro Gly Tyr Ser Gly Asp Gly Thr Ala Glu Gly His
    690                 695                 700

Cys Asn Asp Ile Asp Glu Cys Ala Gly Gln Asn Asp Cys Ala Pro Ala
705                 710                 715                 720

Glu Gln Gly Gly Ile Cys Glu Asn Thr Val Gly Ser Tyr Thr Cys Lys
                725                 730                 735

Cys Lys Glu Gly Tyr Arg Gln Asp Gly Asn Ser Cys Thr Glu Ile Asp
            740                 745                 750

Glu Cys Ala Glu Gly Thr His Asn Cys His Pro Ser Ala Thr Cys Ser
        755                 760                 765

Asn Thr Pro Gly Ser Phe Thr Cys Gln Cys Asn Ser Gly Phe Thr Gly
    770                 775                 780

Ser Gly Val Glu Cys Glu Asp Ile Asp Glu Cys Ser Thr Glu Ala Asp
785                 790                 795                 800

Asp Cys Gly Ala Asn Thr Ile Cys Ser Asn Thr Ile Gly Ala Phe Glu
                805                 810                 815

Cys Asn Cys Arg Glu Gly Tyr Glu Arg Ala Asp Ala Lys Thr Cys Val
            820                 825                 830

Asp Ile Asp Glu Cys Ala Thr Gly Thr His Thr Cys Ser Asn His Ala
        835                 840                 845

Thr Cys Thr Asn Thr Asp Gly Ser Phe Thr Cys Gln Cys Asn Pro Gly
    850                 855                 860

Phe Glu Gly Asp Gly His Lys Cys Glu Asp Ile Asp Phe Cys Gly Ala
865                 870                 875                 880

Gly Gln His Asp Cys Asn Val His Ala Glu Cys Ser Glu Ser Lys Asp
                885                 890                 895

Asn Thr Thr Phe Lys Cys Thr Cys Ile Thr Gly Tyr Ala Gly Asp Gly
            900                 905                 910

His Gly Glu Ala Gly Cys Gln Asp Ile Asp Glu Cys Ala Glu Glu Asn
        915                 920                 925

Ile Cys Gly Ser Asn Ala Val Cys Thr Asn Thr Ala Gly Ser Tyr Gln
```

-continued

```
    930                 935                 940

Cys Ala Cys Arg Glu Gly Phe Val Ala Ser Ala Glu Gln Gln Gln Gln
945                 950                 955                 960

Gly Thr Pro Ala Leu Val Cys Val Asp Val Asp Glu Cys Ser Asp Ala
                965                 970                 975

Ser Lys Asn Thr Cys Ala Lys Pro Ala Asp Gly Gly Ile Cys Thr Asn
            980                 985                 990

Thr Glu Gly Ser Tyr Glu Cys Ala  Cys Lys Pro Gly Tyr  Gln Gly Asp
        995                 1000                1005

Gly His  Ser Cys Ala Asp Ile  Asn Glu Cys Thr Ala  Gln Gly Thr
    1010                 1015                 1020

Cys Gly  Glu His Thr Thr Cys  Lys Asn Thr Pro Gly  Ser Phe Gln
    1025                 1030                 1035

Cys Asp  Cys Val Glu Gly Glu  Glu Arg Ala Asp Glu  Arg Thr Cys
    1040                 1045                 1050

Arg Asp  Ile Asn Glu Cys Glu  Thr Gly Ala Val Val  Leu Pro Pro
    1055                 1060                 1065

Asn Ser  Thr Cys Val Asn Thr  Glu Gly Ser Tyr Asp  Phe Asp Cys
    1070                 1075                 1080

Val Ala  Gly Tyr Arg Arg Thr  Asp Gly Ala Cys Val  Lys Ile Asp
    1085                 1090                 1095

Phe Cys  Lys Glu Lys Gly Cys  Asn Ala Asn Ala Thr  Cys Arg Glu
    1100                 1105                 1110

Asn Asp  Ala Gly Thr Glu Ala  Ile Cys Thr Cys Lys  Glu Gly Tyr
    1115                 1120                 1125

Glu Gly  Ser Gly Glu Gly Glu  Asp Gly Cys Gln Asn  Ile Asn Glu
    1130                 1135                 1140

Cys Glu  Arg Gly Glu Pro Cys  Lys Asp Phe Gly Glu  Gly Gly Val
    1145                 1150                 1155

Cys Val  Asp Thr Pro Gly Ser  Phe Thr Cys Glu Cys  Ala Ala Gly
    1160                 1165                 1170

Phe Ile  Gln Arg Arg Ser Val  Cys Gln Asp Val Asp  Glu Cys Leu
    1175                 1180                 1185

Asp Gly  Lys Leu Asn Thr Cys  Ala Ala Thr Gly Gly  Val Cys Ser
    1190                 1195                 1200

Asn Thr  Val Gly Ser Phe Thr  Cys Ser Cys Ala Ser  Gly Phe Glu
    1205                 1210                 1215

Gly Asp  Gly His Thr Cys Asn  Asp Val Asp Glu Cys  Ala Thr Ala
    1220                 1225                 1230

Gln His  Thr Cys Asp Pro Asn  Ala Thr Cys Val Asn  Thr Glu Gly
    1235                 1240                 1245

Ser Phe  Glu Cys Arg Cys Asn  Ala Gly Phe Glu Gly  Asp Gly His
    1250                 1255                 1260

Thr Cys  Ala Asp Ile Asp Glu  Cys Ala Asp Pro Ala  Lys Asn Thr
    1265                 1270                 1275

Cys Asp  Thr His Lys Gly Val  Cys Gln Asn Thr Thr  Gly Ser Tyr
    1280                 1285                 1290

Thr Cys  Gly Cys Lys Thr Gly  Phe Ser Leu Ala Ala  Asp Gly Ser
    1295                 1300                 1305

Thr Cys  Glu Asn Val Asp Glu  Cys Ala Ala Gly Thr  Ala Asn Cys
    1310                 1315                 1320

Asn Glu  Arg Ser Pro Cys Lys  Asp Thr Glu Gly Ser  Tyr Gln Cys
    1325                 1330                 1335
```

-continued

```
Glu Cys  Lys Asn Gly Tyr Lys  Ala Ala Gly Glu Asp  Cys Val Asp
    1340                 1345                 1350

Val Asp  Glu Cys Glu Ala Gly  Val His Gly Cys Ser  Glu His Ala
    1355                 1360                 1365

Ile Cys  Thr Asn Thr Asp Gly  Ser Tyr Ser Cys Glu  Cys Met Glu
    1370                 1375                 1380

Gly Tyr  Gln Gly Asp Gly Lys  Ala Cys Glu Lys Thr  Val Gly Val
    1385                 1390                 1395

Cys Asp  Ser Ala Pro Cys Gly  Ala His Ala Thr Cys  Glu Pro Ala
    1400                 1405                 1410

Gly Asp  Asn Tyr Thr Cys Thr  Cys His Pro Gly Tyr  Glu Met Arg
    1415                 1420                 1425

Glu Gly  Ala Cys Val Asp Ile  Asp Glu Cys Thr Ala  Gly Ser Leu
    1430                 1435                 1440

Asn Cys  Asp Pro His Ala Ile  Cys Thr Asn Thr Asp  Gly Ser Phe
    1445                 1450                 1455

Thr Cys  Val Cys Gly Ser Gly  Tyr Thr Gly Leu Gly  Thr Ser Cys
    1460                 1465                 1470

Glu Asp  Ile Asp Glu Cys Ala  Gly Asn Ala Ala Gly  Cys Asp Ile
    1475                 1480                 1485

His Ala  Val Cys Thr Asn Thr  Pro Gly Ser Phe Lys  Cys Glu Cys
    1490                 1495                 1500

Lys Ser  Gly Phe Glu Gly Asp  Gly Thr Gln Cys Thr  Glu Lys Val
    1505                 1510                 1515

Leu Leu  Pro Gly Gln Ile His  Cys Glu Ala Trp Thr  Ala Trp Thr
    1520                 1525                 1530

Glu Cys  Thr Asp Gly Ala Lys  Thr Ser Thr Arg Ser  Cys Leu Ala
    1535                 1540                 1545

Leu Pro  Leu Lys Lys Glu Met  Arg Ala Cys Pro Ala  Ala Asp Phe
    1550                 1555                 1560

Ser Gln  Cys Gly Glu Phe Thr  Glu Trp Thr Ala Cys  Pro Gly Thr
    1565                 1570                 1575

Asn Asn  Asn Leu Ser His Arg  Arg Thr Glu Arg Phe  Gly Glu Pro
    1580                 1585                 1590

Gly Cys  Glu Asp Ala Glu Glu  Val Arg Glu Cys Pro  Asp Glu Glu
    1595                 1600                 1605

Thr Glu  Gln Lys Cys Gly Ala  Trp Gly Glu Trp Thr  Ala Cys Gly
    1610                 1615                 1620

Asp Pro  Ser Pro Gly Leu Arg  Thr Arg Ala Arg Glu  Asn Cys Pro
    1625                 1630                 1635

Asp Val  Val Glu Phe Glu Arg  Cys Thr Met Pro Ser  Glu Pro Glu
    1640                 1645                 1650

Ala Gly  Glu Val Thr Glu Pro  His Thr Glu Gly Gly  Ala Gly Val
    1655                 1660                 1665

Gly Gly  Glu Val Thr Glu Pro  Asp Thr Glu Glu Gly  Ala Gly Val
    1670                 1675                 1680

Gly Gly  Glu Val Gln Pro Gly  Thr Glu Glu Gly Ala  Gly Val Gly
    1685                 1690                 1695

Gly Glu  Val Gln Pro Gly Thr  Glu Glu Gly Ala Gly  Val Gly Gly
    1700                 1705                 1710

Glu Val  Gln Pro Gly Thr Glu  Glu Gly Ala Gly Val  Gly Gly Glu
    1715                 1720                 1725
```

-continued

```
Val Gln Pro Gly Thr Glu Glu Gly Ala Gly Ile Gly Gly Glu Val
    1730                1735                1740

Thr Glu Pro Asp Thr Glu Gly Gly Ala Gly Val Ser Gly Glu Pro
    1745                1750                1755

Thr Glu Glu Glu Gly Thr Glu Ser Thr Gly Pro Cys Lys Glu Phe
    1760                1765                1770

Gly Pro Trp Thr Ala Cys Lys Glu Asp Glu Asn Gly Val Gly Ile
    1775                1780                1785

Gln Arg Arg Met Cys Ala Gly Arg Glu Asp Ile Ile Glu Ser Arg
    1790                1795                1800

Ile Cys Thr Val Thr Asp Asp Cys Gly Glu Trp Thr Pro Trp Ser
    1805                1810                1815

Thr Cys Thr Asn Gly Ser Gln Ala Arg Asn Lys Arg Pro Cys Thr
    1820                1825                1830

Asn Val Arg Glu Val Arg Leu Cys Gly Ala Asp Ile Pro Val Thr
    1835                1840                1845

Asp Gly Cys Thr Trp Ser Glu Trp Thr Ser Cys Ser Leu Val Asn
    1850                1855                1860

Glu Glu Gly Gly Tyr Phe Arg Thr Arg Thr Ser Ser Asp Cys Asn
    1865                1870                1875

Met Asn Glu Val Gln Ala Cys Ser Pro Ser Ser Ser Thr Thr Ala
    1880                1885                1890

Asp Ser Glu Thr Glu Gly Thr Cys Ser Ala Trp Asn Pro Trp Thr
    1895                1900                1905

Glu Cys Ser Asn Gly His Gln Thr Arg Lys Cys Ala Thr Met Glu
    1910                1915                1920

Ala Glu Glu Ser Arg Thr Cys Gly Glu Thr Pro Glu Asn Cys Gly
    1925                1930                1935

Glu Phe Gly Pro Phe Glu Pro Ala Asn Cys Thr Ala Gly Gln Met
    1940                1945                1950

Val Thr Arg Thr Arg Thr Cys Gly Glu Thr Glu Gln Lys Glu Thr
    1955                1960                1965

Lys Leu Cys Asp Val Ser Ser Thr Glu Glu Gly Lys Gln Cys Gly
    1970                1975                1980

Gln Trp Gly Pro Trp Ser Glu Cys Asn Thr His Leu Gly Ser Glu
    1985                1990                1995

Asp Asn Val Arg Val Arg Glu Asp Thr Ala Cys Gly Val Thr Glu
    2000                2005                2010

Tyr Glu Glu Cys Ser Lys Pro Ala Asn Asn Ala Phe Val Cys Thr
    2015                2020                2025

Pro Trp Ser Glu Cys Ser Asp Lys Lys Glu Arg Arg Thr Cys Thr
    2030                2035                2040

Ile Arg Lys Asn Gly Leu Val Gln Thr Arg Gln Glu Phe Arg Thr
    2045                2050                2055

Cys Ser Val Asp Ile Ala Thr Thr Cys Gly Asp Phe Gly Ala Trp
    2060                2065                2070

Ser Glu Cys Asn Ala Glu Gly Leu His Gln Arg Ser Leu Glu Lys
    2075                2080                2085

Cys Pro Asp Val Ile Glu Val Ala Thr Cys Gly Ser Glu Asp Cys
    2090                2095                2100

Pro Pro Phe Gly Glu Trp Thr Glu Cys Gly Val Pro Glu Glu Gly
    2105                2110                2115

Met Arg Ser Arg Gln Arg Ile Asp Cys Val Glu Ser Ala Ala Cys
```

-continued

```
    2120                2125                2130

Gln Cys  Thr Glu Val Glu Ser  Cys Phe Asp Thr Glu  Leu His Pro
    2135                2140                2145

Ile Pro  Ala Pro Gly Thr Glu  Thr Gly Glu Gly Glu  Gly Glu Thr
    2150                2155                2160

Glu Thr  Gly Glu Gly Glu Thr  Gly Glu Ala Gly Gly  Glu Glu Gly
    2165                2170                2175

Glu Gln  Thr Gly Glu Gly Glu  Val Gln Pro Pro Glu  Glu Glu Leu
    2180                2185                2190

Pro Gly  Glu Ser Val Thr Glu  Pro Glu Glu Lys Pro  Glu Glu Glu
    2195                2200                2205

Leu Pro  Glu Glu Glu Val Thr  Glu Pro Glu Glu Lys  Pro Glu Glu
    2210                2215                2220

Gly Val  Thr Gln Pro Glu Glu  Thr Pro Glu Gln Pro  Val Glu Gly
    2225                2230                2235

Thr Glu  Glu Glu Gly Lys Gln  Glu Ser Glu Ala Ala  Pro Glu Thr
    2240                2245                2250

Pro Ala  Val Gln Pro Lys Pro  Glu Glu Gly His Glu  Arg Pro Glu
    2255                2260                2265

Pro Glu  Glu Glu Glu Glu Lys  Lys Glu Glu Gly Gly  Gly Phe Pro
    2270                2275                2280

Thr Ala  Ala Val Ala Gly Gly  Val Gly Gly Val Leu  Leu Ile Ala
    2285                2290                2295

Ala Val  Gly Gly Gly Val Ala  Ala Phe Thr Ser Gly  Gly Gly Gly
    2300                2305                2310

Ala Gly  Ala Gln Glu Ala Glu  Gln Val Glu Phe Glu  Gly Glu Asp
    2315                2320                2325

Thr Gly  Ala Ala Thr Ala Glu  Thr Pro Glu Ala Asp  Thr Val Ile
    2330                2335                2340

Asp Ile  Thr Asp Glu Asp Asp  Tyr Trp Ala Asp Ser  Gly Asp Ile
    2345                2350                2355

Gln


<210> SEQ ID NO 7
<211> LENGTH: 2189
<212> TYPE: PRT
<213> ORGANISM: Chicken

<400> SEQUENCE: 7

Met Gly Phe Phe Val Phe Thr Gly Gly Asp Phe Gly Asp Trp Ser Pro
1               5                   10                  15

Pro Leu Ala Gly Asp Cys Val Pro Gly Thr Thr His Thr Arg Gln Arg
            20                  25                  30

Ala Asn Cys Pro Asn His Lys Glu Val Arg Val Cys Gly Ala Phe Asp
        35                  40                  45

Cys Ser Gln Cys Ser Val Asn Ala Thr Cys Asp Pro Leu Gly Ala Thr
    50                  55                  60

Cys Gln Cys Lys Pro Gly Phe Arg Gly Asp Gly Thr Gln Cys Glu Ala
65                  70                  75                  80

Phe Asn Pro Cys Glu Gly Glu Thr Ala Pro Cys Asp Ala Asn Ala Thr
                85                  90                  95

Cys Thr Ala Asp Gly Asn Asp Ala Lys Cys His Cys Asn Lys Gly Trp
            100                 105                 110

Asn Ala Asp Ser Lys Ala Gly Ala Ser Gly His Ala Cys Val Glu Glu
```

-continued

```
        115                 120                 125

Asp Glu Cys Ala Asn Asn Thr His Glu Cys Pro Gln His Ser Thr Cys
    130                 135                 140

Val Asn Thr Glu Gly Ser Tyr Glu Cys Asn Cys Leu Pro Gly Tyr Gln
145                 150                 155                 160

Lys Asp Gln Asp Gly Lys Cys Gln Asp Ile Asp Glu Cys Ala Gly Glu
                165                 170                 175

His Gly Cys Pro Ala His Ser Thr Cys Val Asn Thr Ala Gly Ser Phe
            180                 185                 190

Glu Cys Lys Cys Asp Ala Gly Phe Ser Gly Ser Ala Thr Ser Glu Ser
        195                 200                 205

Pro Cys Ser Asn Ile Asp Glu Cys Gln Asp Pro Asp Ala Cys Ser Ala
    210                 215                 220

Asn Ala Ile Cys Ala Asp Thr Glu Gly Ser Phe Thr Cys Ser Cys Pro
225                 230                 235                 240

Glu Gly Tyr Ser Gly Gly Gly Ser His Asp Ser Pro Cys Ser Lys Ile
                245                 250                 255

Asp Tyr Cys Ala Asp Pro Thr Leu Asn Thr Cys Gly Ala His Ser Thr
            260                 265                 270

Cys Val Asn Thr Leu Thr Thr Phe Lys Cys Val Cys Asp Ala Gly Tyr
        275                 280                 285

Asp Gly Ala Gly Thr His Glu Ser Pro Cys Val Asp Ile Asp Glu Cys
    290                 295                 300

Ser Lys Glu Lys Pro Ser Asn Asp Cys Asn Arg Asn Ala Val Cys Thr
305                 310                 315                 320

Asn Thr Glu Gly Ser Tyr Thr Cys Ala Cys Lys Glu Gly Pro Ser Gly
                325                 330                 335

Glu Gly Phe Gly Ala Ala Gly Cys Ala Asp Val Asp Glu Cys Ala Asn
            340                 345                 350

Ser Pro Cys Asp Ala His Ala Ser Cys Ala Asn Thr Glu Gly Ser Tyr
        355                 360                 365

Val Cys Thr Cys Asn Pro Gly Tyr Glu Pro Ala Ser Ser Asp Gly His
    370                 375                 380

Ala Cys Lys Asp Val Asp Glu Cys Ala Ala Gly Thr Ala Glu Cys His
385                 390                 395                 400

Val Ser Ala Gln Cys Val Asn Val Asp Gly Ser Tyr Glu Cys His Cys
                405                 410                 415

Leu Glu Gly Phe Ile Gly Asp Gly Lys Val Cys Ser Asp Val Asp Glu
            420                 425                 430

Cys Ala Ala Glu Ala Ser Pro Cys Gly Ala Asn Thr His Cys Leu Asn
        435                 440                 445

Thr Ile Gly Ser Tyr Glu Cys Glu Cys Lys Asp Gly Tyr Gly His Met
    450                 455                 460

Glu Gly Asn Ala Cys Glu Asp Ile Asp Glu Cys Ser Glu Ala Ser Thr
465                 470                 475                 480

Glu Ile Pro Glu Asn Cys Asn Cys Val Asn Thr Glu Gly Ser Phe Ser
                485                 490                 495

Leu Glu Ala Lys Pro Gly Tyr Glu Leu Val Asp Gly Lys Cys Val Lys
            500                 505                 510

Ile Asp Phe Cys Ala Arg Gly Ala Cys Asn Ser Leu Ala His Cys Lys
        515                 520                 525

Glu Asn Pro Glu Gly Thr Ala Ala Ile Cys Thr Cys Ile Ala Gly Tyr
    530                 535                 540
```

-continued

```
Ser Gly Asp Gly Thr Ala Gln Gly His Cys Asp Asp Ile Asp Glu Cys
545                 550                 555                 560

Glu Ala Glu Asn Asp Cys Thr Pro Ala Asp Gln Gly Gly Ile Cys Glu
                565                 570                 575

Asn Thr Val Gly Ser Tyr Thr Cys Lys Cys Ala Ala Gly Tyr Gln Gln
            580                 585                 590

Asp Gly Asn Ser Cys Thr Asp Ile Asp Glu Cys Ala Asn Gly Thr His
        595                 600                 605

Asn Cys His Ala Ser Ala Thr Cys Thr Asn Thr Gln Gly Ser Phe Glu
    610                 615                 620

Cys Ala Cys Asn Ala Gly Pro Ser Gly Asn Gly Val Glu Cys Asn Asp
625                 630                 635                 640

Val Asp Glu Cys Ser Thr Asp Ala Asp Asp Cys Gly Glu Asn Thr Leu
                645                 650                 655

Cys Asn Asn Thr Val Gly Ser Phe Glu Cys Thr Cys Met Ala Gly Phe
            660                 665                 670

Glu Ala Ala Asp Ala Lys Thr Cys Lys Asp Ile Asp Glu Cys Ala Ser
        675                 680                 685

Gly Thr His Thr Cys Ser Thr His Ala Thr Cys Thr Asn Thr Ala Gly
    690                 695                 700

Ser Phe Thr Cys Glu Cys Asn Pro Gly Phe Asp Gly Asp Gly His Lys
705                 710                 715                 720

Cys Glu Asp Val Asp Pro Cys Gly Gln Gly Leu His Asp Cys Asn Val
                725                 730                 735

His Ala Glu Cys Ser Glu Ser Asp Asp Asn Thr Thr Lys Phe Cys Thr
            740                 745                 750

Cys Gly Ile Gly Tyr Ser Gly Glu Gly His Gly Glu Asn Gly Cys Gln
        755                 760                 765

Asp Ile Asp Glu Cys Ala Gln Asp Ala Ile Cys Gly Glu Asn Thr Val
    770                 775                 780

Cys Thr Asn Thr Pro Gly Ser Phe Glu Cys Ala Cys Val Glu Gly Phe
785                 790                 795                 800

Val Ala Val Gly Ala Lys Leu Lys Gly Ala Thr Ser Leu Thr Cys Ile
                805                 810                 815

Asp Ile Asp Glu Cys Asn Asp Ala Ser Lys Asn Thr Cys Ala Thr Ser
            820                 825                 830

Ala Asp Gly Gly Ser Cys Lys Asn Thr Ala Gly Ser Tyr Glu Cys Ser
        835                 840                 845

Cys Leu Pro Gly Phe Gln Gly Asp Gly His Ser Cys Thr Asp Ile Asp
    850                 855                 860

Glu Cys Ala Thr Gln Gly Val Cys Gly Glu His Ala Thr Cys Glu Asn
865                 870                 875                 880

Thr Ala Gly Ser Tyr Asn Cys Thr Cys Glu Ala Gly Tyr Thr Gln Gln
                885                 890                 895

Asp Gly Ala Val Gly Cys Ile Asp Ile Asp Glu Cys Ala Ala Ser Thr
            900                 905                 910

Ala Val Leu Pro Ala Asn Ala Thr Cys Val Asn Thr Glu Gly Ser Tyr
        915                 920                 925

Thr Phe Glu Cys Val Pro Gly Tyr Arg His Thr Glu Asn Gly Cys Thr
    930                 935                 940

Lys Ile Asp Phe Cys Ser Glu Lys Gly Cys Asn Ala Asn Ala Ser Cys
945                 950                 955                 960
```

-continued

```
Lys Glu Asn Asp Ala Gly Thr Glu Ala Ile Cys Thr Cys His Ser Gly
                965                 970                 975

Tyr Glu Gly Asn Gly Glu Gly Glu Glu Gly Cys Lys Asn Ile Asp Glu
            980                 985                 990

Cys Ser Val Gly Glu Pro Cys Lys  Asp Phe Gly Glu Gly  Gly Val Cys
        995                 1000                 1005

Val Asp  Ser Pro Gly Ser Phe  Ser Cys Ser Cys Ala  Thr Gly Phe
    1010                 1015                 1020

Ile Lys  Arg Arg Ser Thr Cys  Gln Asp Ile Asp Glu  Cys Leu Asp
    1025                 1030                 1035

Gly Lys  Met Asn Thr Cys Ala  Pro Val Gly Gly Ile  Cys Thr Asn
    1040                 1045                 1050

Thr Val  Gly Ser Phe Thr Cys  Ser Cys Ala Ala Gly  Phe Thr Gly
    1055                 1060                 1065

Asp Gly  Leu Thr Cys Glu Asp  Ile Asp Glu Cys Ala  Thr Ala Ala
    1070                 1075                 1080

His Thr  Cys Asp Pro Asn Ala  Thr Cys Val Asn Thr  Val Gly Ser
    1085                 1090                 1095

Phe Glu  Cys Gly Cys Lys Glu  Gly Phe Ser Gly Asp  Gly His Thr
    1100                 1105                 1110

Cys Thr  Asp Ile Asp Glu Cys  Ala Asp Pro Asn Leu  Asn Lys Cys
    1115                 1120                 1125

Asp Thr  His Lys Gly Ile Cys  Gln Asn Gly Thr Gly  Ser Tyr Thr
    1130                 1135                 1140

Cys Gly  Cys Arg Pro Gly Tyr  Ser Leu Ala Ala Asp  Gly Phe Thr
    1145                 1150                 1155

Cys Asp  Asn Val Asp Glu Cys  Ala Ala Gly Thr Ala  Thr Cys Gly
    1160                 1165                 1170

Glu Arg  Ser Phe Cys Val Asp  Thr Gln Gly Ser Tyr  Lys Cys Glu
    1175                 1180                 1185

Cys Lys  Asn Gly Tyr Arg Gln  Ser Gly Glu Asp Cys  Val Asp Val
    1190                 1195                 1200

Asp Glu  Cys Glu Ala Asp Val  His Thr Cys Ser Glu  His Ala Thr
    1205                 1210                 1215

Cys Thr  Asn Thr Glu Gly Ser  His Thr Cys Thr Cys  Asn Glu Gly
    1220                 1225                 1230

Tyr Gln  Gly Asp Gly Lys Lys  Cys Glu Lys Thr Val  Gly Pro Cys
    1235                 1240                 1245

Asp Asn  Ser Pro Cys Gly Asn  Asn Ala Met Cys Glu  Ala Thr Ala
    1250                 1255                 1260

Asp Ser  Tyr Asn Cys Thr Cys  Lys Ala Gly Tyr Glu  Met Lys Asp
    1265                 1270                 1275

Gly Ala  Cys Val Gln Ile Asp  Glu Cys Gln Ser Gly  Thr His Asn
    1280                 1285                 1290

Cys Asp  Pro His Ala Asp Cys  Ser Asn Thr Asp Gly  Ser Phe Thr
    1295                 1300                 1305

Cys Thr  Cys Gly Ser Gly Tyr  Thr Gly Val Gly Thr  Leu Cys Glu
    1310                 1315                 1320

Asp Val  Asp Glu Cys Ala Gly  Asn His Ala Gly Cys  Asp Ile Asn
    1325                 1330                 1335

Ala Val  Cys Thr Asn Val Pro  Gly Ser Phe Thr Cys  Glu Cys Lys
    1340                 1345                 1350

Ser Gly  Phe Glu Gly Asp Gly  His Glu Cys Thr Glu  Lys Val Leu
```

-continued

```
    1355                1360                1365

Leu Pro  Gly Gln Ile His Cys  Asp Ser Trp Thr Ala  Trp Thr Glu
    1370                1375                1380

Cys Thr  Ala Glu Thr Lys Gln  Ser Thr Arg Lys Cys  Val Ala Leu
    1385                1390                1395

Pro Leu  Lys Val Glu Val Lys  Leu Cys Pro Asp Ala  Asp Ile Ser
    1400                1405                1410

Ala Cys  Gly Glu Leu Gly Glu  Trp Ser Ser Cys Pro  Gly Val Asp
    1415                1420                1425

Asn Asn  Leu Ser His Arg Arg  Ala Glu Lys Phe Gly  Glu Pro Gly
    1430                1435                1440

Cys Glu  His Ala Glu Glu Val  Arg Glu Cys Pro Asp  Glu Glu Val
    1445                1450                1455

Glu Glu  Arg Cys Gly Ala Phe  Gly Glu Trp Thr Ala  Cys Gly Asp
    1460                1465                1470

Pro Ser  Glu Gly Leu Arg Thr  Arg Thr Arg Gln Asn  Cys Pro Glu
    1475                1480                1485

Glu Ala  Glu Phe Glu His Cys  Thr Met Pro Ser Ala  Pro Ser Val
    1490                1495                1500

Pro Glu  Gly Gly Ser Ser Cys  Thr Glu Phe Gly Ala  Trp Ser Glu
    1505                1510                1515

Cys Val  Ala Asp Ala His Gly  Ile Lys Met Gln His  Arg Thr Cys
    1520                1525                1530

Val His  Asn Glu Ala Val Gln  Glu His Arg Ile Cys  Thr Val Glu
    1535                1540                1545

Asp Pro  Gln Gln Cys Gly Glu  Trp Ser Gln Trp Ser  Glu Cys Lys
    1550                1555                1560

Asn Gly  Lys Gln Tyr Arg Gly  Ala Ala Gly Cys Ala  Ser Val Tyr
    1565                1570                1575

Glu Val  Arg Ala Cys Ser Gly  Ala Ser Asp Ala Lys  Glu Cys Ser
    1580                1585                1590

Phe Gly  Ala Trp Ser Gly Cys  Val Val Glu Phe Gly  Gly His Thr
    1595                1600                1605

Tyr Lys  Val Arg Asn Ser Ile  Asp Cys Glu Leu Ser  Glu Leu Gln
    1610                1615                1620

Ala Cys  Lys Pro Ser Ala Ala  Thr Glu Gly Glu Gly  Lys Cys Ala
    1625                1630                1635

Ala Trp  Ser Pro Trp Thr Thr  Cys Arg Asp Gly Met  Gln Thr Arg
    1640                1645                1650

Asp Cys  Lys Ser Leu Gly Val  Gln Glu Ser Arg Pro  Cys Ser Ala
    1655                1660                1665

Glu Gly  Glu Thr Asp Ser Cys  Gly Ala Phe Gly Pro  Phe Glu Pro
    1670                1675                1680

Ala Ala  Cys Lys Ala Gly Glu  Met Val Thr Arg Thr  Arg Glu Cys
    1685                1690                1695

Asn Gly  Ala Gln Gln Lys Glu  Thr Arg Leu Cys Asn  Phe Glu Gly
    1700                1705                1710

Asn Asp  Asn Cys Asn Asn Trp  Gly Ala Trp Thr Glu  Cys Ser Leu
    1715                1720                1725

Ile Val  Gly Gly Ser Ala Leu  Arg Ser Arg Glu Glu  Ser Thr Cys
    1730                1735                1740

Gly Tyr  Val Glu Leu Glu Glu  Cys Ser Gly Ser Ser  Ser Ser Gly
    1745                1750                1755
```

-continued

```
Asp Gln Thr Val His Cys Gly Ser Trp Ser Glu Cys Ser Met Arg
    1760                1765                1770

Lys Thr Glu Arg Thr Cys Asp Val Leu Ser Asp Gly Ser His Thr
    1775                1780                1785

Ser Val Thr Glu Val Leu Thr Cys Asp Asp Val Leu Pro Asp Ser
    1790                1795                1800

Cys Gly Glu Phe Gly Glu Trp Ser Glu Cys Ser Ala Asp Gly Leu
    1805                1810                1815

His Ser Arg Ser Leu Ser Gly Cys Pro Asp Val Thr Glu Val Met
    1820                1825                1830

Thr Cys Gly Ser Glu Asn Cys Pro Ala Pro Gly Glu Trp Ser Glu
    1835                1840                1845

Cys Gly Ser Pro Glu Asp Gly Leu Arg Ser Arg Gln Arg Thr Asn
    1850                1855                1860

Cys Arg Glu Gly Ser Gly Cys Ile Cys Ser Glu Thr Glu Ala Cys
    1865                1870                1875

Val Asn Thr Glu Leu His Pro Ile Pro Leu Pro Val Pro Gly Gly
    1880                1885                1890

Gly Glu Gly Ser Glu Asn Gly Glu Gly Gly Gln Thr Gly Glu Glu
    1895                1900                1905

Gly Thr Glu Gly Gly Ala Gly Gly Ala Gly Gly Ser Gly Gly Ala
    1910                1915                1920

Glu Glu Leu Pro Gly Glu Glu Gly Gly Ala Gly Ala Gly Gly Glu
    1925                1930                1935

Gly Gly Ser Gly Gly Asn Ala Glu Glu Leu Pro Gly Glu Gly Gly
    1940                1945                1950

Ala Gly Glu Ala Gly Gly Ser Gly Gly Ser Ala Glu Glu Leu Pro
    1955                1960                1965

Gly Glu Glu Gly Gly Ala Gly Ala Gly Gly Gly Gly Gly Ser Gly
    1970                1975                1980

Gly Ser Ala Glu Glu Leu Pro Gly Glu Glu Gly Gly Ala Gly Ala
    1985                1990                1995

Gly Gly Glu Gly Gly Ser Gly Gly Asn Ala Glu Glu Leu Pro Gly
    2000                2005                2010

Glu Glu Gly Gly Ala Gly Ala Gly Gly Ala Glu Gly Glu Thr Gly
    2015                2020                2025

Lys Pro Gly Gly Glu Glu Gly Gly Ala Gly Gly Ala Gly Glu Gly
    2030                2035                2040

Ala Gly Gly Glu Gly Gly Glu Val Gln Pro Gly Glu Gly Glu Gly
    2045                2050                2055

Ala Ser Glu Gly Gly Glu Gln Val Pro Glu Thr Pro Glu Thr Pro
    2060                2065                2070

Glu Pro Glu Thr Pro Glu Ala Glu Arg Pro Glu Glu Gln Pro Ser
    2075                2080                2085

Thr Glu Thr Pro Ala Glu Glu Pro Thr Glu Gly Gly Ala Glu Glu
    2090                2095                2100

Glu Glu Lys Glu Glu Gly Ser Gly Phe Pro Thr Ala Ala Val Ala
    2105                2110                2115

Gly Gly Val Gly Gly Val Leu Leu Leu Ala Ala Val Gly Gly Gly
    2120                2125                2130

Val Ala Ala Tyr Ser Gly Gly Gly Gly Gly Gly Gly Ala Glu Glu
    2135                2140                2145
```

-continued

Ala Glu Gln Val Glu Phe Glu Gly Glu Glu Ser Gly Gly Ala Ser
2150 2155 2160

Ala Glu Thr Pro Glu Ala Asp Thr Val Ile Asp Ile Thr Asp Glu
2165 2170 2175

Asp Asp Tyr Trp Ala Asp Ser Gly Asp Ile Gln
2180 2185

<210> SEQ ID NO 8
<211> LENGTH: 16
<212> TYPE: PRT
<213> ORGANISM: Chicken

<400> SEQUENCE: 8

Glu Val Asn Asn Glu Leu Ser Lys Cys Glu Ser Gly Trp Thr Pro Trp
1 5 10 15

<210> SEQ ID NO 9
<211> LENGTH: 7
<212> TYPE: PRT
<213> ORGANISM: Chicken

<400> SEQUENCE: 9

Gln Trp Thr Ala Trp Thr Glu
1 5

<210> SEQ ID NO 10
<211> LENGTH: 6
<212> TYPE: PRT
<213> ORGANISM: Chicken
<220> FEATURE:
<221> NAME/KEY: MISC_FEATURE
<222> LOCATION: (2)..(2)
<223> OTHER INFORMATION: Where X= L/I

<400> SEQUENCE: 10

Glu Xaa Val Asn Trp Phe
1 5

<210> SEQ ID NO 11
<211> LENGTH: 293
<212> TYPE: DNA
<213> ORGANISM: Chicken

<400> SEQUENCE: 11
gtggtgattg aatctgctcc agccaagatg gctcaccctc ctgtggtgat tgagtctgct 60
ccggtcgagg tggtccatcc tcctatggtg attgaatctg ctccacccaa gatggctcaa 120
cctccgatgg tgattgagtc tgctccaccc aagatggctc aaccacctat ggtgattgag 180
tcggctcccg tcgaggtggt ccatcctcct atggtgatgg aagccgctcc caccgtgaag 240
ggaagatacc tcgctgctga ggatgaggtg gaagagcagt ttgaatcgaa cag 293

<210> SEQ ID NO 12
<211> LENGTH: 97
<212> TYPE: PRT
<213> ORGANISM: Chicken

<400> SEQUENCE: 12

Val Val Ile Glu Ser Ala Pro Ala Lys Met Ala His Pro Pro Val Val
1 5 10 15

Ile Glu Ser Ala Pro Val Glu Val Val His Pro Pro Met Val Ile Glu
20 25 30

Ser Ala Pro Pro Lys Met Ala Gln Pro Pro Met Val Ile Glu Ser Ala

-continued

```
        35                  40                  45

Pro Pro Lys Met Ala Gln Pro Pro Met Val Ile Glu Ser Ala Pro Val
    50                  55                  60

Glu Val Val His Pro Pro Met Val Met Glu Ala Ala Pro Thr Val Lys
65                  70                  75                  80

Gly Arg Tyr Leu Ala Ala Glu Asp Glu Val Glu Glu Gln Phe Glu Ser
                85                  90                  95

Asn


<210> SEQ ID NO 13
<211> LENGTH: 196
<212> TYPE: DNA
<213> ORGANISM: Chicken

<400> SEQUENCE: 13

cctgcaggtt gtactaagag cgctttatga ctatcgggag ctcaaatgcg gctcagcatg      60

ccggaacgtg ggcattttgg tacacggagg tatcacctcg agcgaatggg cgggggtctt     120

tccgcaaaca agcgttccac caaaacctaa ggtggaaaac tgttcagttg catttaatta     180

cgcttttgta aatacc                                                     196


<210> SEQ ID NO 14
<211> LENGTH: 65
<212> TYPE: PRT
<213> ORGANISM: Chicken

<400> SEQUENCE: 14

Leu Gln Val Val Leu Arg Ala Leu Tyr Asp Tyr Arg Glu Leu Lys Cys
1               5                   10                  15

Gly Ser Ala Cys Arg Asn Val Gly Ile Leu Val His Gly Gly Ile Thr
            20                  25                  30

Ser Ser Glu Trp Ala Gly Val Phe Pro Gln Thr Ser Val Pro Pro Lys
        35                  40                  45

Pro Lys Val Glu Asn Cys Ser Val Ala Phe Asn Tyr Ala Phe Val Asn
    50                  55                  60

Thr
65


<210> SEQ ID NO 15
<211> LENGTH: 8
<212> TYPE: PRT
<213> ORGANISM: Chicken

<400> SEQUENCE: 15

Ser Trp Thr Ala Trp Thr Glu Cys
1               5


<210> SEQ ID NO 16
<211> LENGTH: 8
<212> TYPE: PRT
<213> ORGANISM: Chicken

<400> SEQUENCE: 16

Glu Phe Gly Ala Trp Ser Glu Cys
1               5


<210> SEQ ID NO 17
<211> LENGTH: 8
<212> TYPE: PRT
<213> ORGANISM: Chicken
```

-continued

<400> SEQUENCE: 17

```
Glu Trp Ser Gln Trp Ser Glu Cys
1               5
```

<210> SEQ ID NO 18
<211> LENGTH: 8
<212> TYPE: PRT
<213> ORGANISM: Chicken

<400> SEQUENCE: 18

```
Ala Trp Ser Pro Trp Thr Glu Cys
1               5
```

<210> SEQ ID NO 19
<211> LENGTH: 8
<212> TYPE: PRT
<213> ORGANISM: Chicken

<400> SEQUENCE: 19

```
Asn Trp Gly Ala Trp Thr Glu Cys
1               5
```

<210> SEQ ID NO 20
<211> LENGTH: 85
<212> TYPE: PRT
<213> ORGANISM: Chicken

<400> SEQUENCE: 20

```
Glu Gln Lys Glu Thr Lys Leu Cys Asp Val Ser Ser Thr Glu Glu Gly
1               5                   10                  15

Lys Gln Cys Gly Gln Trp Gly Pro Trp Ser Glu Cys Asn Ile Tyr Leu
            20                  25                  30

Gly Ser Glu Asp Asn Val Arg Val Arg Glu Asp Thr Ala Cys Gly Val
        35                  40                  45

Thr Glu Cys Glu Glu Cys Ser Lys Pro Ala Asn Asn Ala Phe Val Cys
    50                  55                  60

Thr Pro Trp Ser Glu Cys Ser Asp Lys Lys Glu Arg Arg Thr Cys Thr
65                  70                  75                  80

Ile Arg Lys Asn Gly
                85
```

<210> SEQ ID NO 21
<211> LENGTH: 300
<212> TYPE: DNA
<213> ORGANISM: Chicken

<400> SEQUENCE: 21

```
accttggccc atgtgccaca tggtcatttt tcttcagttt gttcatgaga agagctgcta      60

cagtgtagct cgaactcaac tttaaacgca gccgtttcag cggcgacaat atgctgcatc     120

gcaacccgcg gtgggcgctt tgtgcagccc tcgctgcact ctatggcgga acaggaatcg     180

ccagcgccga agttaacaat gaattgagca agtgcgaatc tgggtggaca ccctggacta     240

cctgcaaccc gcaaactggt ctgcgggaga ggcacaatgc acagtgcgag acatgggtgg     300
```

<210> SEQ ID NO 22
<211> LENGTH: 300
<212> TYPE: DNA
<213> ORGANISM: Chicken

<400> SEQUENCE: 22

-continued

```
tggaaccggg tacacggtgt accagtaaaa agaagtcaaa caagtactct tctcgacgat     60

gtcacatcga gcttgagttg aaatttgcgt cggcaaagtc gccgctgtta tacgacgtag    120

cgttgggcgc cacccgcgaa acacgtcggg agcgacgtga gataccgcct tgtccttagc    180

ggtcgcggct tcaattgtta cttaactcgt tcacgcttag acccacctgt gggacctgat    240

ggacgttggg cgtttgacca gacgccctct ccgtgttacg tgtcacgctc tgtacccacc    300
```

<210> SEQ ID NO 23
<211> LENGTH: 78
<212> TYPE: PRT
<213> ORGANISM: Chicken

<400> SEQUENCE: 23

```
Leu Glu Leu Asn Phe Lys Arg Ser Arg Phe Ser Gly Asp Asn Met Leu
1               5                   10                  15

His Arg Asn Pro Arg Trp Ala Leu Cys Ala Ala Leu Ala Ala Leu Tyr
            20                  25                  30

Gly Gly Thr Gly Ile Ala Ser Ala Glu Val Asn Asn Glu Leu Ser Lys
        35                  40                  45

Cys Glu Ser Gly Trp Thr Pro Trp Thr Thr Cys Asn Pro Gln Thr Gly
    50                  55                  60

Leu Arg Glu Arg His Asn Ala Gln Cys Glu Thr Trp Val Glu
65                  70                  75
```

<210> SEQ ID NO 24
<211> LENGTH: 215
<212> TYPE: DNA
<213> ORGANISM: Chicken

<400> SEQUENCE: 24

```
gacatcgacg aatgcgcgac aggcacacac acttgctcga accacgccac ctgcaccaat     60

accgatgggt cattcacatg ccagtgcaac cccggcttcg aaggtgacgg ccacaagtgc    120

gaggacatcg acttctgcgg tgctggacag cacgactgca atgtgcatgc cgagtgctct    180

gagagcgagg acaacaccac tttcaagtgc acctg                               215
```

<210> SEQ ID NO 25
<211> LENGTH: 7990
<212> TYPE: DNA
<213> ORGANISM: Chicken

<400> SEQUENCE: 25

```
caacatttct tcttcctttt tcttcttcga gcttctttag ctcgattttc tggcccttgc     60

agctctccgc gggtgcaggg cgcagccagc tcactactgc ctttcacagc gtcgttcccc    120

accttggccc atgtgccaca tggtcatttt tcttcagttt gttcatgaga agagctgcta    180

cagtgtagct cgaactcaac tttaaacgca gccgtttcag cggcgacaat atgctgcatc    240

gcaacccgcg gtgggcgctt tgtgcagccc tcgctgcact ctatggcgga acaggaatcg    300

ccagcgccga agttaacaat gaattgagca agtgcgaatc tgggtggaca ccctggacta    360

cctgcaaccc gcaaactggt ctgcgggaga ggcacaatgc acagtgcgag acatgggtgg    420

aggttgagga atgccagaag ctgacaggat gtggcaactg gactccttgg tctcccggcg    480

atatgtcgtg tgtggtggga cagtttcaaa cccgcaacag ggagggctgc ccagaggtgc    540

aggaagtgag ggcatgcagg cctgtacttc tagaatgcaa cgatcaatgg accccctgga    600

caatgtgcga caccaaccgc gtccaggaaa gatacaactc aaagtgcgga cccgtcgaag    660
```

-continued

```
tccgcgagtg caacatggac gacgcagaga tcgagaaatg cggcgagttc gtggaatggg    720
atccccctat gaatggagac tgcgtacgcg ggggtaccca cacgcgttac cgtcaaaact    780
gcccagaccg caaagaggtg cgggtgtgcg gagcctttga ttgcagtagc tgctctgtaa    840
acgccacttg cgatcccatt ggtgcatcct gcgaatgcaa gcctggtttc cgcggcaatg    900
ggaagacctg cgaggccttc aacccctgcg aagataccoc tgcaccttgc gacagcaacg    960
ccatctgcac cccagacggc aatgacgcca aatgccagtg caaggcaggc tgggacgcag   1020
attccggagc aggcagcagc aagaagcctt gcgttgaggt cgacgagtgc gcatccaaca   1080
cccaccagtg cccggcacac tccacatgca tcaacaccaa gggctcttat aagtgcgact   1140
gcaaccaggg atacgtcaag ggagaggacg gacagtgtca tgacgtcgat gaatgcacca   1200
acggagagca cacctgcccc gctcactcca cttgtttgaa tacagctggc agctacgagt   1260
gccgctgcga cactgggtac agcggaaatg caactgcaga cagcccttgc aagaacattg   1320
acgaatgcgc caaccccaac gcctgctcgg ccaacgctat ctgcacagac accgacggct   1380
ccttcacctg cagctgcccc gaagggtaca gcggccaggg aacccatgac tctccctgct   1440
ccaagatcga cttctgcgca gacccctcac tcaatacatg cggagcccac tccacttgcg   1500
tgaacaccct cacatctttc aagtgcatct gcgatgcggg atatgaaggc gccggcactc   1560
gcgagagccc gtgcgtggac gtgaacgagt gctcgaacga gaagcccaca aacaactgca   1620
acagaaacgc aaactgcacc aacaccgagg gatcctacac ttgcgaatgc aagcccggtt   1680
tctctggcga cggcatgggt cccaacgggt gtaccgacat cgacgagtgc gcggcggagc   1740
agtccccctg cgaccctcac gcctcctgca gcaacactga gggctcgtat gtatgcacct   1800
gcaacaccgg ctacgagcca gcttcaaccg acgggcatgc atgcaaagat atcgacgagt   1860
gcgccaccgg tgcagctggg tgccacgtgt cagcacagtg tctgaacacg gacggcagct   1920
acgagtgcaa gtgtcttgag ggcttcgtcg gcgacggaaa gacctgcaac gacgtcgatg   1980
agtgcgctgc ggcgacatct ccttgcggtg acaacactca ctgccagaac acaattggca   2040
gctacgagtg cgagtgcaag gctggctatg gcaacatgca agacaacgca tgcagcgaca   2100
ttgacgagtg caaggatgcg aacaccaaga tccctgacaa ctgtctttgc gtgaacaatg   2160
atggcagcta ctcccttgag gcgaaggctg gatacgaatt ggtgaacggc gagtgcatca   2220
agatcgactt ctgcgcccgc ggcgcatgca actcgctggc ctcctgcaag gagaatgaag   2280
aaggcacagc ggcgatctgc acctgcctgc caggctacag cggcgacggc actgctgaag   2340
gccactgcaa cgacattgac gagtgtgcag gtcagaatga ctgtgctcct gccgagcagg   2400
gaggcatctg cgagaacact gtcggctcgt acacctgcaa gtgcaaagag gggtacaggc   2460
aagatggaaa ctcatgcact gagatcgacg agtgcgctga gggaacccac aactgccacc   2520
cttccgccac ctgcagcaac acccccggaa gcttcacctg ccaatgcaac agtggattca   2580
ctggcagcgg tgtggagtgc gaagacattg acgagtgctc aactgaggca gatgattgtg   2640
gtgcaaacac catctgcagc aacaccattg gtgctttcga gtgcaactgc cgtgaaggct   2700
atgaacgcgc agacgcaaag acgtgcgtcg acatcgacga atgcgcgaca ggcacacaca   2760
cttgctcgaa ccacgccacc tgcaccaata ccgatgggtc attcacatgc cagtgcaacc   2820
ccggcttcga aggtgacggc cacaagtgcg aggacatcga cttctgcggt gctggacagc   2880
acgactgcaa tgtgcatgcc gagtgctctg agagcgagga caacaccact ttcaagtgca   2940
cctgtataac agggtacgct ggagacggcc atggcgaggc aggctgccaa gacattgatg   3000
```

-continued agtgcgcaga agaaaacatc tgcggaagca acgctgtctg cacaaacacc gcaggaagct 3060
accaatgcgc atgccgtgag ggcttcgttg catcagctga acagcagcag cagggaaccc 3120
cagcactggt ttgcgtggac gtcgacgagt gcagcgacgc ttcgaagaac acatgtgcca 3180
agccagccga cggaggcatt tgcacaaaca ctgaaggcag ctacgaatgc gcttgcaagc 3240
caggctacca aggtgacggc cacagctgcg cagacatcaa cgaatgcact gcacagggca 3300
cctgcggcga acacacaact tgcaagaaca cacccggatc cttccagtgc gactgcgttg 3360
agggattcga gcgcgctgat gaacgcacct gccgtgacat caacgagtgc gagacaggag 3420
cagtcgtgct gccaccgaac tccacctgcg tcaacactga aggcagctac gacttcgact 3480
gcgttgctgg gtaccgccgc actgatggag cttgtgtgaa gatcgacttc tgcaaggaga 3540
agggatgcaa cgcaaacgcc acatgccgcg aaaacgatgc cggcaccgag gccatctgca 3600
cttgcaagga aggctatgaa ggcagcggag aaggcgaaga tggttgccag aacatcaatg 3660
agtgcgagag aggcgaaccc tgcaaggact tcggcgaagg cggtgtttgc gtcgacacac 3720
caggatcatt cacttgcgag tgcgctgctg gattcattca acgccgctcc gtttgccaag 3780
atgttgacga atgtctcgac ggaaagctga acacctgcgc tgccaccgga ggcgtctgct 3840
ccaacaccgt cggttccttc acctgctcgt gcgccagcgg cttcgaaggc gatggccaca 3900
cctgcaatga tgtcgacgaa tgcgcaacag cacagcacac ctgtgacccg aatgccactt 3960
gcgtcaacac cgaaggcagc ttcgagtgcc gctgcaatgc cggattcgag ggcgacggac 4020
acacctgcgc agacatcgac gaatgcgcag acccagccaa aaacacatgc gatacacaca 4080
agggtgtatg ccaaaacacc acagggtcct acacctgcgg ctgcaagacc ggattcagtc 4140
ttgcagctga cggaagcaca tgcgaaaacg tcgacgagtg cgcggcggga actgcaaact 4200
gcaacgagcg aagcttctgt aaggacacag agggttccta ccaatgcgag tgcaagaacg 4260
gctacaaggc tgcaggagag gactgtgtgg acgttgacga gtgcgaggct ggcgtgcatg 4320
gatgcagcga gcacgcaatc tgcacaaata cagacggcag ctactcctgc gaatgcatgg 4380
agggatacca gggagacggc aaggcttgcg agaagacagt cggcgtctgc gactccgctc 4440
cctgcggtgc ccacgccacc tgcgagcctg caggggacaa ctacacttgc acatgccacc 4500
caggctacga gatgcgcgaa ggagcctgcg ttgacatcga tgagtgcaca gcaggcagcc 4560
tcaactgcga ccctcatgcc atttgcacaa acaccgacgg ctccttcact tgcgtctgtg 4620
gcagcggcta taccggcctt ggcacatcct gcgaagacat cgacgagtgc gcgggtaacg 4680
cagcaggctg cgacatccac gccgtctgca cgaacactcc cggatcgttc aagtgcgagt 4740
gcaagagcgg cttcgaaggc gatggcacgc aatgcacgga gaaggtgttg ctccccggac 4800
agattcactg cgaagcctgg actgcatgga cagagtgtac cgacggcgcc aaaaccagca 4860
cacgcagctg ccttgcactg ccgcttaaga aggagatgcg cgcctgccct gcagctgact 4920
tctcccagtg cggagagttc actgaatgga ctgcctgccc tggaaccaac aataacctgt 4980
ctcataggcg cactgaaaga ttcggagaac ccggatgcga agatgcagag gaagtccgcg 5040
aatgcccaga tgaagagacc gagcagaaat gcggcgcctg ggtgagtggt accgcctgcg 5100
gcgacccatc ccctggcctg agaactcgcg cacgcgagaa ctgccccgat gtggtagagt 5160
tcgagcgttg cactatgccc agtgagcctg aggctggcga agtgactgag cctcacacag 5220
aaggaggagc cggagttggt ggcgaagtga ctgagcctga cacggaagaa ggagccggag 5280
ttggtggtga agtgcagccc ggtacagaag aaggagcagg agttggtggt gaagtgcagc 5340
ccggtacaga agaaggagcc ggagttggtg gtgaagtgca gcccggtaca gaagaaggag 5400

-continued

```
ccggagttgg tggtgaagtg cagcccggta cggaagaagg agccggcatt ggtggcgaag   5460
tgactgagcc tgacaccgaa ggaggagccg gagttagtgg cgaaccgacc gaagaagagg   5520
gcaccgaaag caccggtcca tgcaaagagt tcggaccctg gacggcctgc aaggaggacg   5580
agaacggagt cggcatccaa cgccgtatgt gcgccggcag agaagacatc atcgaatcca   5640
gaatttgcac tgtcacggat gactgcggag aatggacccc ctggtcaact tgcactaacg   5700
gcagccaggc cagaaacaaa cgcttctgca ccaacgttag ggaagtccgt ctctgcggag   5760
ctgacattcc agttacagac ggatgcacgt ggagcgagtg gacttcttgc agtctagtca   5820
atgaggaggg cggctacttc cgcacgcgca catcctctga ctgcaacatg aatgaagtgc   5880
aggcctgctc tcccagcagc agcacaaccg cagacagcga aacagaaggc acctgctctg   5940
catggaaccc ctggacggag tgctcgaacg gccaccagac acgcaagtgt gccacaatgg   6000
aagcagaaga atcgcgcact tgcggagaga ctccagagaa ctgcggagaa ttcggcccct   6060
tcgaacccgc aaactgcacg gccggccaaa tggtcaccag gacgcgcacc tgcggagaaa   6120
ccgagcagaa ggaaaccaaa ctgtgcgacg tcagctccac cgaagaagga aaacaatgcg   6180
gtcagtgggg cccatggagc gaatgcaaca tccacctggg ctcagaggac aatgtgcgtg   6240
ttcgtgagga caccgcttgc ggcgtgacgg agtacgagga gtgcagcaag ccggcgaaca   6300
acgcctttgt ctgcacacct tggagtgaat gctcggacaa gaaggagcgg agaacgtgca   6360
ccatccgcaa aaacggtctt gttcagacac gtcaagaatt cagaacatgc agtgtagaca   6420
tcgccacaac ttgcggcgat ttcggcgcat ggtctgaatg caacgctgag ggcttgcatc   6480
agcgcagtct cgagaaatgc cccgacgtca tcgaggtcgc aacttgcggc agtgaggatt   6540
gcccgccatt cggcgagtgg actgaatgcg gcgttccaga ggagggcatg cgttctcgcc   6600
aacgcattga ctgcgttgaa tctgcagcct gccagtgcac agaagtggag agctgcttcg   6660
acaccgaatt gcaccccatt ccagcccccg gtacggaaac aggcgaagga gagggagaga   6720
ccgagacagg cgaaggcgaa actggtgaag caggtggcga ggaaggcgag caaacaggag   6780
aaggcgaagt gcagccccca gaagaagagc ttcctgggga gagtgtaact gagcctgagg   6840
agaagcctga ggaggagcta cctgaggagg aggttactga gcctgaggag aagcctgagg   6900
agggtgtgac tcagcctgag gagacacctg agcagcctgt tgagggtacc gaagaagagg   6960
gcaagcagga gtctgaggct gcccccgaaa ctcctgccgt ccagccaaaa ccagaggagg   7020
gtcacgaacg cccagaaccc gaagaggagg aggagaagaa ggaagaaggc ggcggcttcc   7080
caacagctgc agtggcagga ggtgttggtg gtgtgttgct catagctgct gtaggtggtg   7140
gtgttgcagc cttcactagc ggcggaggtg gcgctggcgc acaggaggca gaacaggtcg   7200
agttcgaagg agaagatacc ggagcagcaa ctgccgagac acctgaagcc gatacagtta   7260
tcgacatcac agacgaagac gactactggg ccgacagcgg cgacattcag taaagttgaa   7320
tgtctgtttt cttccaagga gaagatacaa aaccaaaatc ttaacaaaac gaaggatgcg   7380
aaggcgaaac aggccaaagt cgacctgttt tctcattcaa tcaatggttg cagtcgtgaa   7440
ggagctggac tcagttgcat ctccacccca agagctcgcc gttagtgggc aagttggata   7500
gggtgaatgc attttcatct ccgcaggcga aagtcacgac gagggcctgt tcttgtttgt   7560
ttgtttgaat tggttggttg gtgcatcctg ctggatttca acgacggcaa tcatcacgca   7620
gtgagacgga gcagcagcgc atactatttt ctgagcaagt tcatcgttta tttttcgctg   7680
tatctcgtag cgccgaggaa gcaaacaagc aaacgcccac caactgacca accaatgaga   7740
```

-continued

```
gagccgtcct ttaatttcca cccctcttct gtcttccgaa gattcggcgg ggtttcggat   7800

gggggagaaa ttgtggttgg attggtcggg tgttttcgtt ttctttgatt gatgcaacaa   7860

tatctgctag ccagcgtaca aagaatagct gcagttcaaa tgaatgcatc ttaattattc   7920

cacaccgcgg tgcctcttct ttgccgtggc acaccttccg tttattacct ccactcaaga   7980

ttttctcccc                                                          7990


<210> SEQ ID NO 26
<211> LENGTH: 2359
<212> TYPE: PRT
<213> ORGANISM: Chicken

<400> SEQUENCE: 26

Met Leu His Arg Asn Pro Arg Trp Ala Leu Cys Ala Ala Leu Ala Ala
1               5                   10                  15

Leu Tyr Gly Gly Thr Gly Ile Ala Ser Ala Glu Val Asn Asn Glu Leu
            20                  25                  30

Ser Lys Cys Glu Ser Gly Trp Thr Pro Trp Thr Thr Cys Asn Pro Gln
        35                  40                  45

Thr Gly Leu Arg Glu Arg His Asn Ala Gln Cys Glu Thr Trp Val Glu
    50                  55                  60

Val Glu Glu Cys Gln Lys Leu Thr Gly Cys Gly Asn Trp Thr Pro Trp
65                  70                  75                  80

Ser Pro Gly Asp Met Ser Cys Val Val Gly Gln Phe Gln Thr Arg Asn
                85                  90                  95

Arg Glu Gly Cys Pro Glu Val Gln Glu Val Arg Ala Cys Arg Pro Val
            100                 105                 110

Leu Leu Glu Cys Asn Asp Gln Trp Thr Pro Trp Thr Met Cys Asp Thr
        115                 120                 125

Asn Arg Val Gln Glu Arg Tyr Asn Ser Lys Cys Gly Pro Val Glu Val
    130                 135                 140

Arg Glu Cys Asn Met Asp Asp Ala Glu Ile Glu Lys Cys Gly Glu Phe
145                 150                 155                 160

Val Glu Trp Asp Pro Pro Met Asn Gly Asp Cys Val Arg Gly Gly Thr
                165                 170                 175

His Thr Arg Tyr Arg Gln Asn Cys Pro Asp Arg Lys Glu Val Arg Val
            180                 185                 190

Cys Gly Ala Phe Asp Cys Ser Ser Cys Ser Val Asn Ala Thr Cys Asp
        195                 200                 205

Pro Ile Gly Ala Ser Cys Glu Cys Lys Pro Gly Phe Arg Gly Asn Gly
    210                 215                 220

Lys Thr Cys Glu Ala Phe Asn Pro Cys Glu Asp Thr Pro Ala Pro Cys
225                 230                 235                 240

Asp Ser Asn Ala Ile Cys Thr Pro Asp Gly Asn Asp Ala Lys Cys Gln
                245                 250                 255

Cys Lys Ala Gly Trp Asp Ala Asp Ser Gly Ala Gly Ser Ser Lys Lys
            260                 265                 270

Pro Cys Val Glu Val Asp Glu Cys Ala Ser Asn Thr His Gln Cys Pro
        275                 280                 285

Ala His Ser Thr Cys Ile Asn Thr Lys Gly Ser Tyr Lys Cys Asp Cys
    290                 295                 300

Asn Gln Gly Tyr Val Lys Gly Glu Asp Gly Gln Cys His Asp Val Asp
305                 310                 315                 320

Glu Cys Thr Asn Gly Glu His Thr Cys Pro Ala His Ser Thr Cys Leu
```

-continued

```
                325                 330                 335

Asn Thr Ala Gly Ser Tyr Glu Cys Arg Cys Asp Thr Gly Tyr Ser Gly
            340                 345                 350

Asn Ala Thr Ala Asp Ser Pro Cys Lys Asn Ile Asp Glu Cys Ala Asn
        355                 360                 365

Pro Asn Ala Cys Ser Ala Asn Ala Ile Cys Thr Asp Thr Asp Gly Ser
    370                 375                 380

Phe Thr Cys Ser Cys Pro Glu Gly Tyr Ser Gly Gln Gly Thr His Asp
385                 390                 395                 400

Ser Pro Cys Ser Lys Ile Asp Phe Cys Ala Asp Pro Ser Leu Asn Thr
                405                 410                 415

Cys Gly Ala His Ser Thr Cys Val Asn Thr Leu Thr Ser Phe Lys Cys
            420                 425                 430

Ile Cys Asp Ala Gly Tyr Glu Gly Ala Gly Thr Arg Glu Ser Pro Cys
        435                 440                 445

Val Asp Val Asn Glu Cys Ser Asn Glu Lys Pro Thr Asn Asn Cys Asn
    450                 455                 460

Arg Asn Ala Asn Cys Thr Asn Thr Glu Gly Ser Tyr Thr Cys Glu Cys
465                 470                 475                 480

Lys Pro Gly Phe Ser Gly Asp Gly Met Gly Pro Asn Gly Cys Thr Asp
                485                 490                 495

Ile Asp Glu Cys Ala Ala Glu Gln Ser Pro Cys Asp Pro His Ala Ser
            500                 505                 510

Cys Ser Asn Thr Glu Gly Ser Tyr Val Cys Thr Cys Asn Thr Gly Tyr
        515                 520                 525

Glu Pro Ala Ser Thr Asp Gly His Ala Cys Lys Asp Ile Asp Glu Cys
    530                 535                 540

Ala Thr Gly Ala Ala Gly Cys His Val Ser Ala Gln Cys Leu Asn Thr
545                 550                 555                 560

Asp Gly Ser Tyr Glu Cys Lys Cys Leu Glu Gly Phe Val Gly Asp Gly
                565                 570                 575

Lys Thr Cys Asn Asp Val Asp Glu Cys Ala Ala Ala Thr Ser Pro Cys
            580                 585                 590

Gly Asp Asn Thr His Cys Gln Asn Thr Ile Gly Ser Tyr Glu Cys Glu
        595                 600                 605

Cys Lys Ala Gly Tyr Gly Asn Met Gln Asp Asn Ala Cys Ser Asp Ile
    610                 615                 620

Asp Glu Cys Lys Asp Ala Asn Thr Lys Ile Pro Asp Asn Cys Leu Cys
625                 630                 635                 640

Val Asn Asn Asp Gly Ser Tyr Ser Leu Glu Ala Lys Ala Gly Tyr Glu
                645                 650                 655

Leu Val Asn Gly Glu Cys Ile Lys Ile Asp Phe Cys Ala Arg Gly Ala
            660                 665                 670

Cys Asn Ser Leu Ala Ser Cys Lys Glu Asn Glu Glu Gly Thr Ala Ala
        675                 680                 685

Ile Cys Thr Cys Leu Pro Gly Tyr Ser Gly Asp Gly Thr Ala Glu Gly
    690                 695                 700

His Cys Asn Asp Ile Asp Glu Cys Ala Gly Gln Asn Asp Cys Ala Pro
705                 710                 715                 720

Ala Glu Gln Gly Gly Ile Cys Glu Asn Thr Val Gly Ser Tyr Thr Cys
                725                 730                 735

Lys Cys Lys Glu Gly Tyr Arg Gln Asp Gly Asn Ser Cys Thr Glu Ile
            740                 745                 750
```

-continued

```
Asp Glu Cys Ala Glu Gly Thr His Asn Cys His Pro Ser Ala Thr Cys
        755                 760                 765

Ser Asn Thr Pro Gly Ser Phe Thr Cys Gln Cys Asn Ser Gly Phe Thr
    770                 775                 780

Gly Ser Gly Val Glu Cys Glu Asp Ile Asp Glu Cys Ser Thr Glu Ala
785                 790                 795                 800

Asp Asp Cys Gly Ala Asn Thr Ile Cys Ser Asn Thr Ile Gly Ala Phe
                805                 810                 815

Glu Cys Asn Cys Arg Glu Gly Tyr Glu Arg Ala Asp Ala Lys Thr Cys
            820                 825                 830

Val Asp Ile Asp Glu Cys Ala Thr Gly Thr His Thr Cys Ser Asn His
        835                 840                 845

Ala Thr Cys Thr Asn Thr Asp Gly Ser Phe Thr Cys Gln Cys Asn Pro
    850                 855                 860

Gly Phe Glu Gly Asp Gly His Lys Cys Glu Asp Ile Asp Phe Cys Gly
865                 870                 875                 880

Ala Gly Gln His Asp Cys Asn Val His Ala Glu Cys Ser Glu Ser Glu
                885                 890                 895

Asp Asn Thr Thr Phe Lys Cys Thr Cys Ile Thr Gly Tyr Ala Gly Asp
            900                 905                 910

Gly His Gly Glu Ala Gly Cys Gln Asp Ile Asp Glu Cys Ala Glu Glu
        915                 920                 925

Asn Ile Cys Gly Ser Asn Ala Val Cys Thr Asn Thr Ala Gly Ser Tyr
    930                 935                 940

Gln Cys Ala Cys Arg Glu Gly Phe Val Ala Ser Ala Glu Gln Gln Gln
945                 950                 955                 960

Gln Gly Thr Pro Ala Leu Val Cys Val Asp Val Asp Glu Cys Ser Asp
                965                 970                 975

Ala Ser Lys Asn Thr Cys Ala Lys Pro Ala Asp Gly Gly Ile Cys Thr
            980                 985                 990

Asn Thr Glu Gly Ser Tyr Glu Cys  Ala Cys Lys Pro Gly  Tyr Gln Gly
        995                 1000                 1005

Asp Gly  His Ser Cys Ala Asp  Ile Asn Glu Cys Thr  Ala Gln Gly
    1010                 1015                 1020

Thr Cys  Gly Glu His Thr Thr  Cys Lys Asn Thr Pro  Gly Ser Phe
    1025                 1030                 1035

Gln Cys  Asp Cys Val Glu Gly  Phe Glu Arg Ala Asp  Glu Arg Thr
    1040                 1045                 1050

Cys Arg  Asp Ile Asn Glu Cys  Glu Thr Gly Ala Val  Val Leu Pro
    1055                 1060                 1065

Pro Asn  Ser Thr Cys Val Asn  Thr Glu Gly Ser Tyr  Asp Phe Asp
    1070                 1075                 1080

Cys Val  Ala Gly Tyr Arg Arg  Thr Asp Gly Ala Cys  Val Lys Ile
    1085                 1090                 1095

Asp Phe  Cys Lys Glu Lys Gly  Cys Asn Ala Asn Ala  Thr Cys Arg
    1100                 1105                 1110

Glu Asn  Asp Ala Gly Thr Glu  Ala Ile Cys Thr Cys  Lys Glu Gly
    1115                 1120                 1125

Tyr Glu  Gly Ser Gly Glu Gly  Glu Asp Gly Cys Gln  Asn Ile Asn
    1130                 1135                 1140

Glu Cys  Glu Arg Gly Glu Pro  Cys Lys Asp Phe Gly  Glu Gly Gly
    1145                 1150                 1155
```

-continued

```
Val Cys Val Asp Thr Pro Gly Ser Phe Thr Cys Glu Cys Ala Ala
    1160                1165                1170

Gly Phe Ile Gln Arg Arg Ser Val Cys Gln Asp Val Asp Glu Cys
    1175                1180                1185

Leu Asp Gly Lys Leu Asn Thr Cys Ala Ala Thr Gly Gly Val Cys
    1190                1195                1200

Ser Asn Thr Val Gly Ser Phe Thr Cys Ser Cys Ala Ser Gly Phe
    1205                1210                1215

Glu Gly Asp Gly His Thr Cys Asn Asp Val Asp Glu Cys Ala Thr
    1220                1225                1230

Ala Gln His Thr Cys Asp Pro Asn Ala Thr Cys Val Asn Thr Glu
    1235                1240                1245

Gly Ser Phe Glu Cys Arg Cys Asn Ala Gly Phe Glu Gly Asp Gly
    1250                1255                1260

His Thr Cys Ala Asp Ile Asp Glu Cys Ala Asp Pro Ala Lys Asn
    1265                1270                1275

Thr Cys Asp Thr His Lys Gly Val Cys Gln Asn Thr Thr Gly Ser
    1280                1285                1290

Tyr Thr Cys Gly Cys Lys Thr Gly Phe Ser Leu Ala Ala Asp Gly
    1295                1300                1305

Ser Thr Cys Glu Asn Val Asp Glu Cys Ala Ala Gly Thr Ala Asn
    1310                1315                1320

Cys Asn Glu Arg Ser Phe Cys Lys Asp Thr Glu Gly Ser Tyr Gln
    1325                1330                1335

Cys Glu Cys Lys Asn Gly Tyr Lys Ala Ala Gly Glu Asp Cys Val
    1340                1345                1350

Asp Val Asp Glu Cys Glu Ala Gly Val His Gly Cys Ser Glu His
    1355                1360                1365

Ala Ile Cys Thr Asn Thr Asp Gly Ser Tyr Ser Cys Glu Cys Met
    1370                1375                1380

Glu Gly Tyr Gln Gly Asp Gly Lys Ala Cys Glu Lys Thr Val Gly
    1385                1390                1395

Val Cys Asp Ser Ala Pro Cys Gly Ala His Ala Thr Cys Glu Pro
    1400                1405                1410

Ala Gly Asp Asn Tyr Thr Cys Thr Cys His Pro Gly Tyr Glu Met
    1415                1420                1425

Arg Glu Gly Ala Cys Val Asp Ile Asp Glu Cys Thr Ala Gly Ser
    1430                1435                1440

Leu Asn Cys Asp Pro His Ala Ile Cys Thr Asn Thr Asp Gly Ser
    1445                1450                1455

Phe Thr Cys Val Cys Gly Ser Gly Tyr Thr Gly Leu Gly Thr Ser
    1460                1465                1470

Cys Glu Asp Ile Asp Glu Cys Ala Gly Asn Ala Ala Gly Cys Asp
    1475                1480                1485

Ile His Ala Val Cys Thr Asn Thr Pro Gly Ser Phe Lys Cys Glu
    1490                1495                1500

Cys Lys Ser Gly Phe Glu Gly Asp Gly Thr Gln Cys Thr Glu Lys
    1505                1510                1515

Val Leu Leu Pro Gly Gln Ile His Cys Glu Ala Trp Thr Ala Trp
    1520                1525                1530

Thr Glu Cys Thr Asp Gly Ala Lys Thr Ser Thr Arg Ser Cys Leu
    1535                1540                1545

Ala Leu Pro Leu Lys Lys Glu Met Arg Ala Cys Pro Ala Ala Asp
```

-continued

```
    1550                1555                1560

Phe Ser  Gln Cys Gly Glu Phe  Thr Glu Trp Thr Ala  Cys Pro Gly
    1565                1570                1575

Thr Asn  Asn Asn Leu Ser His  Arg Arg Thr Glu Arg  Phe Gly Glu
    1580                1585                1590

Pro Gly  Cys Glu Asp Ala Glu  Glu Val Arg Glu Cys  Pro Asp Glu
    1595                1600                1605

Glu Thr  Glu Gln Lys Cys Gly  Ala Trp Gly Glu Trp  Thr Ala Cys
    1610                1615                1620

Gly Asp  Pro Ser Pro Gly Leu  Arg Thr Arg Ala Arg  Glu Asn Cys
    1625                1630                1635

Pro Asp  Val Val Glu Phe Glu  Arg Cys Thr Met Pro  Ser Glu Pro
    1640                1645                1650

Glu Ala  Gly Glu Val Thr Glu  Pro His Thr Glu Gly  Gly Ala Gly
    1655                1660                1665

Val Gly  Gly Glu Val Thr Glu  Pro Asp Thr Glu Glu  Gly Ala Gly
    1670                1675                1680

Val Gly  Gly Glu Val Gln Pro  Gly Thr Glu Glu Gly  Ala Gly Val
    1685                1690                1695

Gly Gly  Glu Val Gln Pro Gly  Thr Glu Glu Gly Ala  Gly Val Gly
    1700                1705                1710

Gly Glu  Val Gln Pro Gly Thr  Glu Glu Gly Ala Gly  Val Gly Gly
    1715                1720                1725

Glu Val  Gln Pro Gly Thr Glu  Glu Gly Ala Gly Ile  Gly Gly Glu
    1730                1735                1740

Val Thr  Glu Pro Asp Thr Glu  Gly Gly Ala Gly Val  Ser Gly Glu
    1745                1750                1755

Pro Thr  Glu Glu Glu Gly Thr  Glu Ser Thr Gly Pro  Cys Lys Glu
    1760                1765                1770

Phe Gly  Pro Trp Thr Ala Cys  Lys Glu Asp Glu Asn  Gly Val Gly
    1775                1780                1785

Ile Gln  Arg Arg Met Cys Ala  Gly Arg Glu Asp Ile  Ile Glu Ser
    1790                1795                1800

Arg Ile  Cys Thr Val Thr Asp  Asp Cys Gly Glu Trp  Thr Pro Trp
    1805                1810                1815

Ser Thr  Cys Thr Asn Gly Ser  Gln Ala Arg Asn Lys  Arg Phe Cys
    1820                1825                1830

Thr Asn  Val Arg Glu Val Arg  Leu Cys Gly Ala Asp  Ile Pro Val
    1835                1840                1845

Thr Asp  Gly Cys Thr Trp Ser  Glu Trp Thr Ser Cys  Ser Leu Val
    1850                1855                1860

Asn Glu  Glu Gly Gly Tyr Phe  Arg Thr Arg Thr Ser  Ser Asp Cys
    1865                1870                1875

Asn Met  Asn Glu Val Gln Ala  Cys Ser Pro Ser Ser  Ser Thr Thr
    1880                1885                1890

Ala Asp  Ser Glu Thr Glu Gly  Thr Cys Ser Ala Trp  Asn Pro Trp
    1895                1900                1905

Thr Glu  Cys Ser Asn Gly His  Gln Thr Arg Lys Cys  Ala Thr Met
    1910                1915                1920

Glu Ala  Glu Glu Ser Arg Thr  Cys Gly Glu Thr Pro  Glu Asn Cys
    1925                1930                1935

Gly Glu  Phe Gly Pro Phe Glu  Pro Ala Asn Cys Thr  Ala Gly Gln
    1940                1945                1950
```

-continued

```
Met Val  Thr Arg Thr Arg Thr  Cys Gly Glu Thr Glu  Gln Lys Glu
    1955                 1960                 1965

Thr Lys  Leu Cys Asp Val Ser  Ser Thr Glu Glu Gly  Lys Gln Cys
    1970                 1975                 1980

Gly Gln  Trp Gly Pro Trp Ser  Glu Cys Asn Ile His  Leu Gly Ser
    1985                 1990                 1995

Glu Asp  Asn Val Arg Val Arg  Glu Asp Thr Ala Cys  Gly Val Thr
    2000                 2005                 2010

Glu Tyr  Glu Glu Cys Ser Lys  Pro Ala Asn Asn Ala  Phe Val Cys
    2015                 2020                 2025

Thr Pro  Trp Ser Glu Cys Ser  Asp Lys Lys Glu Arg  Arg Thr Cys
    2030                 2035                 2040

Thr Ile  Arg Lys Asn Gly Leu  Val Gln Thr Arg Gln  Glu Phe Arg
    2045                 2050                 2055

Thr Cys  Ser Val Asp Ile Ala  Thr Thr Cys Gly Asp  Phe Gly Ala
    2060                 2065                 2070

Trp Ser  Glu Cys Asn Ala Glu  Gly Leu His Gln Arg  Ser Leu Glu
    2075                 2080                 2085

Lys Cys  Pro Asp Val Ile Glu  Val Ala Thr Cys Gly  Ser Glu Asp
    2090                 2095                 2100

Cys Pro  Pro Phe Gly Glu Trp  Thr Glu Cys Gly Val  Pro Glu Glu
    2105                 2110                 2115

Gly Met  Arg Ser Gln Arg Ile  Asp Cys Val Glu Ser  Ala Ala Cys
    2120                 2125                 2130

Gln Cys  Thr Glu Val Glu Ser  Cys Phe Asp Thr Glu  Leu His Pro
    2135                 2140                 2145

Ile Pro  Ala Pro Gly Thr Glu  Thr Gly Glu Gly Glu  Gly Glu Thr
    2150                 2155                 2160

Glu Thr  Gly Glu Gly Glu Thr  Gly Glu Ala Gly Gly  Glu Glu Gly
    2165                 2170                 2175

Glu Gln  Thr Gly Glu Gly Glu  Val Gln Pro Pro Glu  Glu Glu Leu
    2180                 2185                 2190

Pro Gly  Glu Ser Val Thr Glu  Pro Glu Glu Lys Pro  Glu Glu Glu
    2195                 2200                 2205

Leu Pro  Glu Glu Glu Val Thr  Glu Pro Glu Glu Lys  Pro Glu Glu
    2210                 2215                 2220

Gly Val  Thr Gln Pro Glu Glu  Thr Pro Glu Gln Pro  Val Glu Gly
    2225                 2230                 2235

Thr Glu  Glu Glu Gly Lys Gln  Glu Ser Glu Ala Ala  Pro Glu Thr
    2240                 2245                 2250

Pro Ala  Val Gln Pro Lys Pro  Glu Glu Gly His Glu  Arg Pro Glu
    2255                 2260                 2265

Pro Glu  Glu Glu Glu Glu Lys  Lys Glu Glu Gly Gly  Gly Phe Pro
    2270                 2275                 2280

Thr Ala  Ala Val Ala Gly Gly  Val Gly Gly Val Leu  Leu Ile Ala
    2285                 2290                 2295

Ala Val  Gly Gly Gly Val Ala  Ala Phe Thr Ser Gly  Gly Gly Gly
    2300                 2305                 2310

Ala Gly  Ala Gln Glu Ala Glu  Gln Val Glu Phe Glu  Gly Glu Asp
    2315                 2320                 2325

Thr Gly  Ala Ala Thr Ala Glu  Thr Pro Glu Ala Asp  Thr Val Ile
    2330                 2335                 2340
```

-continued

```
Asp Ile  Thr Asp Glu Asp Asp  Tyr Trp Ala Asp Ser  Gly Asp Ile
    2345                2350                2355

Gln


<210> SEQ ID NO 27
<211> LENGTH: 75
<212> TYPE: PRT
<213> ORGANISM: Chicken

<400> SEQUENCE: 27

Ala Ala Val Ala Gly Gly Val Gly Gly Val Leu Leu Ile Ala Ala Val
1               5                   10                  15

Gly Gly Gly Val Ala Ala Phe Thr Ser Gly Gly Gly Gly Ala Gly Ala
            20                  25                  30

Gln Glu Ala Glu Gln Val Glu Phe Glu Gly Glu Asp Thr Gly Ala Ala
        35                  40                  45

Thr Ala Glu Thr Pro Glu Ala Asp Thr Val Ile Asp Ile Thr Asp Glu
    50                  55                  60

Asp Asp Tyr Trp Ala Asp Ser Gly Asp Ile Gln
65                  70                  75


<210> SEQ ID NO 28
<211> LENGTH: 75
<212> TYPE: PRT
<213> ORGANISM: Chicken

<400> SEQUENCE: 28

Ala Ala Val Ala Gly Gly Val Gly Gly Val Leu Leu Leu Ala Ala Val
1               5                   10                  15

Gly Gly Gly Val Ala Ala Tyr Ser Gly Gly Gly Gly Gly Gly Gly Ala
            20                  25                  30

Glu Glu Ala Glu Gln Val Glu Phe Glu Gly Glu Glu Ser Gly Gly Ala
        35                  40                  45

Ser Ala Glu Thr Pro Glu Ala Asp Thr Val Ile Asp Ile Thr Asp Glu
    50                  55                  60

Asp Asp Tyr Trp Ala Asp Ser Gly Asp Ile Gln
65                  70                  75


<210> SEQ ID NO 29
<211> LENGTH: 67
<212> TYPE: PRT
<213> ORGANISM: Chicken

<400> SEQUENCE: 29

Leu Ala Ile Ala Val Gly Leu Pro Val Gly Ile Leu Gly Leu Cys Ile
1               5                   10                  15

Ile Ala Gly Ser Leu Phe Leu Ile Gly Gly Arg Ser Gly Asp Gln Glu
            20                  25                  30

Glu Asp Glu Thr Asn Tyr Gln Tyr Phe Asp Gln Ser Ser Ala Thr Leu
        35                  40                  45

Asp Gln Asp Ser Glu Tyr Val Gln Glu Ile Gly Pro Glu Ser Gln Asn
    50                  55                  60

Trp Ala Ser
65


<210> SEQ ID NO 30
<211> LENGTH: 73
<212> TYPE: PRT
<213> ORGANISM: Chicken
```

<400> SEQUENCE: 30

```
Val Ala Ala Ile Ala Gly Gly Ile Val Gly Gly Leu Ile Leu Leu Gly
1               5                   10                  15

Ala Ala Gly Gly Gly Ala Tyr Tyr Tyr Phe Gly Gly Gly Lys Ala Asn
            20                  25                  30

Glu Ser Leu Ala Glu Met Asp Phe Asp Val Asp Ser Gly Ala Thr Lys
        35                  40                  45

Val Val Met Glu Glu Glu Lys Glu Thr Leu Val Pro Val Asp Asp Asp
    50                  55                  60

Ser Asp Met Trp Met Gly Ala Asp His
65                  70
```

<210> SEQ ID NO 31
<211> LENGTH: 63
<212> TYPE: PRT
<213> ORGANISM: Chicken

<400> SEQUENCE: 31

```
Ile Ala Gly Gly Ile Ala Gly Gly Leu Ala Leu Leu Ala Cys Ala Gly
1               5                   10                  15

Leu Ala Tyr Lys Phe Val Val Pro Gly Ala Ala Thr Pro Tyr Ala Gly
            20                  25                  30

Glu Pro Ala Pro Phe Asp Glu Thr Leu Gly Glu Glu Asp Lys Asp Leu
        35                  40                  45

Asp Glu Pro Glu Gln Phe Arg Leu Pro Glu Glu Asn Glu Trp Asn
    50                  55                  60
```

<210> SEQ ID NO 32
<211> LENGTH: 63
<212> TYPE: PRT
<213> ORGANISM: Chicken

<400> SEQUENCE: 32

```
Ile Ala Gly Gly Ile Ile Gly Gly Leu Ala Ile Ile Gly Cys Ile Gly
1               5                   10                  15

Val Gly Tyr Asn Phe Ile Ala Gly Ser Ser Ala Ala Ala Met Ala Gly
            20                  25                  30

Glu Ala Ala Pro Phe Glu Asp Val Met Ala Asp Asp Glu Lys Gly Ile
        35                  40                  45

Val Glu Asn Glu Gln Phe Lys Leu Pro Glu Asp Asn Asp Trp Asn
    50                  55                  60
```

<210> SEQ ID NO 33
<211> LENGTH: 55
<212> TYPE: PRT
<213> ORGANISM: Chicken

<400> SEQUENCE: 33

```
Ile Ala Gly Gly Ile Ile Gly Gly Leu Ala Leu Leu Gly Cys Ala Gly
1               5                   10                  15

Phe Ala Tyr Lys Phe Leu Ala His Ala Pro Thr Pro Pro Met Thr Ser
            20                  25                  30

Glu Gly Ala Pro Phe Asn Asp Val Leu Gly Glu Gly Glu Lys Asp Ile
        35                  40                  45

Glu Glu Asn Glu Gln Phe Lys
    50                  55
```

-continued

<210> SEQ ID NO 34
<211> LENGTH: 65
<212> TYPE: PRT
<213> ORGANISM: Chicken

<400> SEQUENCE: 34

```
Ile Val Tyr Phe Ala Thr Gly Gly Ala Phe Leu Ile Ile Leu Leu Leu
1               5                   10                  15

Phe Ala Ser Trp Asn Ala Ala Ser Asn Asp Tyr Glu Glu Glu Ala Thr
            20                  25                  30

Phe Asp Glu Phe Val Glu Tyr Ser Asp Asp Ile His Arg Thr Pro Leu
        35                  40                  45

Met Pro Asn Asp Ile Glu His Met Gln Gln Phe Thr Pro Leu Asp Tyr
    50                  55                  60

Ser
65
```

<210> SEQ ID NO 35
<211> LENGTH: 70
<212> TYPE: PRT
<213> ORGANISM: Chicken

<400> SEQUENCE: 35

```
Ala Ala Ile Ala Gly Gly Ile Val Gly Gly Val Leu Leu Leu Gly Ala
1               5                   10                  15

Ala Gly Gly Gly Ala Ala Tyr Met Met Lys Gly Gly Gly Gly Pro Gly
            20                  25                  30

Gly Glu Ala Glu Gln Val Val Phe Glu Gly Glu Gly Ala Asp Thr Gly
        35                  40                  45

Ala Gly Glu Ala Pro Pro Glu Ser Glu Thr Val Ile Glu Ile Glu Asp
    50                  55                  60

Asp Ala Trp Ala Asp Thr
65                  70
```

<210> SEQ ID NO 36
<211> LENGTH: 71
<212> TYPE: PRT
<213> ORGANISM: Chicken

<400> SEQUENCE: 36

```
Ile Ala Gly Ala Ile Ala Gly Gly Val Ile Gly Gly Leu Ile Leu Leu
1               5                   10                  15

Gly Ala Ala Gly Gly Ala Ser Tyr His Tyr Tyr Leu Ser Ser Ser Val
            20                  25                  30

Gly Ser Pro Ser Ala Glu Ile Glu Tyr Glu Ala Asp Asp Gly Ala Thr
        35                  40                  45

Lys Val Val Met Glu Glu Glu Lys Glu Thr Leu Val Pro Val Asp Asp
    50                  55                  60

Asp Ser Asp Met Trp Met Glu
65                  70
```

<210> SEQ ID NO 37
<211> LENGTH: 62
<212> TYPE: PRT
<213> ORGANISM: Chicken

<400> SEQUENCE: 37

```
Ala Gly Ala Ile Ala Gly Gly Val Ile Gly Gly Leu Leu Leu Leu Ser
1               5                   10                  15
```

-continued

```
Ala Ala Gly Ala Gly Val Ala Tyr Met Arg Lys Ser Gly Ser Gly Gly
            20                  25                  30

Gly Glu Glu Ile Glu Tyr Glu Arg Gly Ile Glu Ala Ala Glu Ala Ser
        35                  40                  45

Glu Val Glu Val Leu Val Asp Leu Asp Ser Lys Thr Trp Asp
    50                  55                  60
```

<210> SEQ ID NO 38
<211> LENGTH: 57
<212> TYPE: PRT
<213> ORGANISM: Chicken

<400> SEQUENCE: 38

```
Thr Pro Leu Trp Leu Trp Cys Cys Val Ala Leu Ala Ala Val Ile Phe
1               5                   10                  15

Val Gly Ala Val Val Tyr Gly Val Arg Tyr Phe Leu Lys Lys Trp Lys
            20                  25                  30

Lys Thr Asn Glu Ser Glu Asp Asp Ala Leu Leu Arg Tyr Gly Tyr Asp
        35                  40                  45

Tyr Gly Ala Ala His Ser Phe Arg Gly
    50                  55
```

<210> SEQ ID NO 39
<211> LENGTH: 77
<212> TYPE: PRT
<213> ORGANISM: Chicken

<400> SEQUENCE: 39

```
Ile Ala Leu Val Val Val Gly Cys Val Ala Leu Leu Gly Ile Ile Ala
1               5                   10                  15

Gly Gly Ile Ser Tyr Ala Arg Asn Arg Gly Gly Glu Arg Asp Asp Glu
            20                  25                  30

Asp Leu Ala Pro Pro Pro Arg Ser Thr Arg Glu Arg Arg Leu Ser Ser
        35                  40                  45

Met Gly Glu Gly Phe Glu Asn Ala Ser Trp Ala Ser Ser Val Ser Met
    50                  55                  60

Ile Pro Ser Ala Pro Ala Pro Pro Pro Ser Gly Gly Ile
65                  70                  75
```

<210> SEQ ID NO 40
<211> LENGTH: 44
<212> TYPE: PRT
<213> ORGANISM: Chicken

<400> SEQUENCE: 40

```
Met Thr Gln Trp Tyr Val Ala Gly Gly Ile Gly Gly Cys Leu Cys Leu
1               5                   10                  15

Phe Ala Val Val Tyr Leu Thr Ser Ser Arg Gln Ser Pro Asn Ser Asn
            20                  25                  30

Asp Ala Leu Tyr Ala His Asp Phe Glu Gly Met Tyr
        35                  40
```

<210> SEQ ID NO 41
<211> LENGTH: 86
<212> TYPE: PRT
<213> ORGANISM: Chicken

<400> SEQUENCE: 41

```
Ala Leu Ile Ala Gly Leu Ala Val Gly Gly Val Leu Leu Leu Ala Leu
1               5                   10                  15
```

-continued

```
Leu Gly Gly Gly Cys Tyr Phe Ala Lys Arg Leu Asp Arg Asn Lys Gly
            20                  25                  30

Val Gln Ala Ala His His Glu His Glu Phe Gln Ser Asp Arg Gly Ala
        35                  40                  45

Arg Lys Lys Arg Pro Ser Asp Leu Met Gln Glu Ala Glu Pro Ser Phe
    50                  55                  60

Trp Asp Glu Ala Glu Glu Asn Ile Glu Gln Asp Gly Glu Thr His Val
65                  70                  75                  80

Met Val Glu Gly Asp Tyr
                85


<210> SEQ ID NO 42
<211> LENGTH: 68
<212> TYPE: PRT
<213> ORGANISM: Chicken

<400> SEQUENCE: 42

Ala Ala Val Ala Gly Gly Val Ala Gly Gly Val Leu Ala Ile Ala Ala
1               5                   10                  15

Gly Ala Gly Ala Phe Tyr Gly Leu Ser Gly Gly Ala Ala Ser Ala Ala
            20                  25                  30

Gly Gly Ala Ala Ala Glu Val Met Val Glu Ser Gly Thr Ala Asn Pro
        35                  40                  45

Pro Glu Val Glu Lys Glu Ser Leu Ile Thr Ala Gly Glu Gln Ser Glu
    50                  55                  60

Met Trp Ala Ser
65


<210> SEQ ID NO 43
<211> LENGTH: 68
<212> TYPE: PRT
<213> ORGANISM: Chicken

<400> SEQUENCE: 43

Ala Ala Val Ala Gly Gly Val Ala Gly Gly Val Leu Ala Ile Ala Ala
1               5                   10                  15

Gly Ala Gly Ala Phe Tyr Gly Leu Ser Gly Gly Ser Ala Ala Ala Ala
            20                  25                  30

Thr Glu Ala Gly Ala Glu Val Met Thr Glu Ala Gly Thr Ser Asn Ala
        35                  40                  45

Ala Glu Val Glu Lys Glu Ser Leu Ile Ser Ala Gly Glu Gln Ser Glu
    50                  55                  60

Met Trp Ala Ser
65


<210> SEQ ID NO 44
<211> LENGTH: 88
<212> TYPE: PRT
<213> ORGANISM: Chicken

<400> SEQUENCE: 44

Ile Ala Ile Gln Ala Ala Gly Gly Ala Ser Ala Ala Val Gly Leu Val
1               5                   10                  15

Ala Ala Val Gly Ala Trp Tyr Ala Ser Arg Asn Arg Gln Glu Gly Glu
            20                  25                  30

Asp Asp Asp Asp Tyr Gln Met Asp Leu Lys Gln Asn Met Lys Lys Lys
        35                  40                  45
```

-continued

```
Arg Lys Lys Arg Val Met Lys Gln Gln Met Lys Leu Leu Leu Gln Leu
    50                  55                  60

Ser Val Ile His His Ser Gly Thr Asn Leu Lys Arg Arg Lys Asp Phe
65                  70                  75                  80

Ser Asn Ser Lys Lys Phe Arg Ile
                85


<210> SEQ ID NO 45
<211> LENGTH: 64
<212> TYPE: PRT
<213> ORGANISM: Chicken

<400> SEQUENCE: 45

Leu Ala Ala Gly Val Ile Gly Leu Val Ala Leu Ala Ala Gly Gly Leu
1               5                   10                  15

Ile Tyr Gly Tyr Asn Thr Leu Asn Gly Gly Glu Pro Pro His Ser Ser
            20                  25                  30

Asn Met Glu Phe Glu Asn Val Glu Asn Asn Ser Gly Thr Glu Glu Glu
        35                  40                  45

Glu Asn Glu Asp Phe Glu Val Val Asp Ala Asp Asp Pro Met Trp Asn
    50                  55                  60


<210> SEQ ID NO 46
<211> LENGTH: 8
<212> TYPE: PRT
<213> ORGANISM: Chicken

<400> SEQUENCE: 46

Glu Val Asn Asn Glu Leu Ser Lys
1               5
```